US009484540B2

(12) United States Patent
Ito et al.

(10) Patent No.: US 9,484,540 B2
(45) Date of Patent: Nov. 1, 2016

(54) OXYGEN-CONTAINING FUSED RING DERIVATIVE AND ORGANIC ELECTROLUMINESCENCE DEVICE COMPRISING THE SAME

(75) Inventors: Hirokatsu Ito, Sodegaura (JP);
Masahiro Kawamura, Sodegaura (JP);
Yuichiro Kawamura, Sodegaura (JP);
Yumiko Mizuki, Sodeguara (JP);
Hiroyuki Saito, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 592 days.

(21) Appl. No.: 13/988,920

(22) PCT Filed: Nov. 22, 2011

(86) PCT No.: PCT/JP2011/006486
§ 371 (c)(1),
(2), (4) Date: Aug. 7, 2013

(87) PCT Pub. No.: WO2012/070226
PCT Pub. Date: May 31, 2012

(65) Prior Publication Data
US 2013/0306958 A1    Nov. 21, 2013

(30) Foreign Application Priority Data
Nov. 22, 2010  (JP) .................. 2010-260653

(51) Int. Cl.
H01L 51/50    (2006.01)
H01L 51/00    (2006.01)
C07D 405/10   (2006.01)
C07D 493/04   (2006.01)
C09K 11/06    (2006.01)
H05B 33/14    (2006.01)

(52) U.S. Cl.
CPC ........ *H01L 51/0067* (2013.01); *C07D 405/10* (2013.01); *C07D 493/04* (2013.01); *C09K 11/06* (2013.01); *H01L 51/0072* (2013.01); *H01L 51/0073* (2013.01); *H05B 33/14* (2013.01); *C09K 2211/1011* (2013.01); *H01L 51/0055* (2013.01); *H01L 51/0058* (2013.01); *H01L 51/0059* (2013.01); *H01L 51/0061* (2013.01); *H01L 51/5076* (2013.01); *H01L 51/5096* (2013.01)

(58) Field of Classification Search
None
See application file for complete search history.

(56) References Cited

U.S. PATENT DOCUMENTS

| | | | |
|---|---|---|---|
| 4,578,469 A | 3/1986 | Deger et al. | |
| 5,942,532 A | 8/1999 | Ohemeng et al. | |
| 6,440,586 B1 | 8/2002 | Yanagi et al. | |
| 7,018,723 B2 | 3/2006 | Thompson et al. | |
| 2003/0168970 A1 | 9/2003 | Tominaga et al. | |
| 2003/0215667 A1 | 11/2003 | Xie | |
| 2004/0091816 A1 | 5/2004 | Matsumura et al. | |
| 2004/0150327 A1 | 8/2004 | Kawai et al. | |
| 2010/0087429 A1 | 4/2010 | White et al. | |
| 2010/0112478 A1 | 5/2010 | Furukawa | |
| 2011/0136201 A1 | 6/2011 | Mao et al. | |
| 2011/0168992 A1 | 7/2011 | Bae et al. | |

FOREIGN PATENT DOCUMENTS

| | | | |
|---|---|---|---|
| JP | 57-198756 | 12/1982 | |
| JP | 3-200880 | 9/1991 | |
| JP | 5-202356 | 8/1993 | |
| JP | 6-9952 | 1/1994 | |
| JP | 8-334898 | 12/1996 | |
| JP | 2000-252069 | 9/2000 | |
| JP | 2000-344780 | 12/2000 | |
| JP | 2001-11079 | 1/2001 | |
| JP | 2001-11080 | 1/2001 | |
| JP | 2001-81347 | 3/2001 | |
| JP | 2002-525808 | 8/2002 | |
| JP | 2004-170762 | 6/2004 | |
| JP | 2004-214180 | 7/2004 | |
| JP | 2010-045281 | * 2/2010 | ............ H01L 51/50 |
| KR | 10-2011-0111093 | 10/2011 | |
| KR | 10-2011-0113470 | 10/2011 | |

| WO | WO 99/11627 | | 3/1999 |
| WO | WO 00/16593 A1 | | 3/2000 |
| WO | WO 02/43449 A1 | | 5/2002 |
| WO | WO 2008/117738 A1 | | 10/2008 |
| WO | WO 2010/030954 A1 | | 3/2010 |
| WO | WO 2010/036027 A2 | | 4/2010 |
| WO | WO 2010/107244 | * | 9/2010 ............. C09K 11/06 |
| WO | WO 2010/107244 A2 | | 9/2010 |

OTHER PUBLICATIONS

International Preliminary Report on Patentability and Written Opinion issued Jun. 20, 2013 in Application No. PCT/JP2011/006486 (English Translation).
International Search Report issued Feb. 21, 2012 in Application No. PCT/JP2011/006486.
Ron T. F. Jukes, et al., "Synthesis, Photophysical, Photochemical, and Redox Properties of Nitrospiropyrans Substituted with with Ru or Os Tris(bipyridine) Complexes", Inorganic Chemistry, vol. 45, No. 20, 2006, pp. 8326-8341.
Ron T. F. Jukes, et al., "Photophysical and Redox Properties of Dinuclear Ru or Os Polypyridyl Complexes with Incorporated Photostable Spiropyran Bridge" Inorganic Chemistry, vol. 48, No. 4, 20069 pp. 1711-1721.
D. D. Rajadhyaksha, et al., "Synthesis of furo[3', 2' :5,6] pyrido [1,2-a] benzimidazole derivatives and their fluorescence properties", STN Online Capsul File, 1988, 1 page.
Yousuke Ooyama, et al., "Dye-Sensitized Solar Cells Based on a Novel Fluorescent Dye with a Pyridine Ring and Pyridinium Dye with the Pyridinium Ring Forming Strong Interactions with Nanocrystalline $TiO_2$ Films", Eur. J. Org. Chem., 2010, pp. 92-100.
D. Y. Kondakov, "Characterization of triplet-triplet annihilation in organic light-emitting diodes based on anthracene derivatives", Journal of Applied Physics, vol. 102, 114504,2007, 5 pages.
Masakazu Funahashi, et al., "47.3; Highly Efficient Fluorescent Deep Blue Dopant for "Super Top Emission" Device", SID 08 Digest, 2008, 709-711.

* cited by examiner

*Primary Examiner* — Gregory Clark
(74) *Attorney, Agent, or Firm* — Oblon, McClelland, Maier & Neustadt, L.L.P.

(57) ABSTRACT

An oxygen-containing fused ring derivative represented by the following formula (1) wherein $Ar^1$ is an m-valent fused ring group in which four or more rings including one or more rings selected from a furan ring and a pyran ring are fused and HAr is any of the nitrogen-containing heterocyclic group represented by the following formulas (2) to (5):

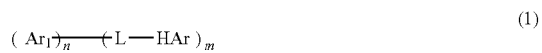

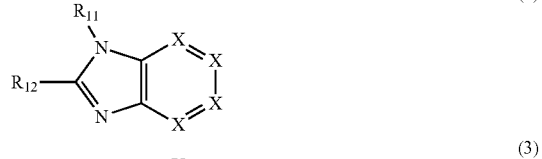

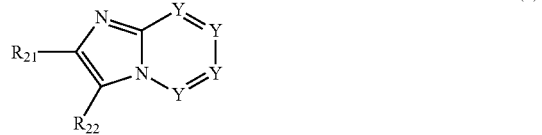

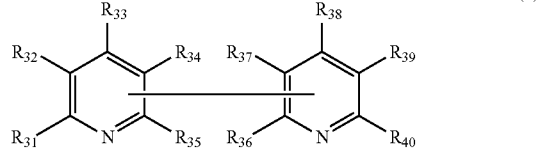

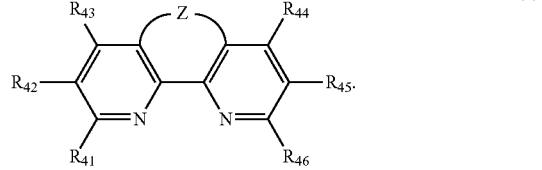

14 Claims, 2 Drawing Sheets

OXYGEN-CONTAINING FUSED RING DERIVATIVE AND ORGANIC ELECTROLUMINESCENCE DEVICE COMPRISING THE SAME

TECHNICAL FIELD

The invention relates to an oxygen-containing fused ring derivative and an organic electroluminescence device comprising the same.

BACKGROUND ART

An organic electroluminescence (EL) device is a self-emission device utilizing the principle that a fluorescent compound emits light by the recombination energy of holes injected from an anode and electrons injected from a cathode when an electric field is impressed.

An organic EL device is provided with a pair of electrodes formed of an anode and a cathode and an organic thin film layer between them. The organic thin film layer is a stacked body of layers having their respective functions. For example, the organic thin film layer is a stacked body of an anode, a hole-injecting layer, a hole-transporting layer, an emitting layer, a blocking layer, an electron-transporting layer and an electron-injecting layer in this sequence.

An organic EL device can be classified into two types, i.e. a fluorescent device and a phosphorescent device according to its emission principle. In a fluorescent organic EL device, emission derived from singlet excitons is used, and in a phosphorescent organic EL device, emission derived from triplet excitons is used. It is known that, in a phosphorescent device, in order to prevent diffusion of triplet excitons which have a longer exciton life than singlet excitons to the outside of an emitting layer, a material having a high triplet energy is used in a layer which is adjacent to the interface on the cathode side of the emitting layer, whereby a high efficiency is attained.

Patent Document 1 discloses a technology in which a blocking layer comprising BCP (bathocuproine), which is a phenanthroline derivative, is provided in adjacent to an emitting layer, whereby efficiency is increased by confining triplet excitons. Further, in Patent Document 2, in order to increase efficiency and prolong the lifetime, a specific aromatic ring compound is used in a hole-barrier layer.

On the other hand, in a fluorescent organic EL device, emission derived from triplet excitons has recently been reported (for example, Non-Patent Documents 1 and 2, Patent Document 3).

RELATED ART DOCUMENTS

Patent Documents

Patent Document 1: JP-T-2002-525808
Patent Document 2: U.S. Pat. No. 7,018,723
Patent Document 3: JP-A-2004-214180

Non-Patent Documents

Non-Patent Document 1: Journal of Applied Physics, 102, 114504 (2007)
Non-Patent Document 2: SID2008 DIGEST, 709 (2008)

SUMMARY OF THE INVENTION

An object of the invention is to provide a novel oxygen-containing fused ring derivative which enables highly efficient emission of an organic EL device by preventing an increase in an applied voltage and utilizing a TTF (Triplet-Triplet Fusion) phenomenon.

An object of the invention is to provide a material for a blocking layer which is optimum for promoting a TTF phenomenon.

According to the invention, the following oxygen-containing fused ring derivative or the like are provided.

1. An oxygen-containing fused ring derivative represented by the following formula (1):

wherein $Ar_1$ is an m-valent fused ring group in which four or more rings comprising one or more rings selected from a furan ring and a pyran ring are fused;

HAr is any of the nitrogen-containing heterocyclic group represented by the following formulas (2) to (5);

n and m are independently an integer of 1 to 5, and at least one of n and m is 1; and L is a single bond, a substituted or unsubstituted n+1 valent aryl group having 6 to 30 carbon atoms that form a ring (hereinafter referred to as "ring carbon atoms"), a substituted or unsubstituted n+1 valent heterocyclic group 5 to 30 atoms that form a ring (hereinafter referred to as "ring atoms") or an n+1 valent group obtained by combining, through a single bond, two or three selected from a substituted or unsubstituted aryl group having 6 to 30 ring carbon atoms and a substituted or unsubstituted heterocyclic group having 5 to 30 ring atoms:

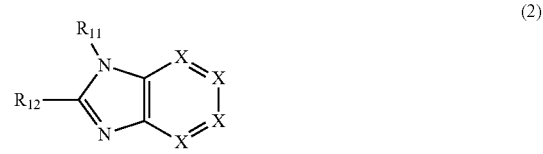

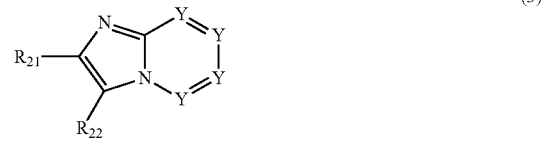

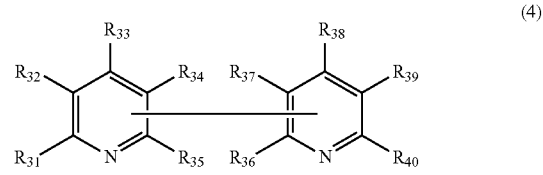

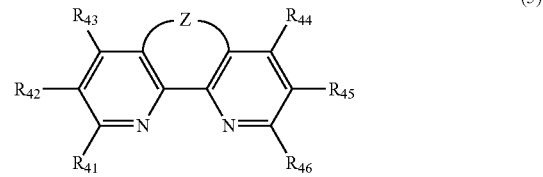

wherein $R_{11}$, $R_{12}$, $R_{21}$, $R_{22}$, $R_{31}$ to $R_{40}$ and $R_{41}$ to $R_{46}$ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms;

any one of $R_{31}$ to $R_{35}$ and any one of $R_{36}$ to $R_{40}$ is a single bond which bonds two pyridine rings in the formula (4);

X is selected from N or $CR_{13}$, and $R_{13}$ is a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms;

when plural $R_{13}$s are present, the $R_{13}$s may be the same or different;

Y is selected from N or $CR_{23}$, and $R_{23}$ is a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms;

when plural $R_{23}$s are present, the $R_{23}$s may be the same or different;

Z is a cross-linking group, which is a substituted or unsubstituted alkylene group or a substituted or unsubstituted alkenylene group; and any one of $R_{11}$ to $R_{13}$, any one of $R_{21}$ to $R_{23}$, any one of $R_{31}$ to $R_{40}$ and any one of $R_{41}$ to $R_{46}$ is a single bond which bonds to L.

2. The oxygen-containing fused ring derivative according to 1, wherein $Ar_1$ is represented by the following formula (6):

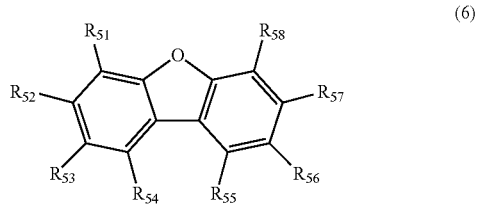

(6)

wherein $R_{51}$ to $R_{58}$ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms, or a substituted or unsubstituted heterocyclic group having 5 to 30 ring atoms;

at least one pair of $R_{51}$ and $R_{52}$, $R_{52}$ and $R_{53}$, $R_{53}$ and $R_{54}$, $R_{54}$ and $R_{55}$, $R_{55}$ and $R_{56}$, $R_{56}$ and $R_{57}$ or $R_{57}$ and $R_{58}$ is bonded with each other to form a ring in the form represented by the following formula (7) or (8);

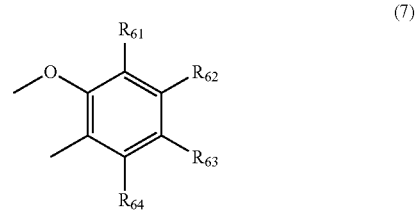

(7)

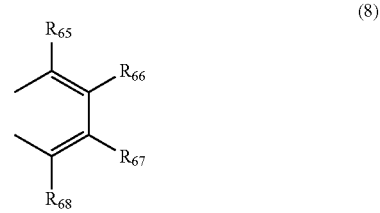

(8)

wherein $R_{61}$ to $R_{68}$ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms;

any "m" of $R_{61}$ to $R_{68}$ is (or are) a single bond which bonds to L.

3. The oxygen-containing fused ring derivative according to 1 or 2 wherein $Ar_1$ is a fused ring group represented by the following formula (9) or (10):

(9)
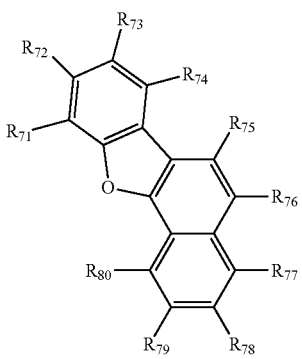

(12)
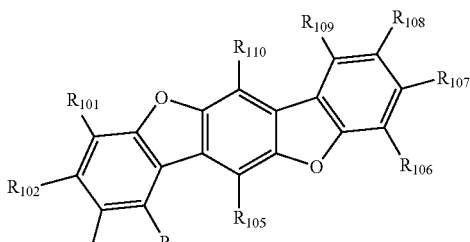

(10)
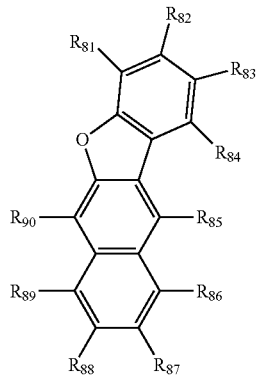

(13)
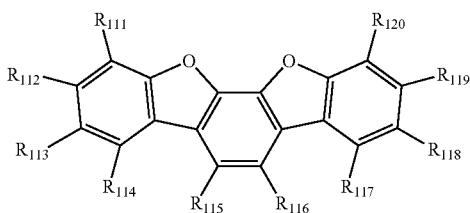

(14)
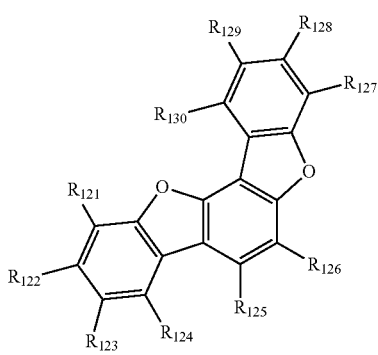

wherein $R_{71}$ to $R_{90}$ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms;

any "m" of $R_{71}$ to $R_{80}$ and any "m" of $R_{81}$ to $R_{90}$ are a single bond which bonds to L.

4. The oxygen-containing fused ring derivative according to 1 or 2, wherein $Ar_1$ is a fused ring group represented by the following formula (11), (12), (13) or (14):

(11)
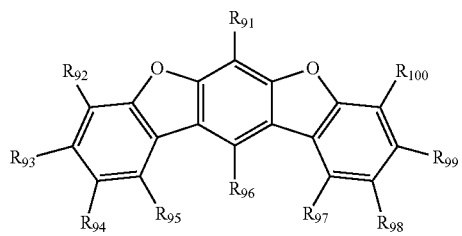

wherein $R_{91}$ to $R_{130}$ are independently a hydrogen atoms, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms; and any "m" of $R_{91}$ to $R_{100}$, any "m" of $R_{101}$ to $R_{110}$, any "m" of $R_{111}$ to $R_{120}$ and any "m" of $R_{121}$ to $R_{130}$ are a single bond which bonds to L.

5. The oxygen-containing fused ring derivative according to 1, wherein $Ar_1$ is a fused ring group represented by the following formula (15):

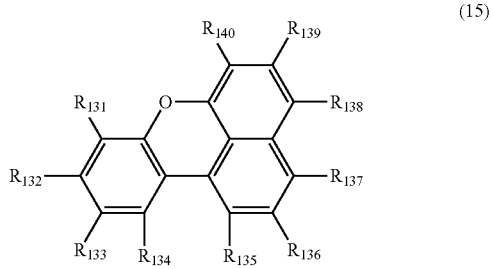

(15)

wherein $R_{131}$ to $R_{140}$ are independently a hydrogen atoms, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms; and any "m" of $R_{131}$ to $R_{140}$ is (or are) a single bond which bonds to L.

6. The oxygen-containing fused ring derivative according to any of 1 to 5, wherein m is 1 and n is 1.

7. The oxygen-containing fused ring derivative according to any of 1 to 6, which is a material for an organic electroluminescence device.

8. The oxygen-containing fused ring derivative according to 7, wherein the material for an organic electroluminescence device is a material for a blocking layer.

9. An organic electroluminescence device comprising an anode, an emitting layer, a blocking layer and a cathode in this sequence, the blocking layer comprising the oxygen-containing fused ring derivative according to any of 1 to 6.

10. The organic electroluminescence device according to 9, which has an electron-injecting layer and/or an electron-transporting layer between the blocking layer and the cathode and at least one layer of the electron-injecting layer and the electron-transporting layer comprises a hetero ring-containing derivative.

11. The organic electroluminescence device according to 10 wherein the electron-injecting layer and/or the electron-transporting layer comprise(s) an electron-donating dopant.

12. The organic electroluminescence device according to 11, wherein the electron-donating dopant is one or two or more selected from an alkali metal, an alkaline-earth metal, a rare earth metal and an oxide of an alkali metal, a halide of an alkali metal, an oxide of an alkaline-earth metal, a halide of an alkaline-earth metal, an oxide of a rare earth metal, a halide of a rare earth metal, an organic complex of an alkali metal, an organic complex of an alkaline-earth metal and an organic complex of a rare earth metal.

13. The organic electroluminescence device according to any of 9 to 12, wherein the emitting layer comprises an anthracene derivative represented by the following formula (16):

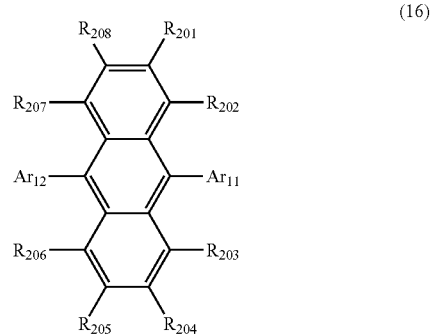

(16)

wherein $Ar_{11}$ and $Ar_{12}$ are independently a substituted or unsubstituted aryl group having 6 to 30 ring carbon atoms or a substituted or unsubstituted heterocyclic group having 5 to 30 ring atoms;

$R_{201}$ to $R_{208}$ are independently a hydrogen atom, a fluorine atom, a substituted or unsubstituted alkyl group having 1 to 10 carbon atoms, a substituted or unsubstituted cycloalkyl group having 3 to 10 ring carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms or a substituted or unsubstituted heterocyclic group having 5 to 30 ring atoms.

14. The organic electroluminescence device according to 13, wherein the emitting layer comprising the anthracene derivative represented by the formula (16) is in contact with the blocking layer comprising the oxygen-containing fused ring derivative.

15. The organic electroluminescence device according to any of 9 to 14, wherein the emitting layer comprises a fluorescent dopant having a main peak wavelength of 500 nm or less.

According to the invention, it is possible to provide a novel oxygen-containing fused ring derivative which enables highly efficient emission of a organic EL device by preventing an increase in an applied voltage and by utilizing a TTF (Triplet-Triplet Fusion) phenomenon.

MODE FOR CARRYING OUT THE INVENTION

Figure 1:
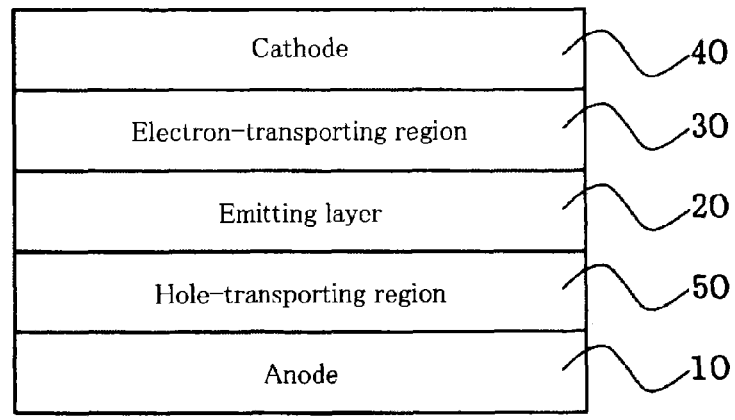
FIG. 1 is a view showing one example of the first embodiment of the invention.

The oxygen-containing fused ring derivative of the invention is represented by the following formula (1):

(1)

wherein Ar₁ is an m-valent fused ring group in which four or more rings comprising one or more rings selected from a furan ring and a pyran ring are fused;

HAr is any of the nitrogen-containing heterocyclic group represented by the following formulas (2) to (5);

n and m are independently an integer of 1 to 5, and at least one of n and m is 1; and L is a single bond, a substituted or unsubstituted n+1 valent aryl group having 6 to 30 carbon atoms that form a ring (hereinafter referred to as the "ring carbon atoms"), a substituted or unsubstituted n+1 valent heterocyclic group 5 to 30 atoms that form a ring (hereinafter referred to as the "ring atoms") or an n+1 valent group obtained by combining, through a single bond, two or three selected from a substituted or unsubstituted aryl group having 6 to 30 ring carbon atoms and a substituted or unsubstituted heterocyclic group having 5 to 30 ring atoms:

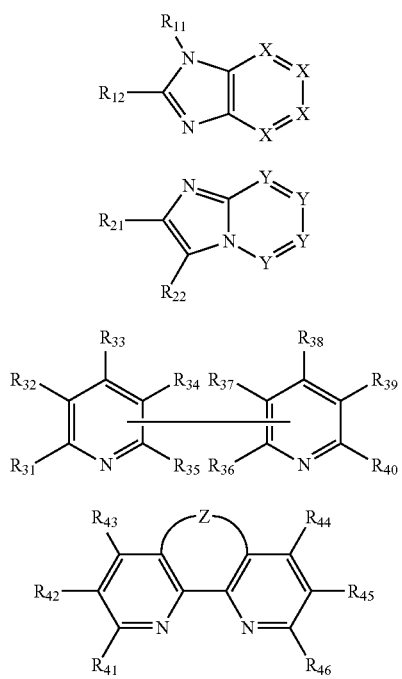

wherein $R_{11}$, $R_{12}$, $R_{21}$, $R_{22}$, $R_{31}$ to $R_{40}$ and $R_{41}$ to $R_{46}$ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms;

any one of $R_{31}$ to $R_{35}$ and any one of $R_{36}$ to $R_{40}$ is a single bond which bonds two pyridine rings in the formula (4);

X is selected from N or $CR_{13}$, and $R_{13}$ is a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms;

when plural $R_{13}$s are present, the $R_{13}$s may be the same or different;

Y is selected from N or $CR_{23}$, and $R_{23}$ is a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms;

when plural $R_{23}$s are present, the $R_{23}$s may be the same or different;

Z is a cross-linking group, which is a substituted or unsubstituted alkylene group or a substituted or unsubstituted alkenylene group; and any one of $R_{11}$ to $R_{13}$, any one of $R_{21}$ to $R_{23}$, any one of $R_{31}$ to $R_{40}$ and any one of $R_{41}$ to $R_{46}$ is a single bond which bonds to L.

The HAr represented by the formula (2) is preferably any of the following nitrogen-containing heterocyclic groups.

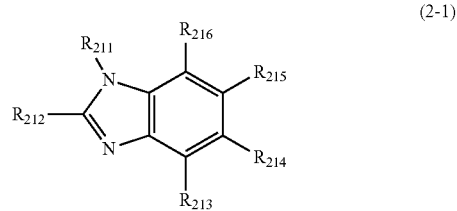

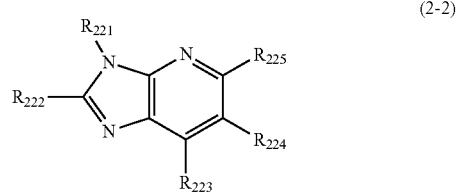

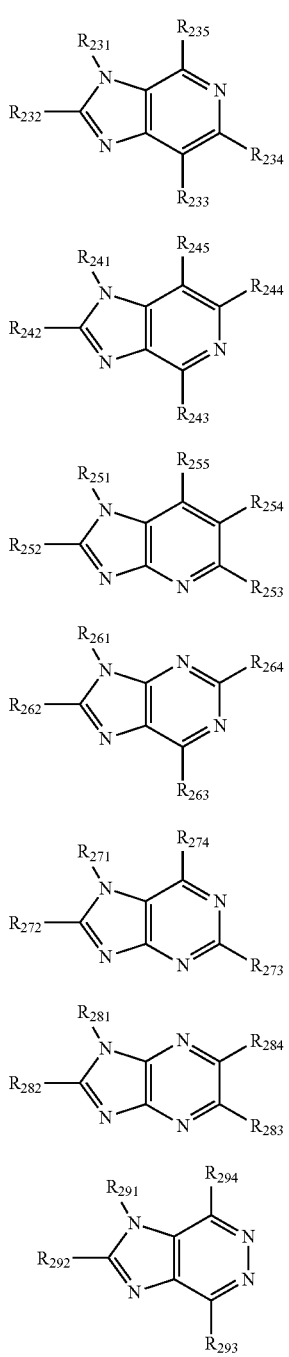

(2-3)

(2-4)

(2-5)

(2-6)

(2-7)

(2-8)

(2-9)

wherein $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, and $R_{291}$ to $R_{294}$ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms, or a substituted or unsubstituted heterocyclic group having 5 to 30 ring atoms.

In each heterocyclic group, any one of $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, and $R_{291}$ to $R_{294}$ is a single bond which bonds to L.

The HAr represented by the formula (3) is preferably any of the following nitrogen-containing heterocyclic groups.

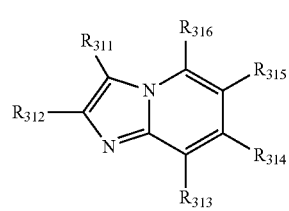

(3-1)

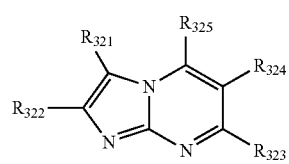

(3-2)

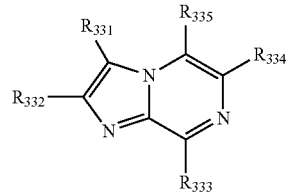

(3-3)

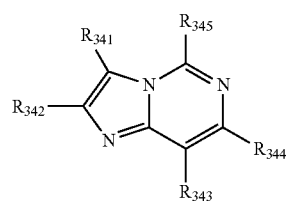

(3-4)

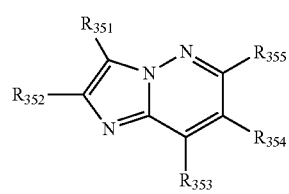

(3-5)

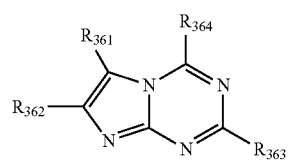

(3-6)

wherein $R_{311}$ to $R_{316}$, $R_{321}$ to $R_{325}$, $R_{331}$ to $R_{335}$, $R_{341}$ to $R_{345}$, $R_{351}$ to $R_{355}$, and $R_{361}$ to $R_{364}$ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms, or a substituted or unsubstituted heterocyclic group having 5 to 30 ring atoms. In each heterocyclic group, any one of $R_{311}$ to $R_{316}$, $R_{321}$ to $R_{326}$, $R_{331}$ to $R_{336}$, $R_{341}$ to $R_{346}$, $R_{351}$ to $R_{355}$, and $R_{361}$ to $R_{364}$ is a single bond which bonds to L.

The HAr represented by the formula (4) is preferably any of the following nitrogen-containing heterocyclic groups.

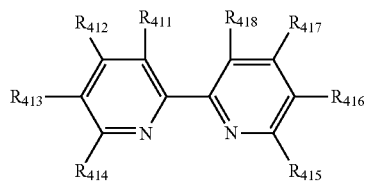

(4-1)

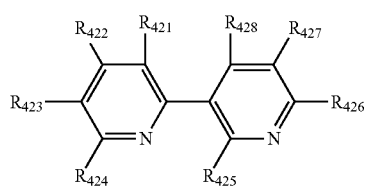

(4-2)

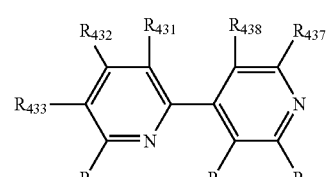

(4-3)

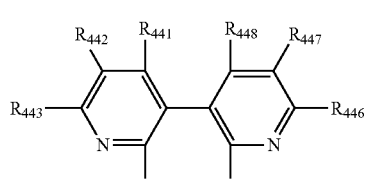

(4-4)

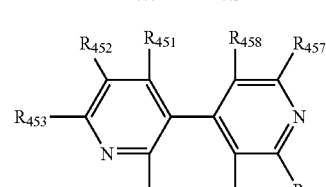

(4-5)

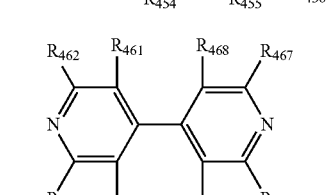

(4-6)

wherein $R_{411}$ to $R_{418}$, $R_{421}$ to $R_{428}$, $R_{431}$ to $R_{438}$, $R_{441}$ to $R_{448}$, $R_{451}$ to $R_{458}$, and $R_{461}$ to $R_{468}$ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms, or a substituted or unsubstituted heterocyclic group having 5 to 30 ring atoms. In each heterocyclic group, any one of $R_{411}$ to $R_{418}$, $R_{421}$ to $R_{428}$, $R_{431}$ to $R_{438}$, $R_{441}$ to $R_{446}$, $R_{451}$ to $R_{458}$, and $R_{461}$ to $R_{468}$ is a single bond which bonds to L.

The HAr represented by the formula (4) is preferably a structure represented by the formula (4-1). In the structure represented by the formula (4-1), the nitrogen atoms in the two pyridine rings are close to each other. When a material having such a structure is co-deposited with an electron-donating dopant having a metal ion represented by Li, Na or the like, in the two nitrogen atoms in the pyridine structure represented by the formula (4-1), a chelate structure in which coordination occurs in a metal atom or a metal ion can be formed. It can be considered that, as a result, the reactivity with the above-mentioned electron-donating dopant is increased, whereby effects of the electron-donating dopant can be obtained more effectively.

The HAr represented by the formula (5) is preferably any of the following nitrogen-containing heterocyclic groups.

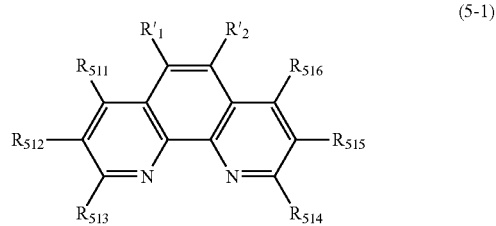

(5-1)

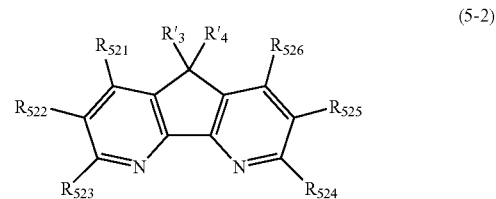

(5-2)

wherein $R_{511}$ to $R_{516}$, $R_{521}$ to $R_{526}$ and $R'_1$ to $R'_4$ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms, or a substituted or unsubstituted heterocyclic group having 5 to 30 ring atoms. In each heterocyclic group, any one of Rs bonds to L as a single bond. R's are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, an amino group, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms.

As for the fused ring group represented by $Ar_1$ in which four or more rings comprising one or more rings selected from a furan ring and a pyran ring (hereinafter often referred to as the "oxygen-containing ring") are fused, the "fused ring group in which four or more rings are fused" means a fused ring group having one or more rings selected from a furan ring and a pyran ring, and a ring selected from a substituted or unsubstituted benzene ring, a substituted or unsubstituted pyridine ring, a substituted or unsubstituted pyrimidine ring, a substituted or unsubstituted pyrazine ring and a substituted or unsubstituted pyridazine ring is fused to the structure containing the oxygen-containing ring, whereby 4 or more rings are fused in total.

$Ar_1$ is preferably a fused ring group having one or more rings selected from a furan ring and a pyran ring, and a benzene ring is fused to the structure containing the oxygen-containing ring, whereby 4 or more rings are fused in total. Particularly preferably, $Ar_1$ is a fused ring group having one or two rings selected from a furan ring and a pyran ring, and a benzene ring is fused to the structure containing the oxygen-containing ring, whereby 4 or more rings are fused in total.

In this specification, the "fused ring" is a polycyclic ring in which adjacent rings share two atoms.

The ring structure formed by fusing of 4 or more rings of $Ar_1$ has a high flatness. It is thought that when an organic EL material has a structure having a high flatness, the degree of overlapping of molecules becomes large, and as a result, the distance between the molecules is reduced to increase the charge transporting property, whereby a low-voltage driving of a device is realized.

Further, the fused ring structure having the oxygen-containing ring has a large triplet energy. Since the compound having this fused ring having the oxygen-containing ring has a large triplet energy, when used as a material for a blocking layer which is in contact with an emitting layer of an organic EL device, a TTF phenomenon can be promoted. In this respect, it is more preferred that the oxygen-containing fused ring structure of $Ar_1$ be one which does not include an anthracene structure in which three benzene rings are linearly fused as a partial structure.

For example, if $Ar_1$ is a fused ring group in which four or more rings including one or more furan rings are fused, the following fused ring groups can be given.

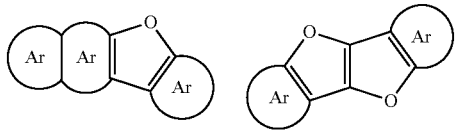

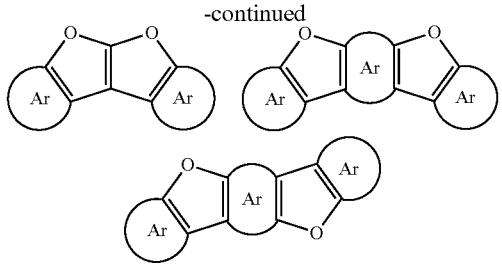

wherein Ar are independently a substituted or unsubstituted benzene ring, a substituted or unsubstituted pyridine ring, a substituted or unsubstituted pyrimidine ring, a substituted or unsubstituted pyrazine ring or a substituted or unsubstituted pyridazine ring. Each of these rings forms a fused ring with an adjacent ring. Further, these fused rings may form a fused ring structure with a benzene ring, a pyridine ring, a pyrimidine ring, a pyrazine ring or a pyridazine ring.

The fused ring group having the above-mentioned furan ring is preferably a fused ring group represented by the following formula (6), more preferably a fused ring group represented by any of the following formulas (9) to (10) having one furan ring or a fused ring group represented by any of the following formulas (11) to (14) having two furan rings.

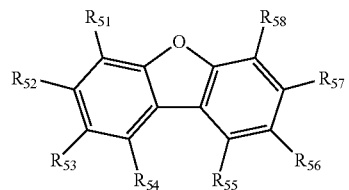

wherein $R_{51}$ to $R_{58}$ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms, or a substituted or unsubstituted heterocyclic group having 5 to 30 ring atoms;

at least one pair of $R_{51}$ and $R_{52}$, $R_{52}$ and $R_{53}$, $R_{53}$ and $R_{54}$, $R_{54}$ and $R_{55}$, $R_{55}$ and $R_{56}$, $R_{56}$ and $R_{57}$ and $R_{57}$ and $R_{58}$ is bonded with each other to form a ring in the form represented by the following formula (7) or (8);

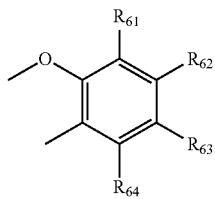
(7)

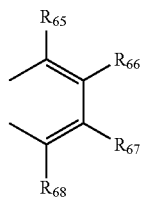
(8)

wherein R₆₁ to R₆₈ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms;

any "m" of R₆₁ to R₆₈ is (or are) a single bond which bonds to L.

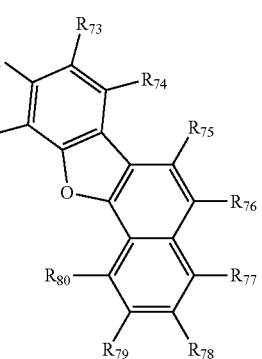
(9)

(10)

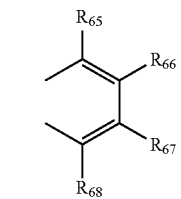

wherein R₇₁ to R₉₀ are independently a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms;

any "m" of R₇₁ to R₈₀ and any "m" of R₈₁ to R₉₀ are a single bond which bonds to L.

(11)

(12)

(13)

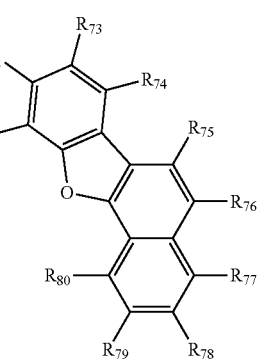

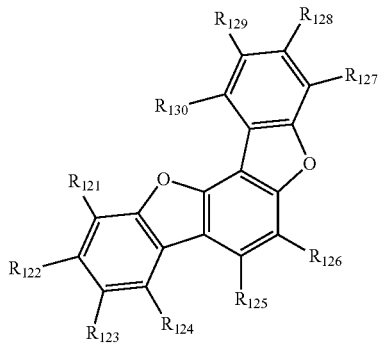

(14)

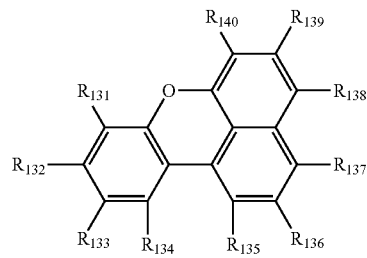

(15)

wherein $R_{91}$ to $R_{130}$ are independently a hydrogen atoms, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted arylthio group having 6 to 30 carbon atoms, a substituted or unsubstituted arylamino group having 6 to 30 carbon atoms, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms; and any "m" of $R_{91}$ to $R_{100}$, any "m" of $R_{101}$ to $R_{110}$, any "m" of $R_{111}$ to $R_{120}$ and any "m" of $R_{121}$ to $R_{130}$ are a single bond which bonds to L.

In the above-mentioned fused ring group having a furan ring, it is particularly preferred that it be a fused ring group represented by any of the following formulas (11) to (14) having two furan rings. It is considered that the compound of the invention having these fused rings has a larger triplet energy, and hence, it has a higher capability of confining triplet excitons. This works advantageously to allow a TTF phenomenon, which is mentioned later, to occur more effectively, and becomes one factor to increase the luminous efficiency of an organic EL device.

When $Ar_1$ is a fused ring group in which four or more rings having one or more pyran rings are fused, the following fused ring groups can be given.

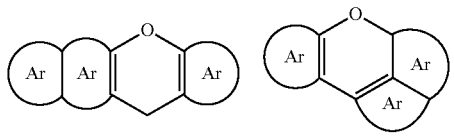

wherein Ars are independently a substituted or unsubstituted benzene ring, a substituted or unsubstituted pyridine ring, a substituted or unsubstituted pyrimidine ring, a substituted or unsubstituted pyrazine ring or a substituted or unsubstituted pyridazine ring, and each of them forms a fused ring with adjacent rings. Further, these fused rings may form a fused ring structure with a benzene ring, a pyridine ring, a pyrimidine ring, a pyrazine ring or a pyridazine ring.

The above-mentioned fused ring group having a pyran ring is preferably a fused ring group represented by the following formula (15).

wherein $R_{131}$ to $R_{140}$ are independently a hydrogen atoms, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, an amino group, a substituted or unsubstituted mono- or dialkylamino group having 1 to 20 carbon atoms, a substituted or unsubstituted aryl group having 6 to 30 ring carbon atoms or a substituted or unsubstituted heterocyclic group having 5 to 30 ring atoms; and any "m" of $R_{131}$ to $R_{140}$ is (or are) a single bond which bonds to L.

In the formula (1), when n is 2 or more, plural $Ar_1$s may be the same or different. Similarly, when m is 2 or more, plural (L-HAr)s may be the same or different. When m is 2 or more, plural Ls and plural HArs may be the same or different.

m and n in the formula (1) preferably satisfies m=n=1.

Hereinbelow, an explanation will be made on each substituent of the oxygen-containing fused ring derivative of the invention.

As the aryl group having 6 to 30 ring carbon atoms of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$, and $R'_1$ to $R'_4$, a phenyl group, a naphthyl group, a phenanthryl group, a biphenyl group, a terphenyl group, a chrysenyl group, a benzophenanthryl group, a benzanthryl group, a benzochrysenyl group, a fluorenyl group, a fluoranthenyl group, a pyrenyl group, a benzofluoranthenyl group, a triphenylenyl group or the like can be given. The aryl group has preferably 6 to 20 ring carbon atoms, with 6 to 14 ring carbon atoms being particularly preferable.

As the heterocyclic group having 5 to 30 ring atoms of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{455}$, $R_{461}$ to $R_{468}$, $R_{511}$ to $R_{516}$, $R_{521}$ to $R_{526}$, and $R'_1$ to $R'_4$, a pyridinyl group, a pyrazinyl group, a pyrimidyl group, a pyridazinyl group, a triazinyl group, an indolyl group, a quinolynyl group, an acrydinyl group, a pyrrolidinyl group, a dioxanyl group, a piperidinyl group, a morpholyl group, a piperazinyl group, a carbazolyl group, a furanyl group, a thiophenyl group, an oxazolyl group, an oxadiazolyl group, a benzoxazolyl group, a thiozolyl group, a thiadiazolyl group, a benzothiazolyl group, a triazolyl group, an imidazolyl group, a benzoimidazolyl group, an imidazopyridyl group, a benzofuranyl group, a dibenzofuranyl group, a dibenzothiophenyl group, a pyrrolyl group, an indazolyl group or the like can be given. The heterocyclic group preferably has 5 to 20, particularly preferably 5 to 14 ring atoms.

As the alkyl group having 1 to 10 carbon atoms of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$, and $R'_1$ to $R'_4$, an ethyl group, a methyl group, an i-propyl group, an n-propyl group, an s-butyl group, a t-butyl group, a pentyl group, a hexyl group or the like can be given. The alkyl group has preferably 1 to 8, particularly preferably 1 to 6 carbon atoms.

As the cycloalkyl group having 3 to 8 carbon atoms of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{65}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$, and $R'_1$ to $R'_4$, a cyclopropyl group, a cyclobutyl group, a cyclopentyl group, a cyclohexyl group, a 4-methylcyclohexyl group or the like can be given. The cycloalkyl group has preferably 3 to 6 carbon atoms.

The substituted silyl group having 3 to 30 carbon atoms of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$ and $R'_1$ to $R'_4$ includes an alkylsilyl group having 3 to 30 carbon atoms and an arylsilyl group having 8 to 30 ring carbon atoms.

As the alkylsilyl group having 3 to 30 carbon atoms, a trimethylsilyl group, a triethylsilyl group, a t-butyldimethylsilyl group, a vinyldimethylsilyl group, a propyldimethylsilyl group or the like can be given. The alkylsilyl group preferably has 3 to 20 carbon atoms, more preferably 3 to 10 carbon atoms, with 3 to 6 carbon atoms being particularly preferable.

As the arylsilyl group having 8 to 30 ring carbon atoms, a triphenylsilyl group, a phenydimethylsilyl group, a t-butyldiphenylsilyl group, a tritolylsilyl group, a trixylylsilyl group, a trinaphthylsilyl group or the like can be given. The arylsilyl group preferably has 8 to 20 ring carbon atoms, with 8 to 18 ring carbon atoms being particularly preferable.

The alkoxy group having 1 to 20 carbon atoms of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$, and $R'_1$ to $R'_4$ is a group represented by —OY. Examples of Y include the same groups as those exemplified above regarding the alkyl group.

The aryloxy group having 6 to 20 ring carbon atoms of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to 364, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$, and $R'_1$ to $R'_4$ is a group represented by —OAr. Examples of Ar are the same as those exemplified above regarding the aryl group. The aryloxy group has preferably 6 to 16 ring carbon atoms, with 6 to 12 ring carbon atoms being particularly preferable.

The alkylamino group of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$, and $R'_1$ to $R'_4$ is represented by —$NY_1Y_2$. Examples of $Y_1$ and $Y_2$ include a hydrogen atom and the above-mentioned examples of the alkyl group. $Y_1$ and $Y_2$ may be the same or different.

The arylamino group of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$, and $R'_1$ to $R'_4$ is represented by —$NZ_1Z_2$. Examples of $Z_1$ and $Z_2$ include a hydrogen atom and those exemplified above referring to the aryl group. $Z_1$ and $Z_2$ may be the same or different.

The substituted or unsubstituted alkylthio group having 1 to 20 ring carbon atoms of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$, and $R'_1$ to $R'_4$ is represented by —SA. A is the above-mentioned alkyl group.

The substituted or unsubstituted arylthio group having 1 to 20 ring carbon atoms of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{90}$, $R_{91}$ to $R_{130}$, $R_{131}$ to $R_{140}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$, and $R'_1$ to $R'_4$ is represented by —SB. B is the above-mentioned aryl group.

As the n+m valent aryl group having 6 to 30 ring carbon atoms of L, a divalent arylene group can be given, for example. A phenylene group, a naphthylene group, a biphenylene group, a terphenylene group, a pocenylene group, a pyrenylene group, a fluorenylene group, a chrysenylene group or the like can be given.

When the valence of L is trivalent or larger, residues corresponding to the divalent arylene group can be given as L.

As the n+m valent heterocyclic group having 5 to 30 ring atoms of L, if it is a divalent heterocyclic group, for example, a pyridinylene group, a pyrazinylene group, a pyrimidinylene group, a pyridazinylene group, a triazinylene group, an indolylene group, a quinolynylene group, an acrydinylene group, a pyrrolidinylene group, a dioxanylene group, a piperidinylene group, a morpholidinylene group, a piperazinylene group, a carbazolylene group, a furanylene group, a thiophenylene group, an oxazolylene group, an oxadiazolylene group, a benzoxazolylene group, a thiazolylene group, a thiadiazolylene group, a benzothiazolylene group, a triazolylene group, an imidazolylene group, a benzimidazolylene group, an imidazopyridinylene group, a benzofuranylene group, a dibenzofuranylene group, a dibenzothiophenylene group, a pyrrolyl group, an indazolyl group or the like can be given.

When the valence of L is trivalent or larger, residues corresponding to the divalent heterocyclic group can be given as L.

If the substituent of $R_{11}$, $R_{12}$, $R_{21}$, $R_{22}$, $R_{31}$ to $R_{40}$, $R_{41}$ to $R_{46}$, $R_{51}$ to $R_{58}$, $R_{61}$ to $R_{68}$, $R_{71}$ to $R_{99}$, $R_{91}$ to $R_{130}$, $R_{131}$ to $R_{149}$, $R_{211}$ to $R_{216}$, $R_{221}$ to $R_{225}$, $R_{231}$ to $R_{235}$, $R_{241}$ to $R_{245}$, $R_{251}$ to $R_{255}$, $R_{261}$ to $R_{264}$, $R_{271}$ to $R_{274}$, $R_{281}$ to $R_{284}$, $R_{291}$ to $R_{294}$, $R_{311}$ to $R_{316}$, $R_{321}$ to $R_{325}$, $R_{331}$ to $R_{335}$, $R_{341}$ to $R_{345}$, $R_{351}$ to $R_{355}$, $R_{361}$ to $R_{364}$, $R_{411}$ to $R_{418}$, $R_{421}$ to $R_{428}$, $R_{431}$ to $R_{438}$, $R_{441}$ to $R_{448}$, $R_{451}$ to $R_{458}$, $R_{461}$ to $R_{468}$, $R_{511}$ to $R_{516}$, $R_{521}$ to $R_{526}$, $R'_1$ to $R'_4$ and L has a further substituent, as the substituent, an alkyl group, an alkylsilyl group, a halogenated alkyl group, an aryl group, a cycloalkyl group, an alkoxy group, a heterocyclic group, an aralkyl group, an aryloxy group, an arylthio group, an alkoxycarbonyl group, a halogen atom, a hydroxyl group, a nitro group, a cyano group, a carboxyl group, a dibenzofuranyl group, a fluorenyl group or the like as mentioned above can be given.

As for each substituent of the oxygen-containing fused ring derivative of the invention, the "unsubstituted" means that a hydrogen atom is substituted. The hydrogen atom of the oxygen-containing fused ring derivative of the invention includes protium and deuterium.

Specific examples of the oxygen-containing fused ring derivative represented by the formula (1) are given below:

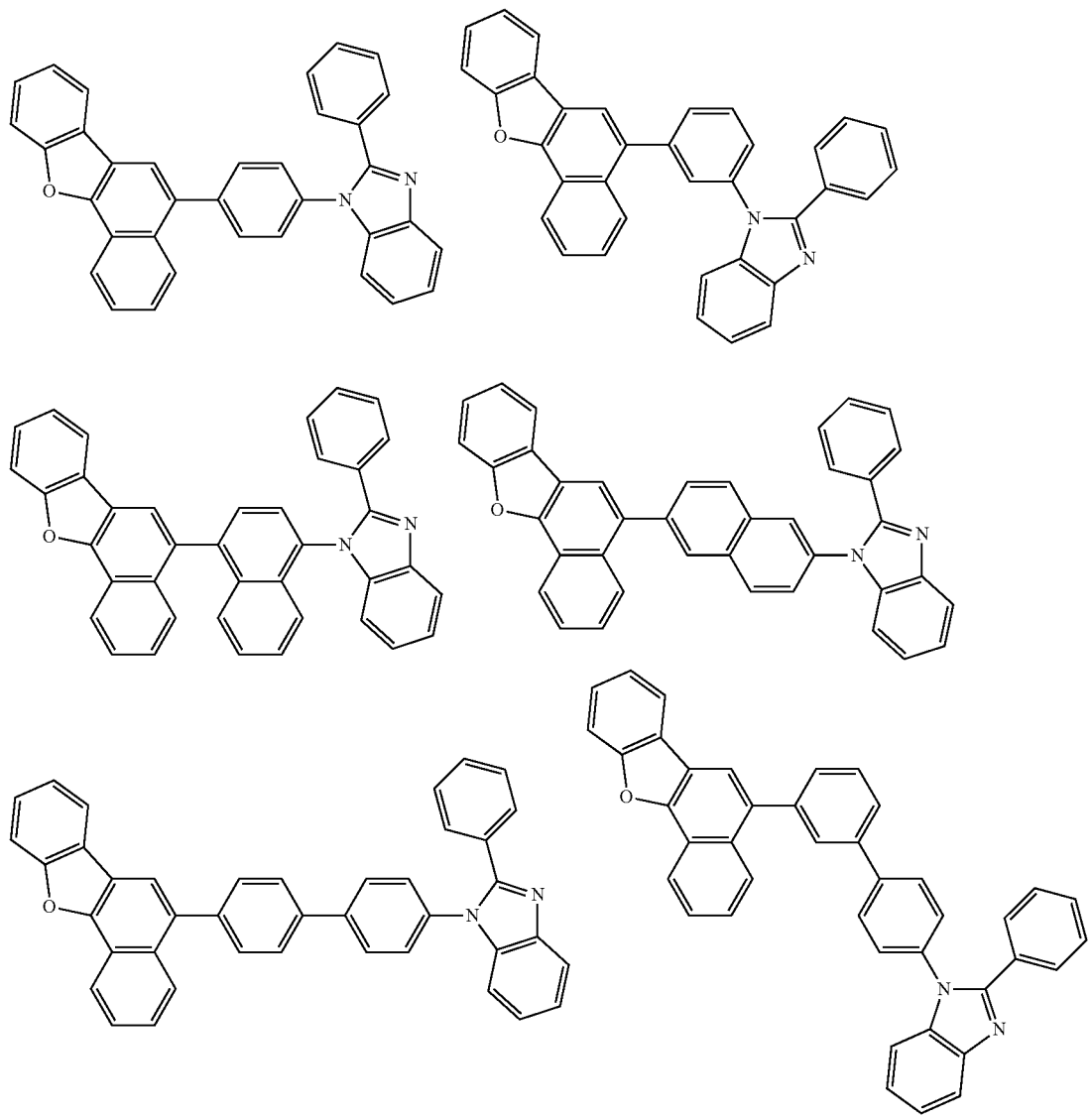

-continued
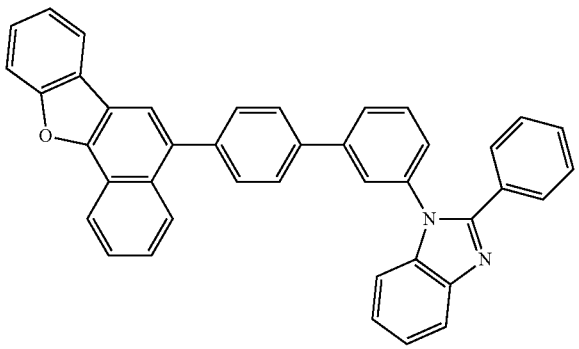
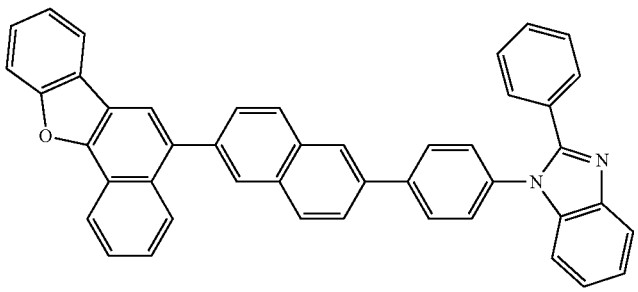
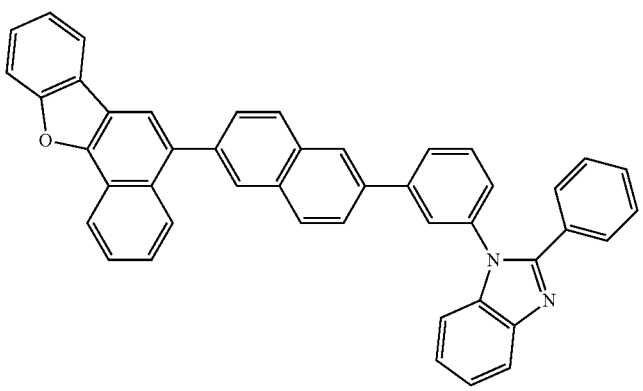
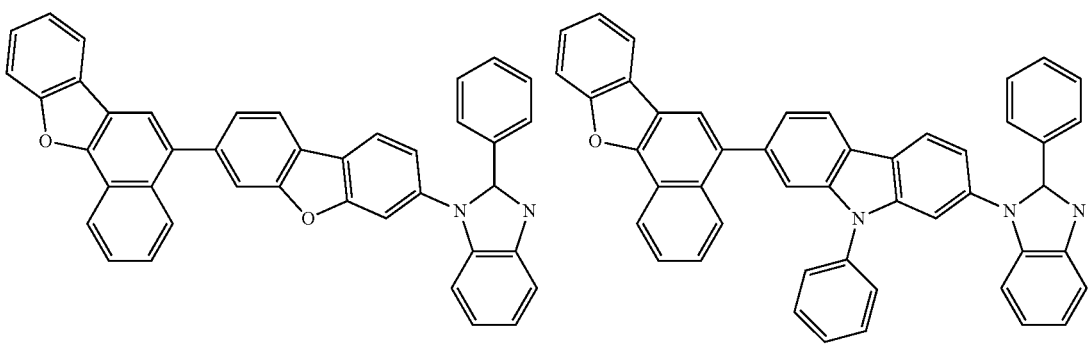
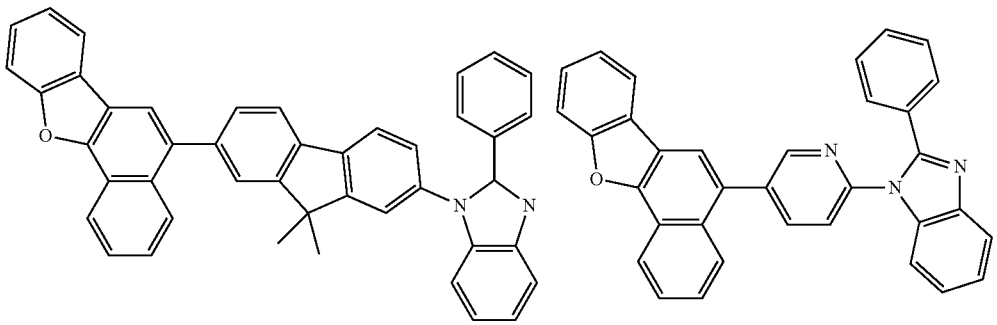

-continued
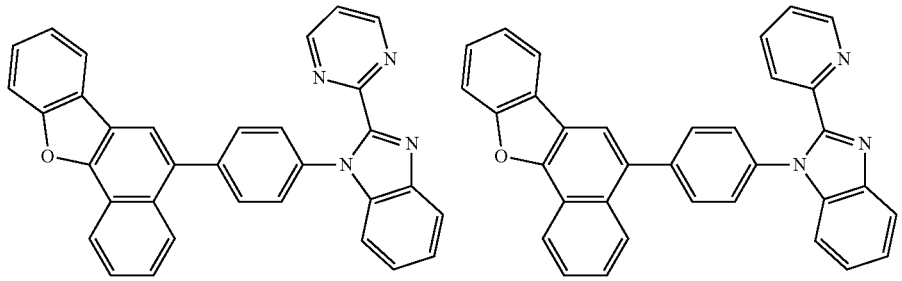
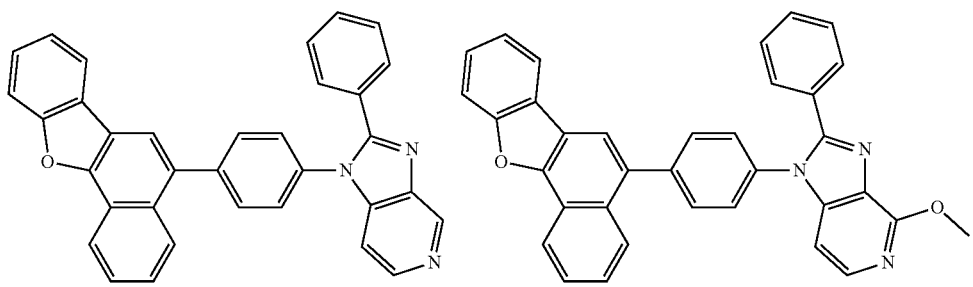
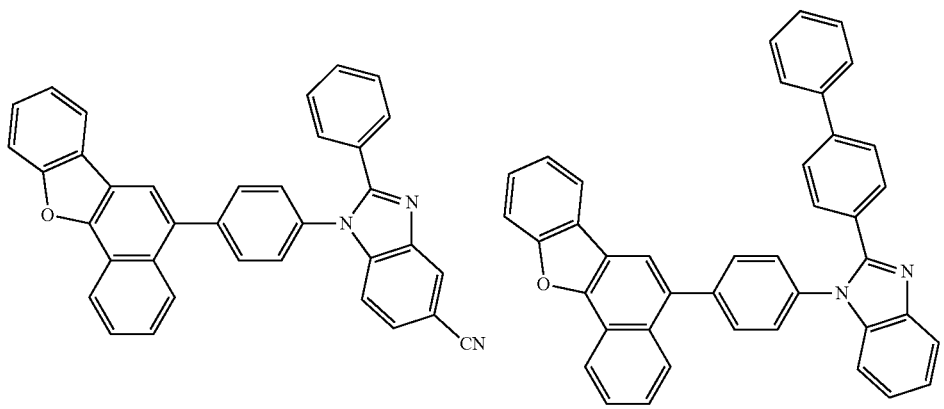
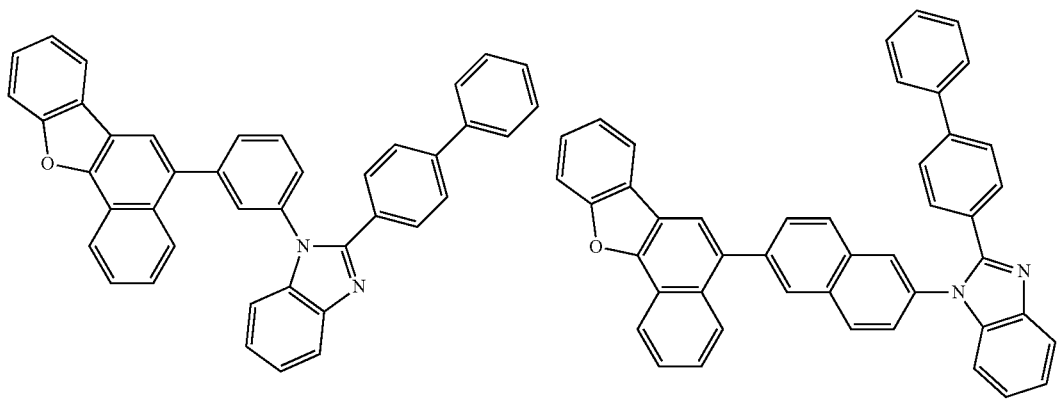

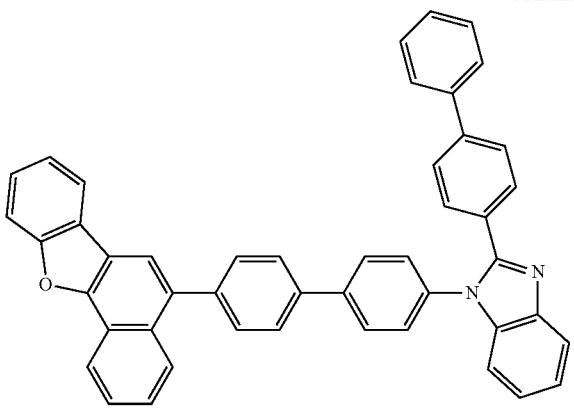
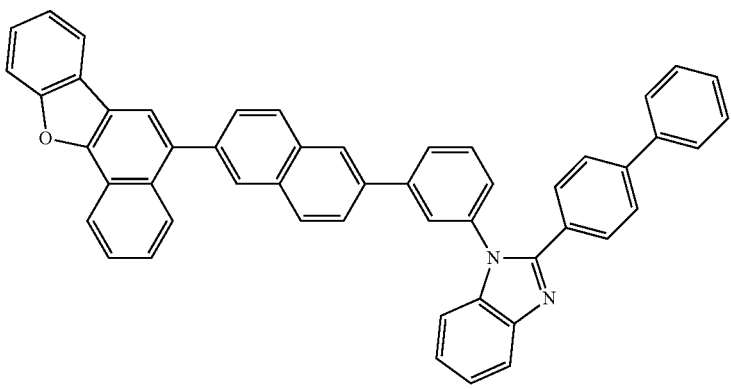
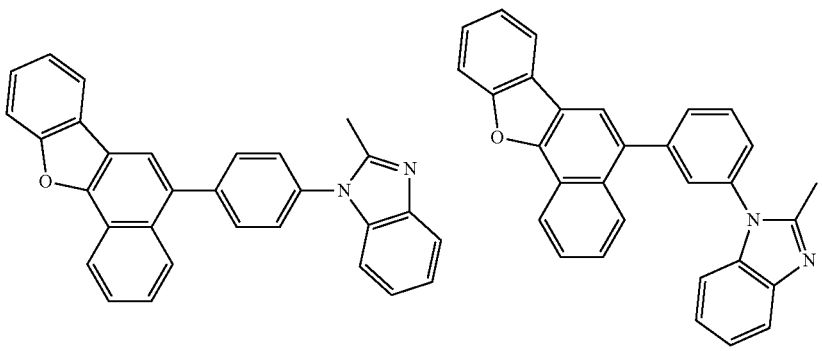
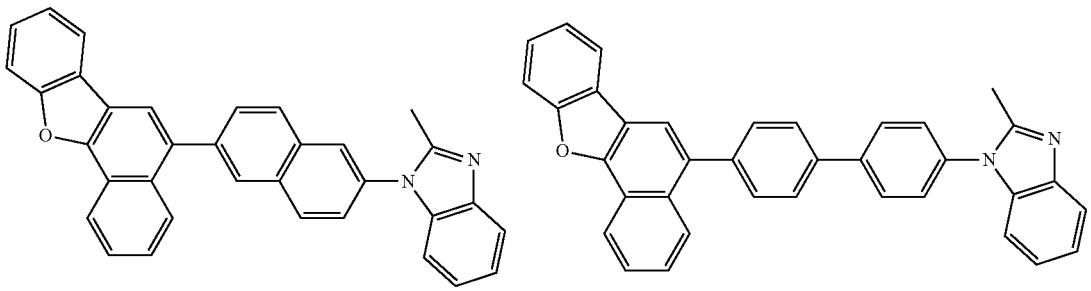

-continued
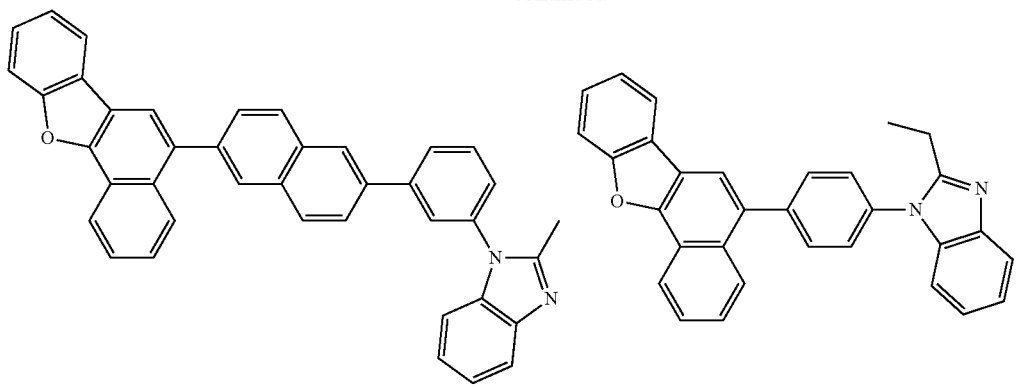
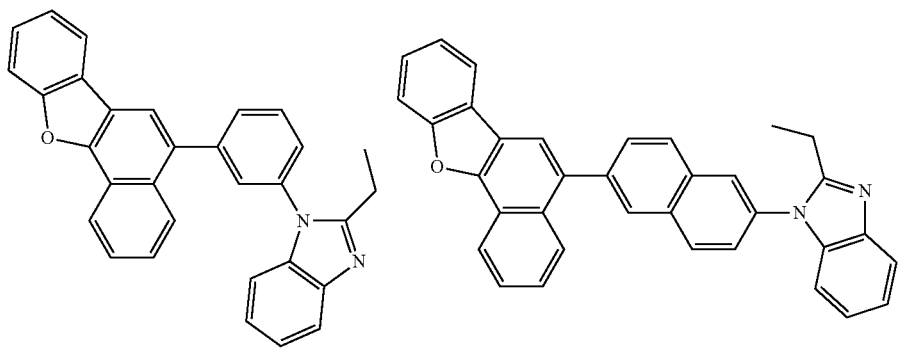
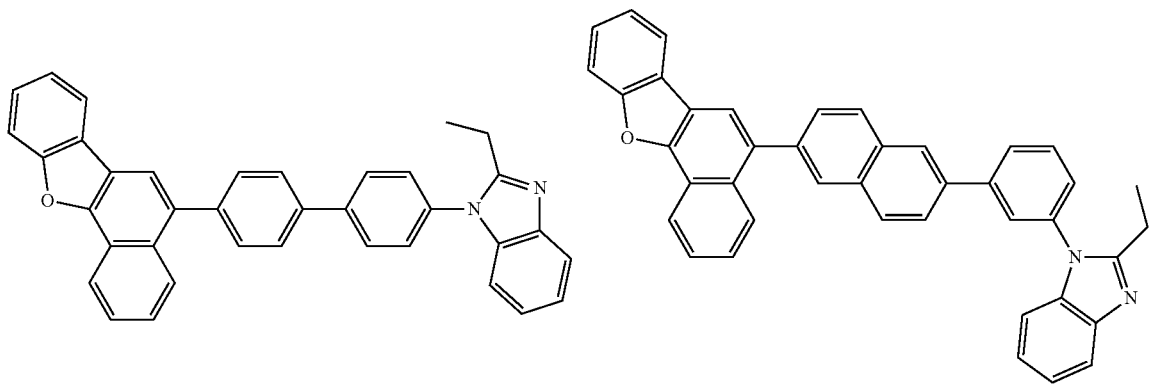
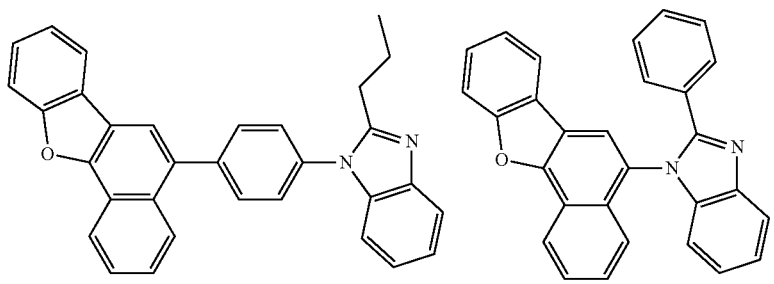
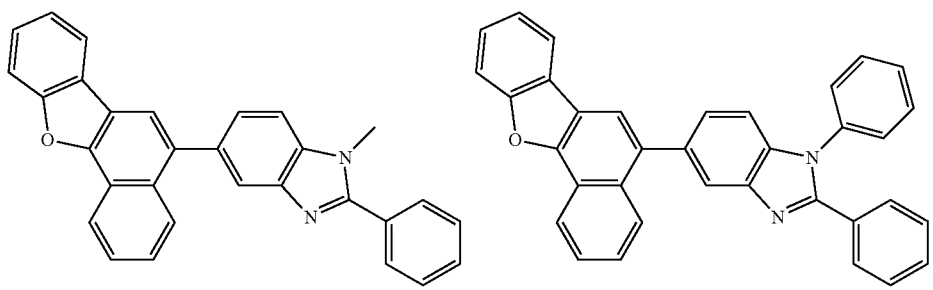

-continued
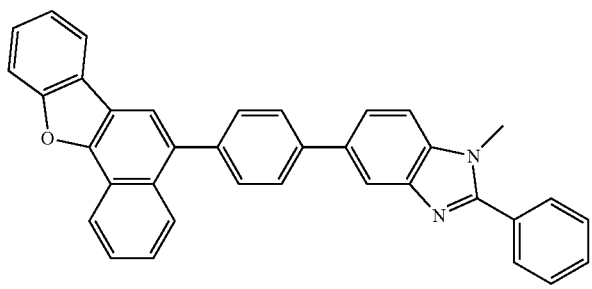
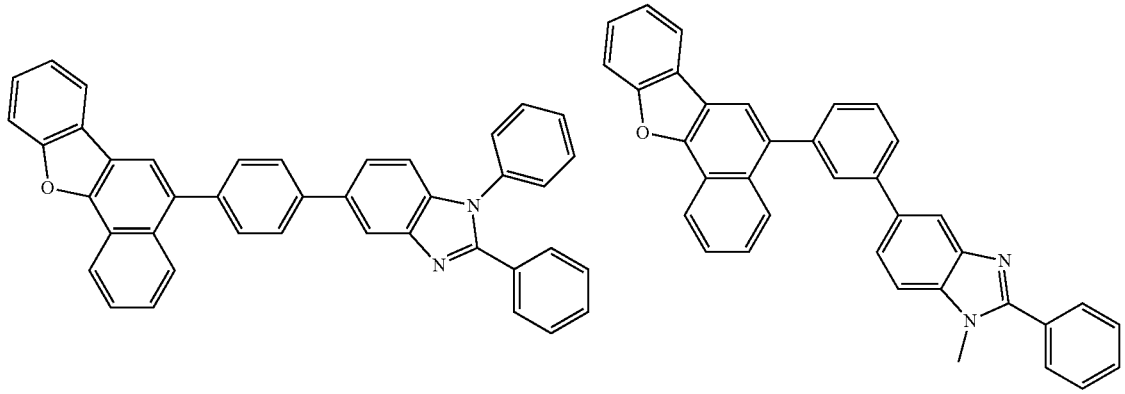
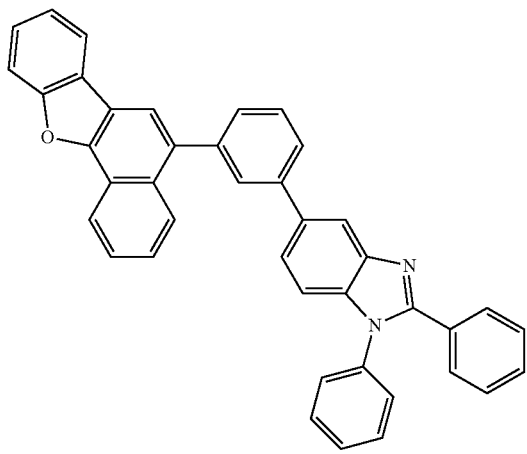
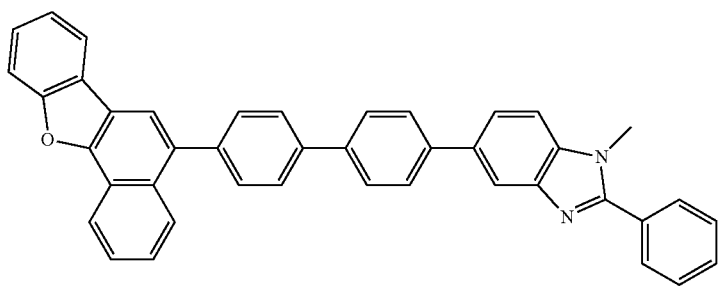
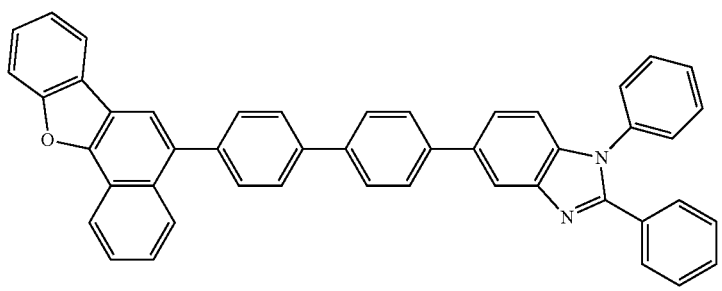

-continued
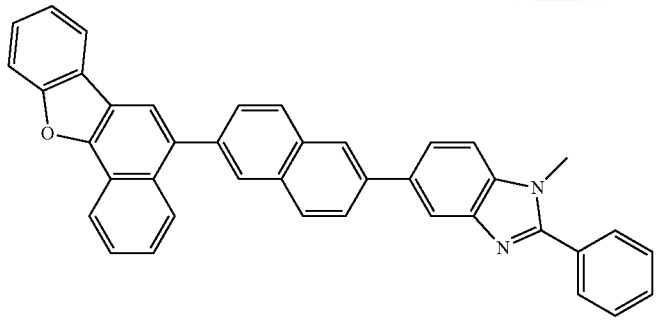
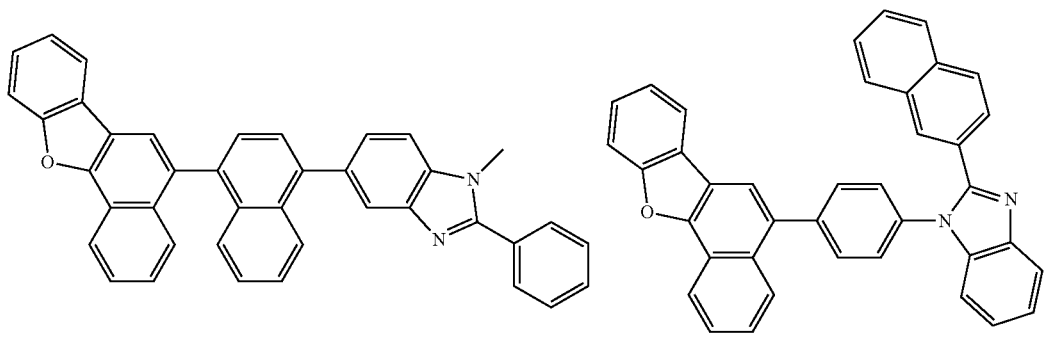
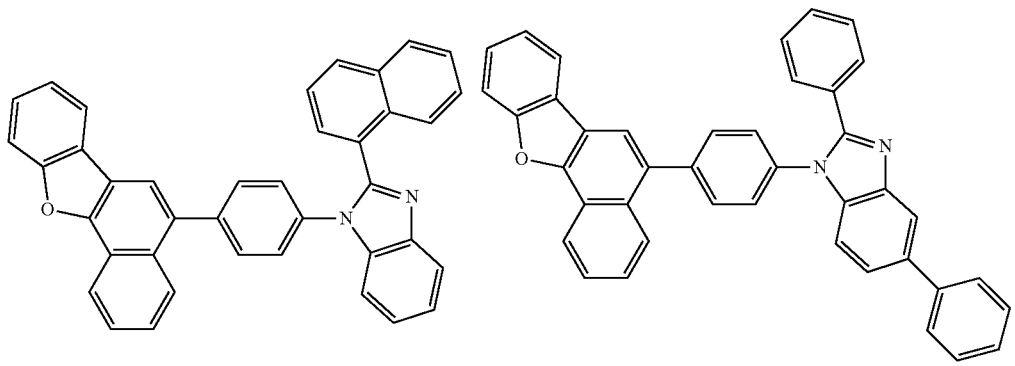
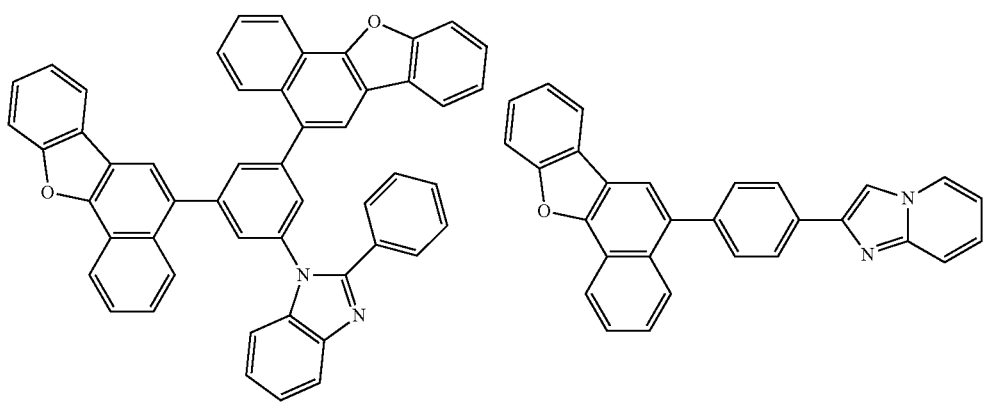

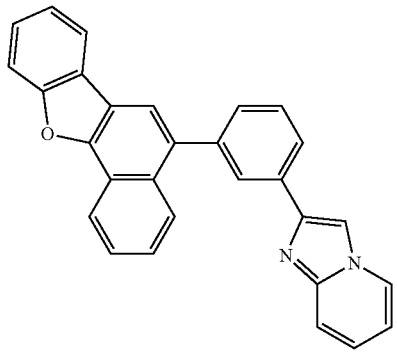
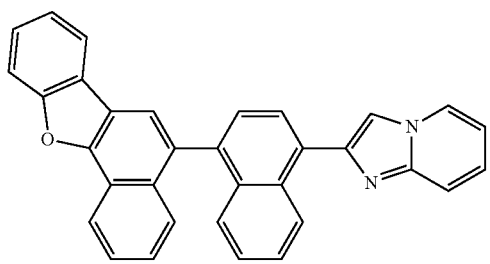
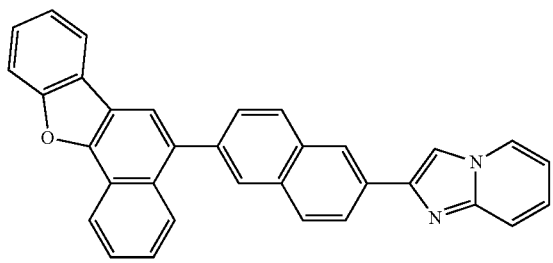
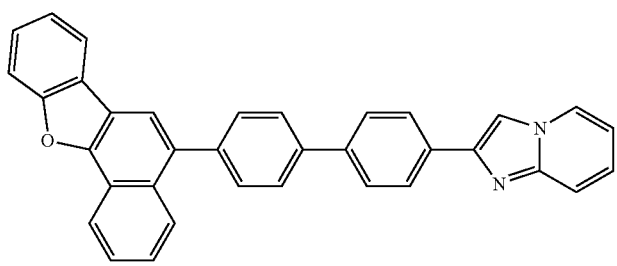
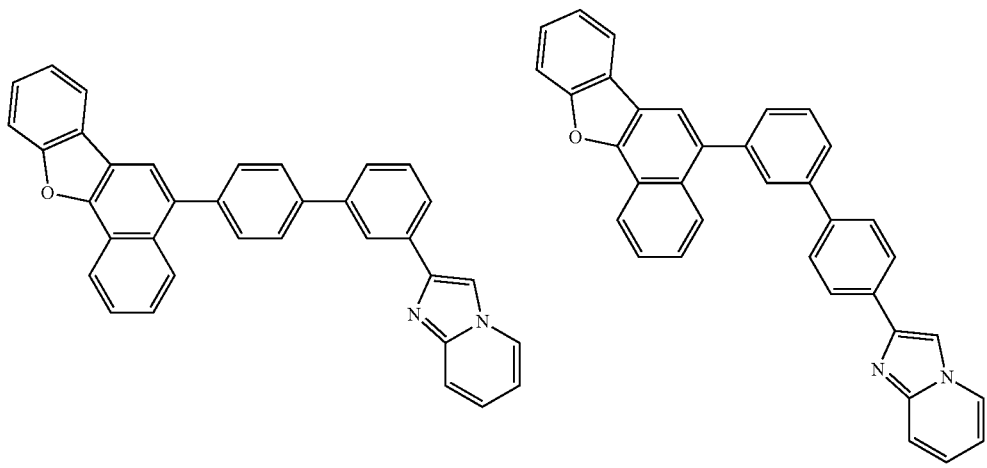
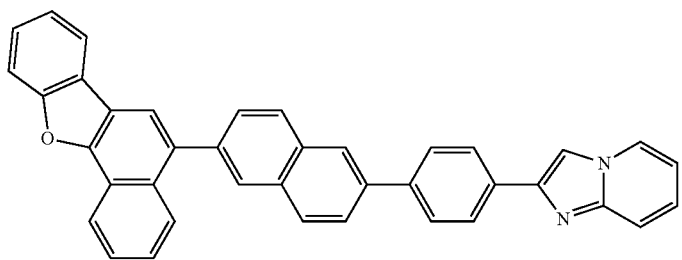

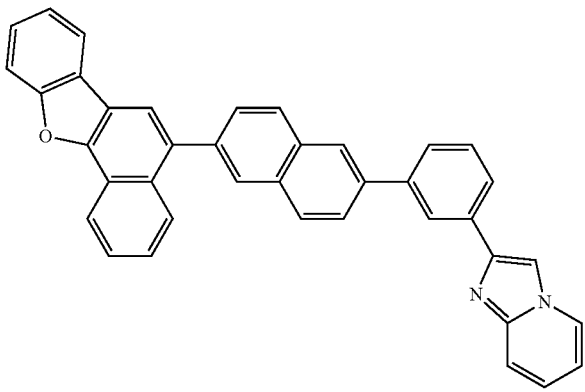
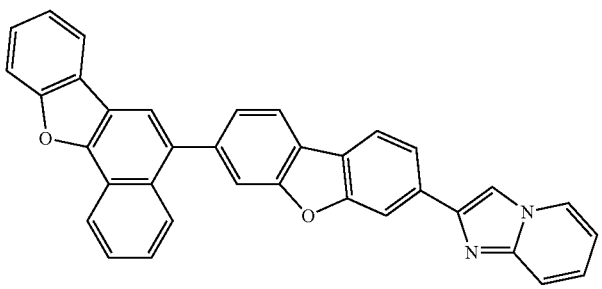
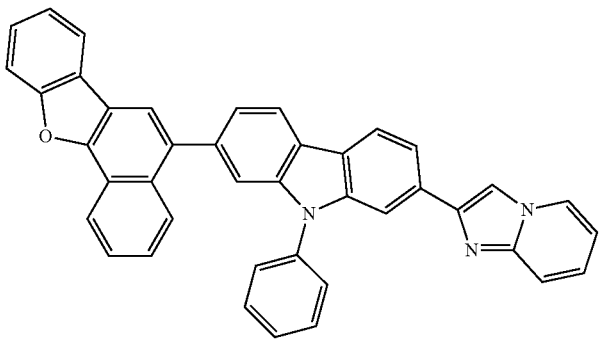
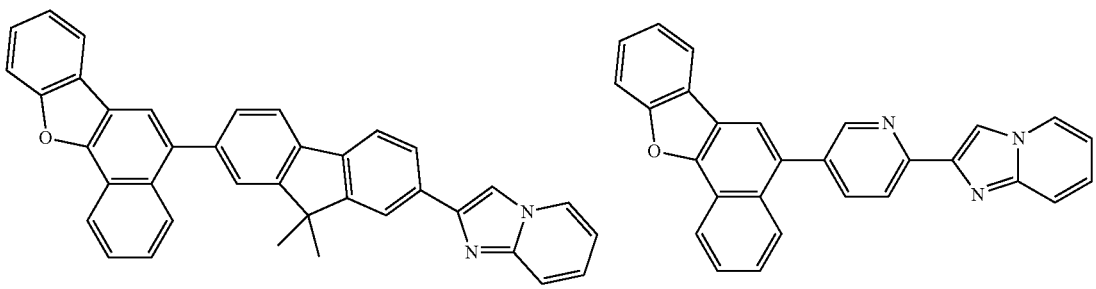
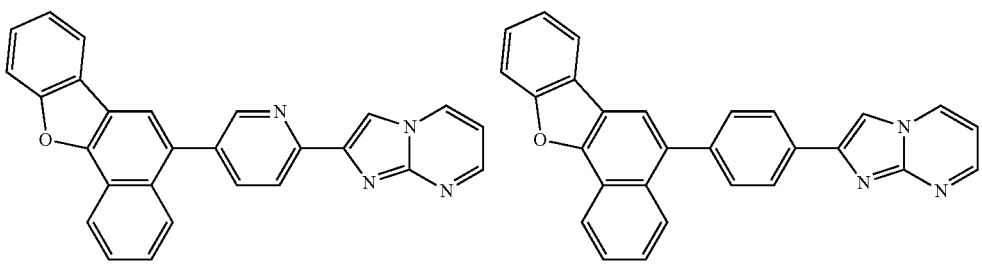

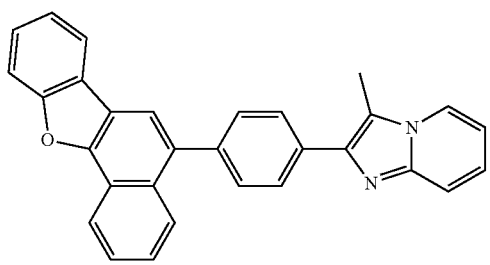
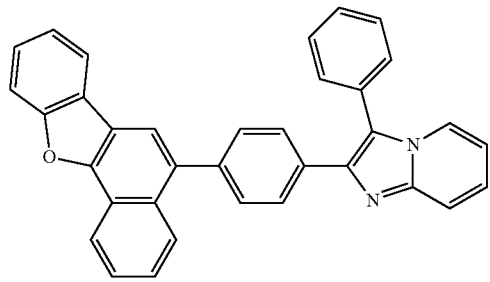
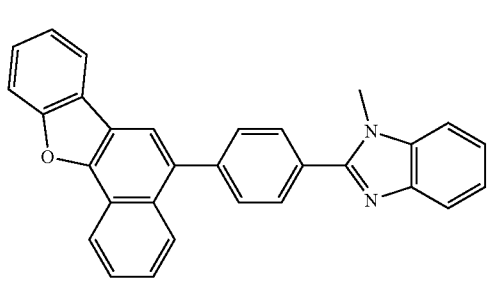
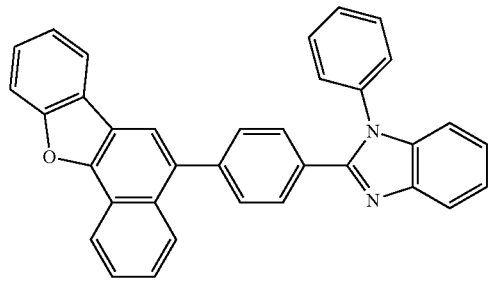
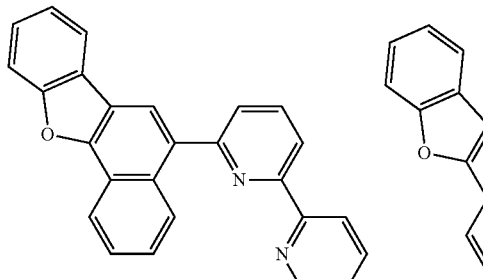
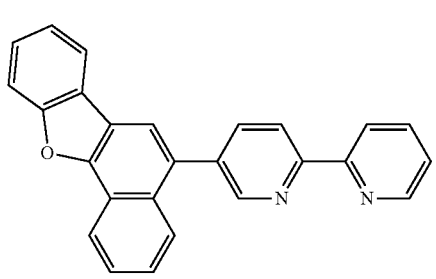
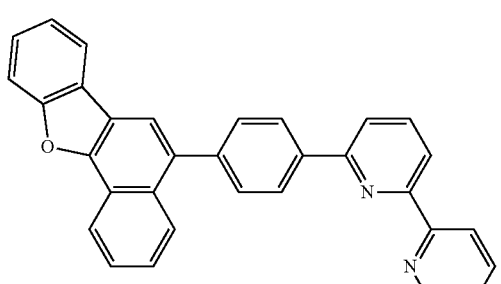
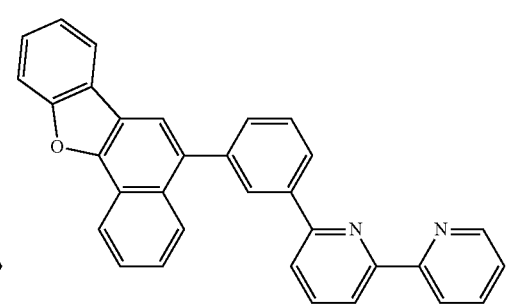
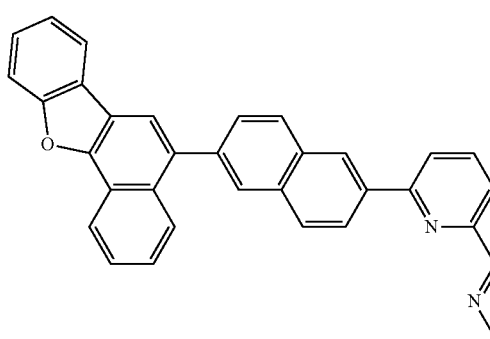
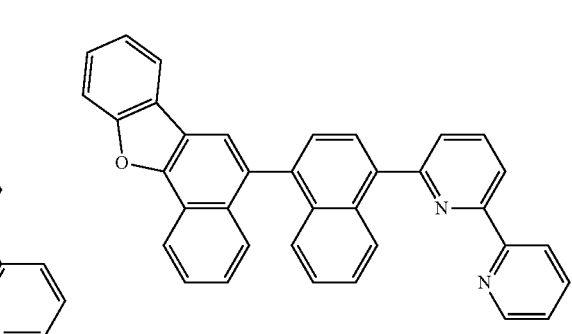

-continued
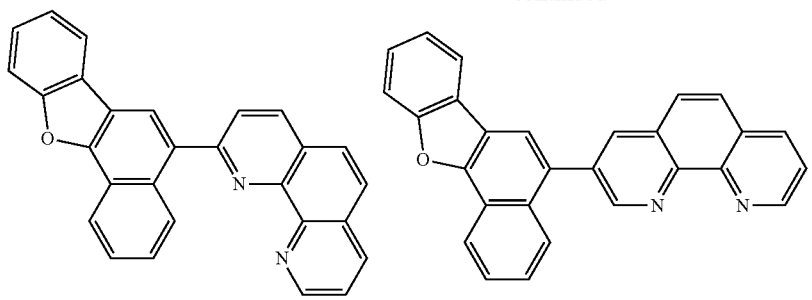
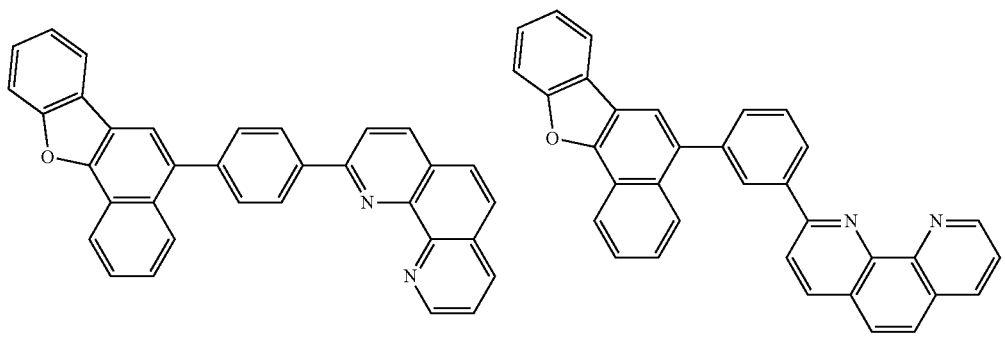
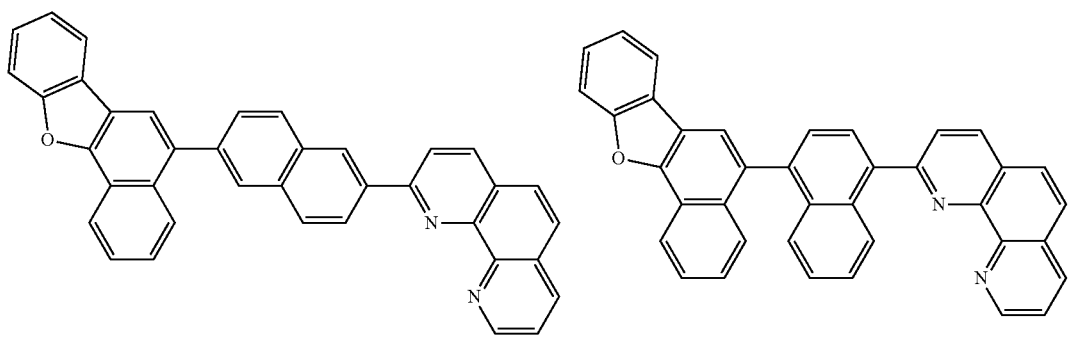
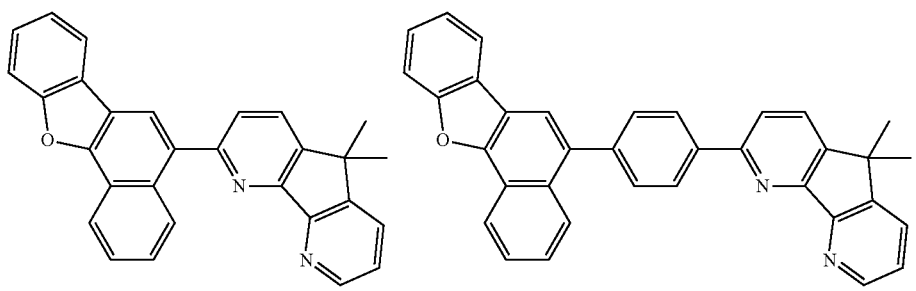
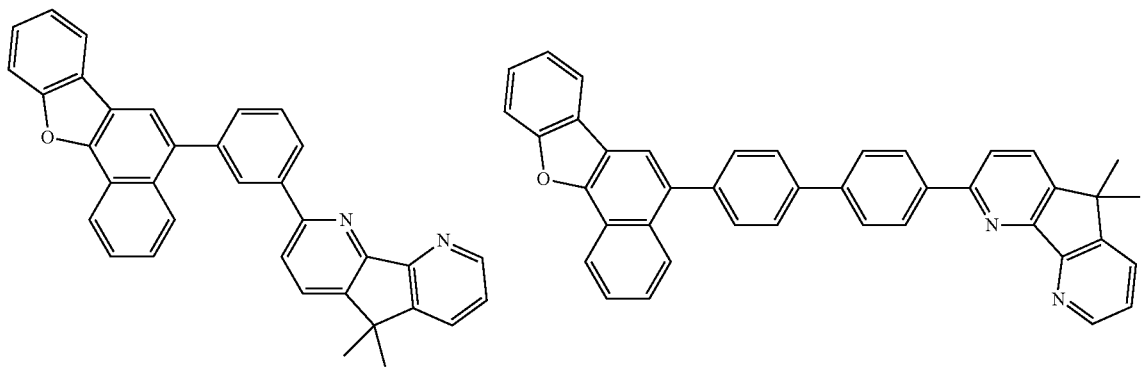

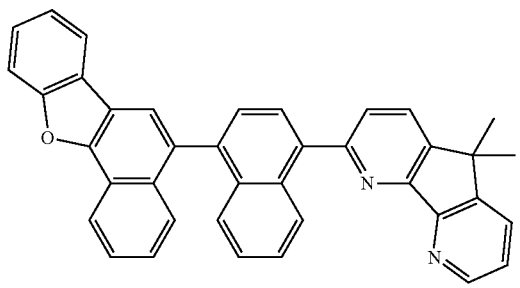
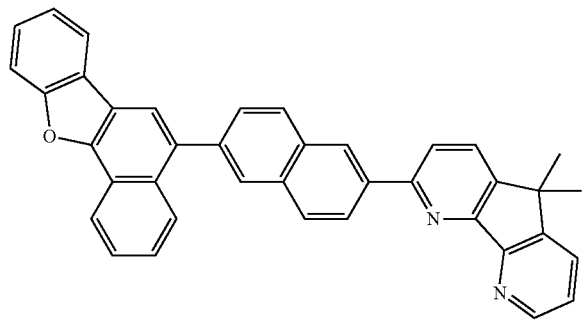
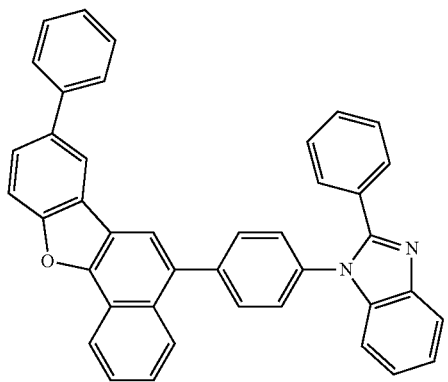
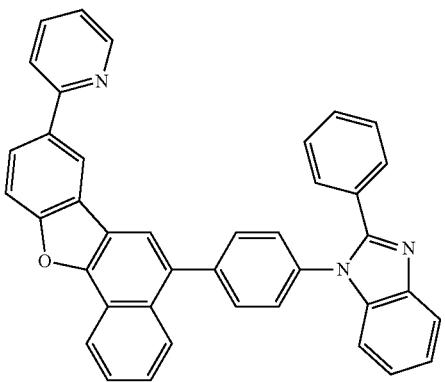
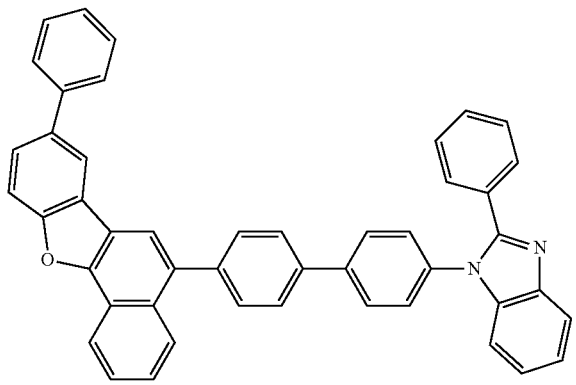
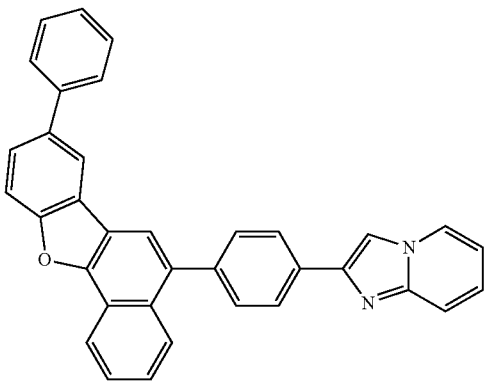
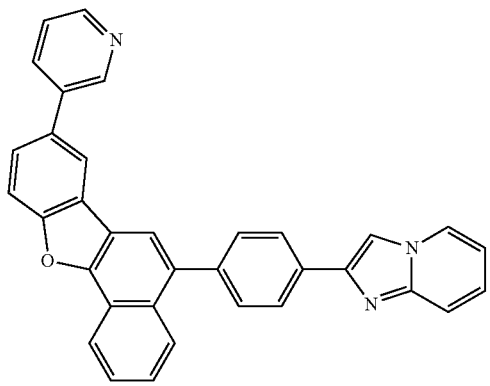
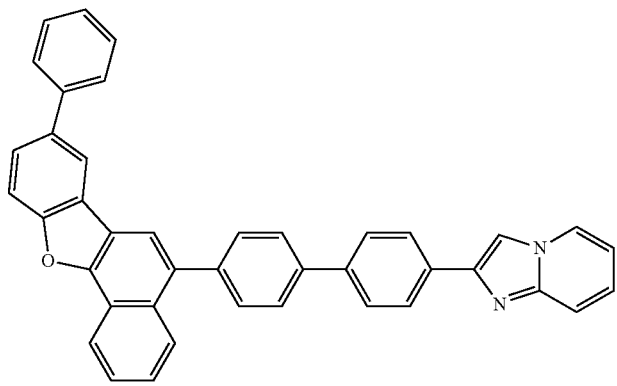

-continued
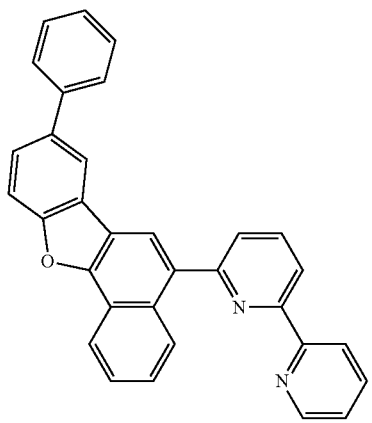
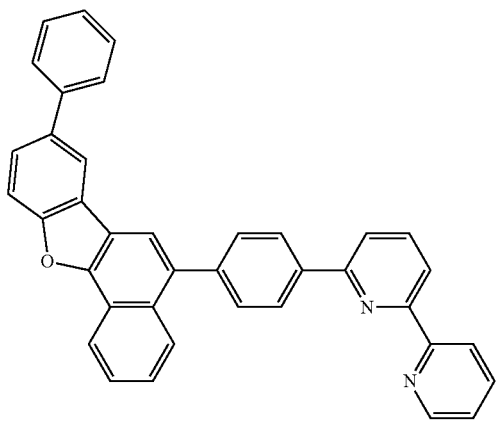
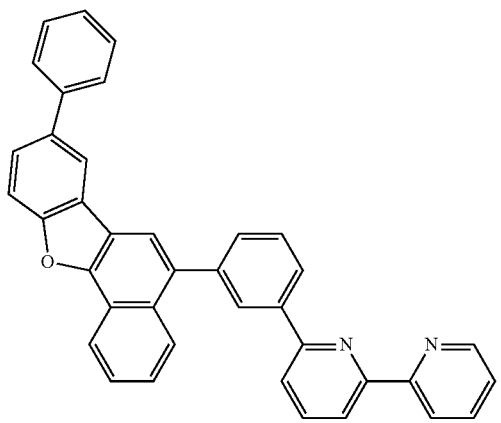
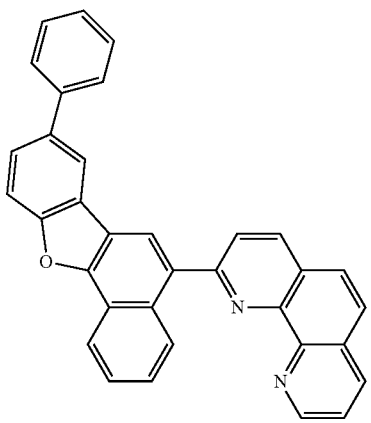
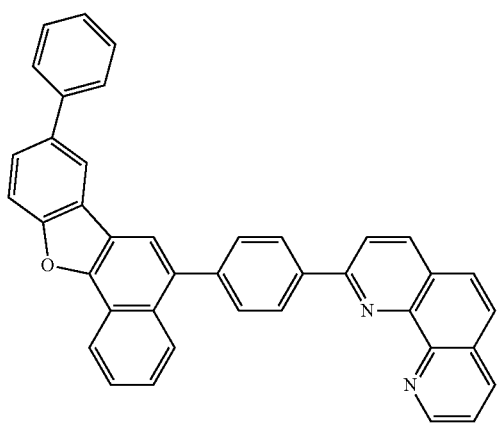
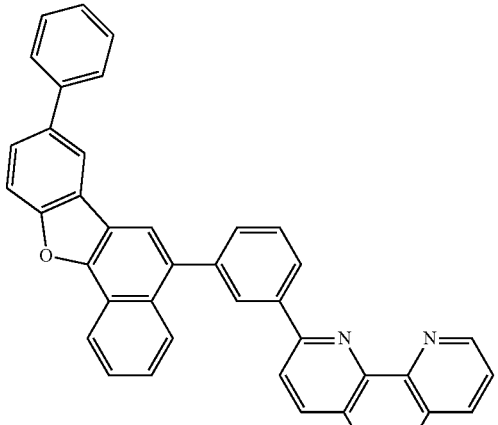
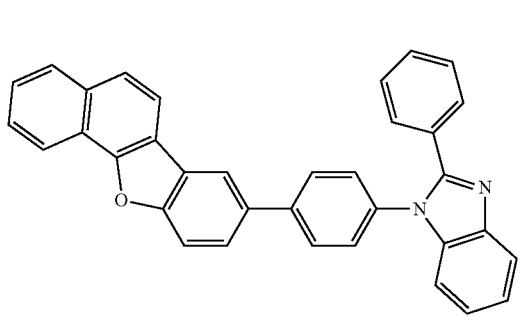
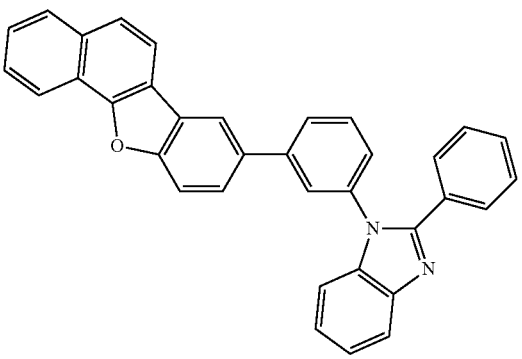

-continued
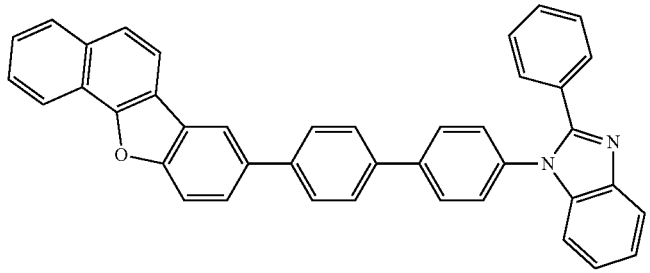
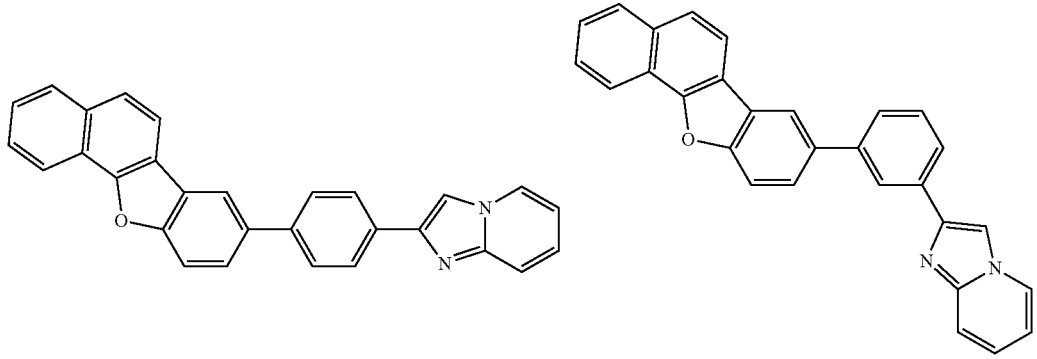
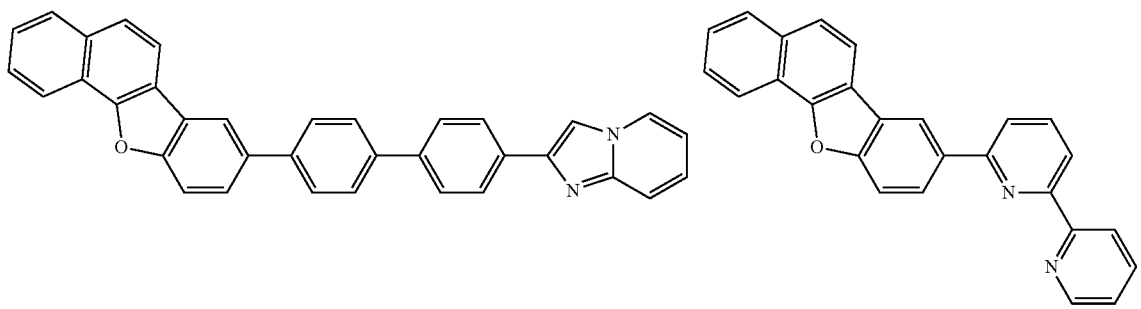
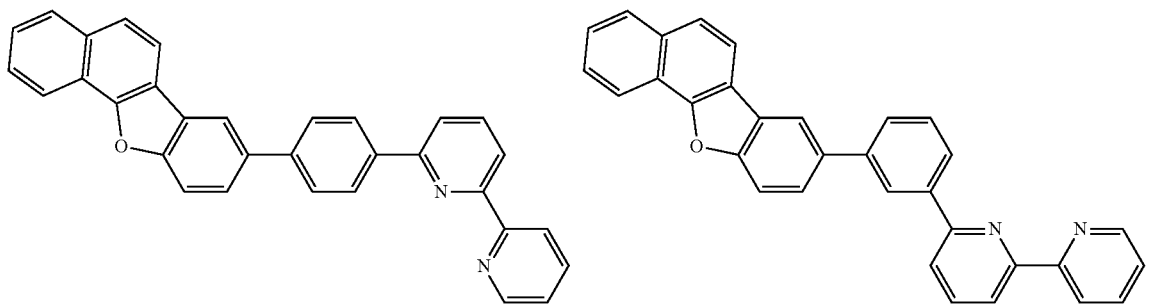
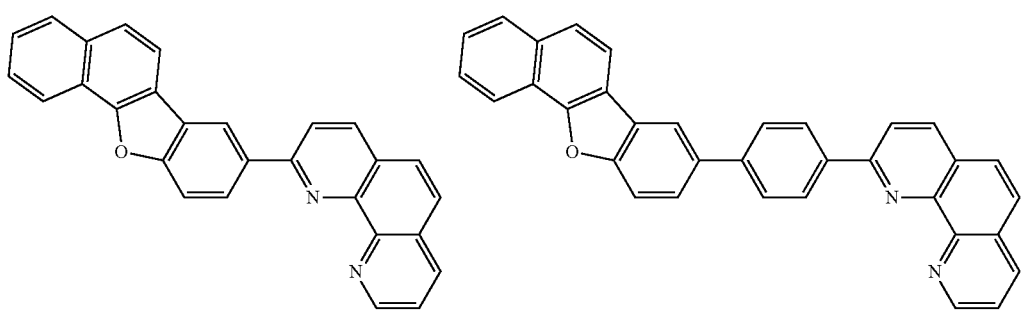

-continued
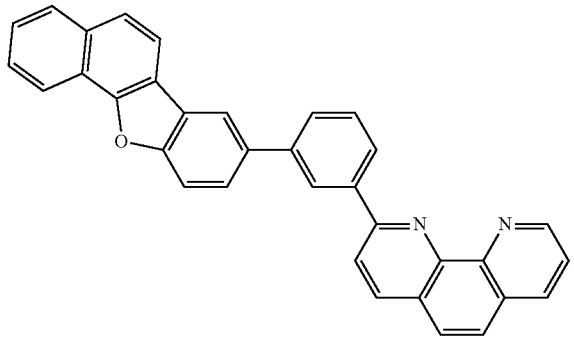
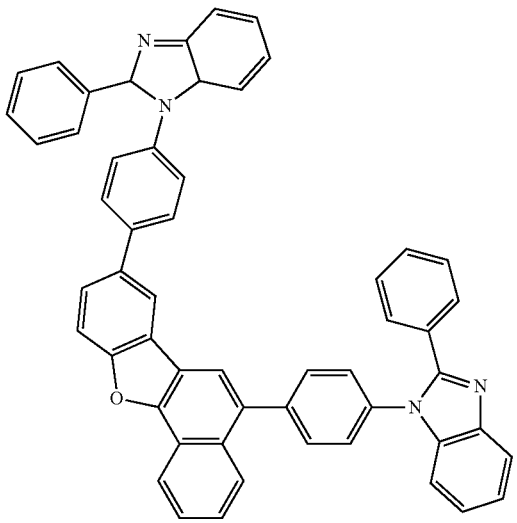
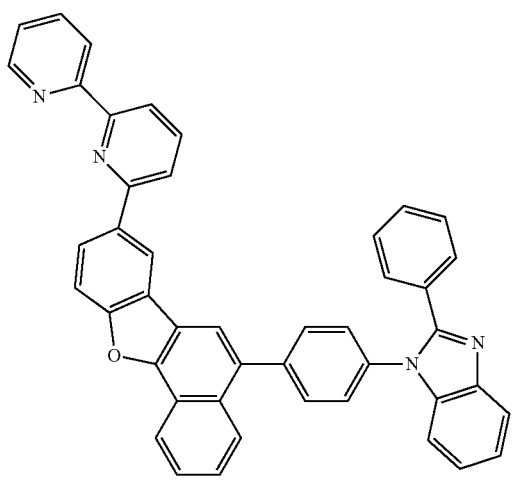
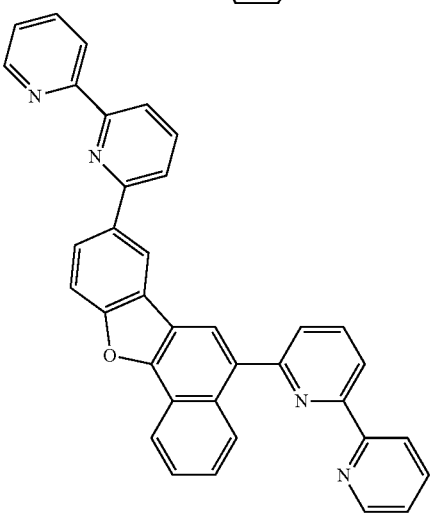
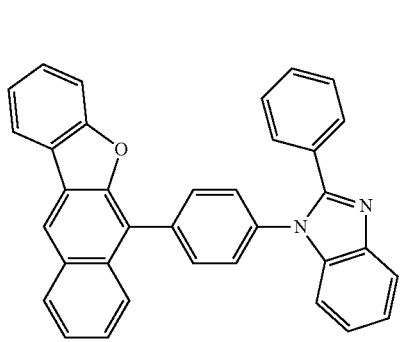
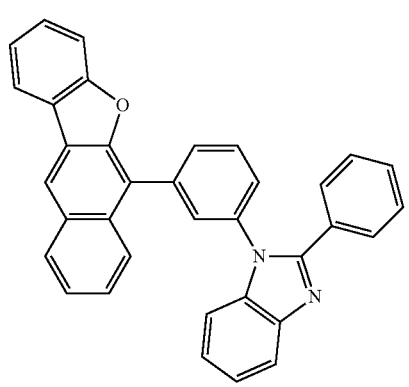
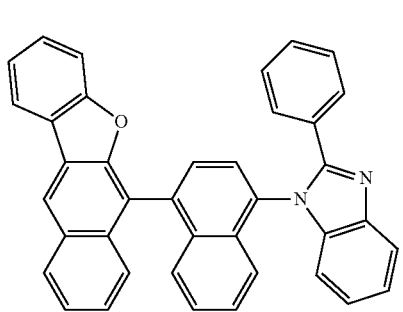
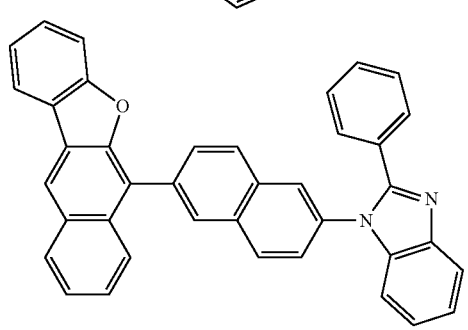

-continued
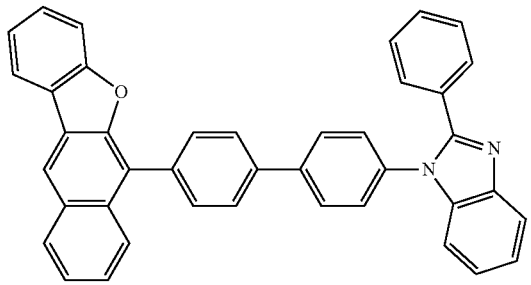
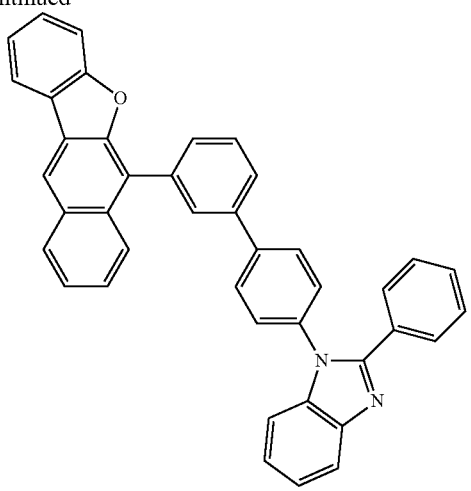
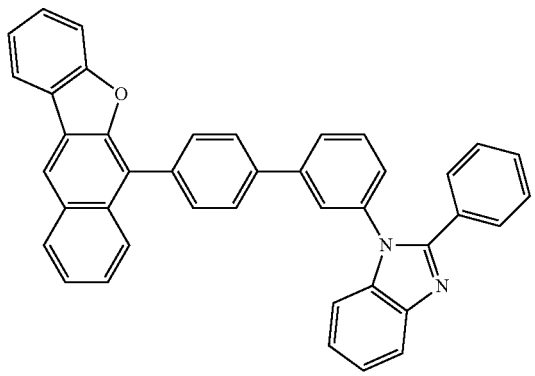
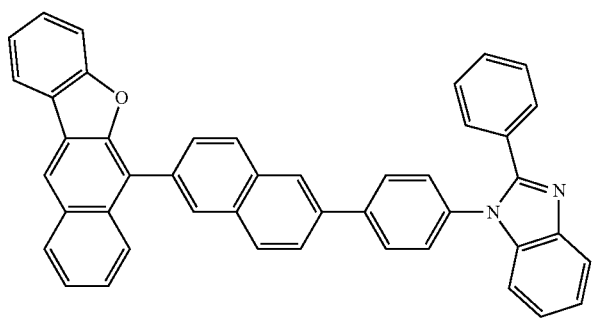
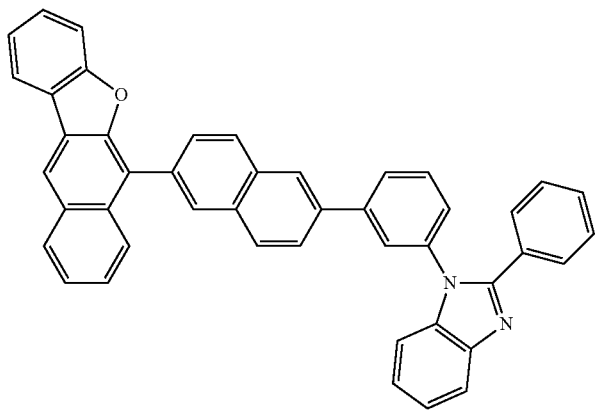
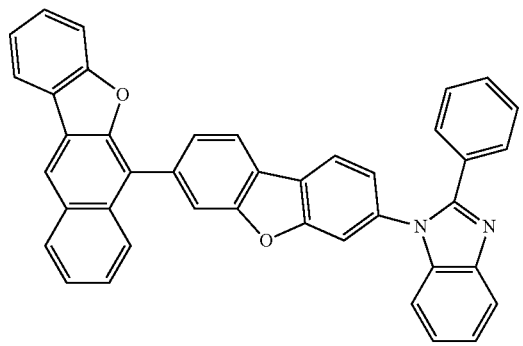
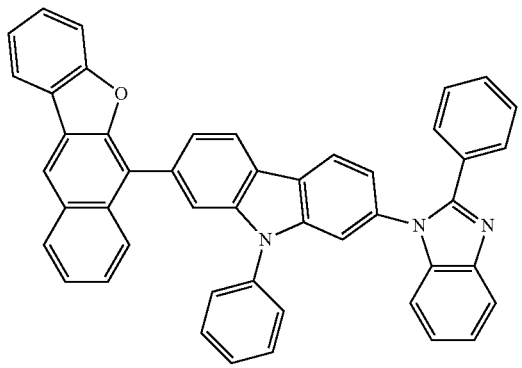
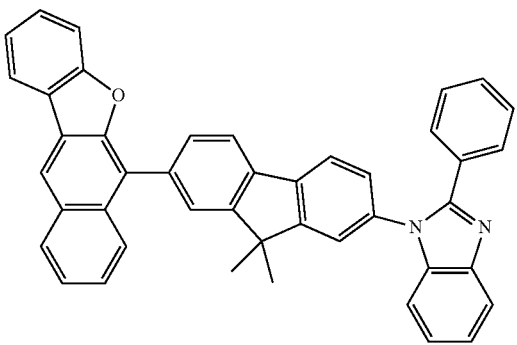

-continued
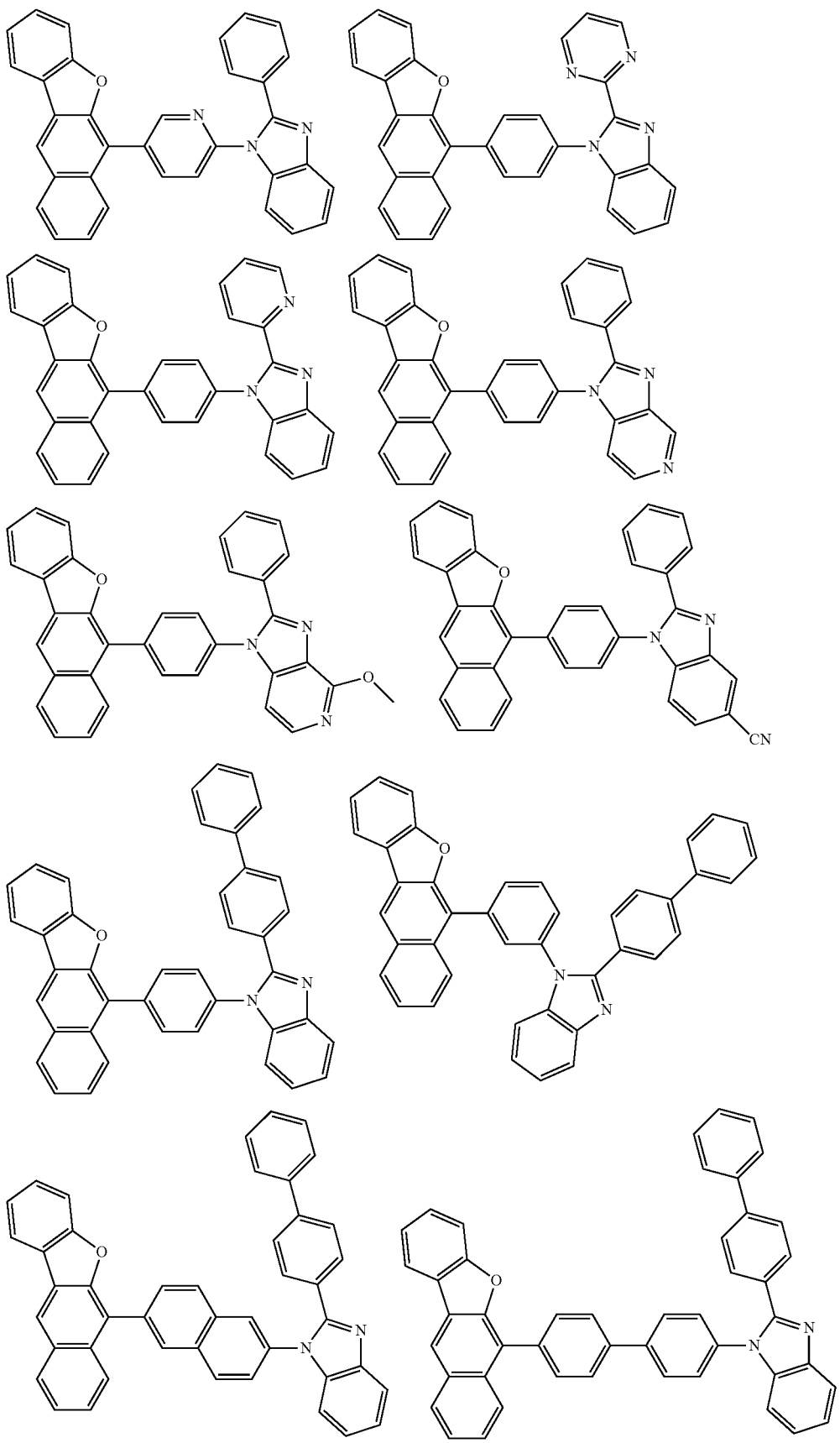

-continued
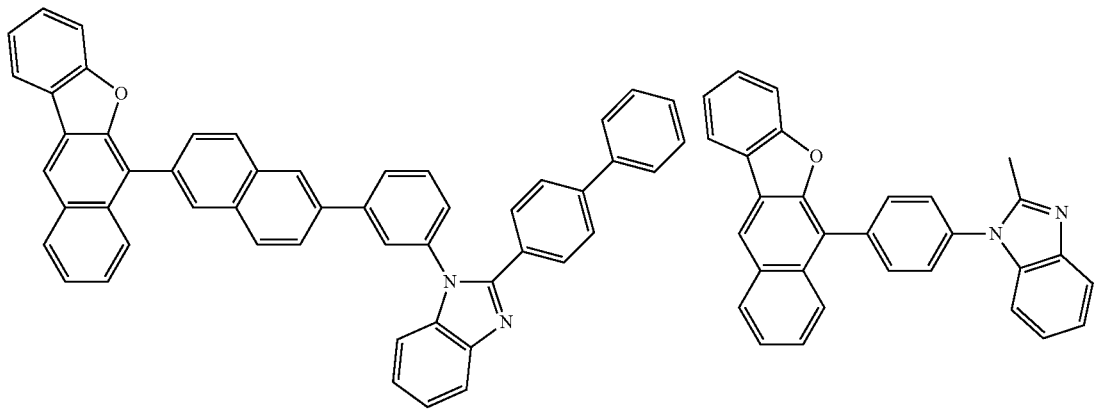
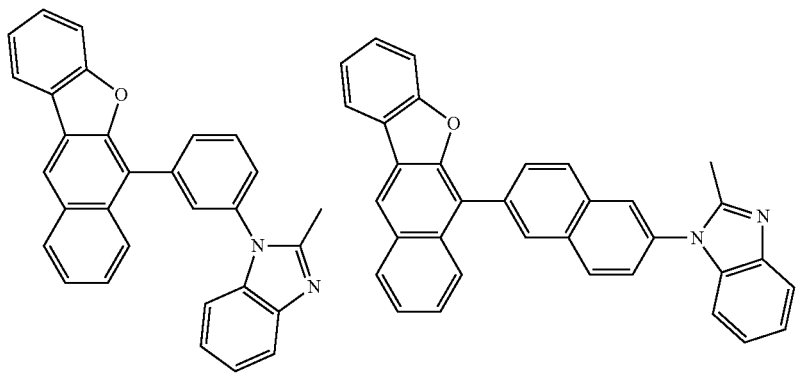
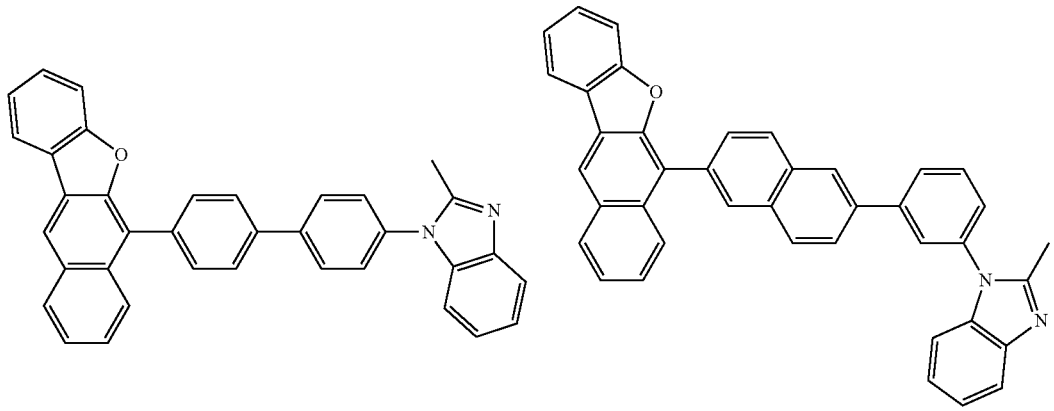
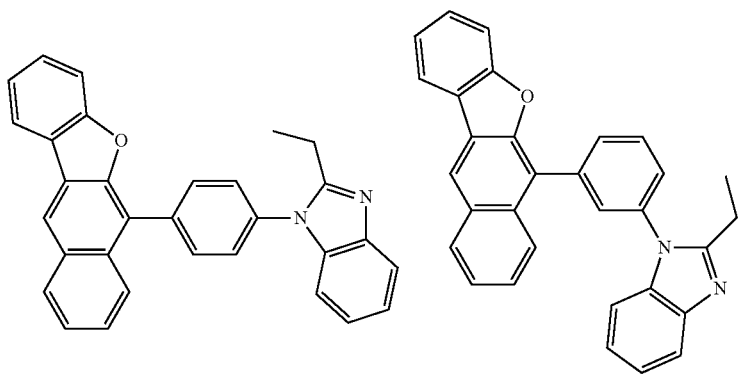

59 60
-continued
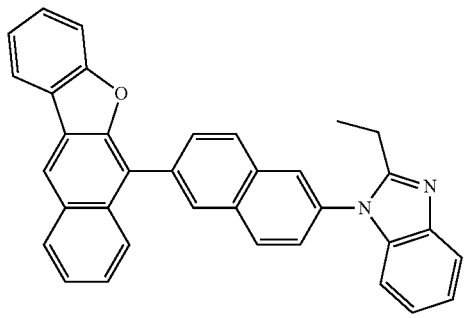
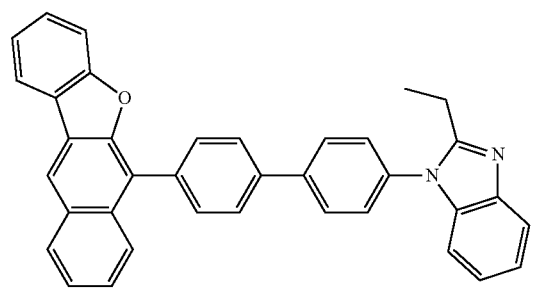
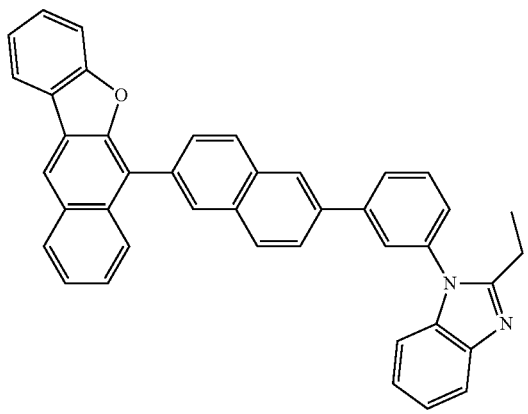
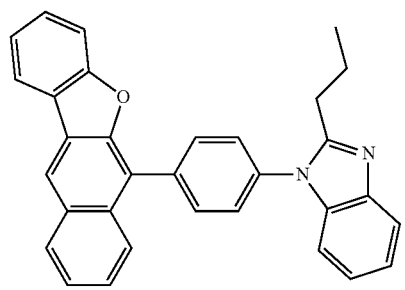
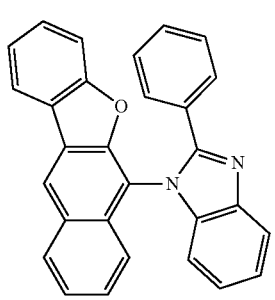
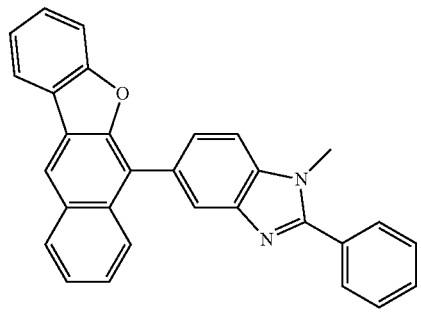
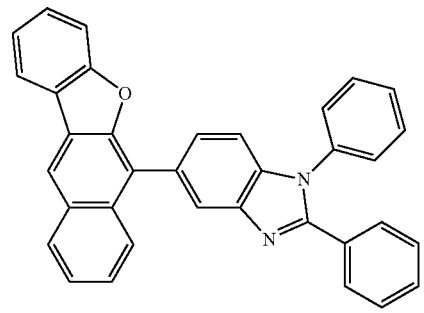
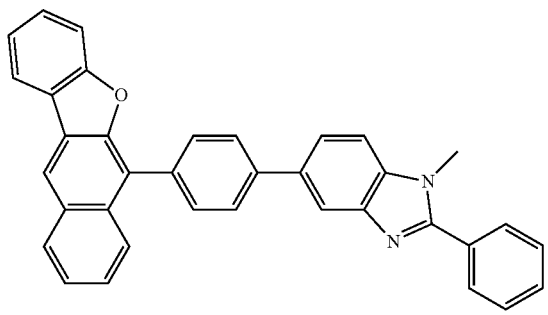
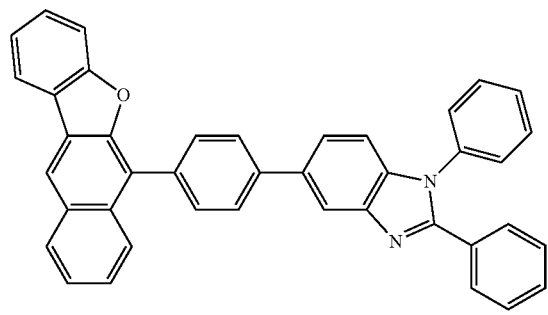

-continued
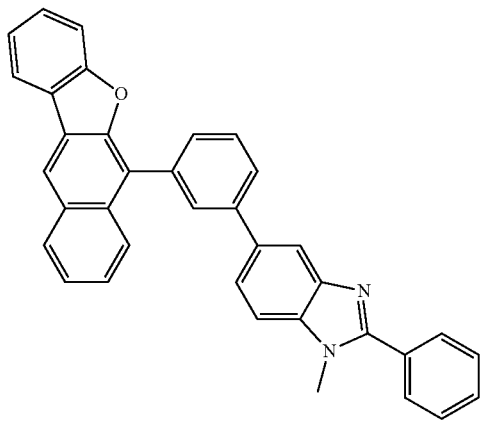
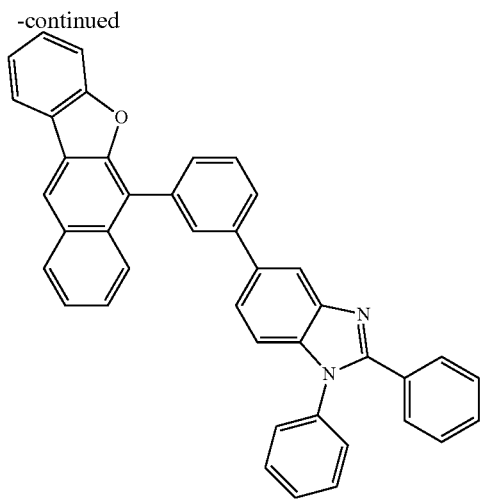
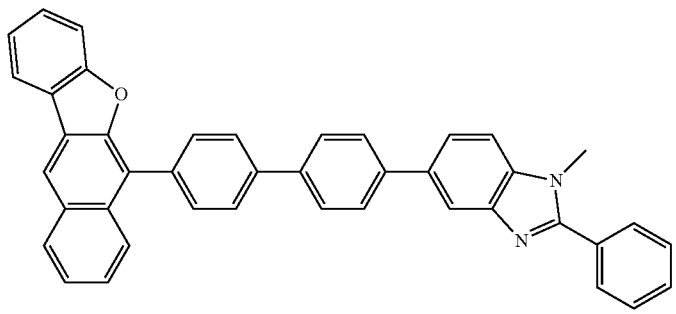
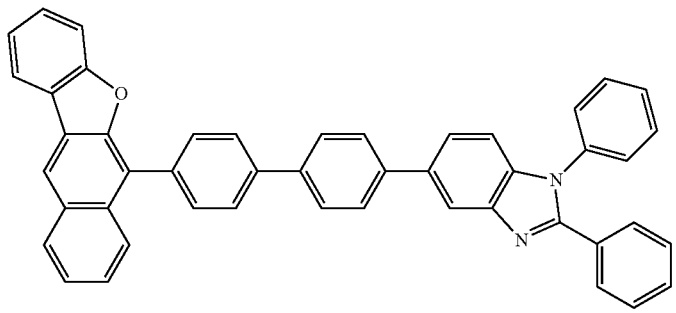
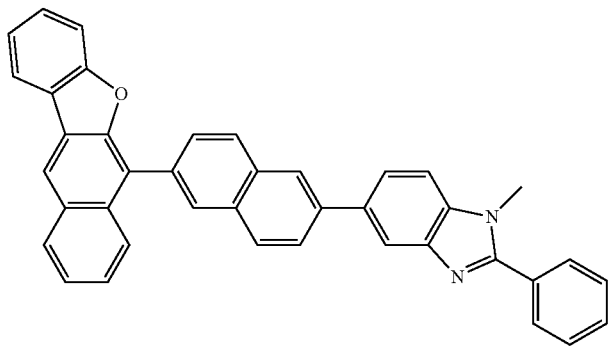

-continued
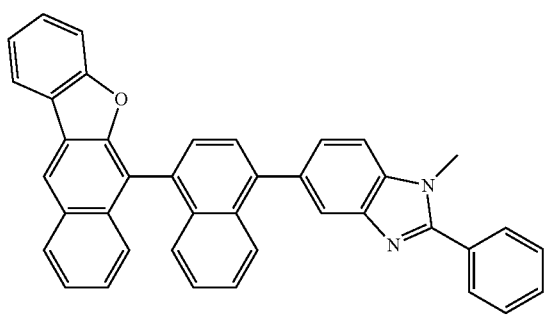
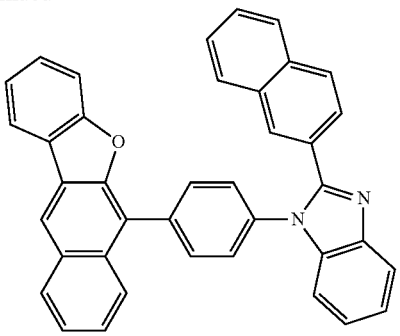
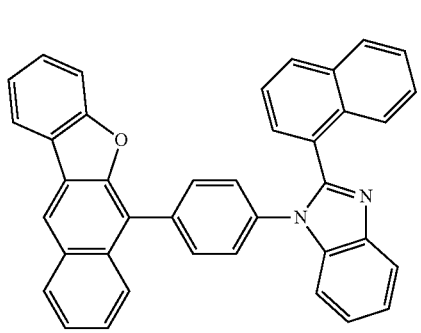
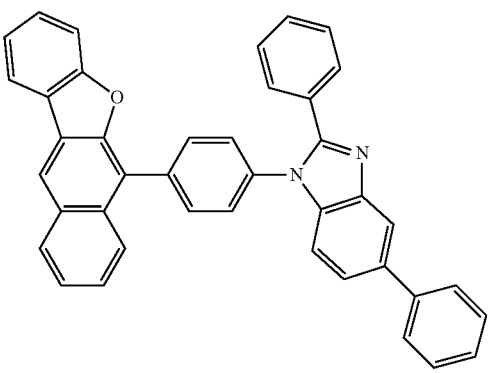
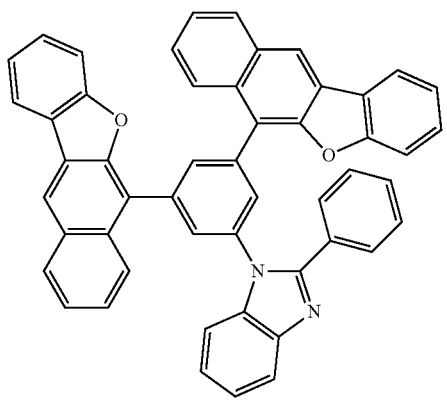
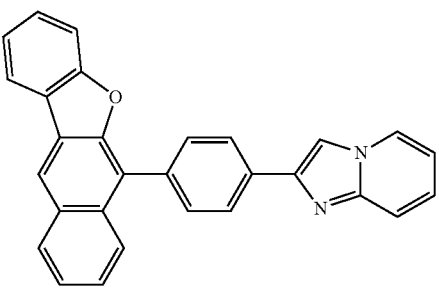
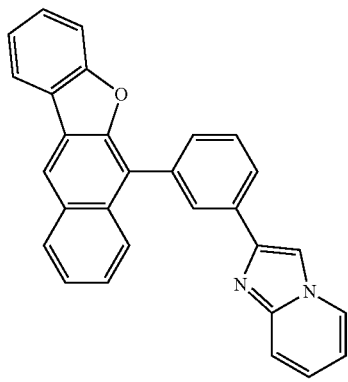
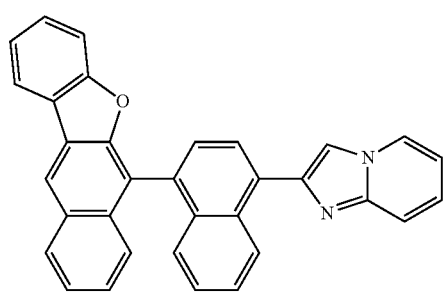

-continued
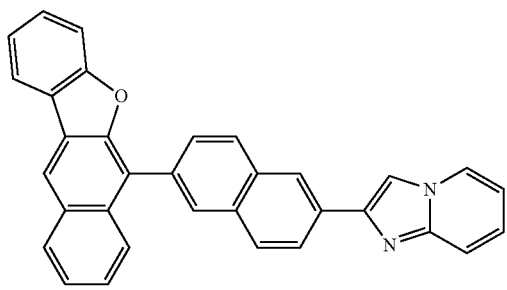
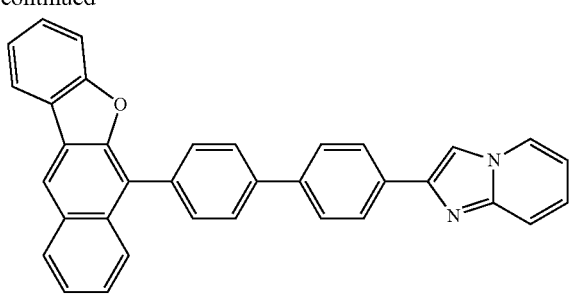
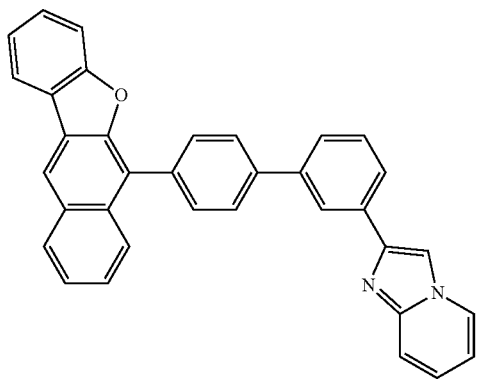
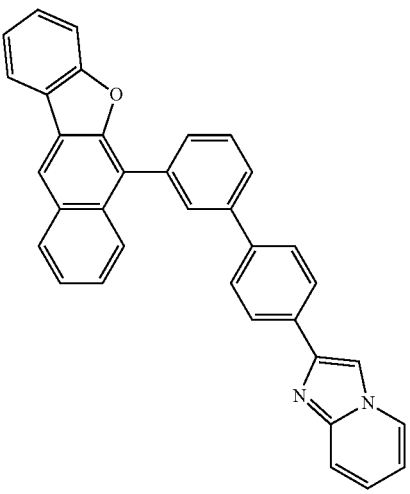
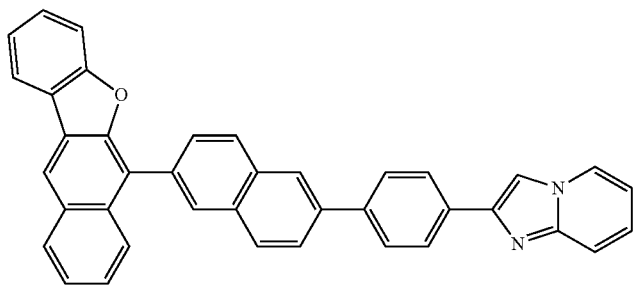
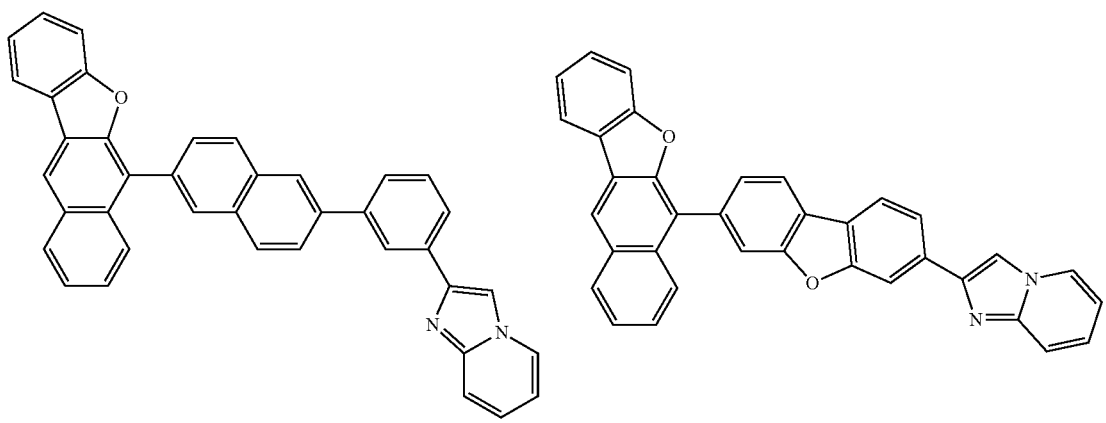

-continued
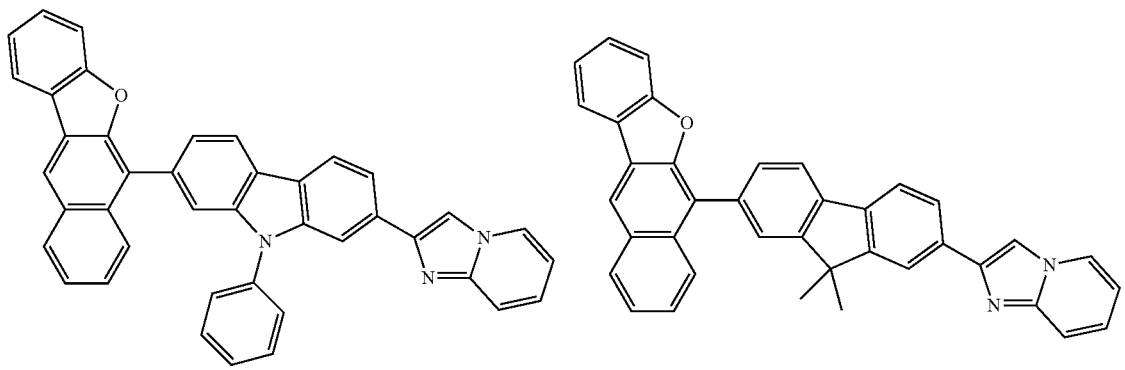
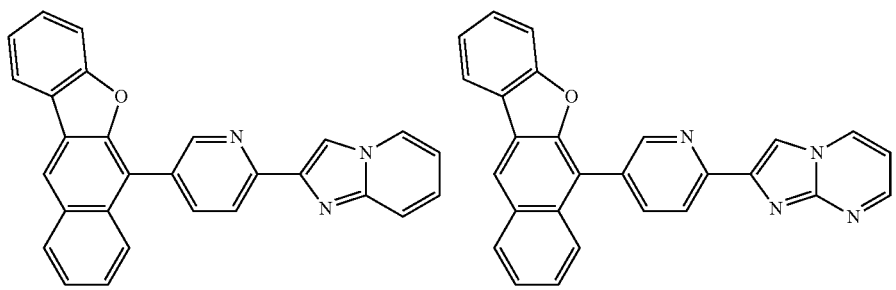
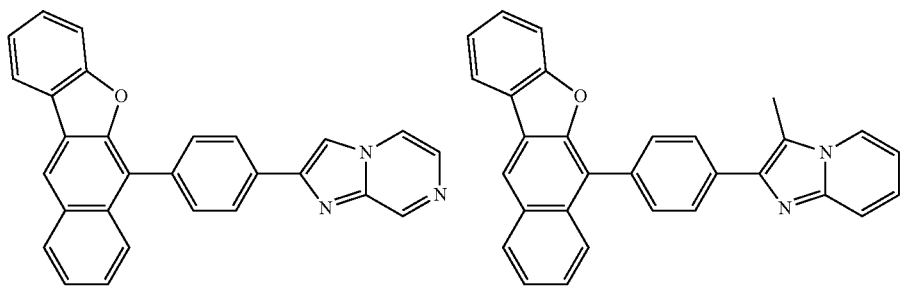
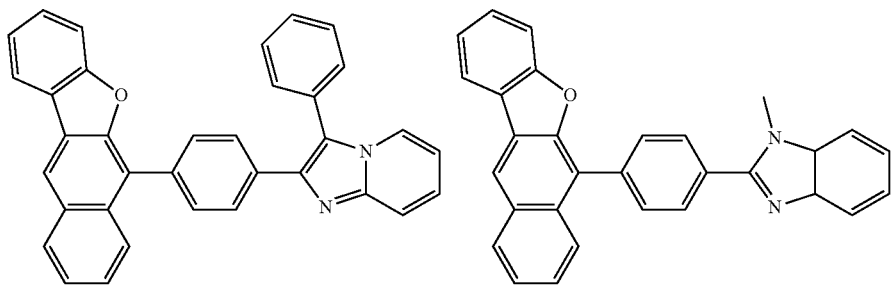
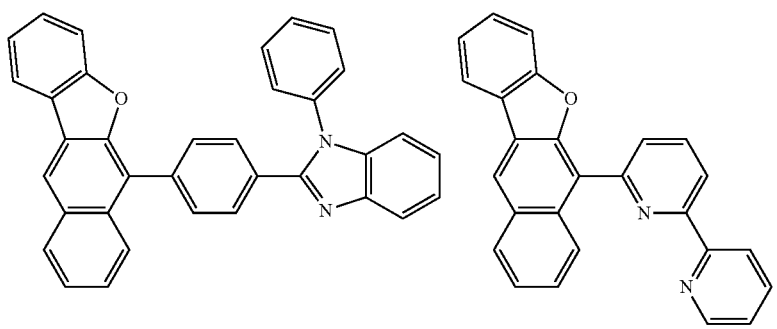

-continued
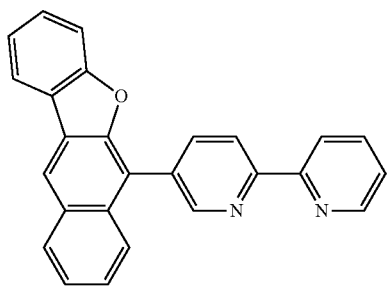
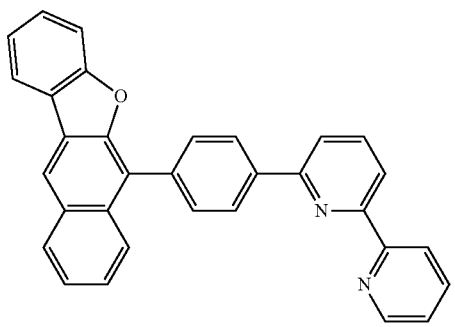
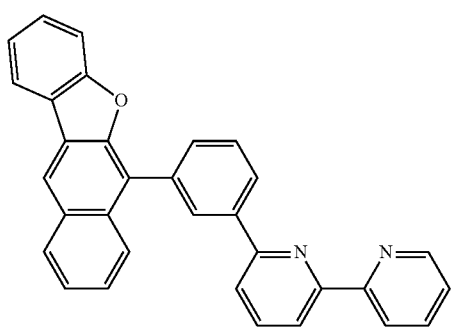
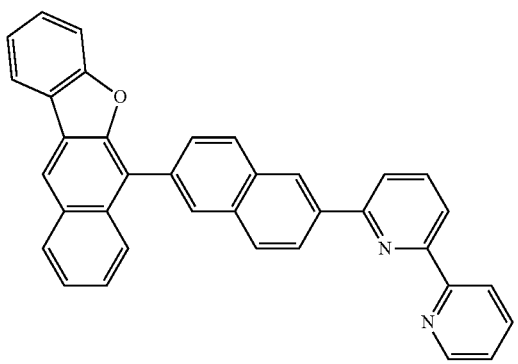
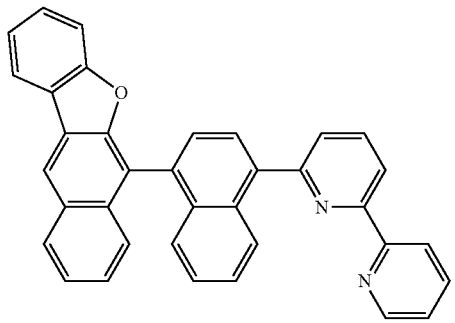
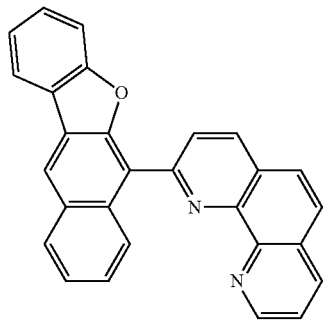
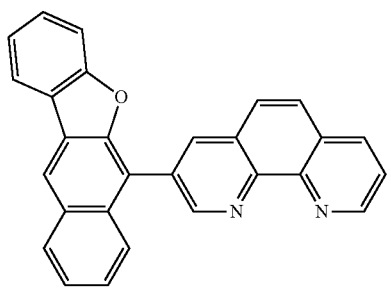
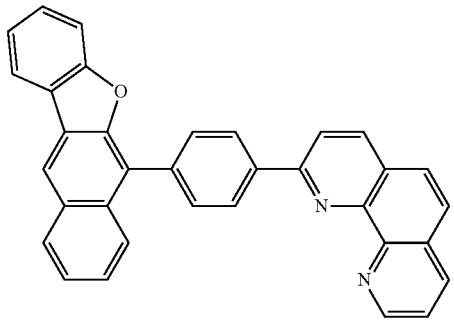
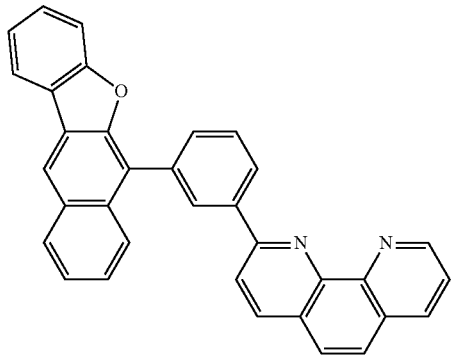
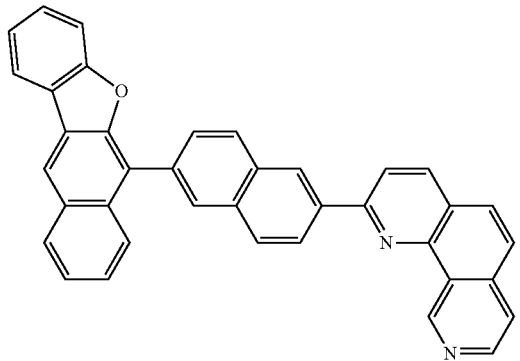

-continued
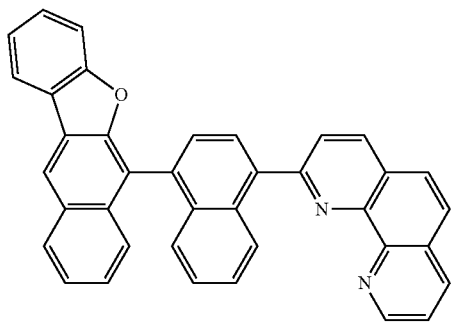
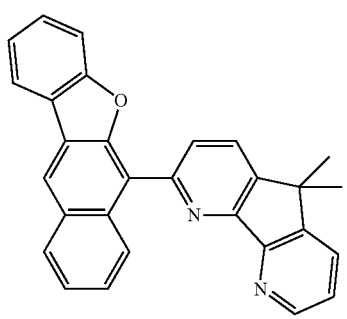
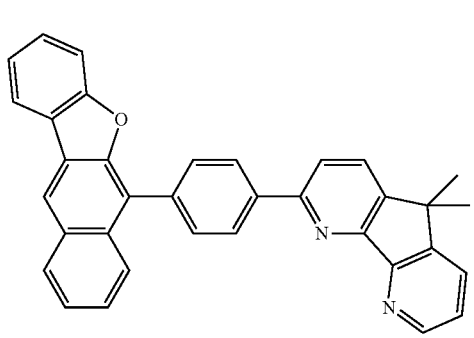
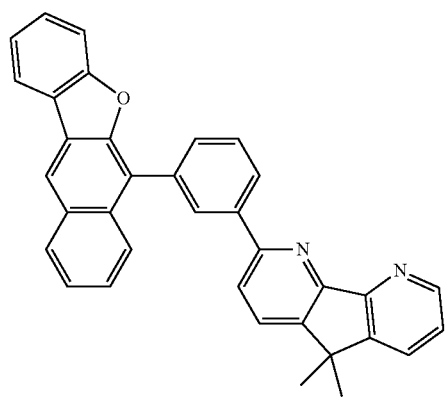
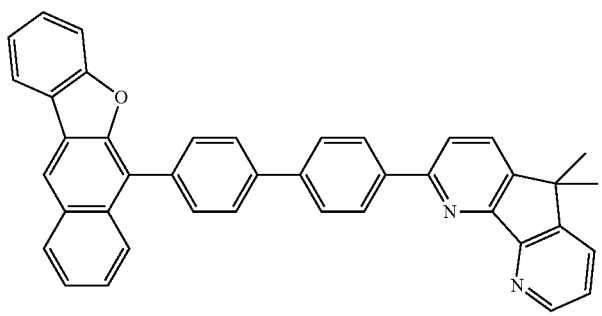
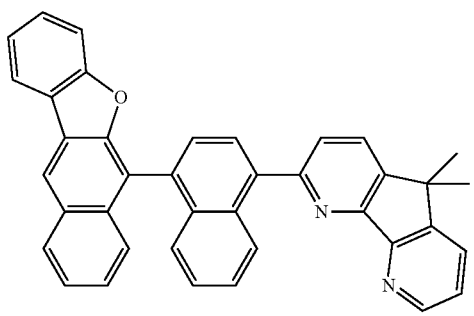
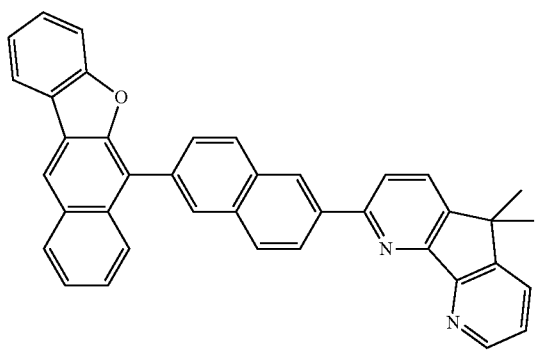
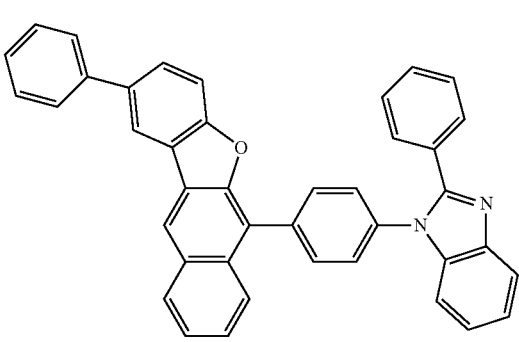
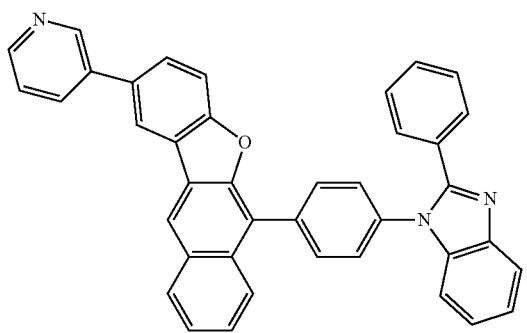

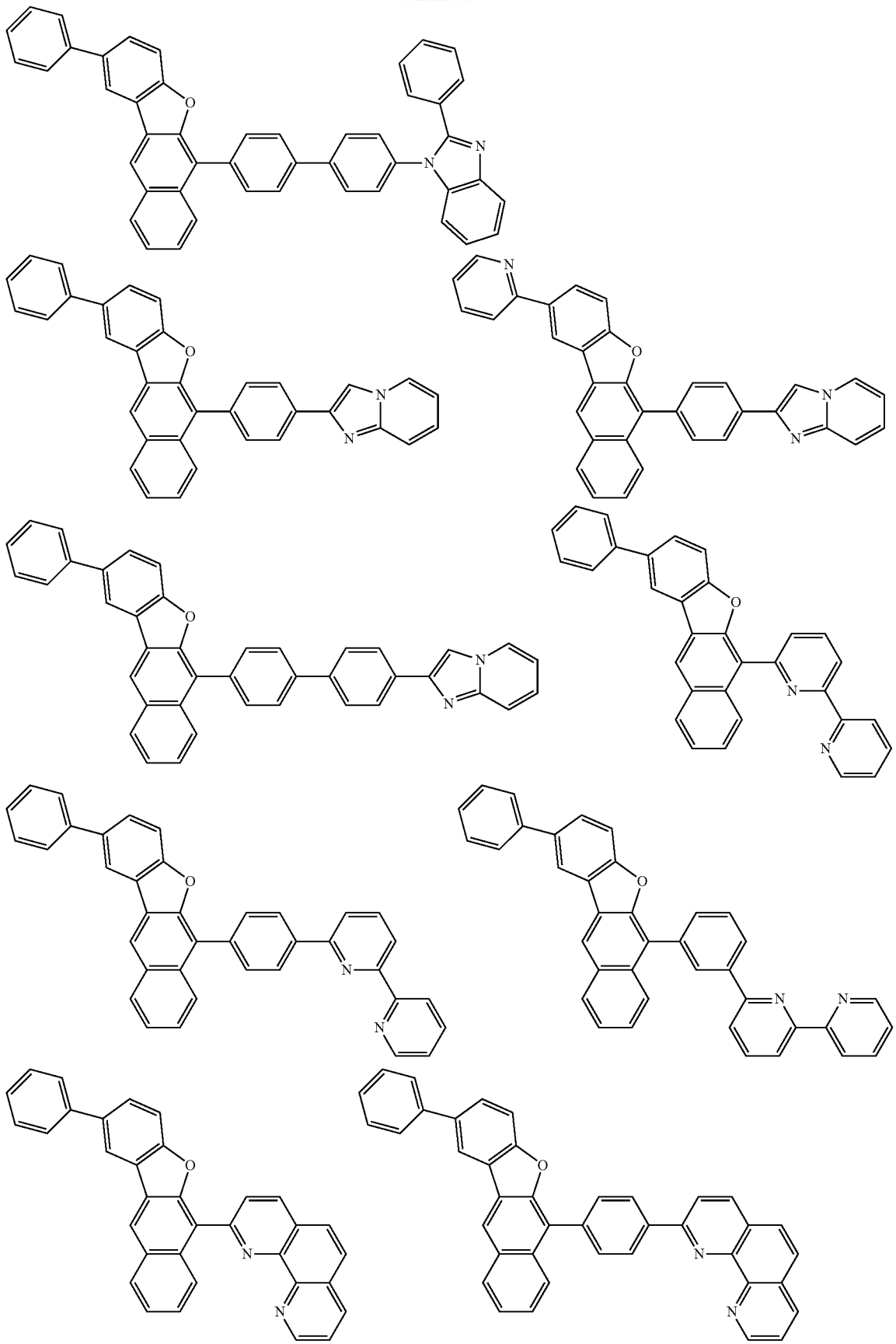

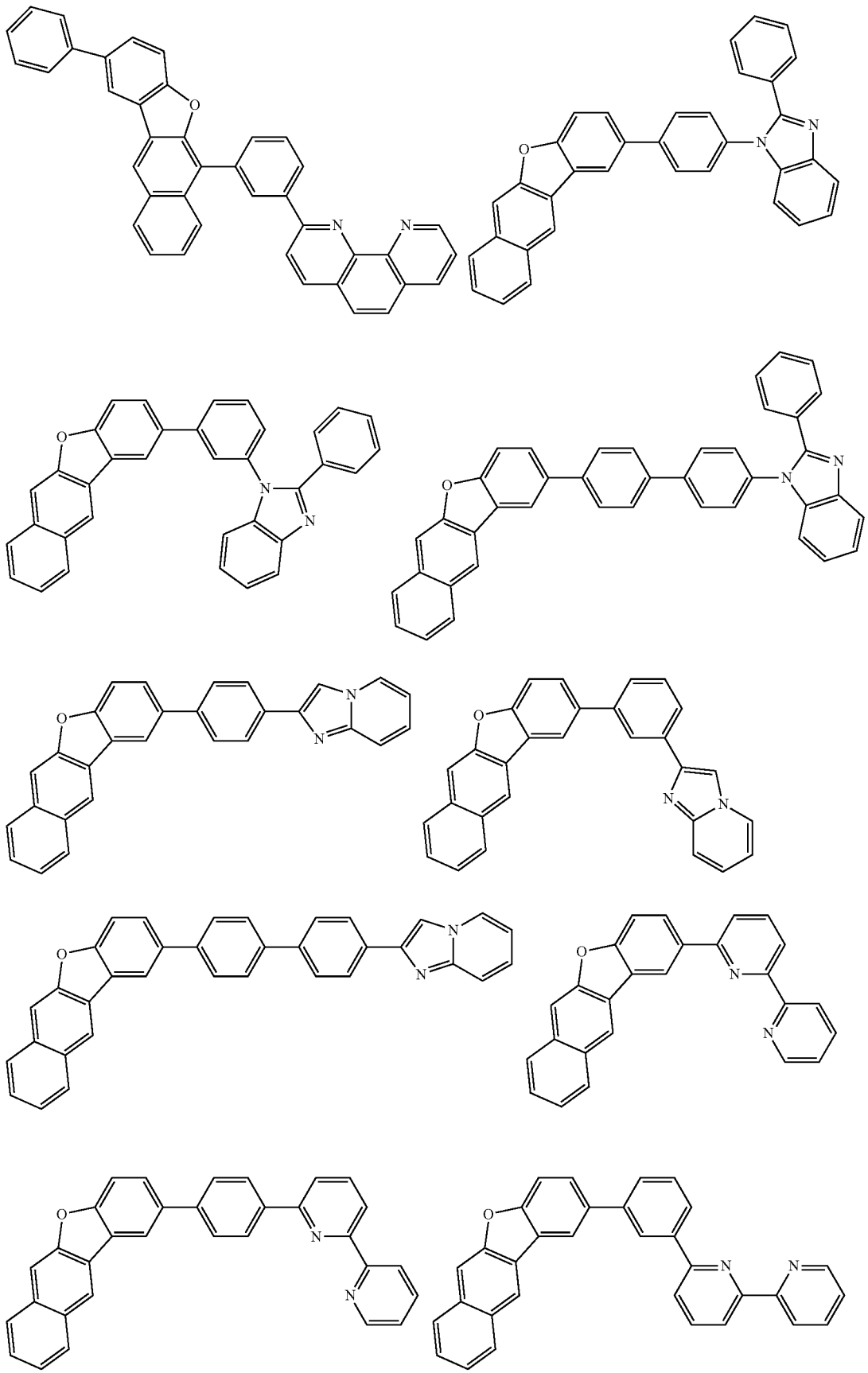

77
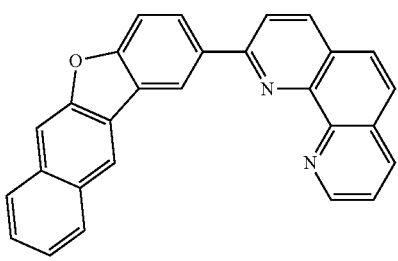
78
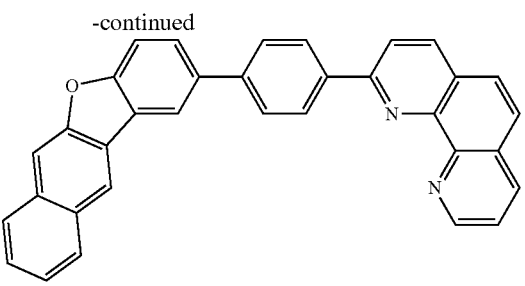
-continued
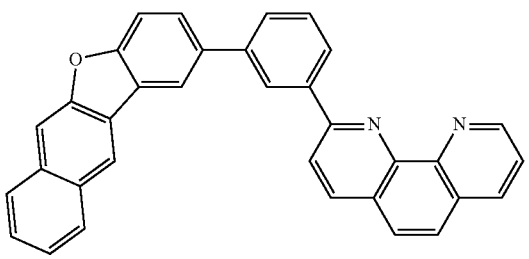
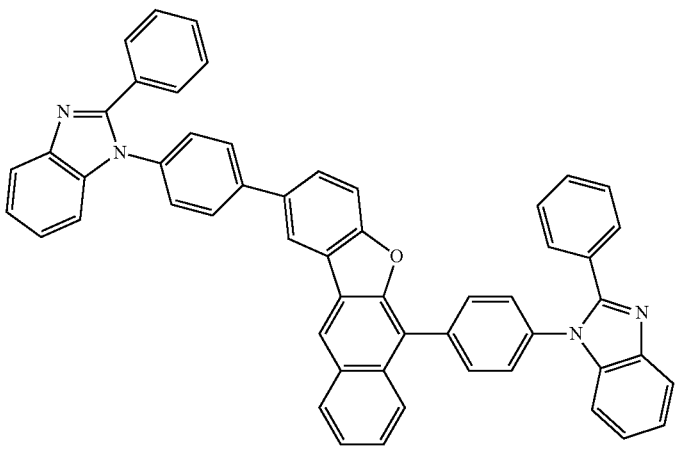
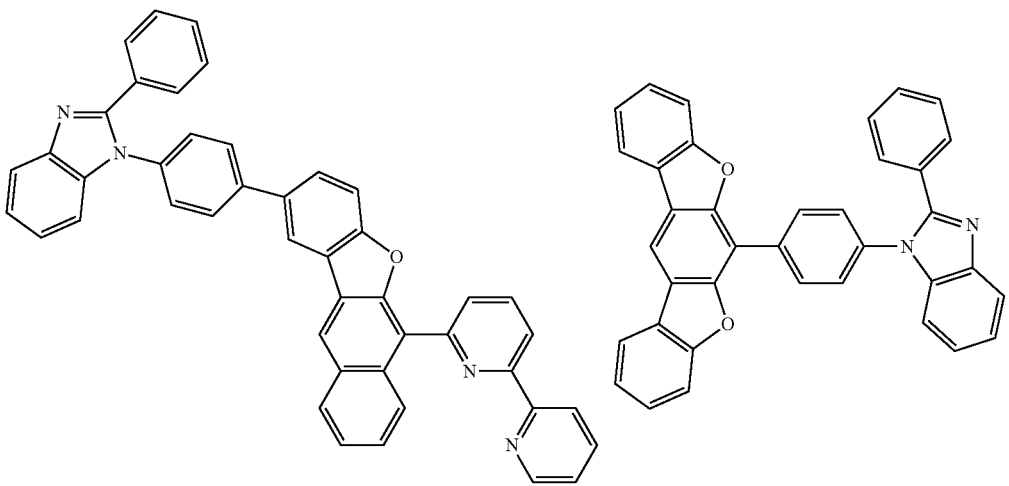

-continued
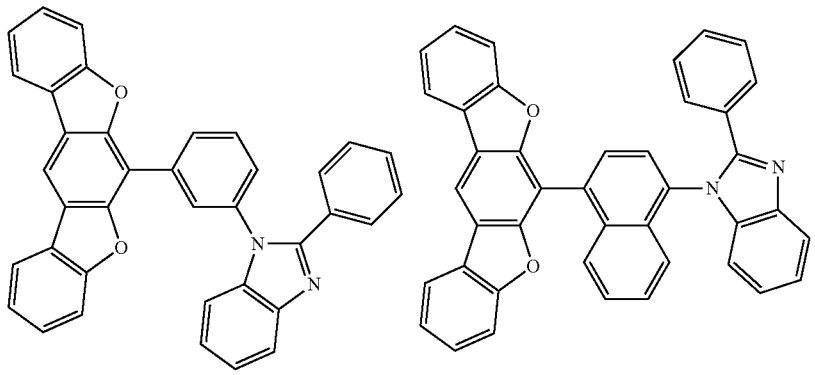
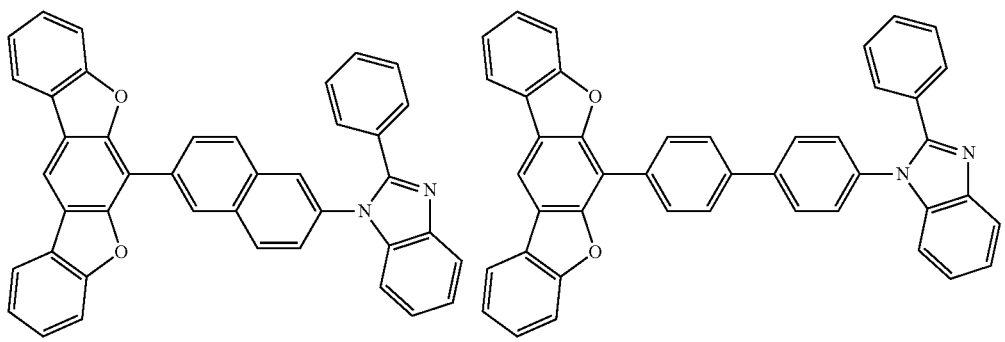
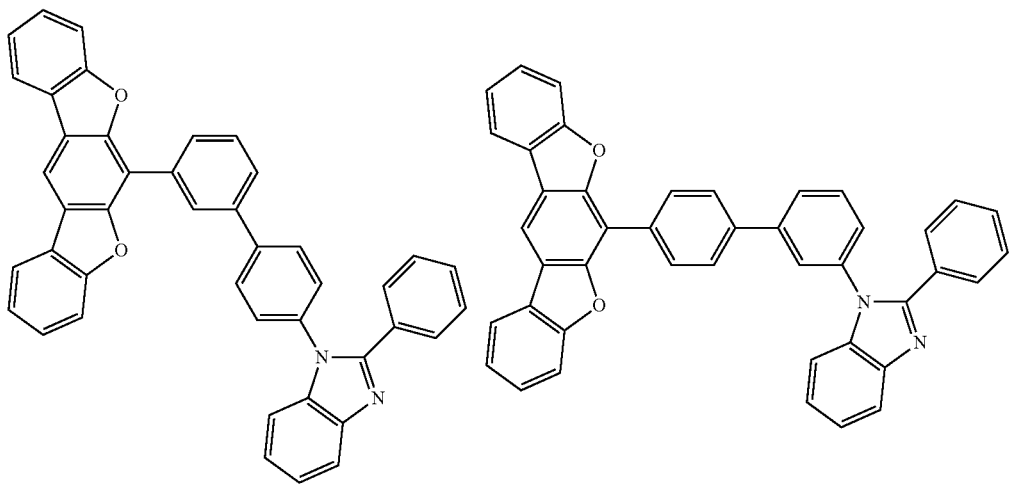
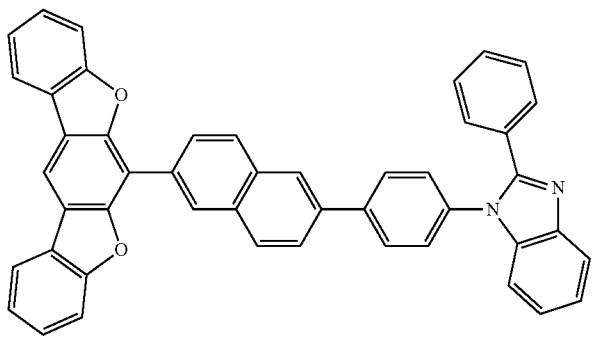

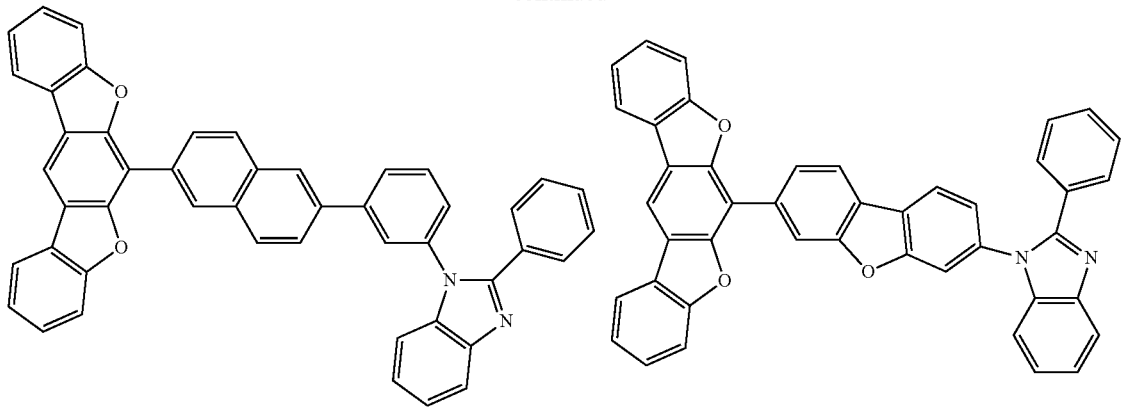
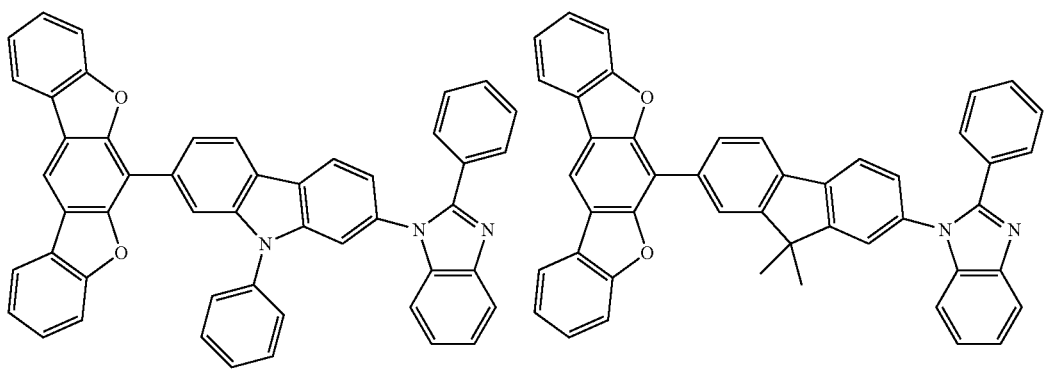
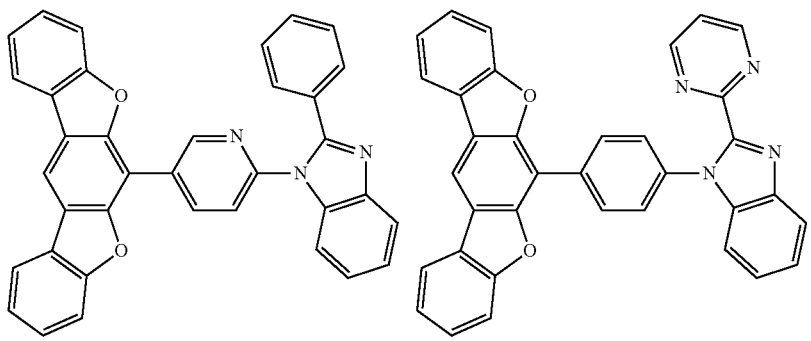
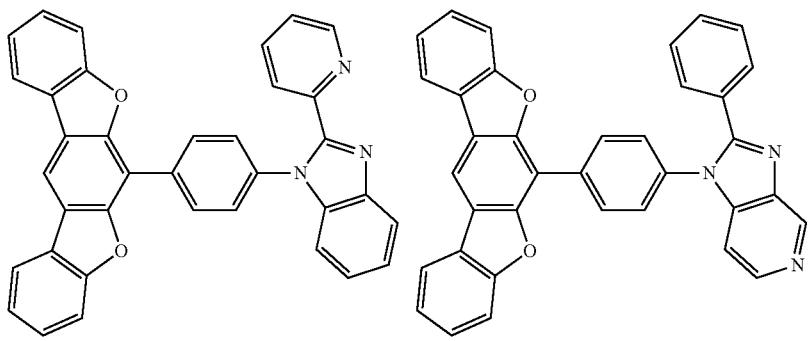

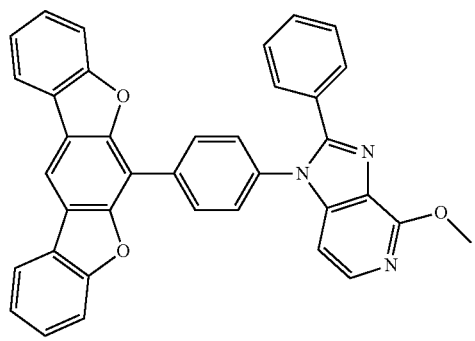
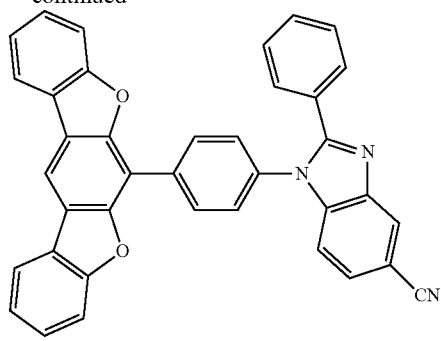
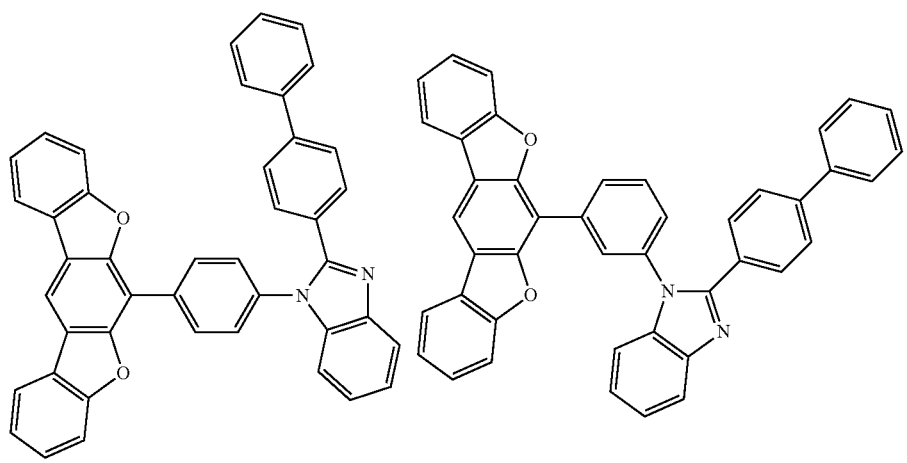
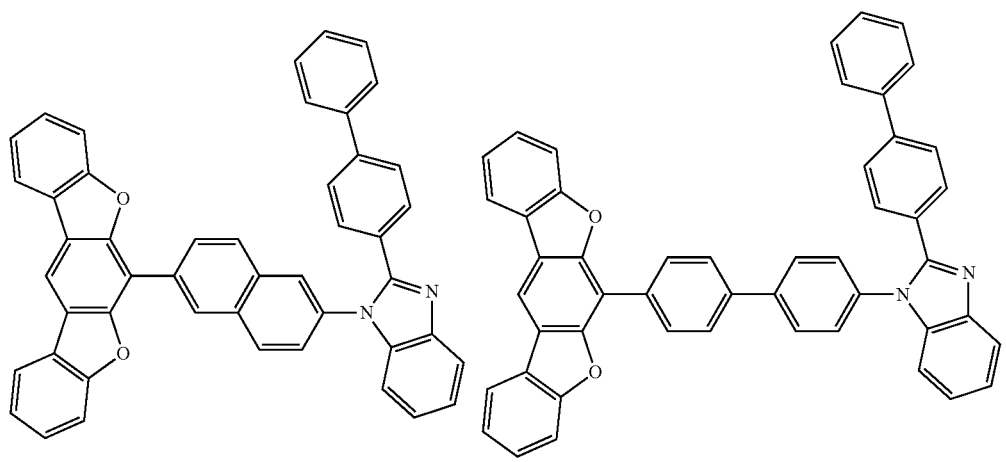
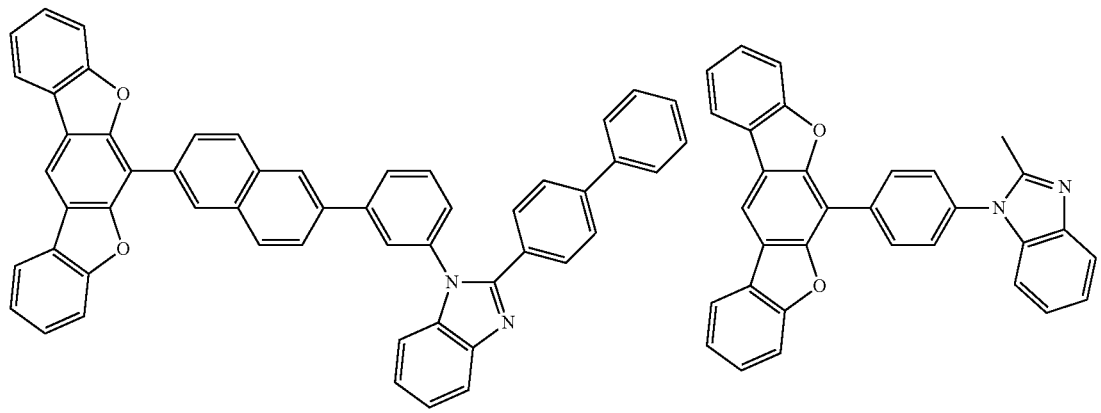

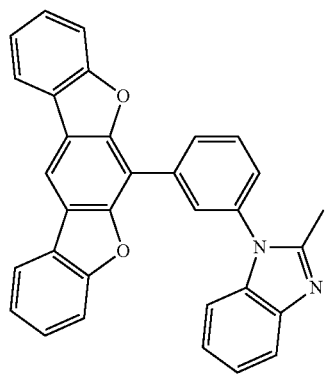
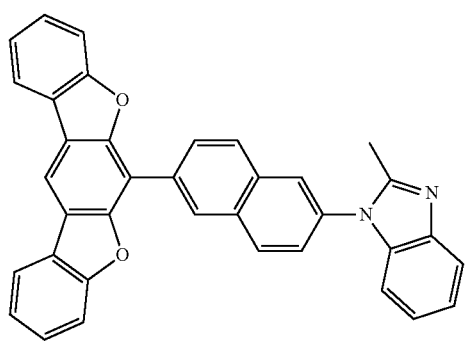
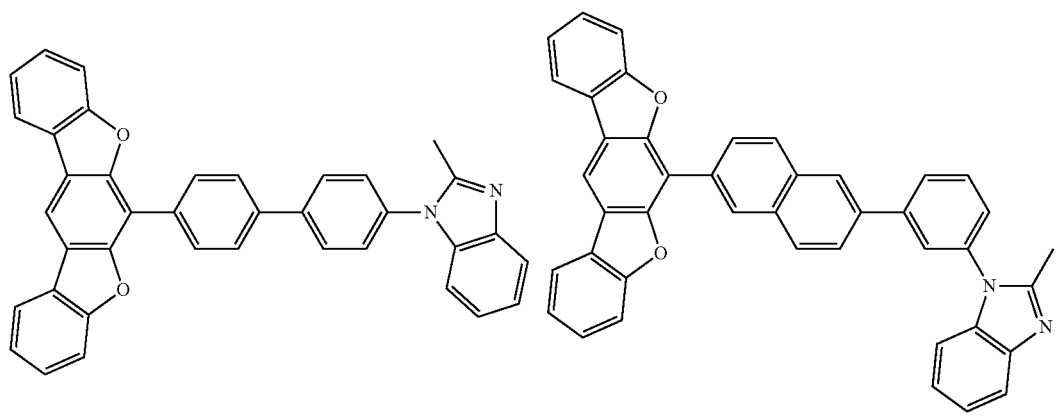
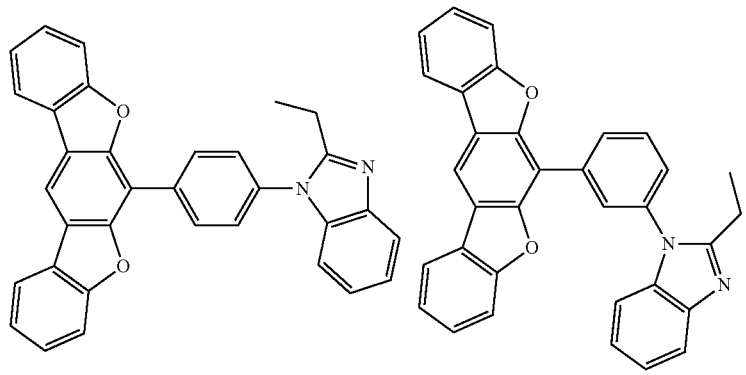
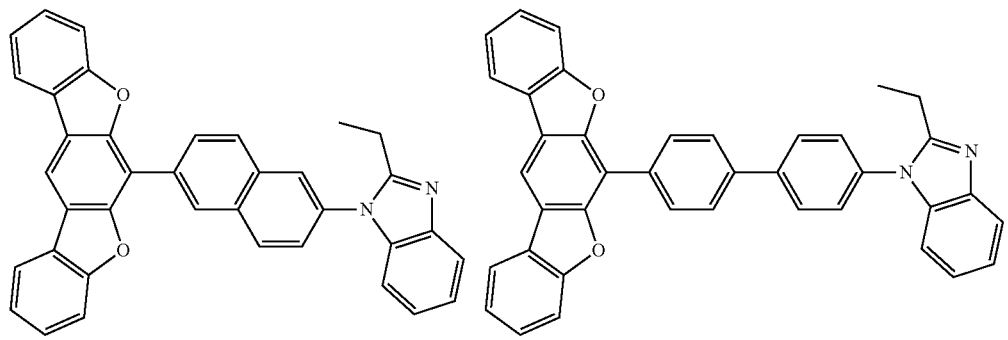

-continued
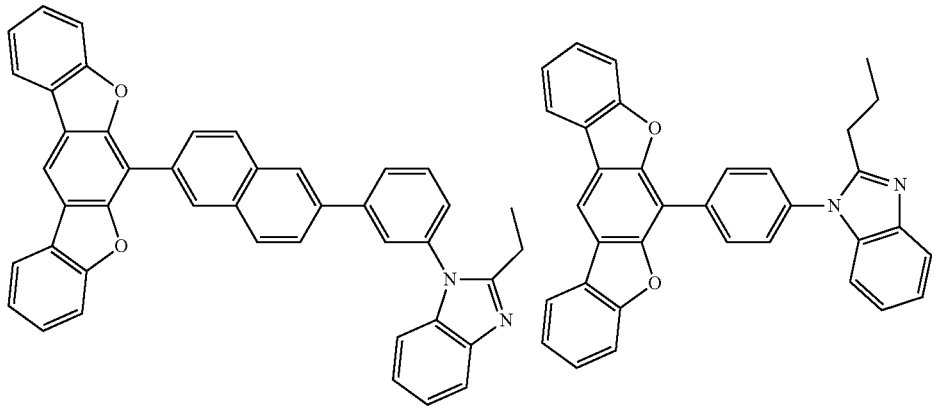
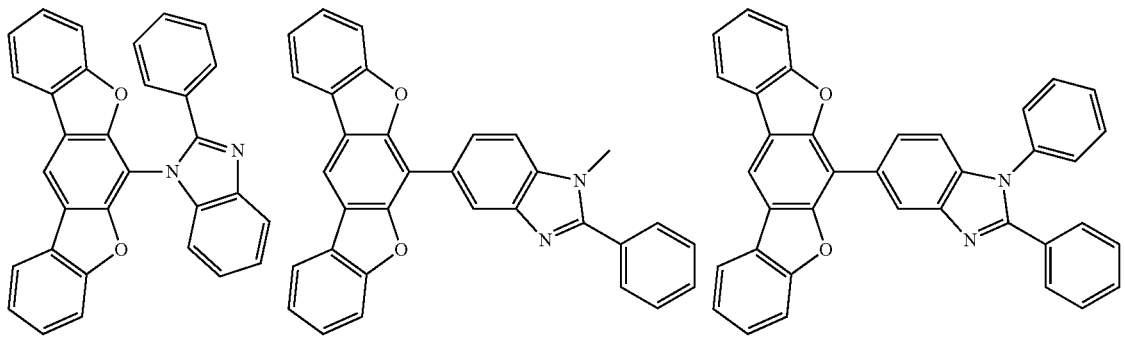
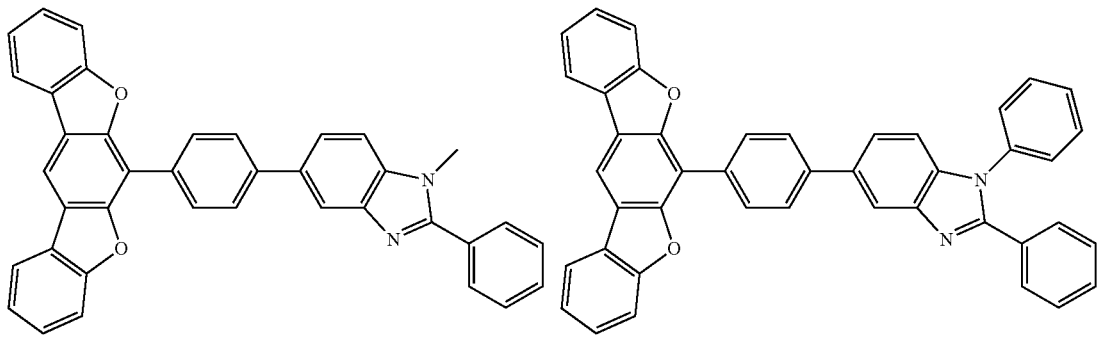
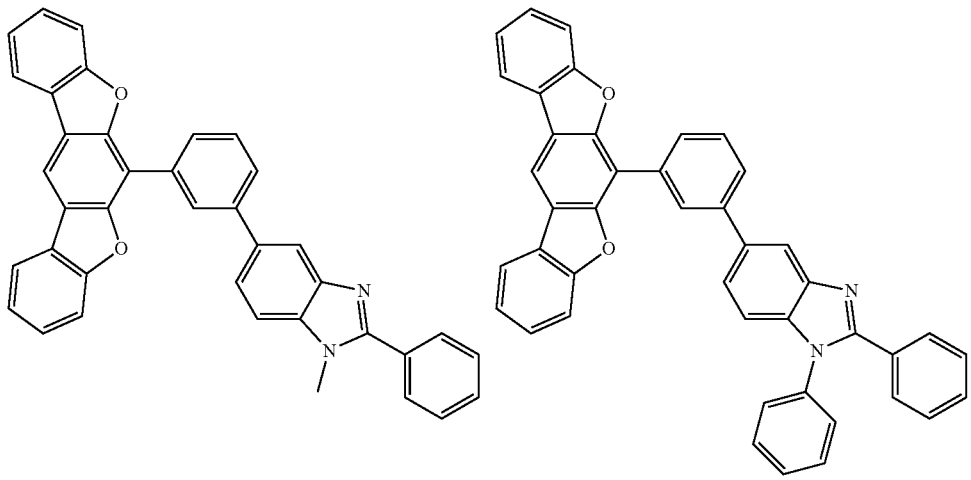

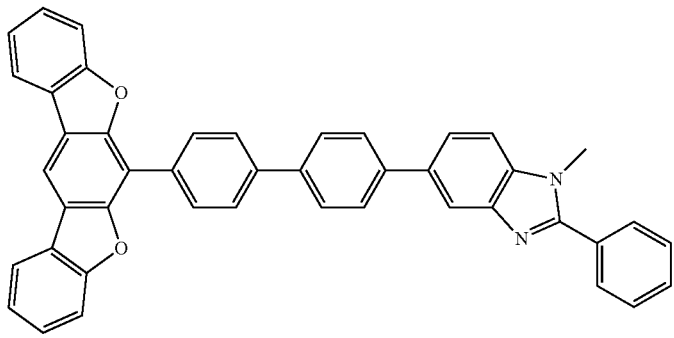
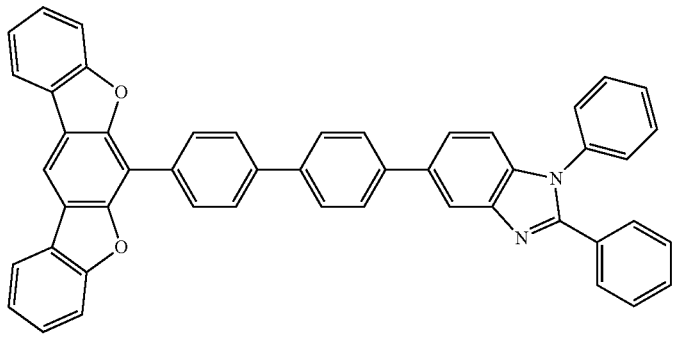
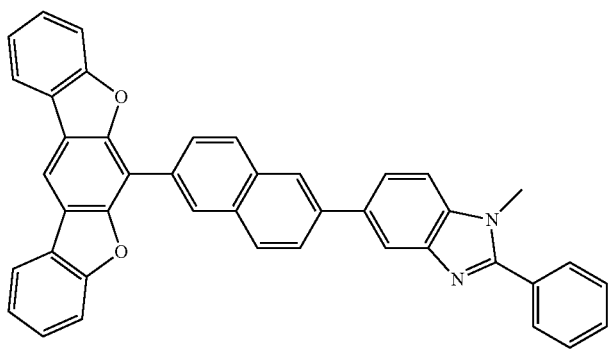
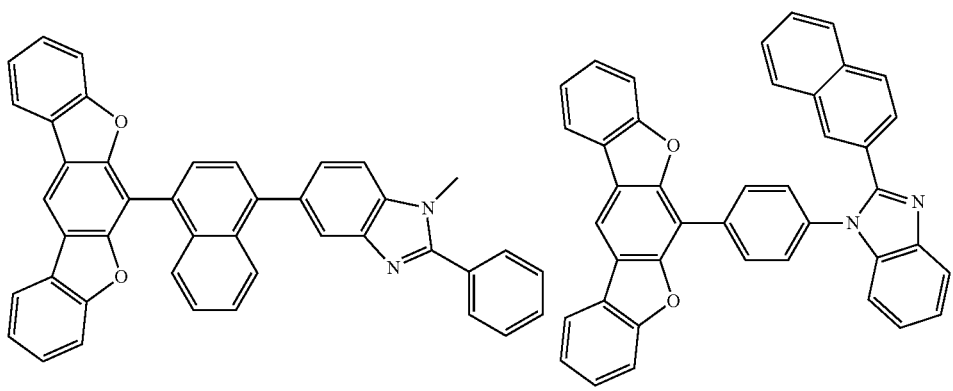

-continued
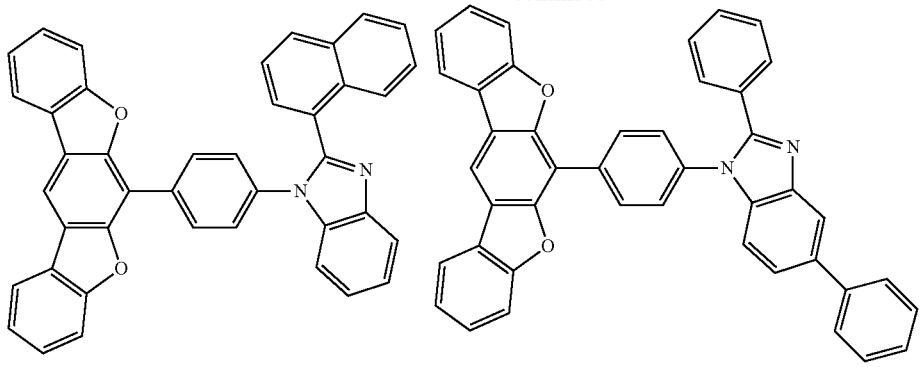
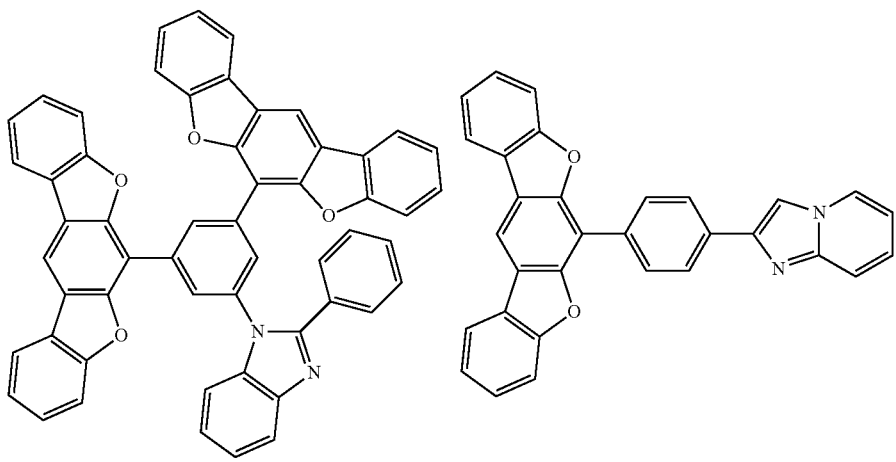
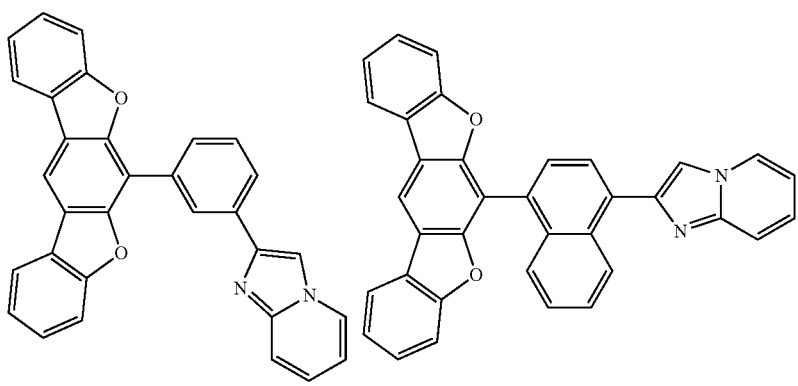
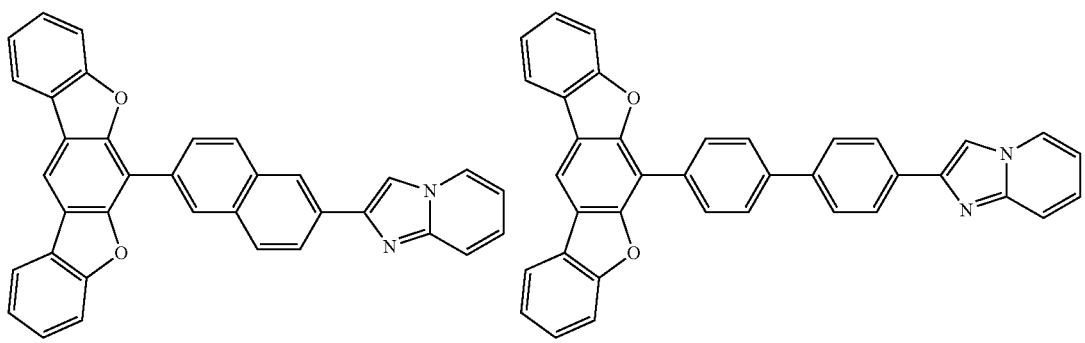

-continued
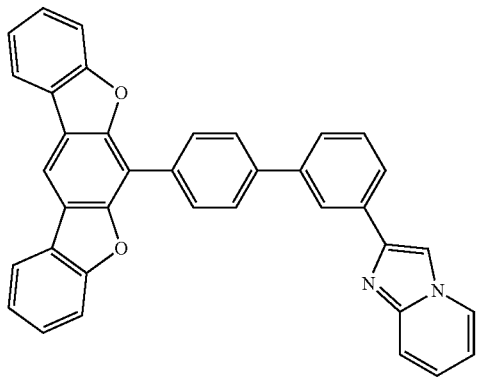
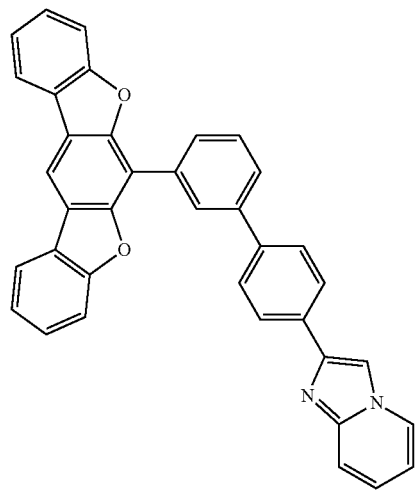
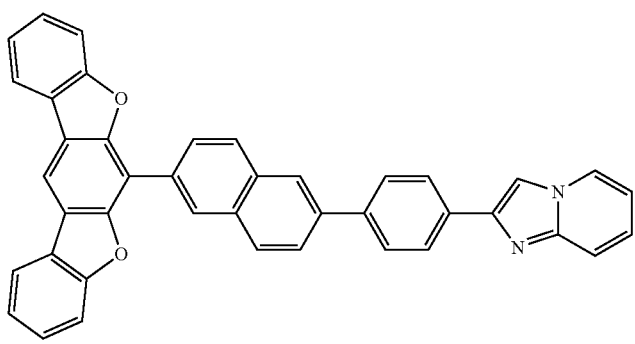
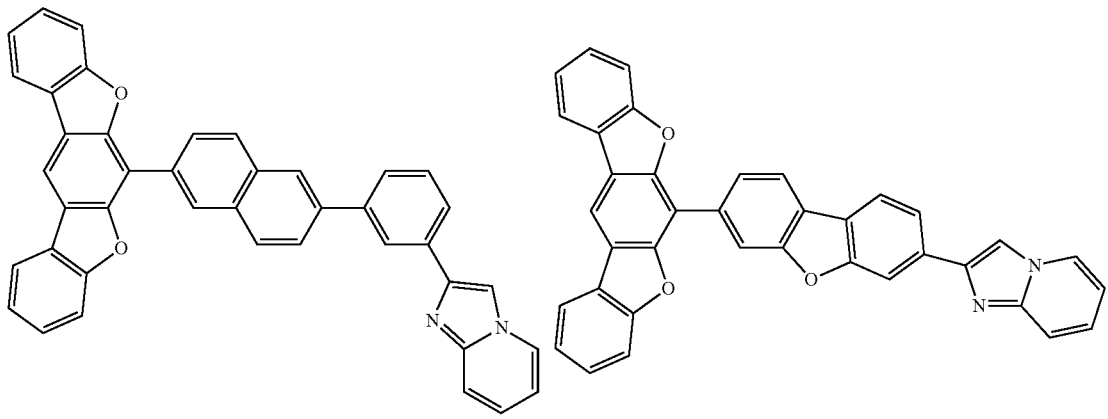
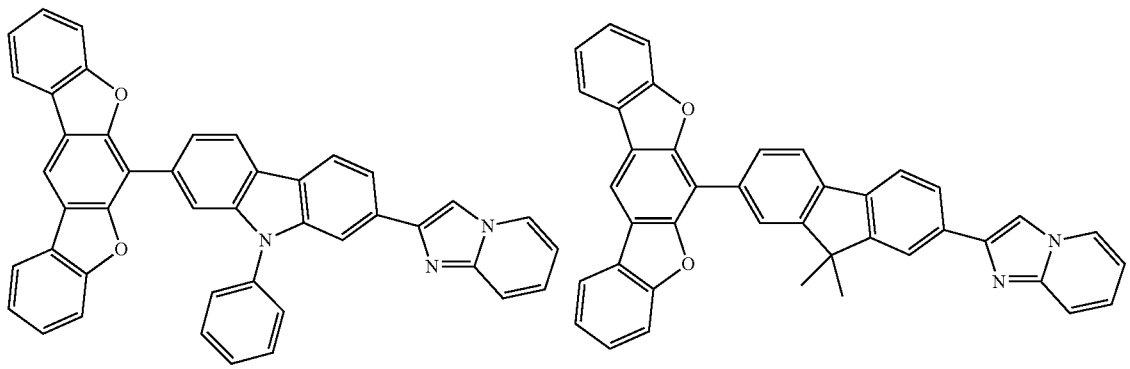

-continued
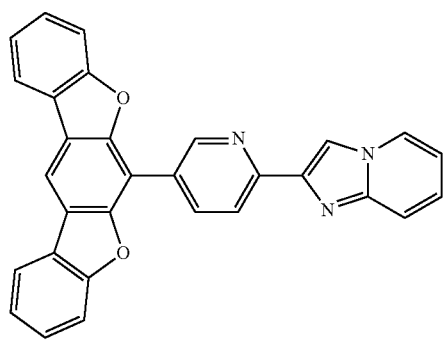 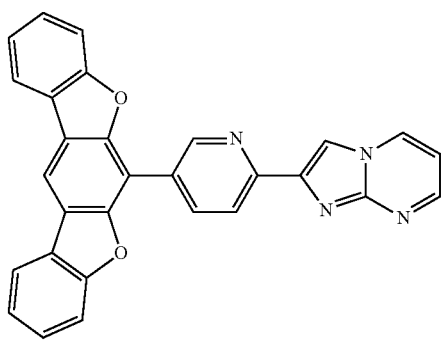
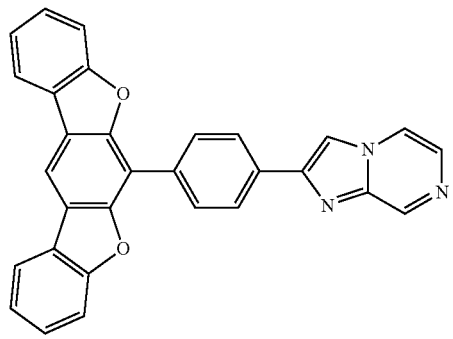 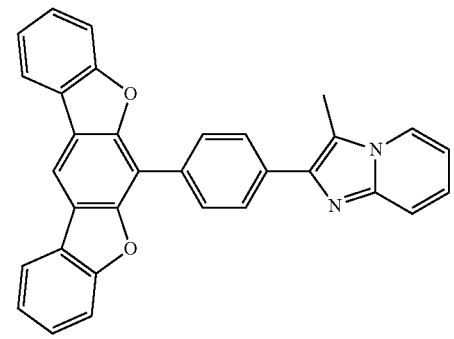
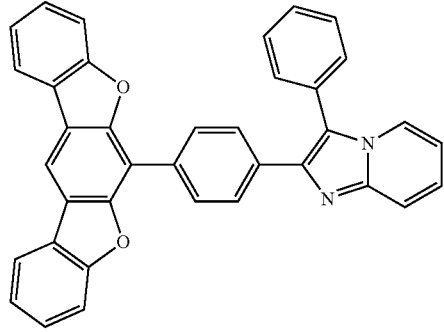 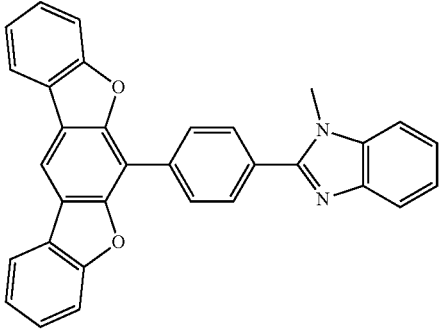
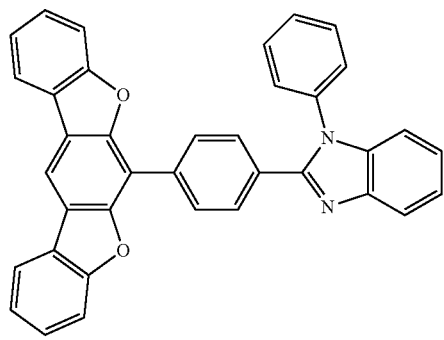 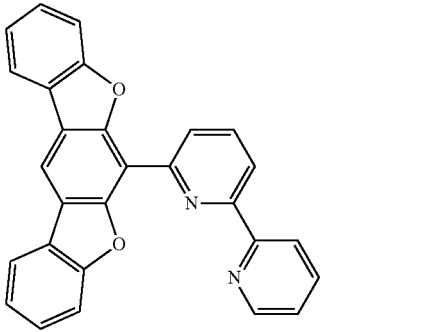
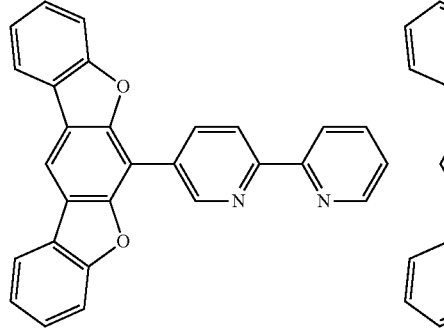 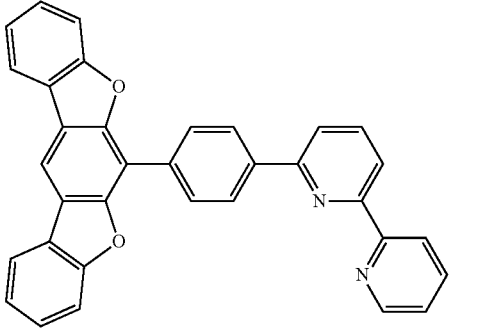

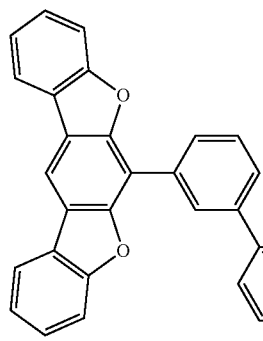
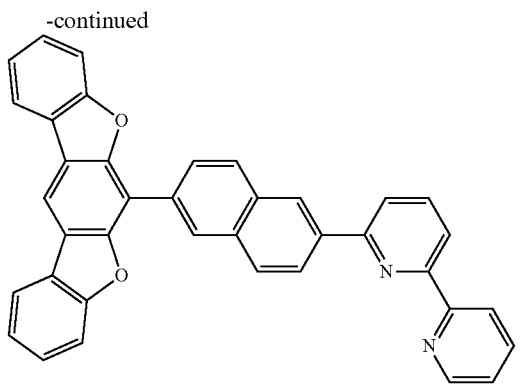
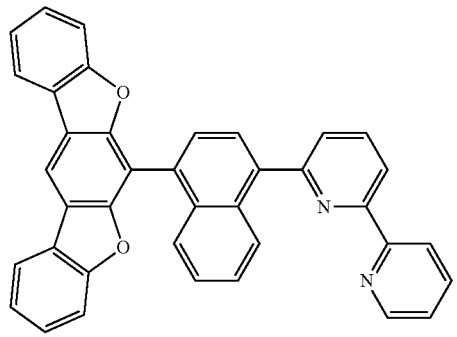
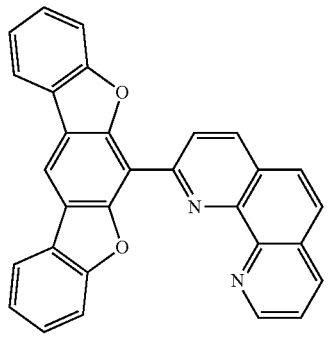
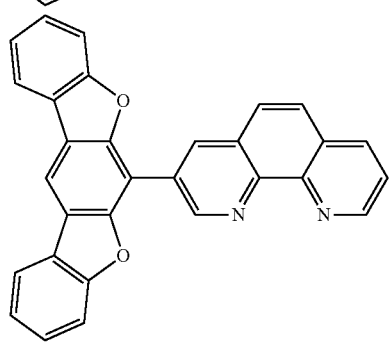
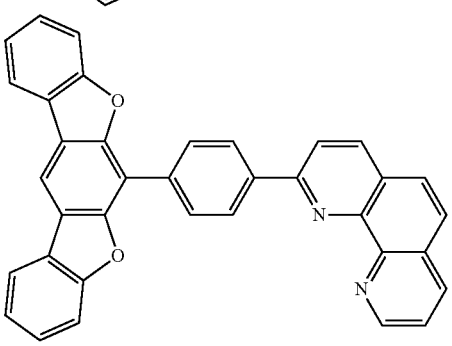
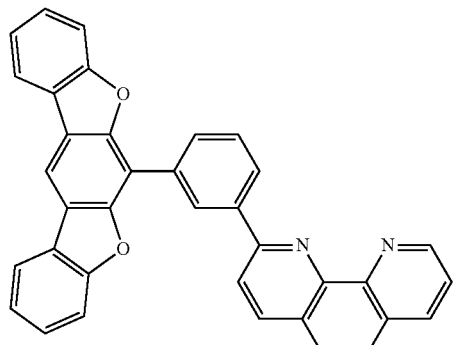
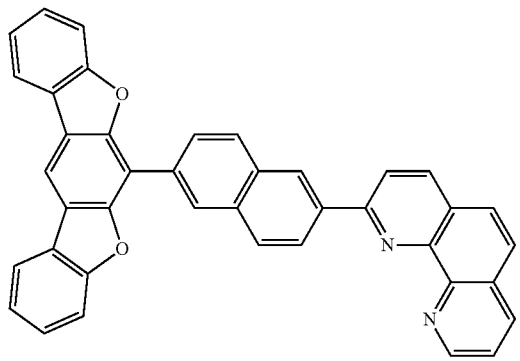
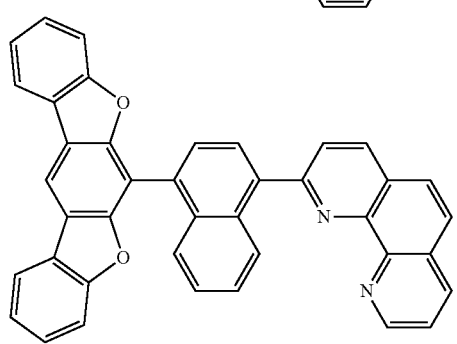
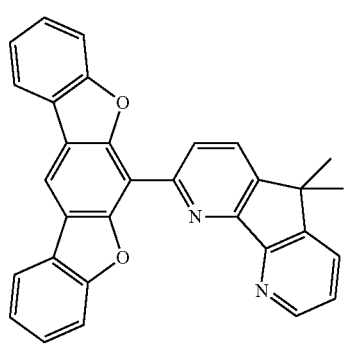

-continued
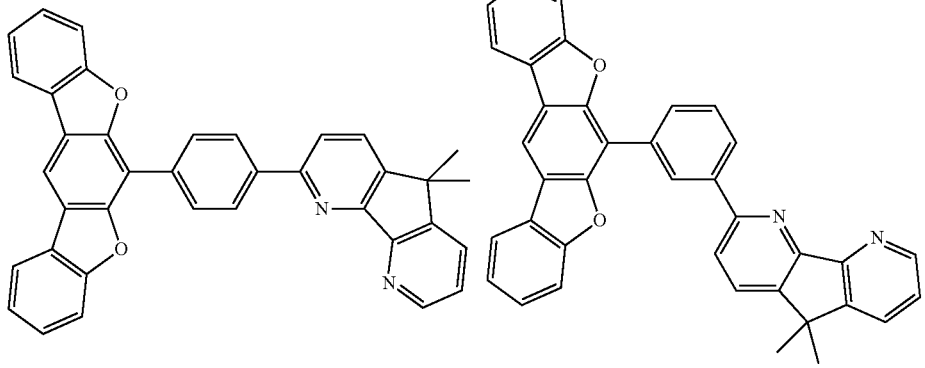
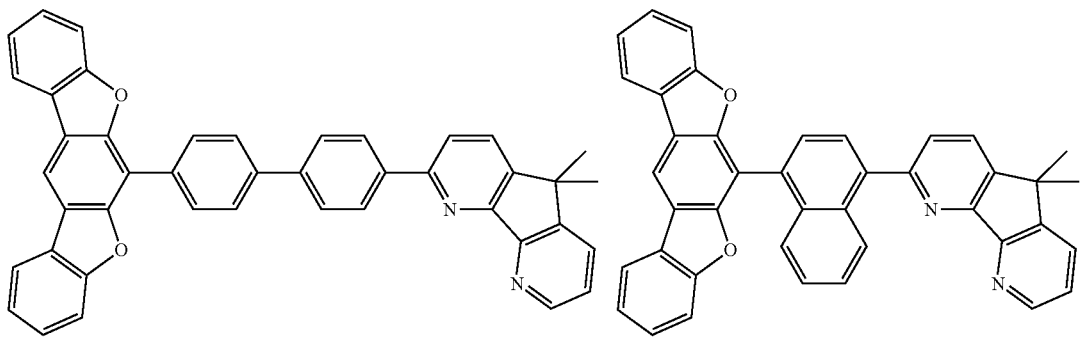
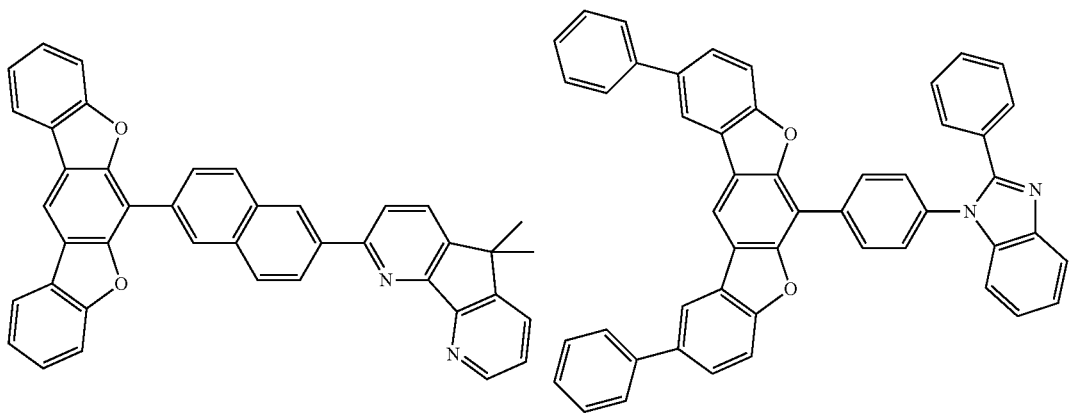
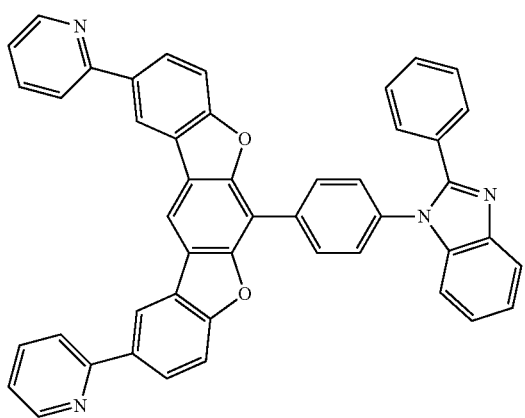

-continued
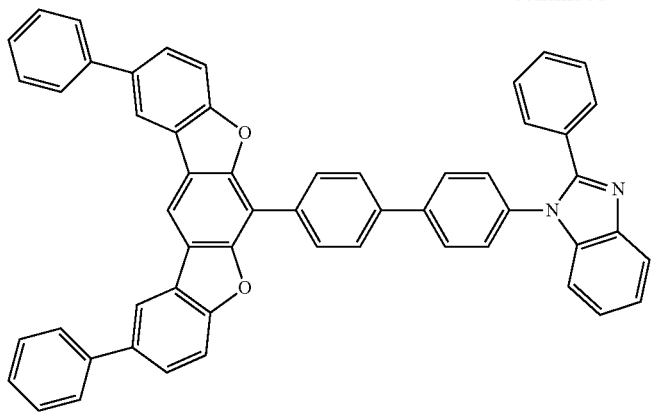
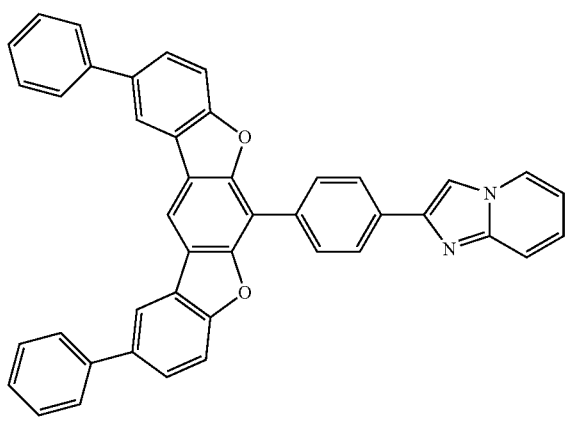
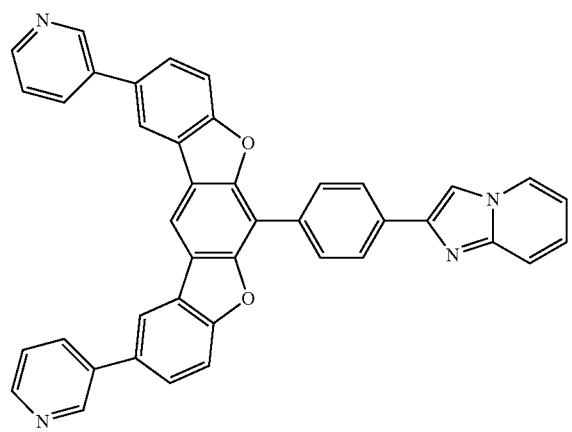
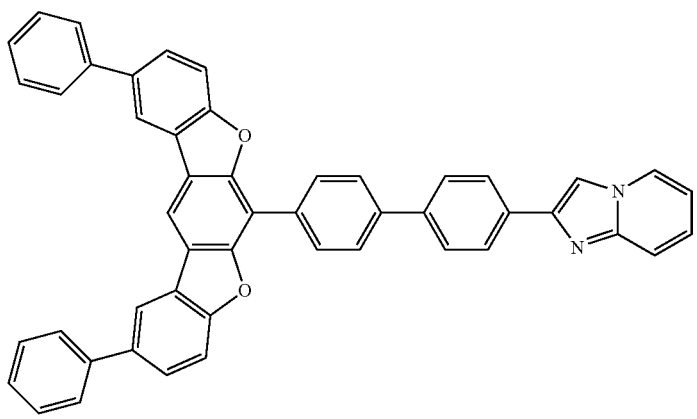
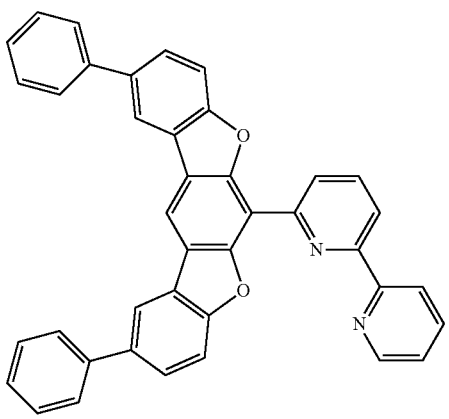
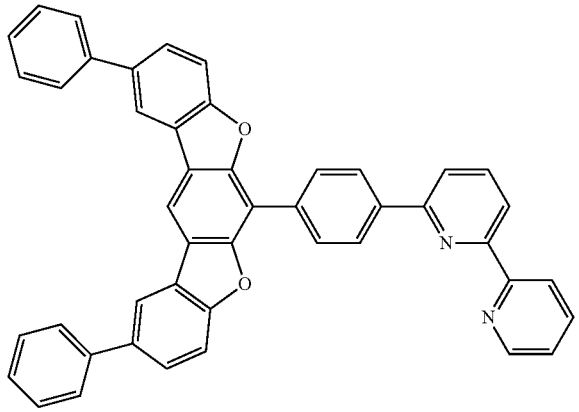
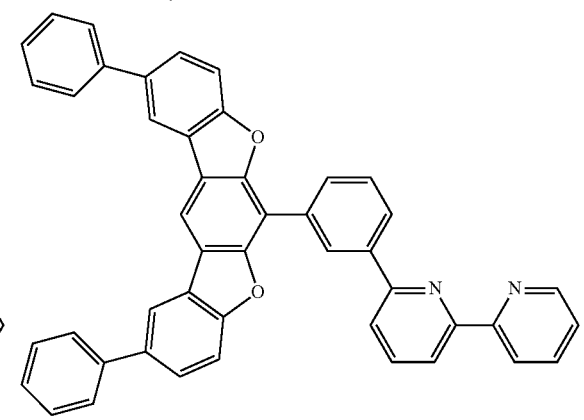

103
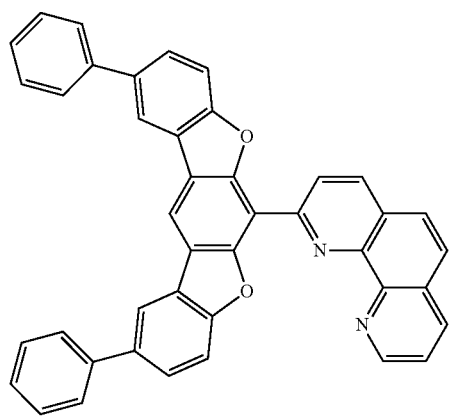
104
-continued
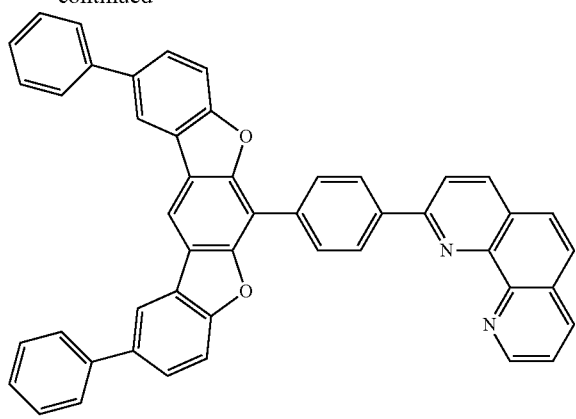
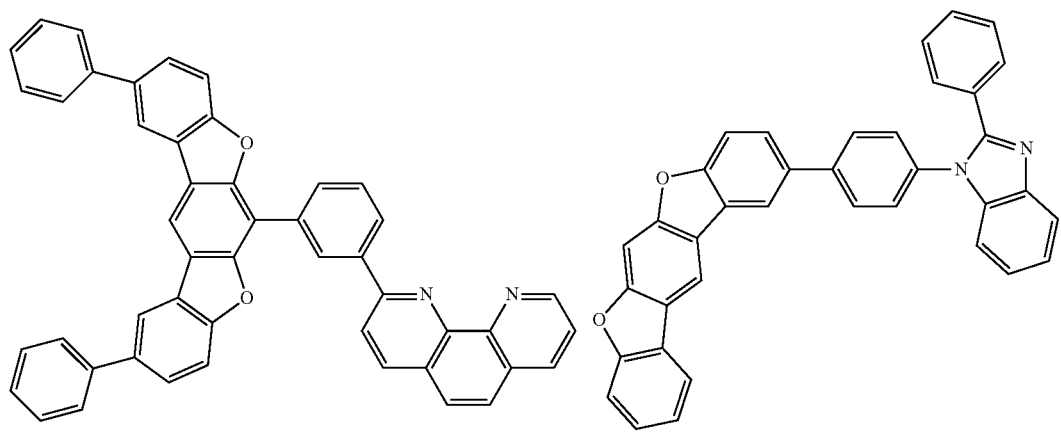
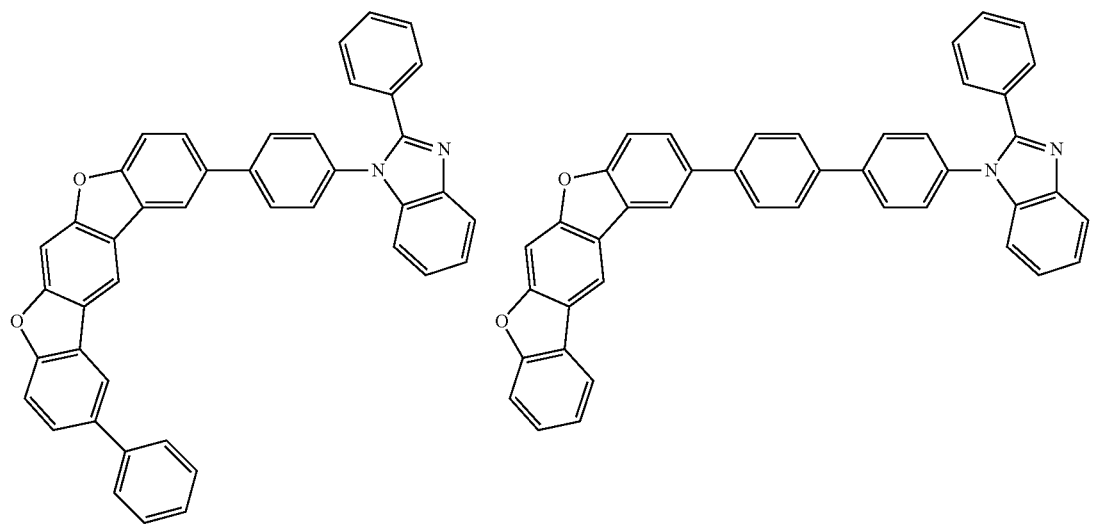

105 106
-continued
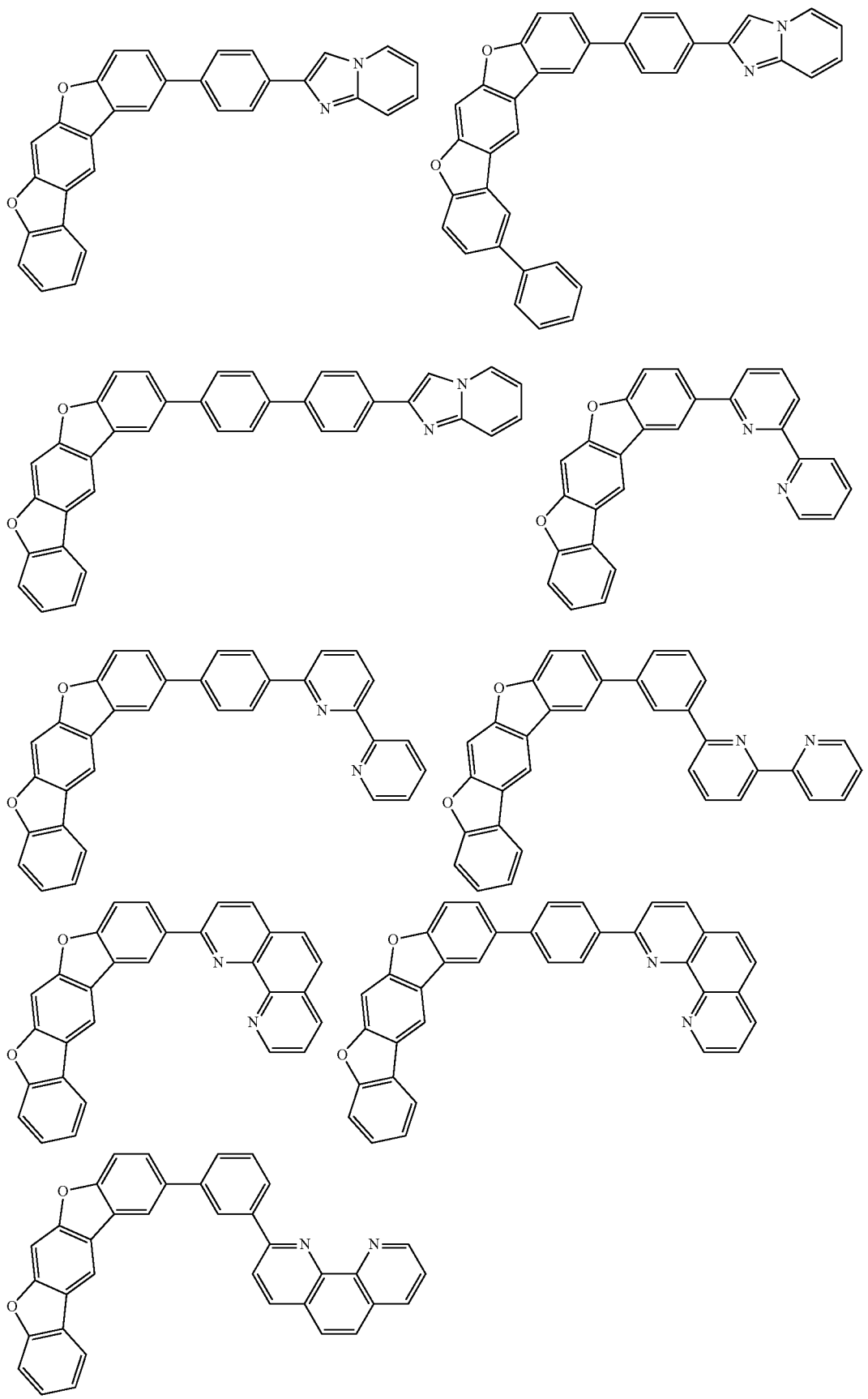

-continued
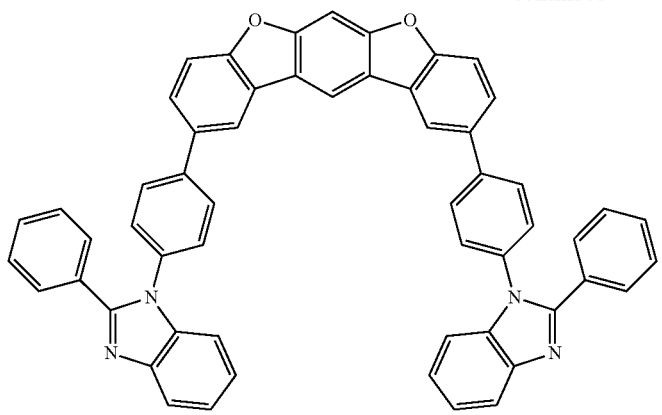
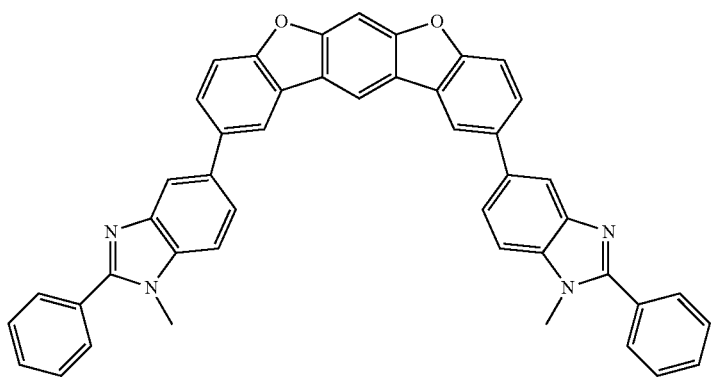
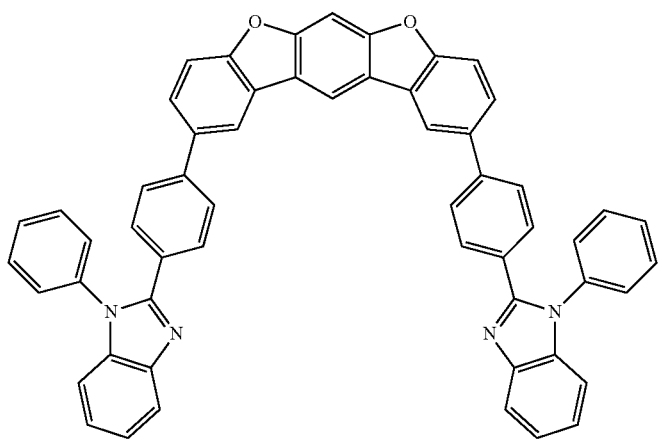
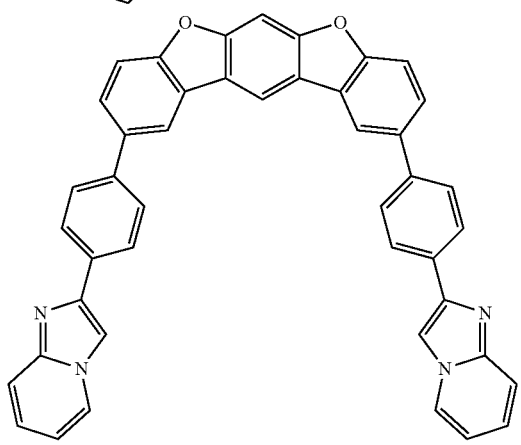

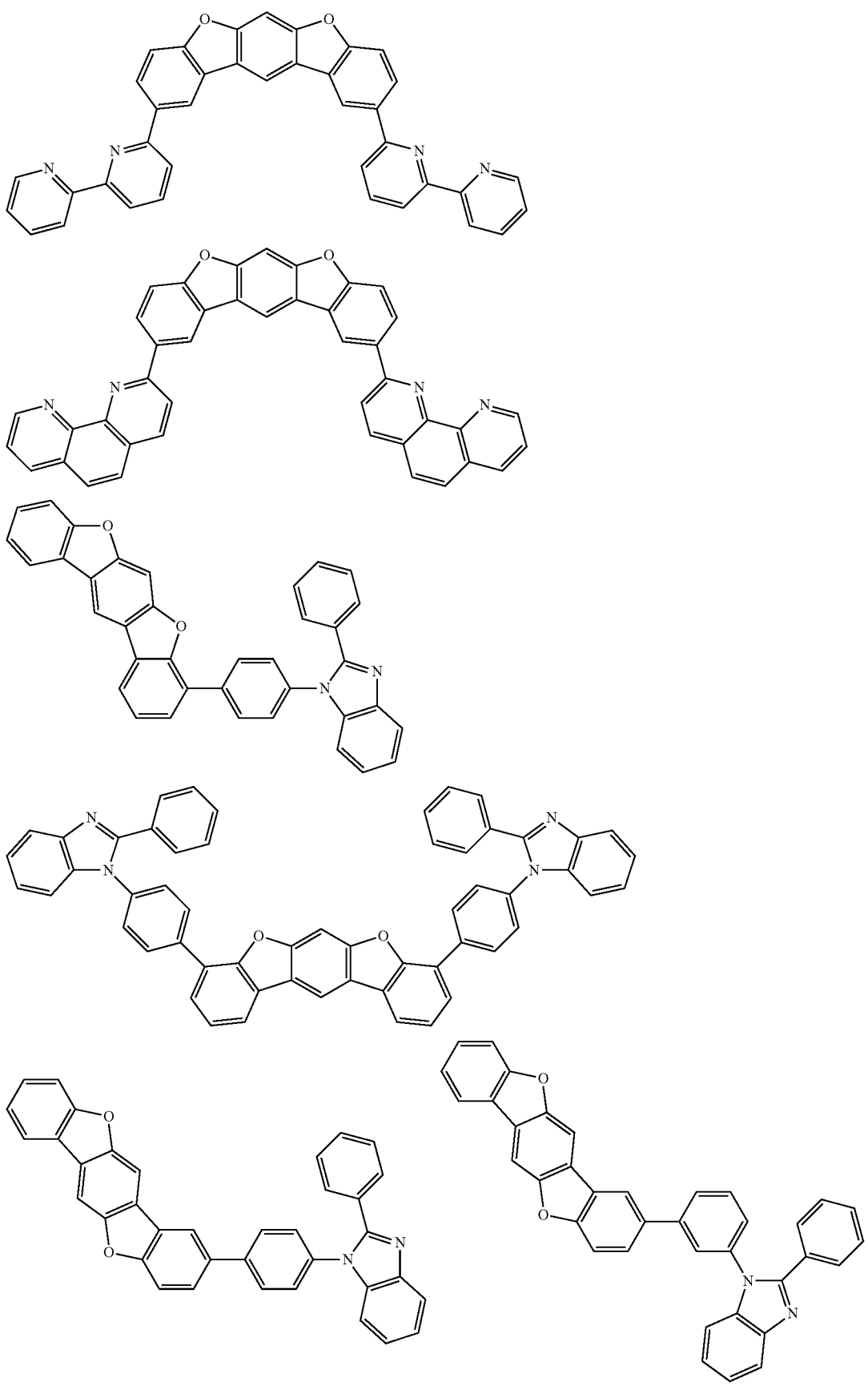

111
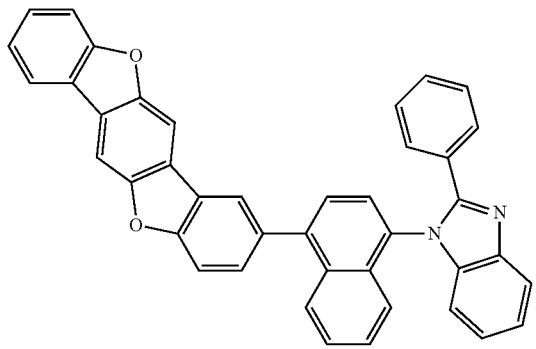
112
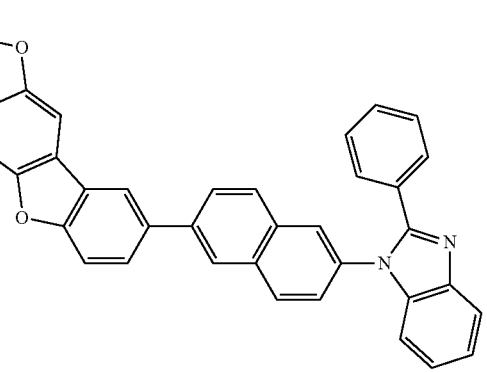
-continued
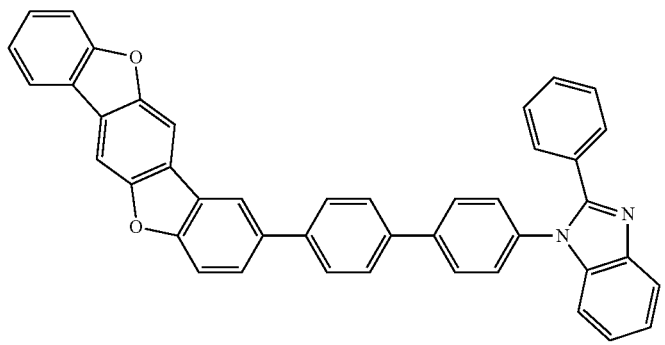
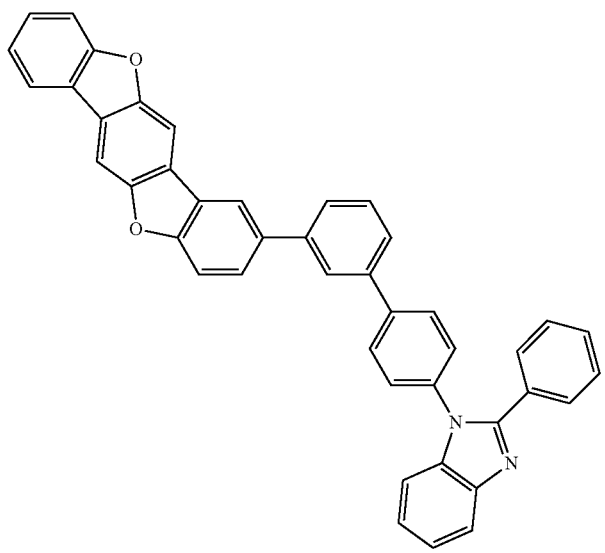
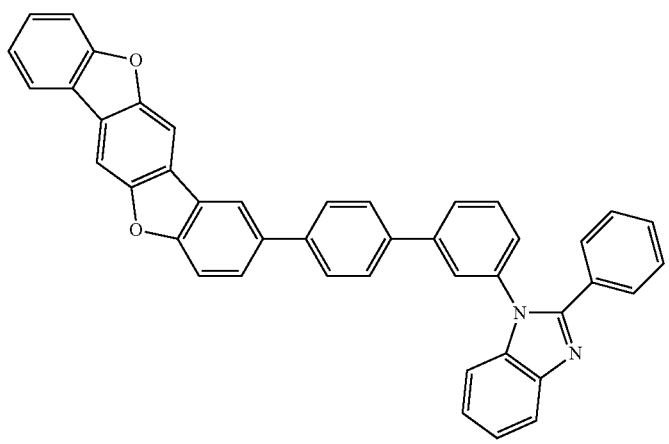

-continued
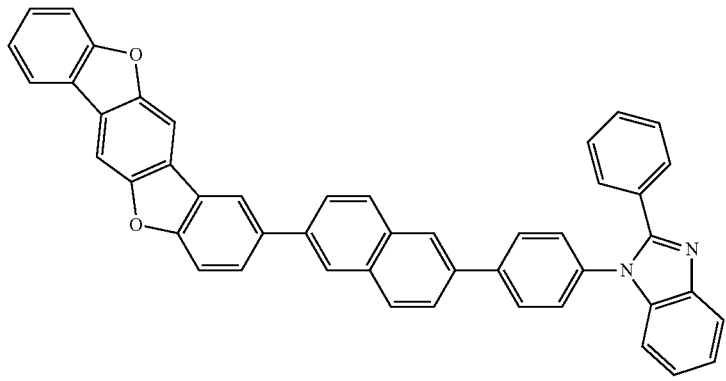
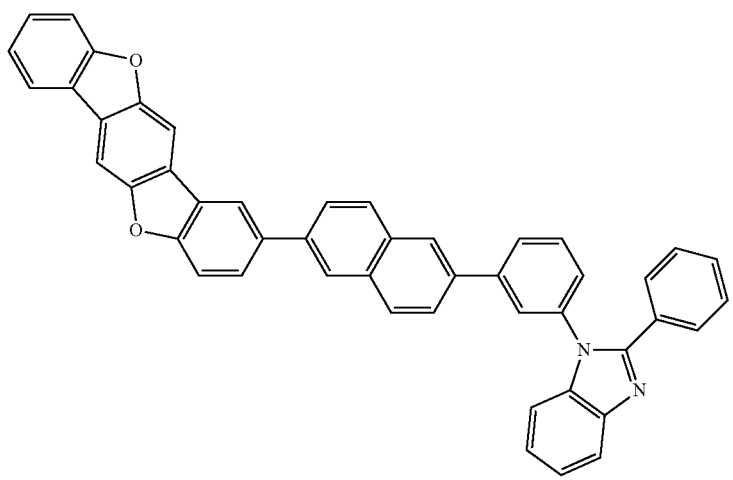
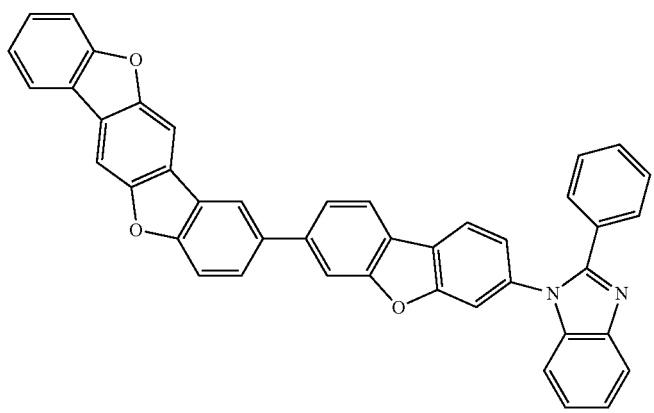
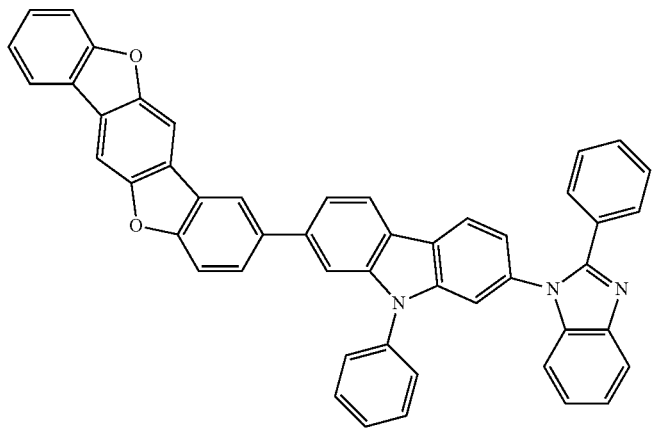

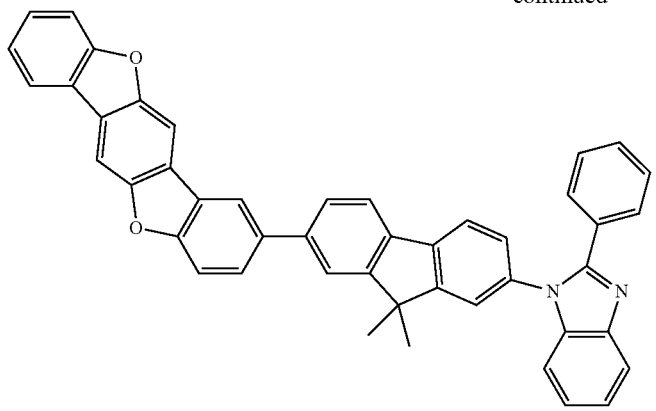
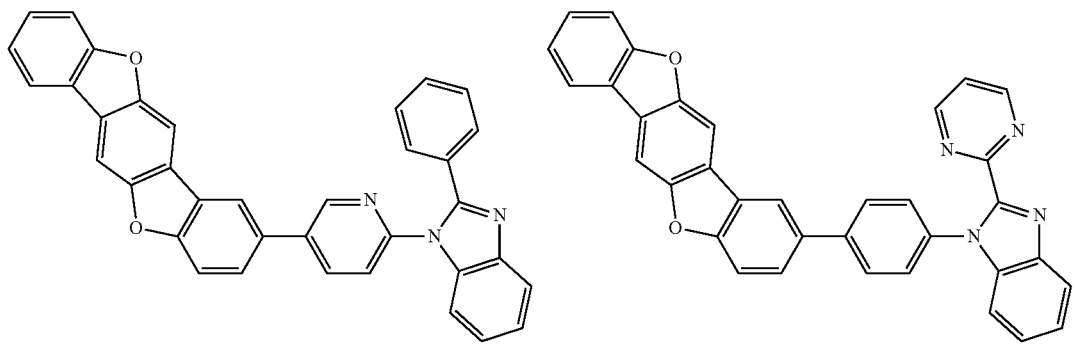
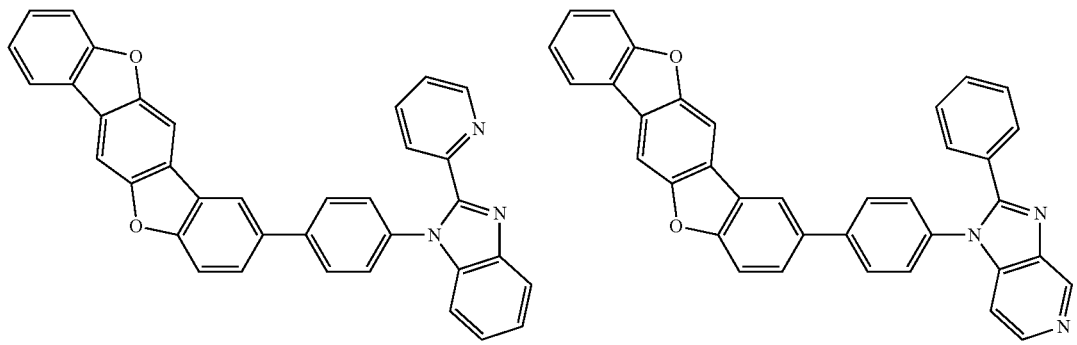
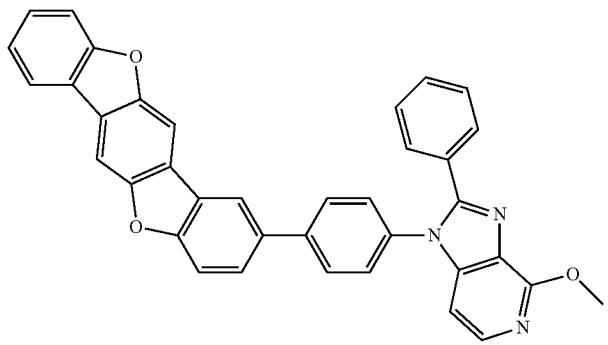

117 118
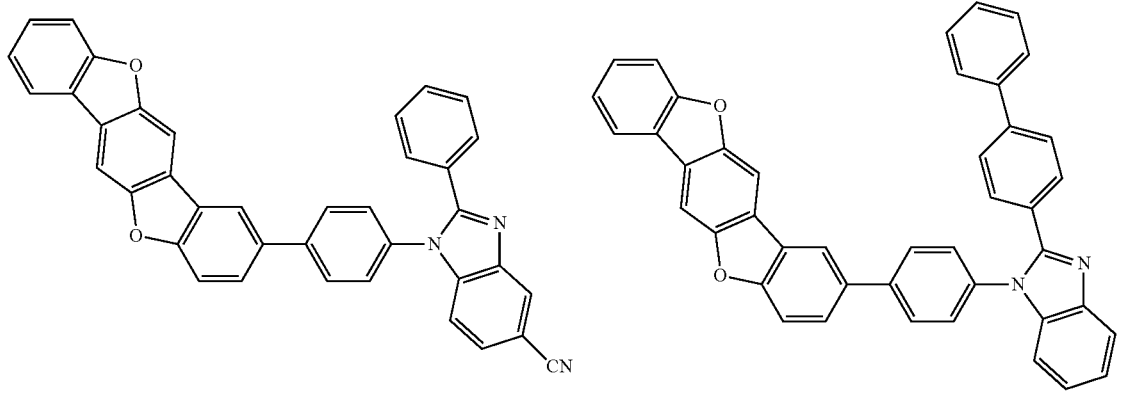
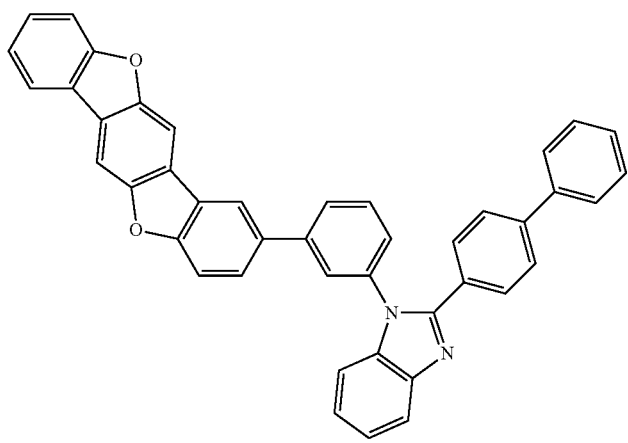
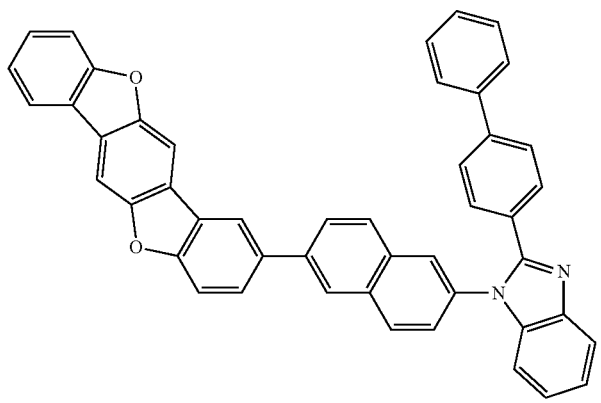
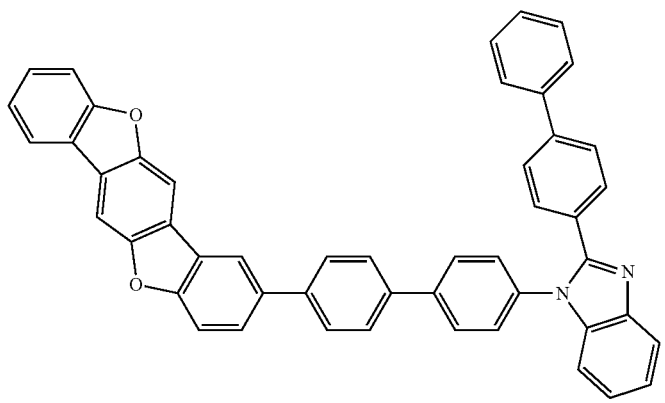

-continued
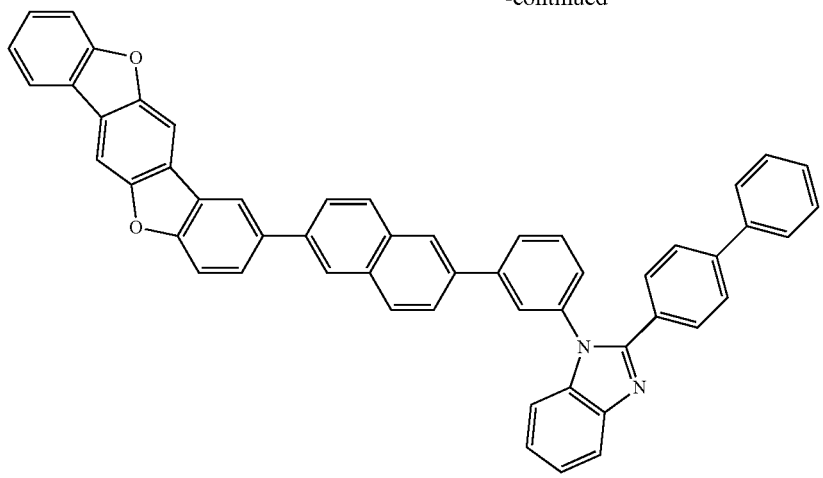
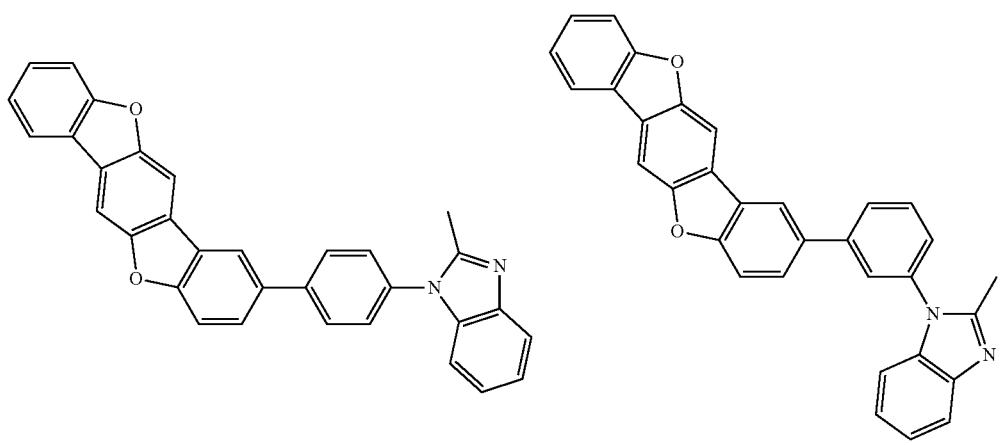
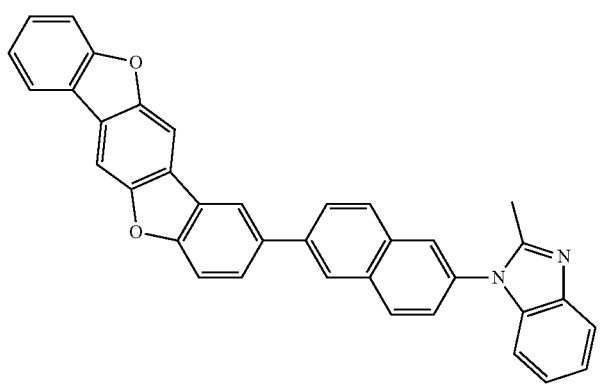
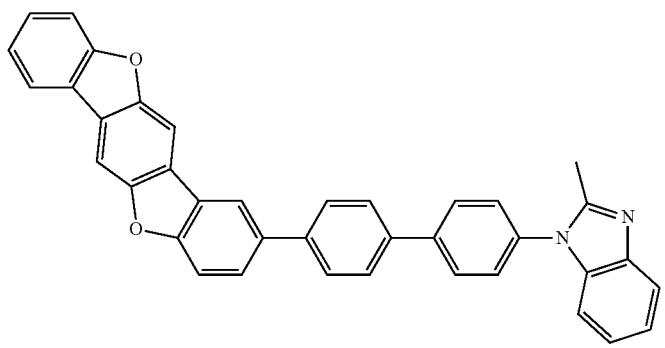

-continued
121
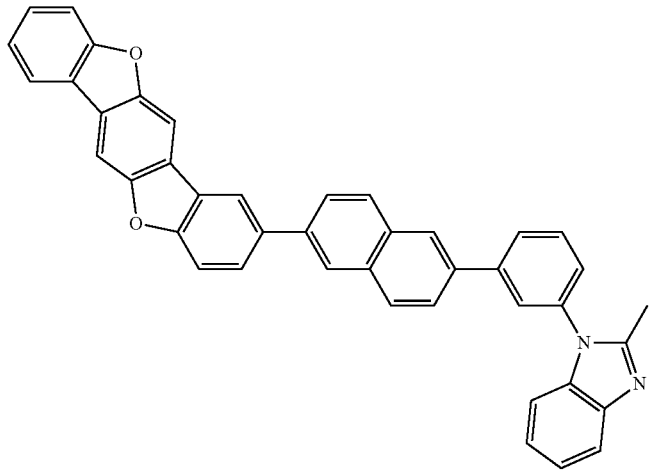
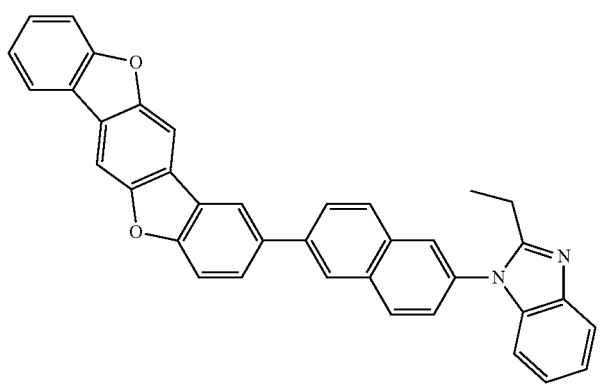
122
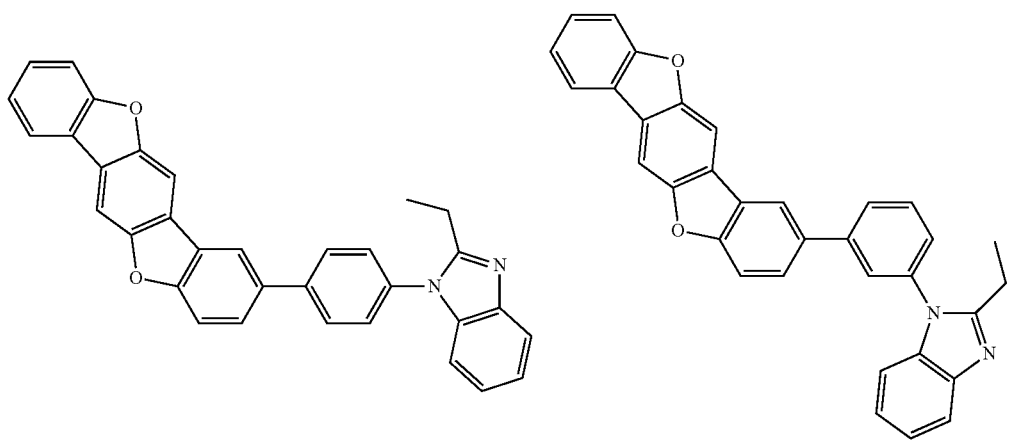
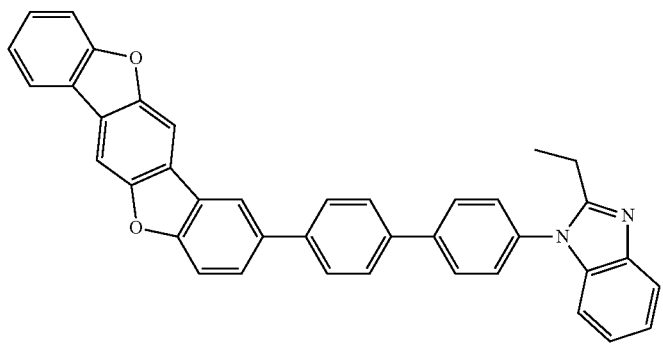

-continued
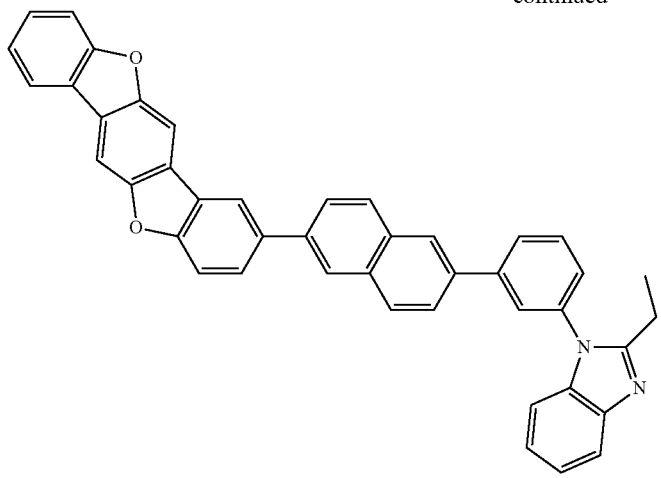
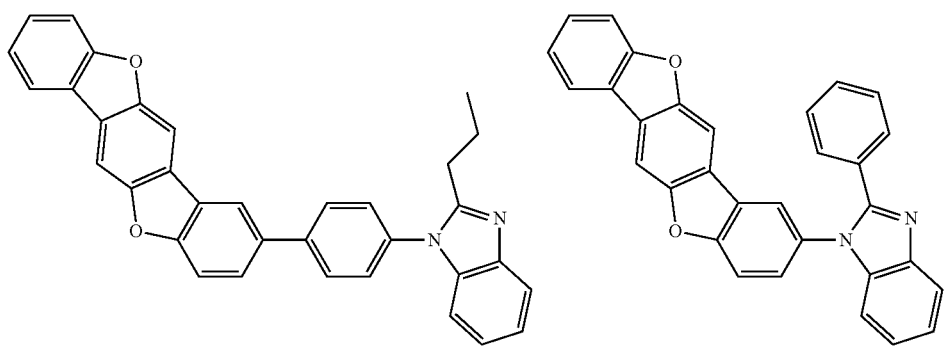
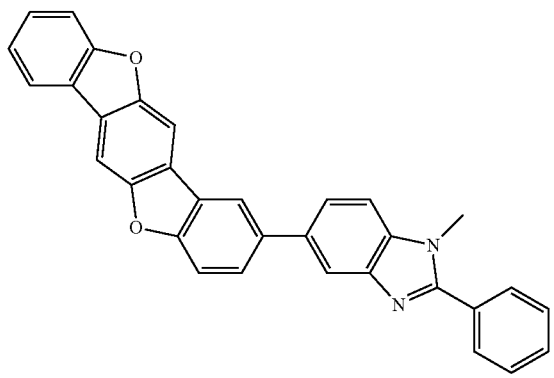
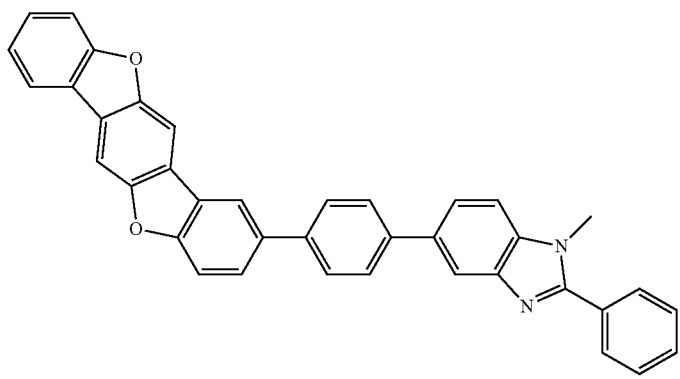

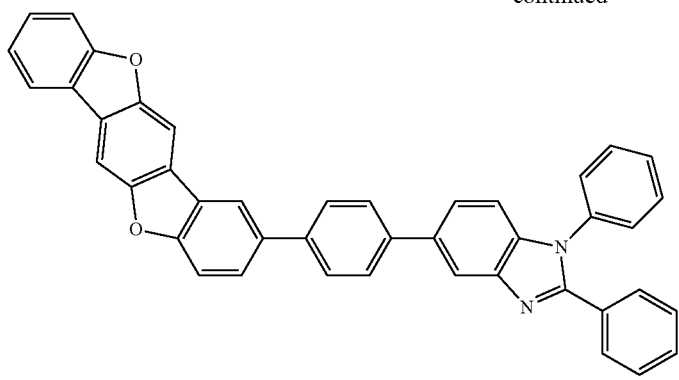
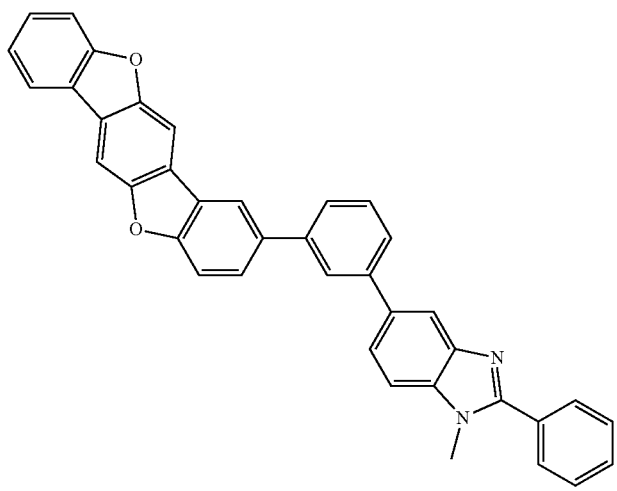
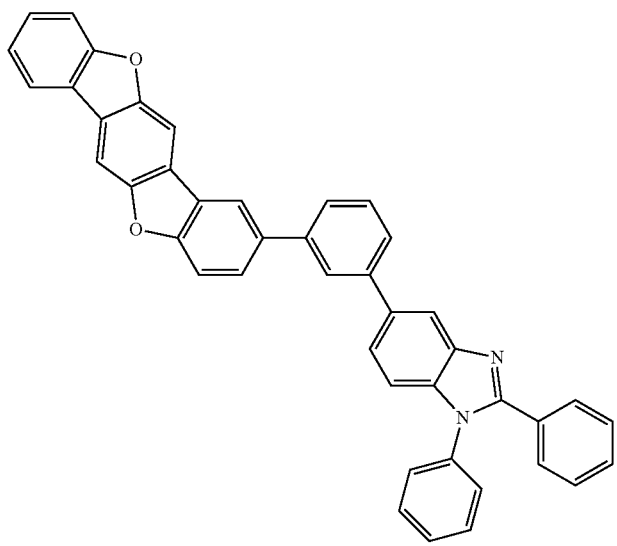

-continued
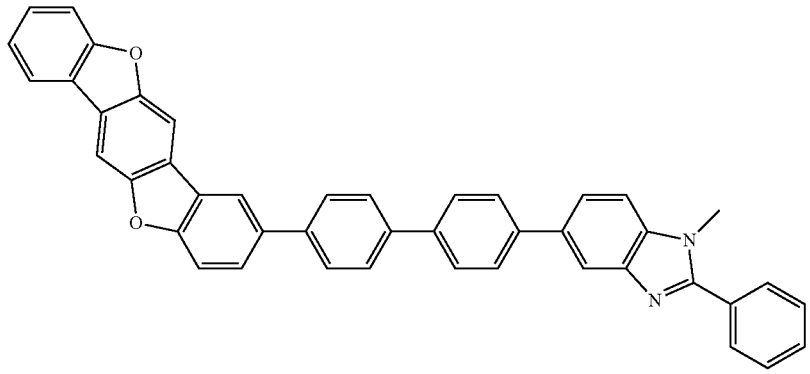
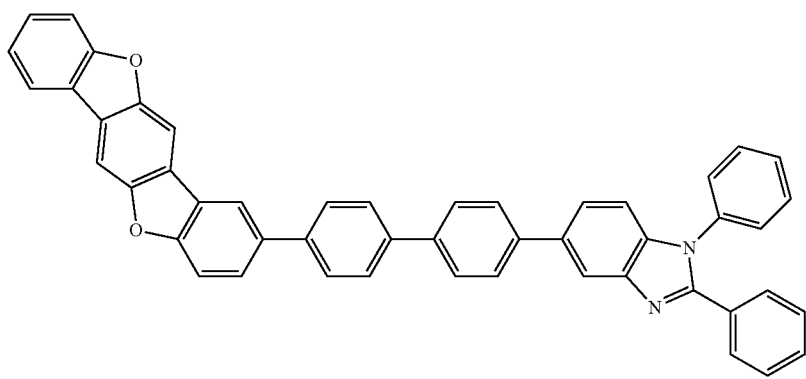
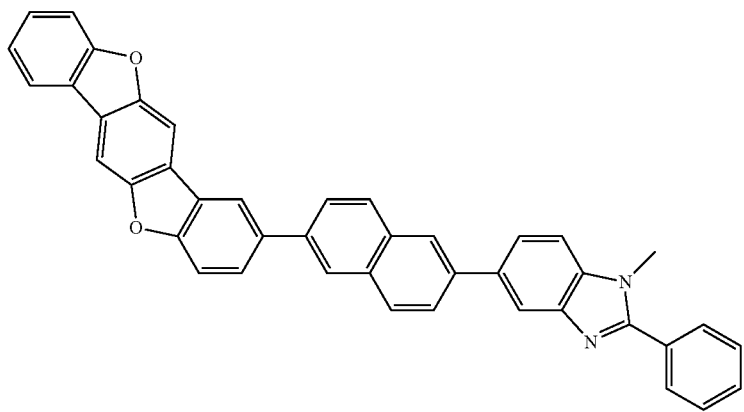
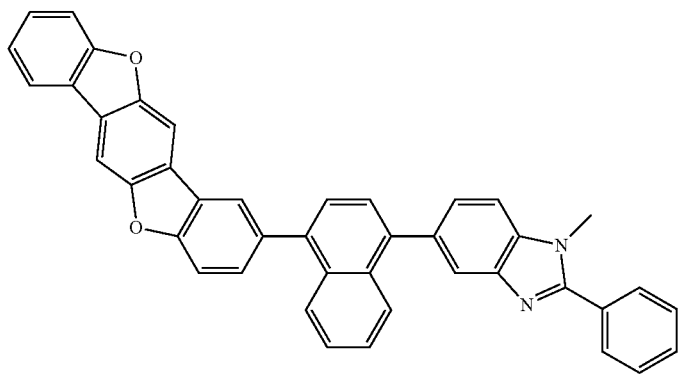

-continued
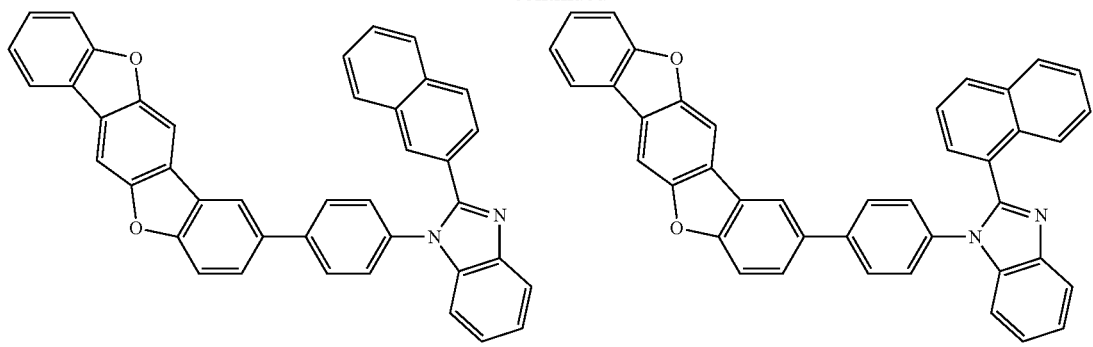
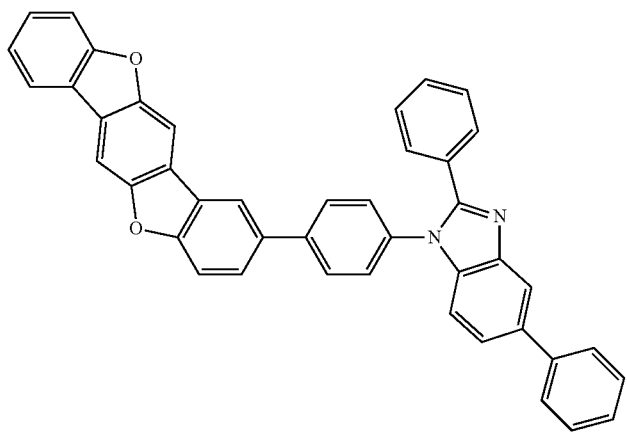
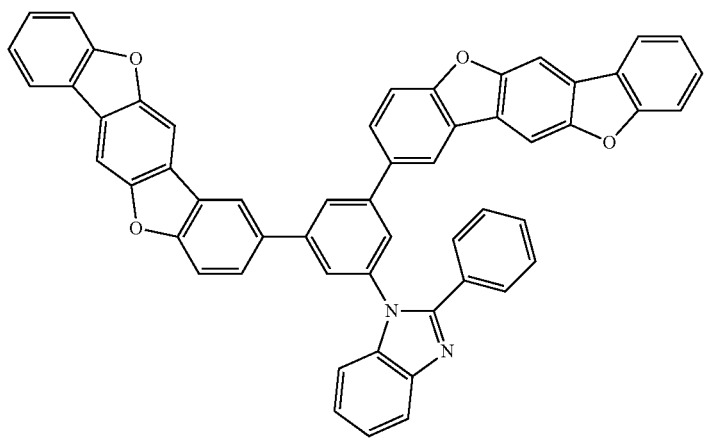 [SMILES: c1ccc(-c2nc3ccccc3n2-c2cc(-c3ccc4oc5cc6c(cc5c4c3)oc3ccccc36)cc(-c3ccc4oc5cc6c(cc5c4c3)oc3ccccc36)c2)cc1]
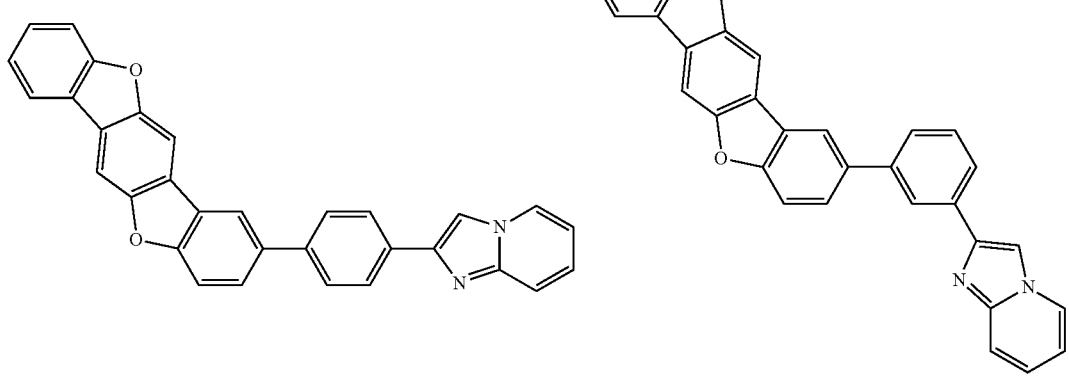

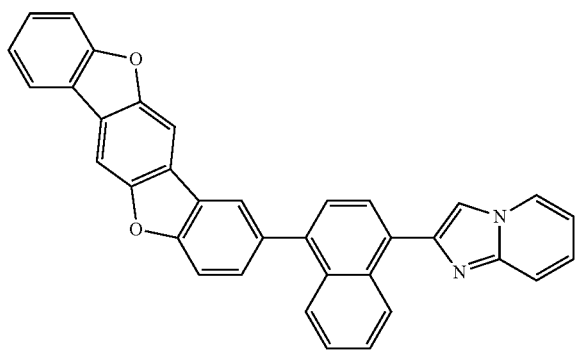
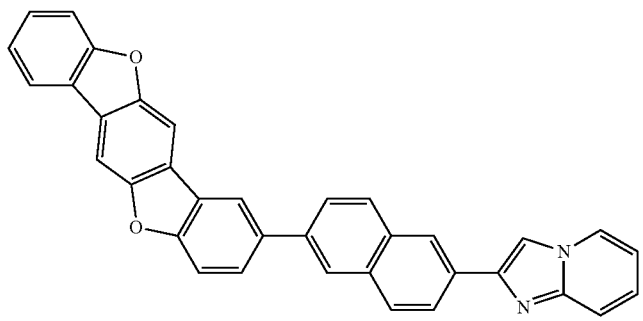
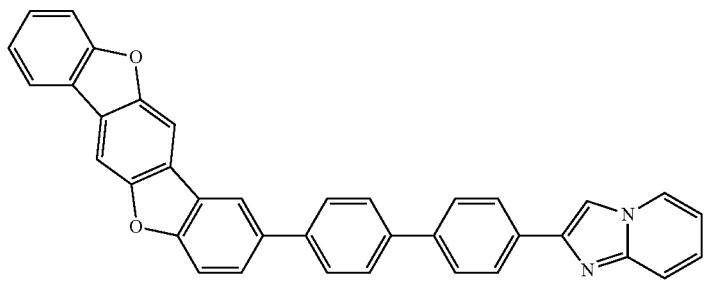
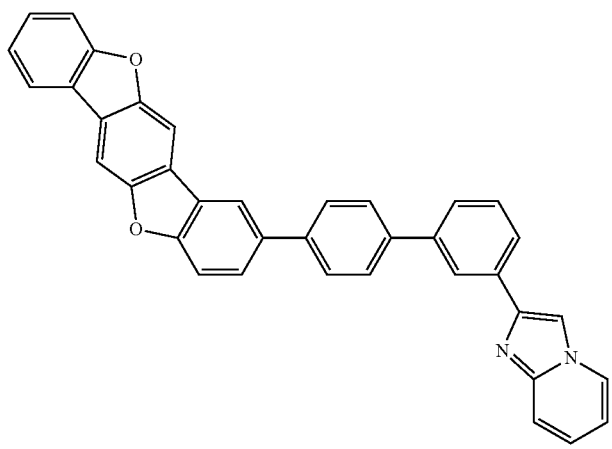

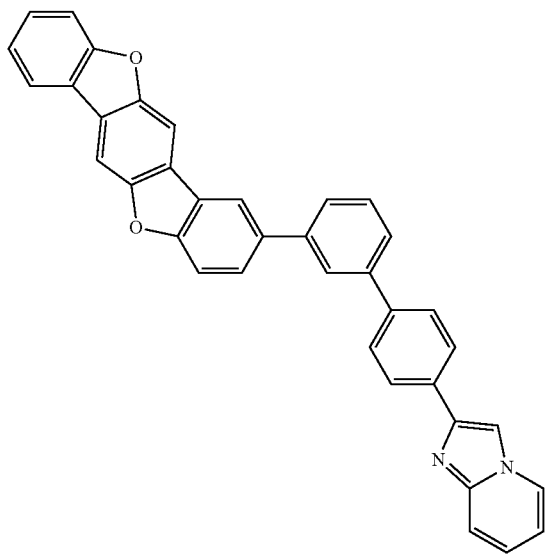
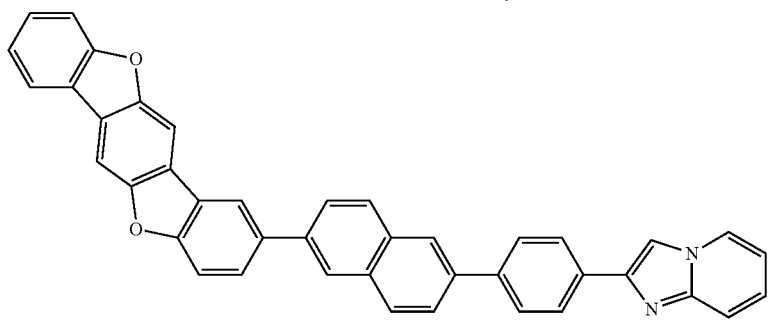
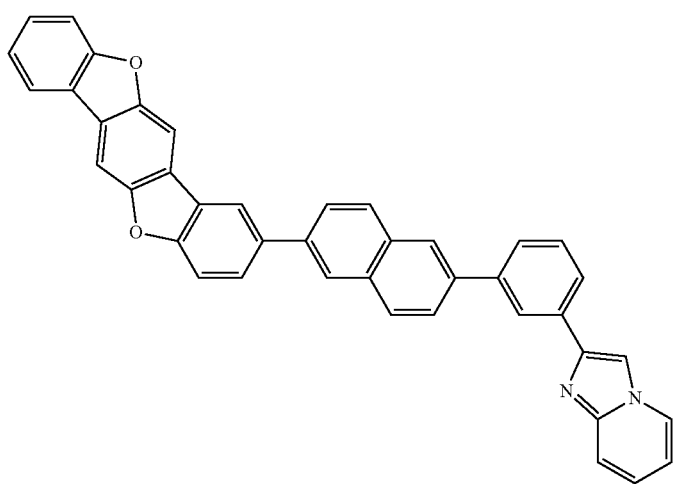
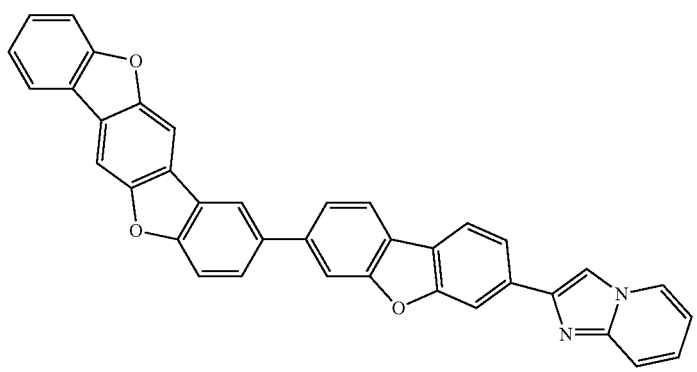

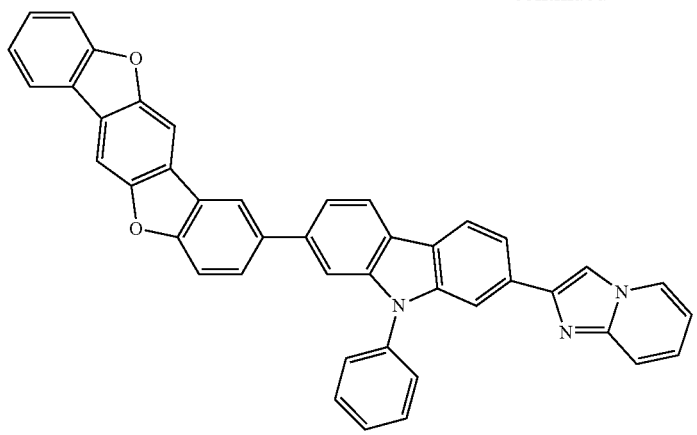
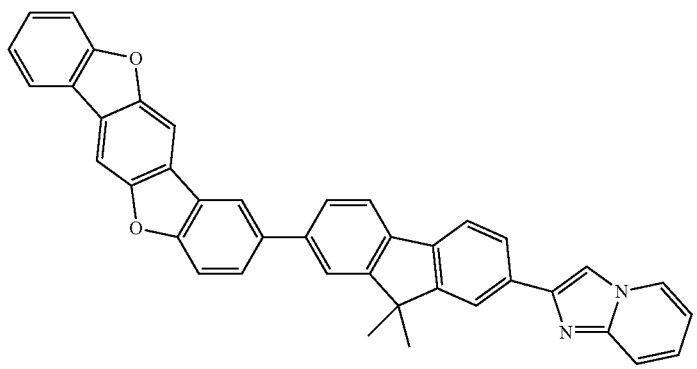
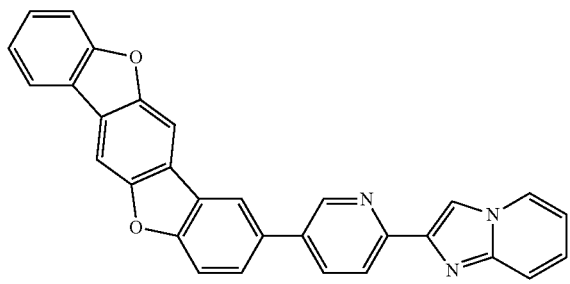
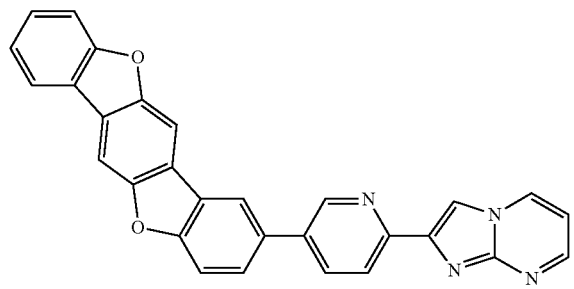
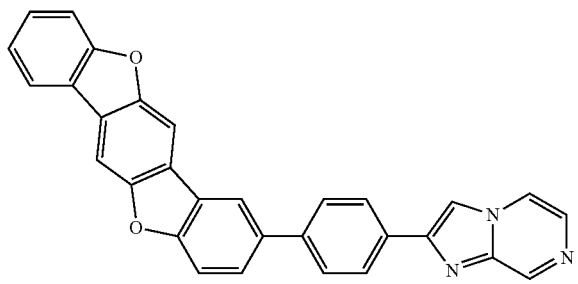
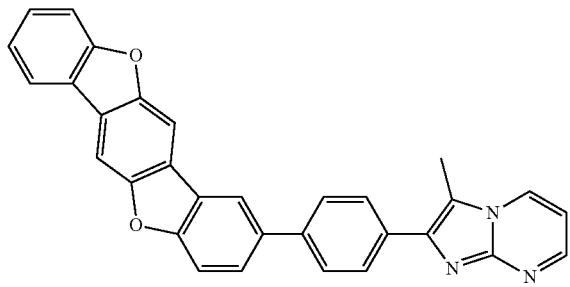
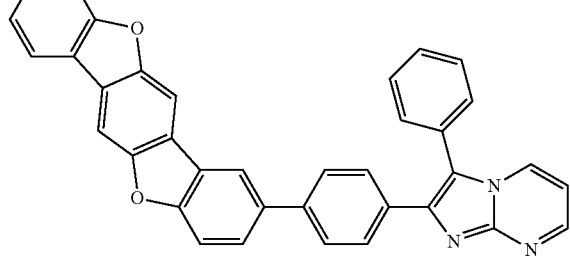

-continued
| 137 | 138 |
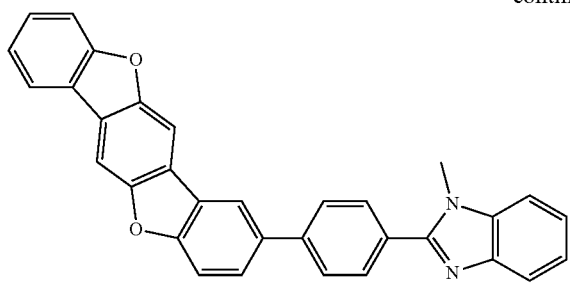
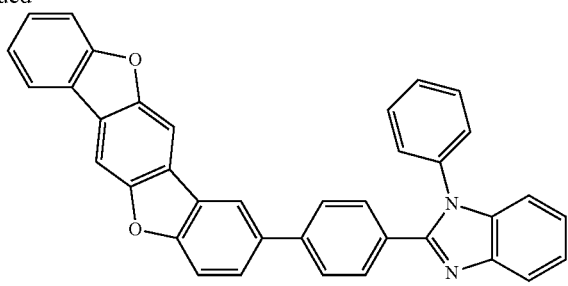
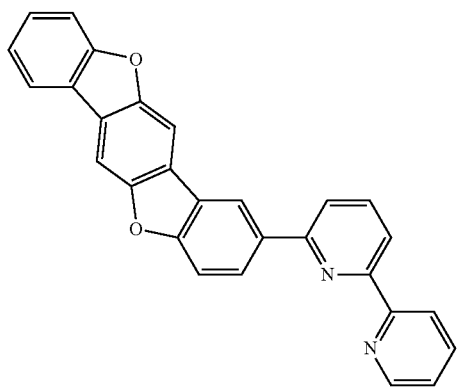
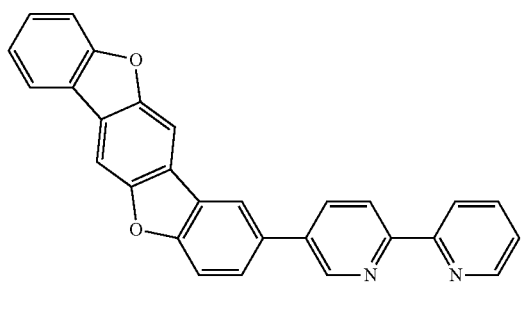
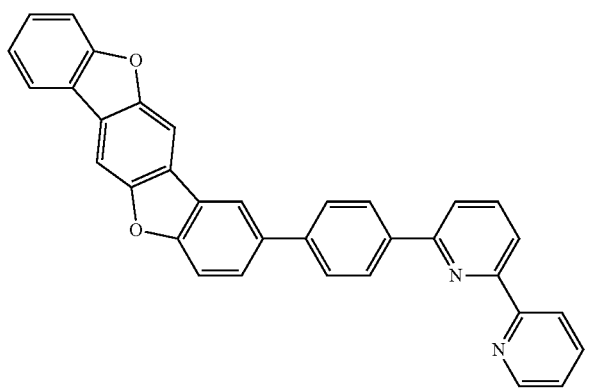
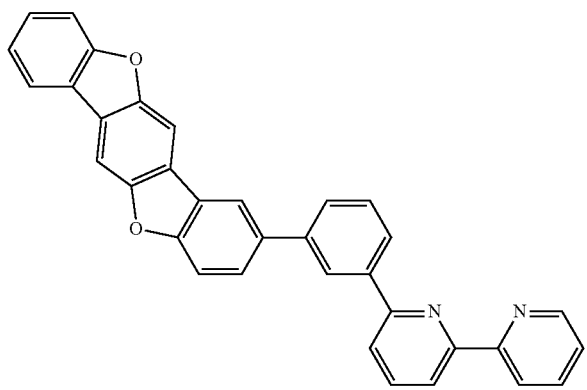

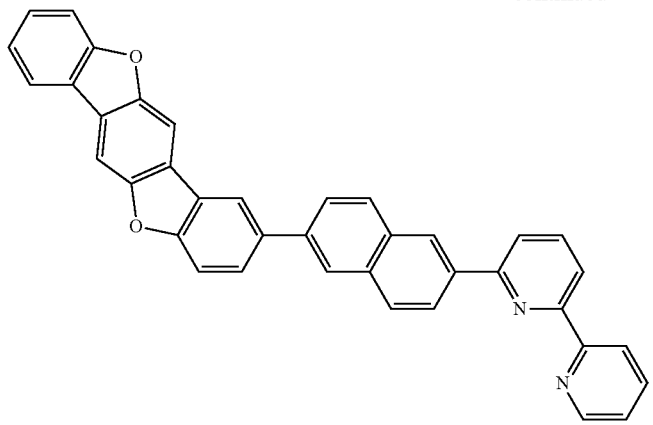
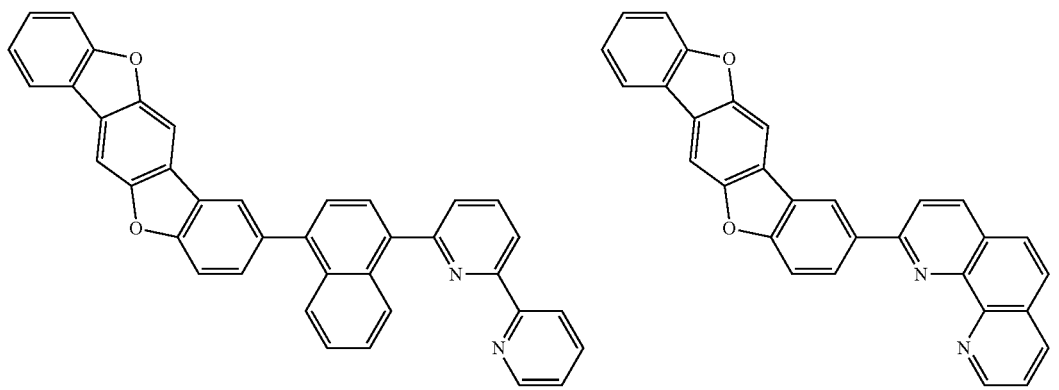
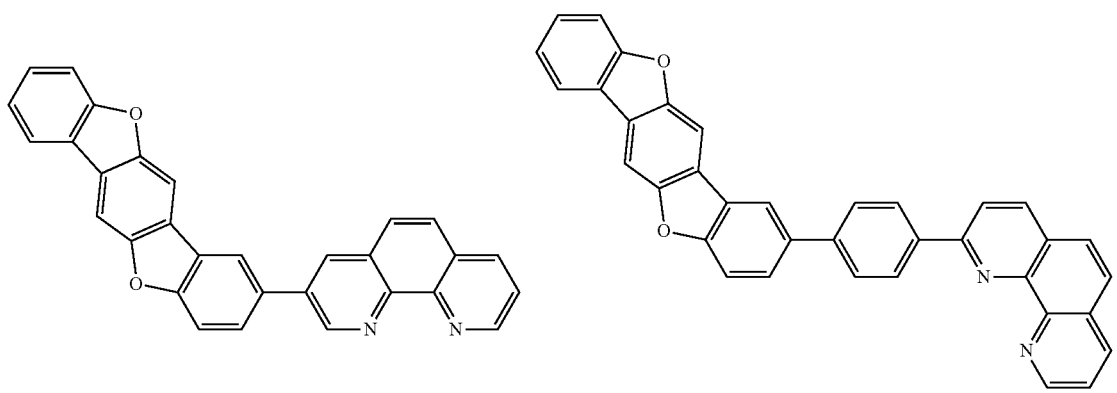
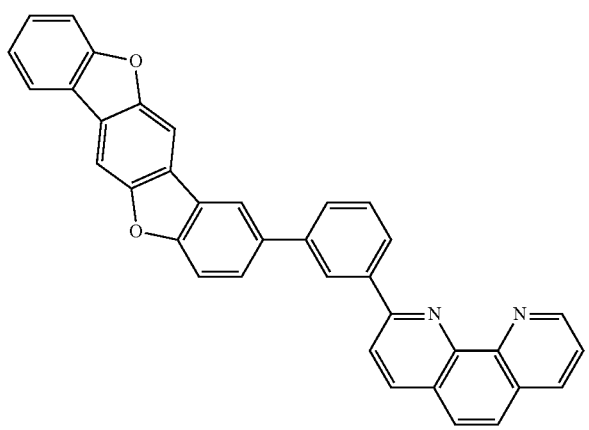

-continued
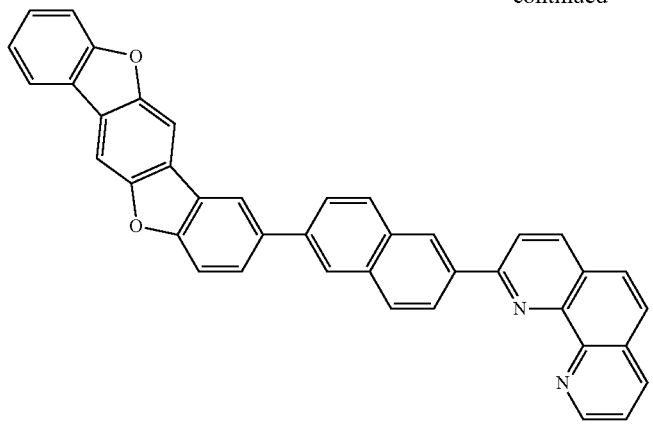
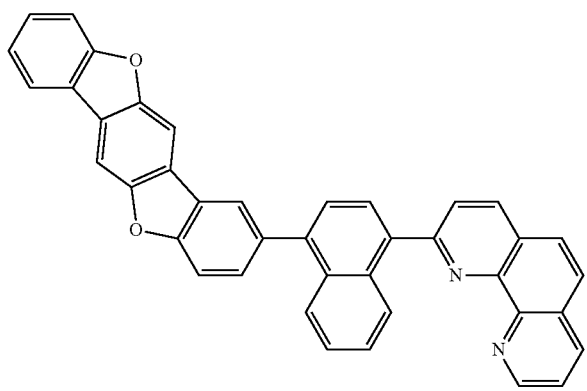
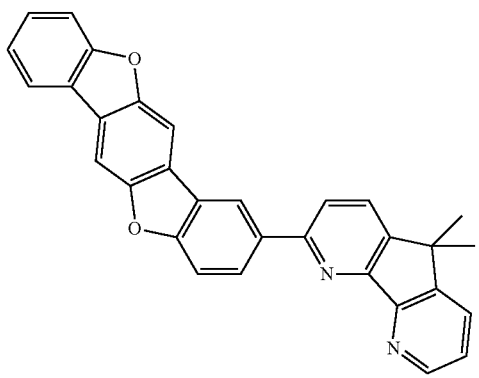
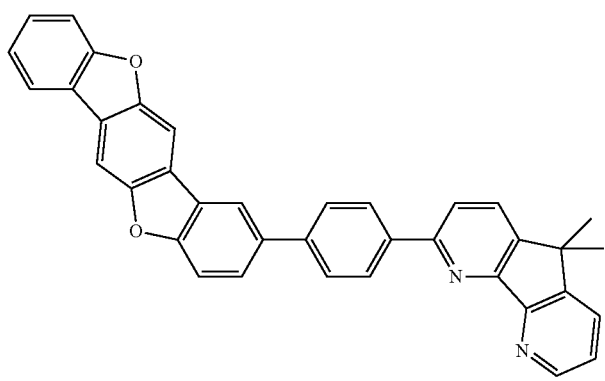
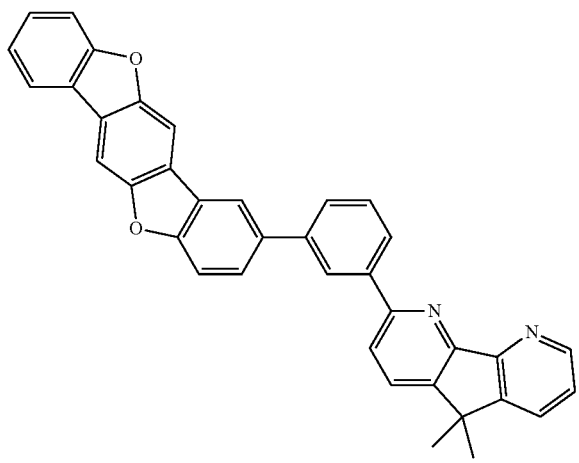

-continued
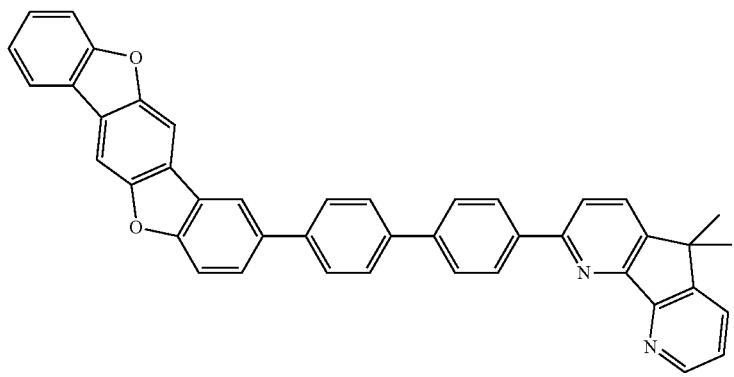
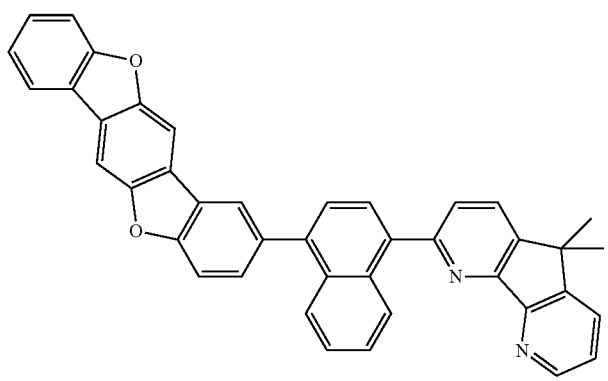
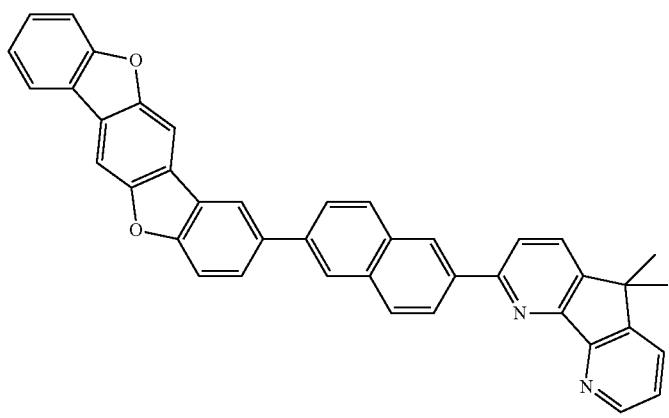
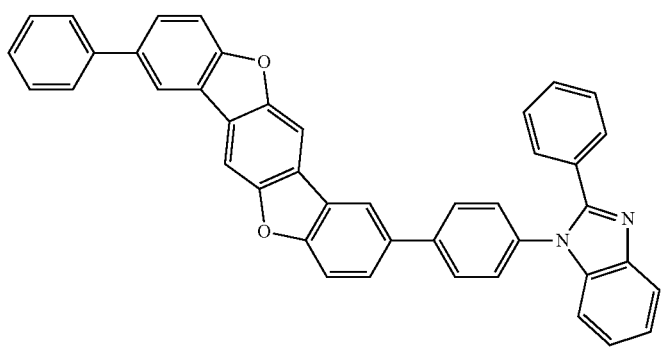

-continued
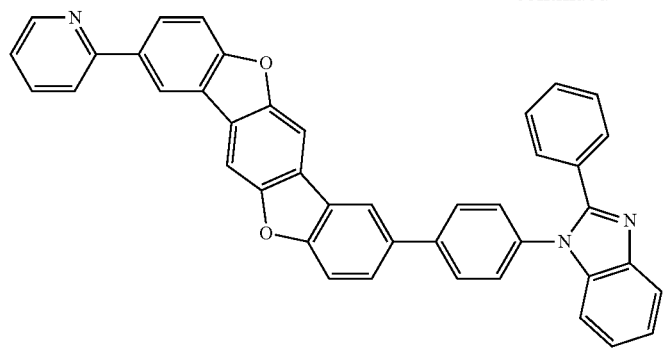
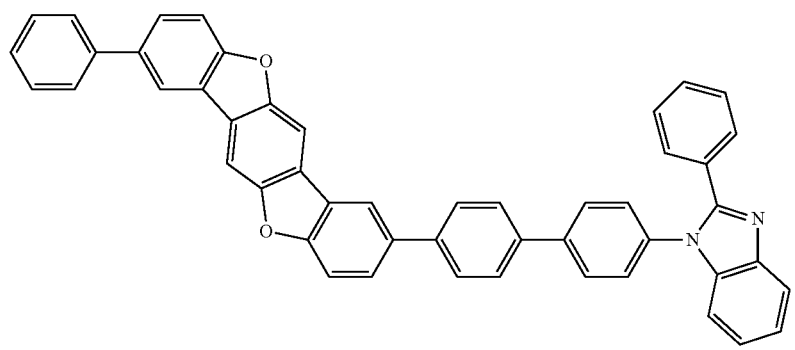
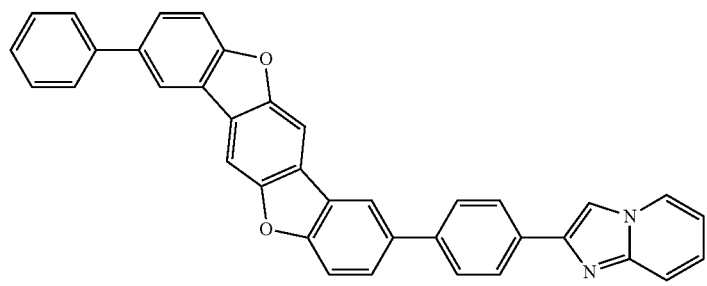
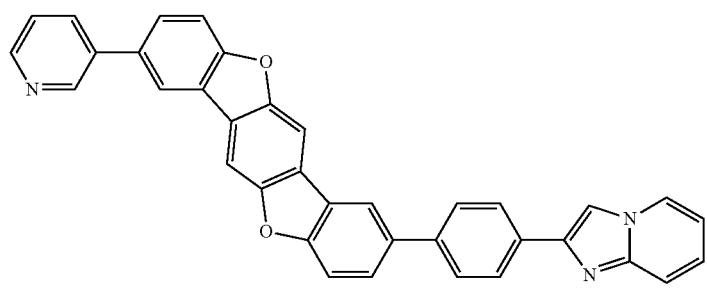
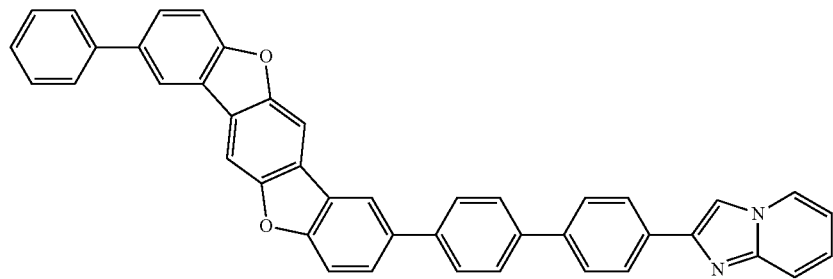

-continued
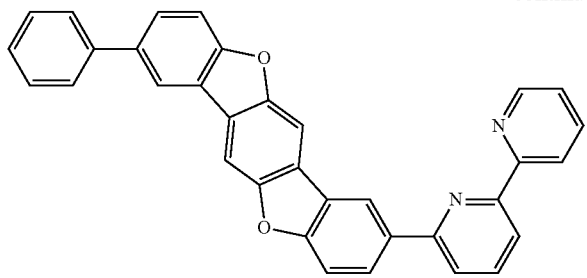
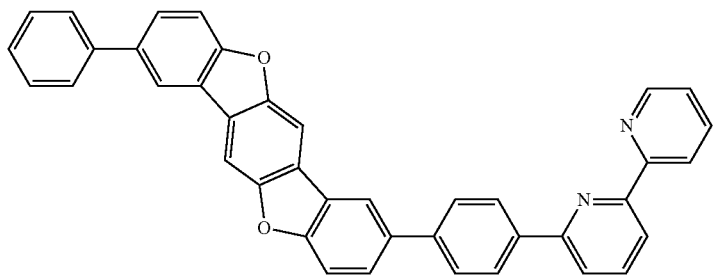
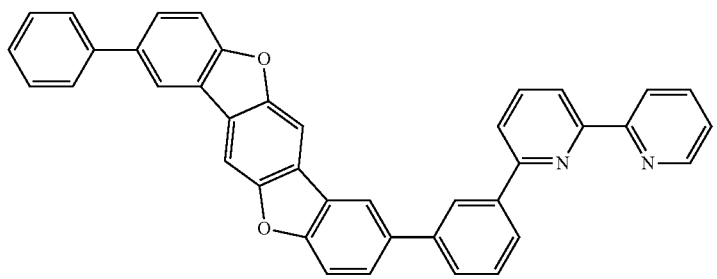
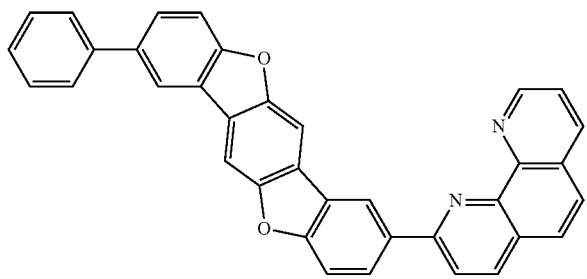
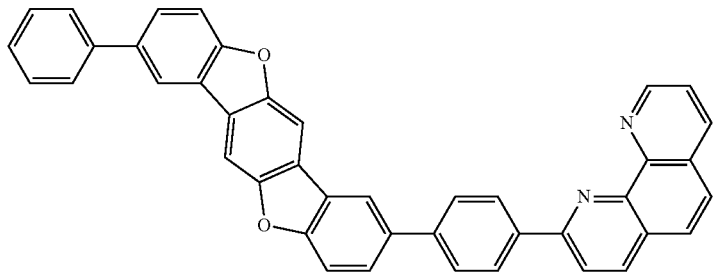
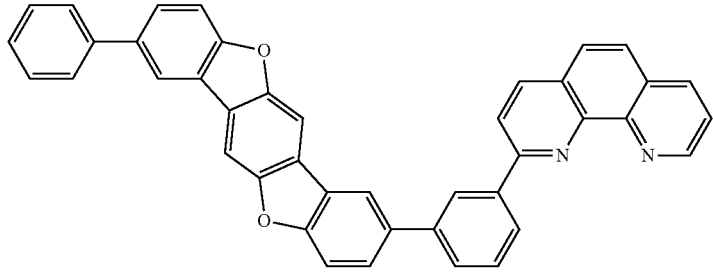

-continued
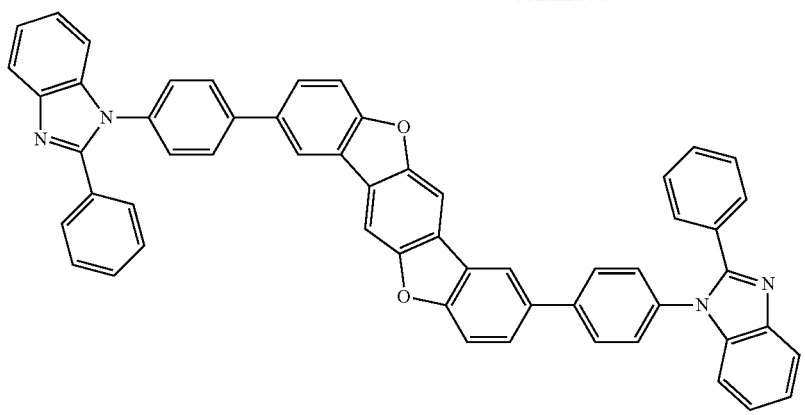
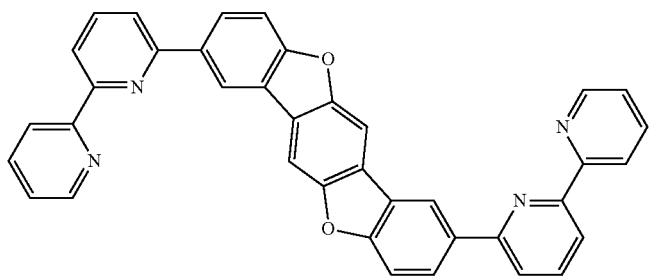
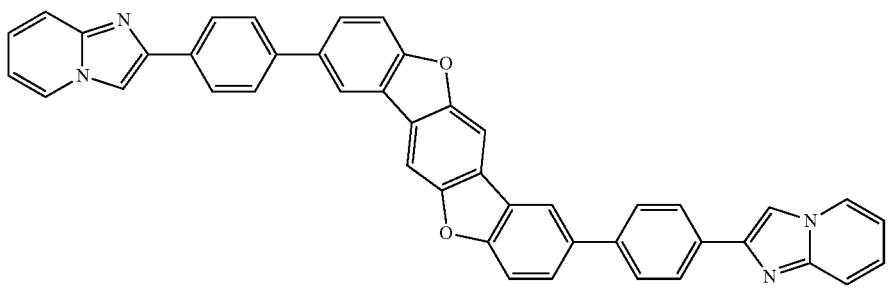
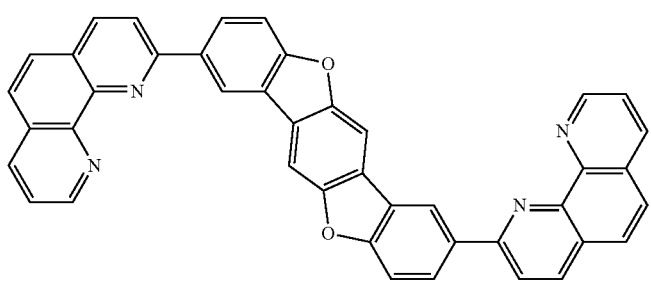
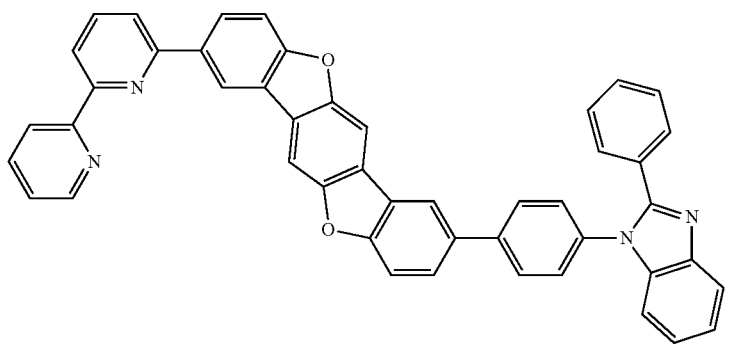

151 152
-continued
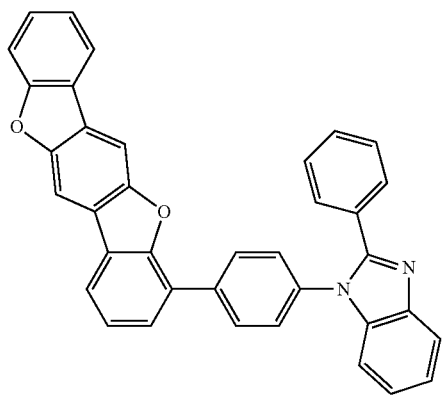
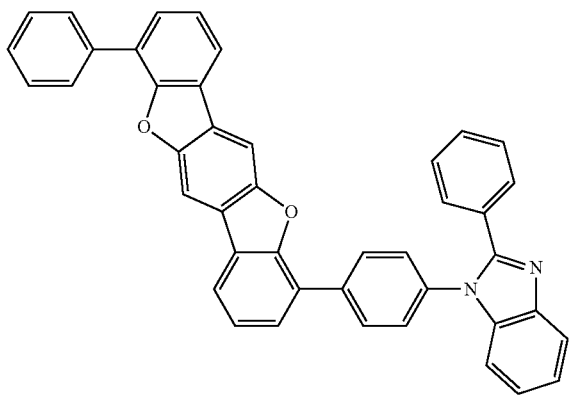
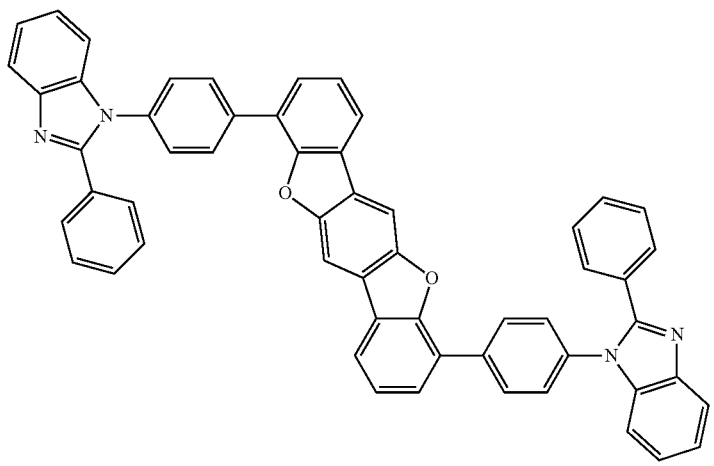
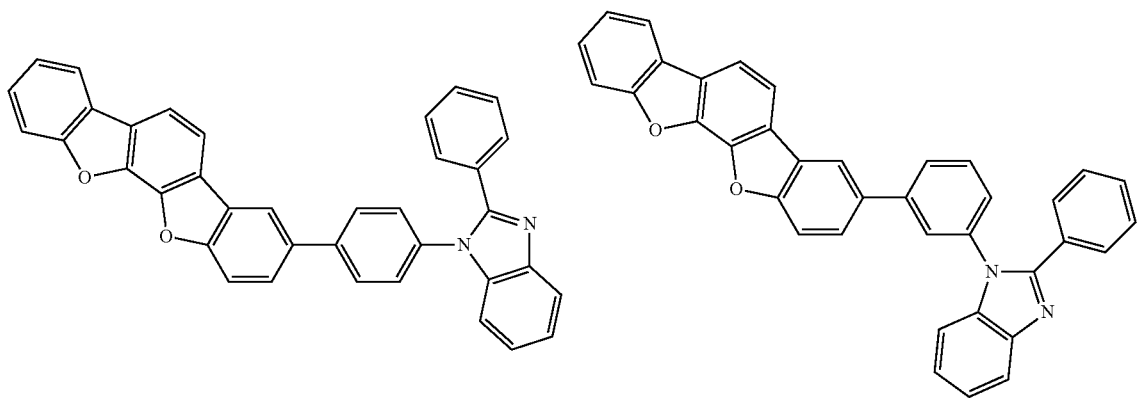
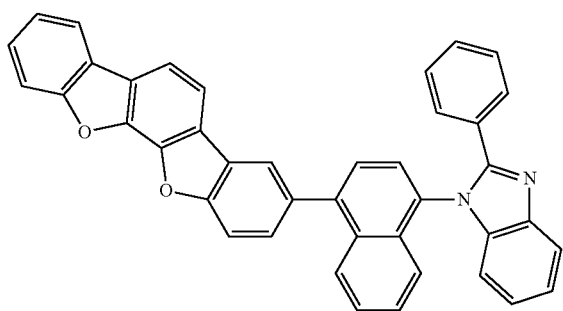

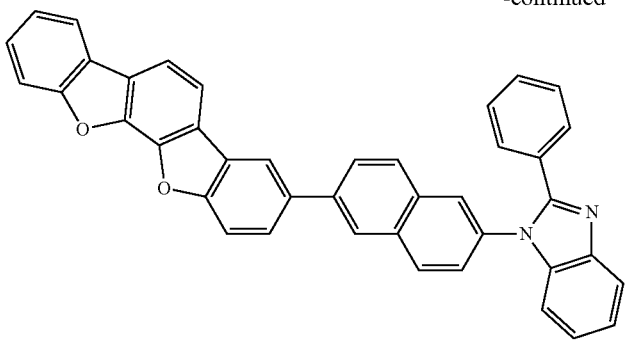
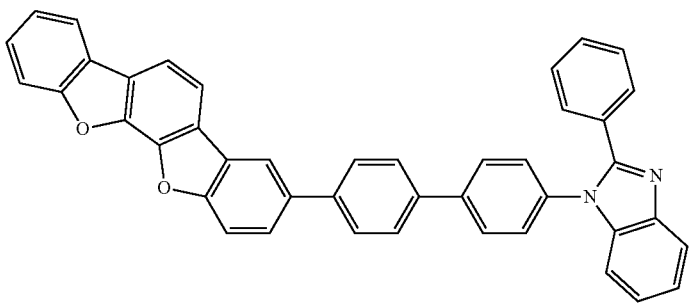
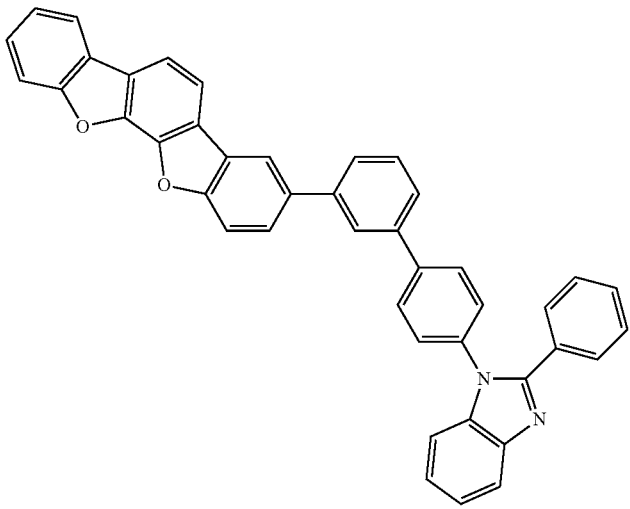
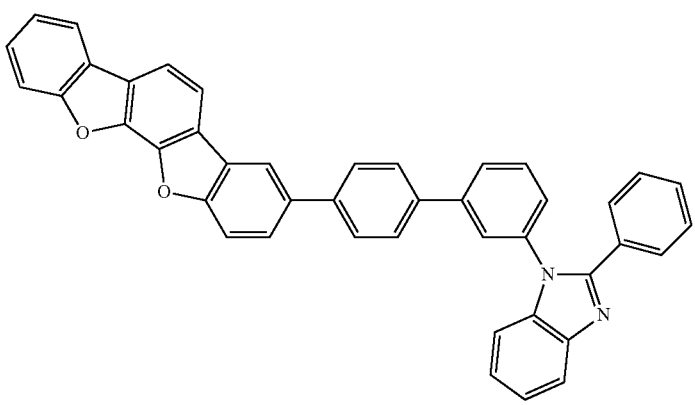

-continued
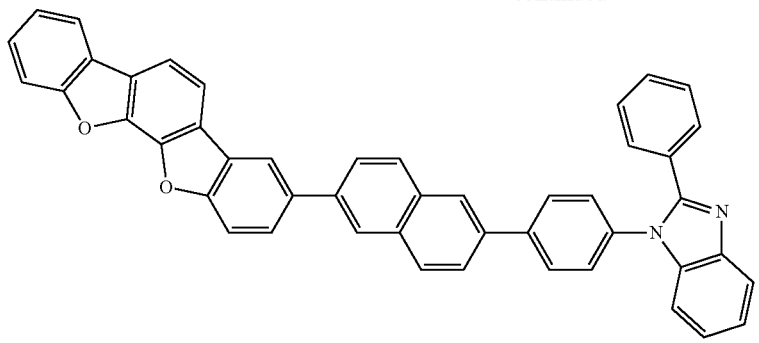
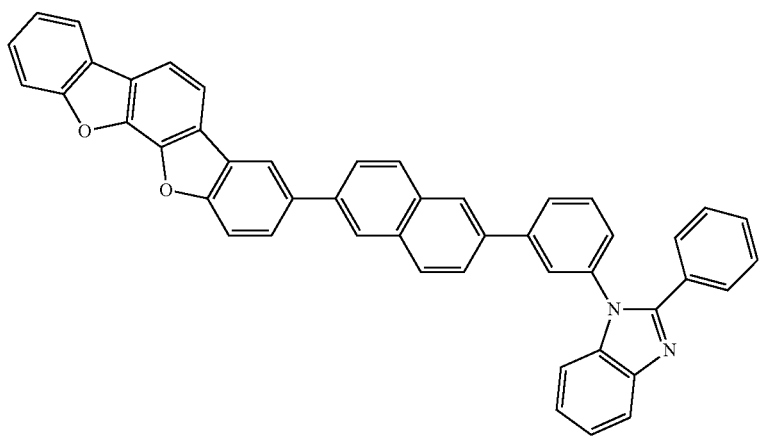
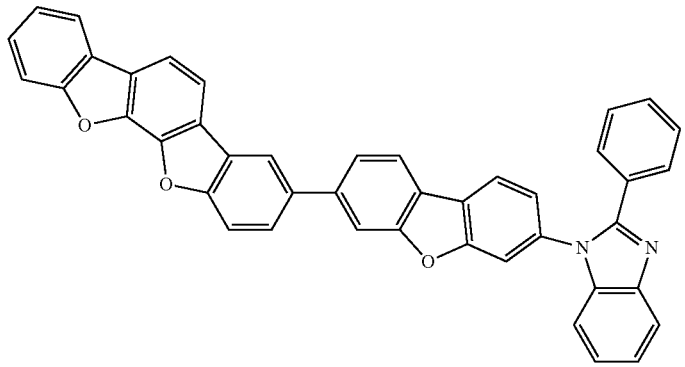
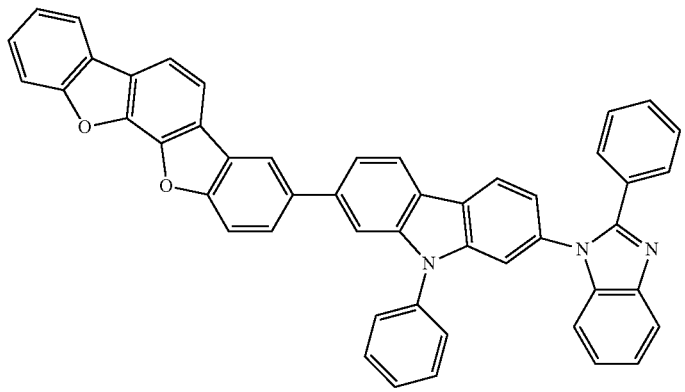

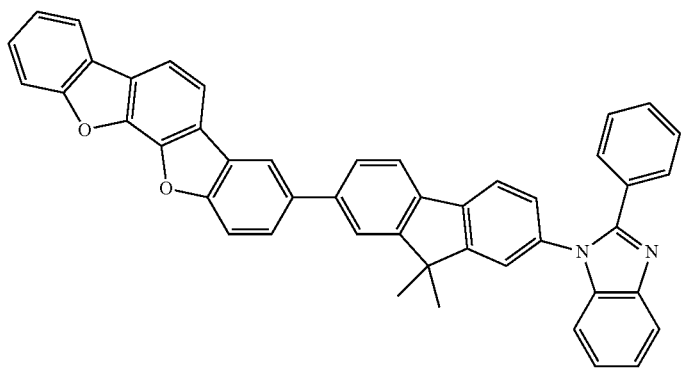
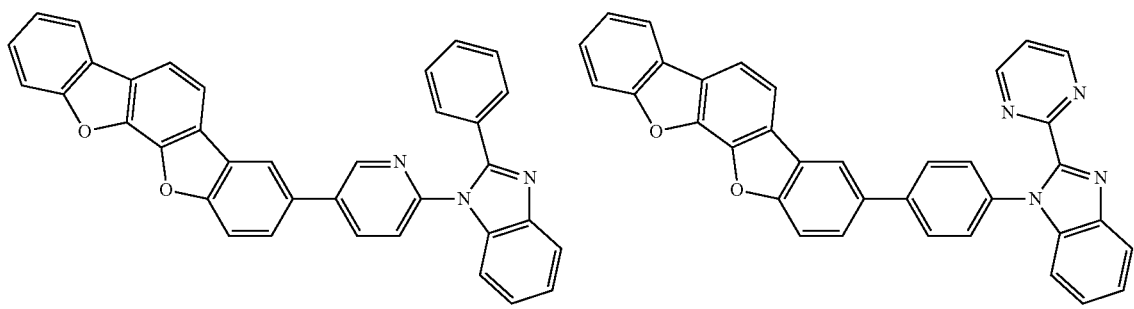
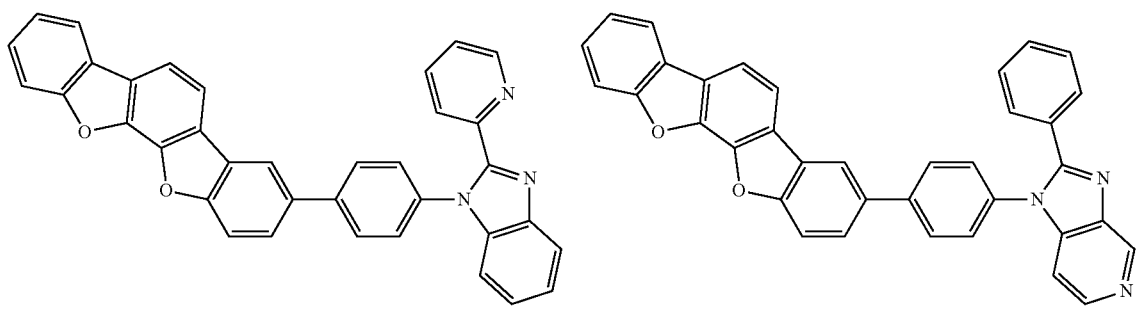
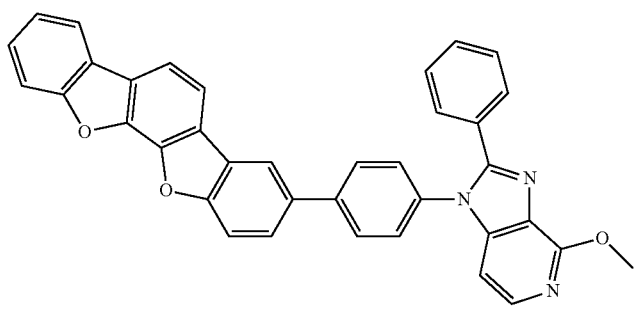
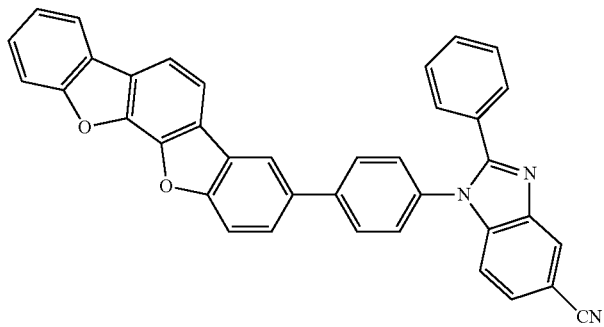 [SMILES: N#Cc1ccc2c(c1)nc(-c1ccccc1)n2-c1ccc(-c2ccc3oc4c(ccc5c6ccccc6oc54)c3c2)cc1]

-continued
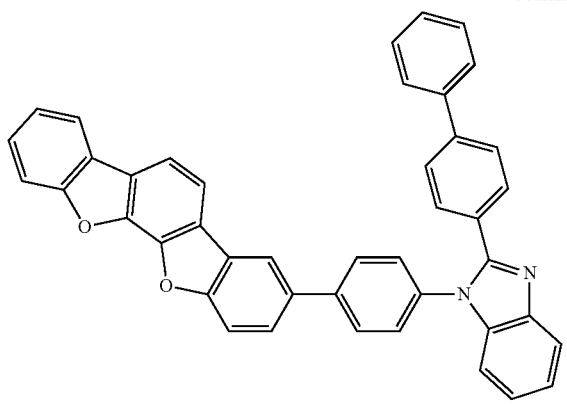
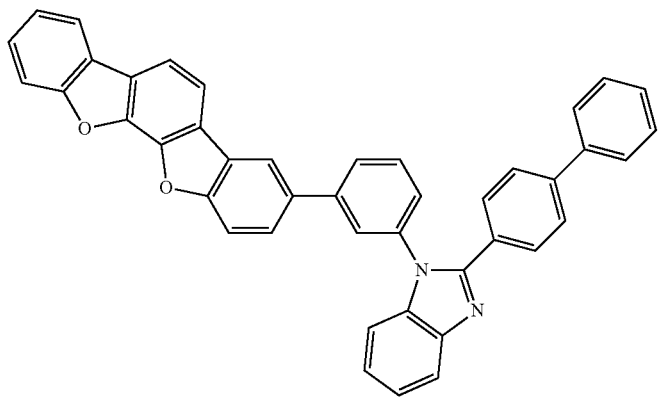
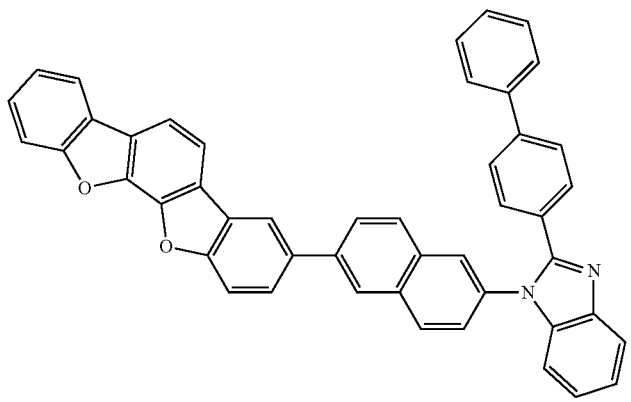
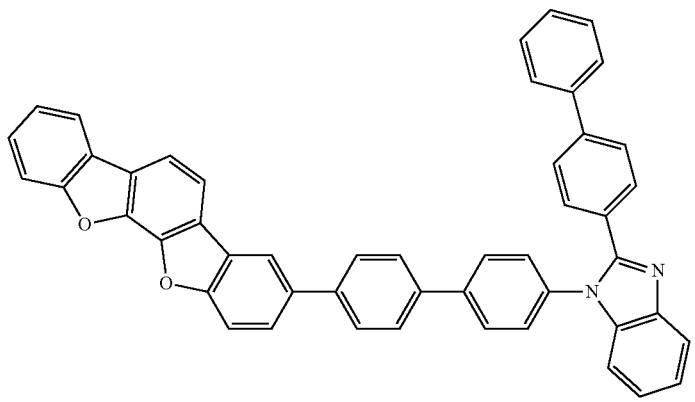

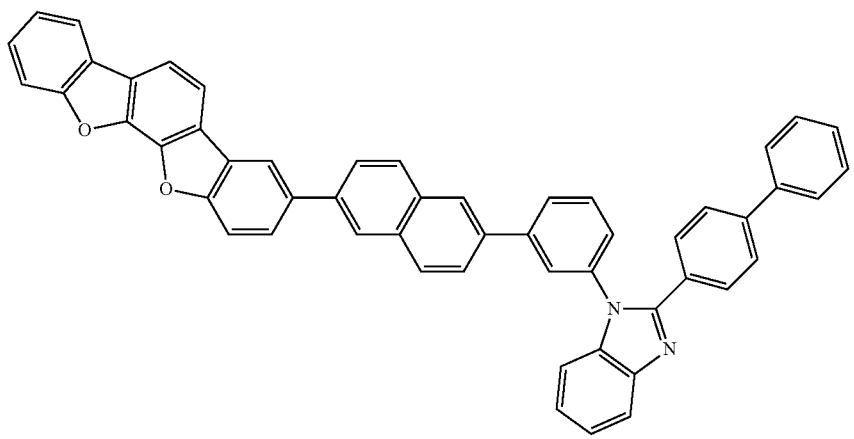
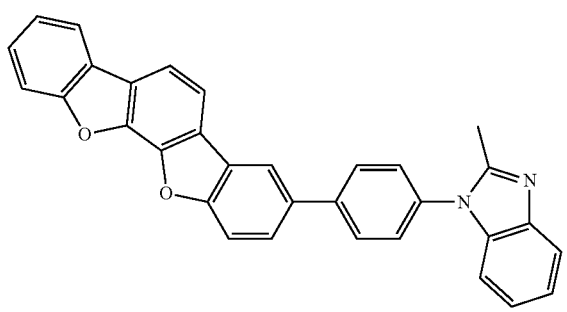
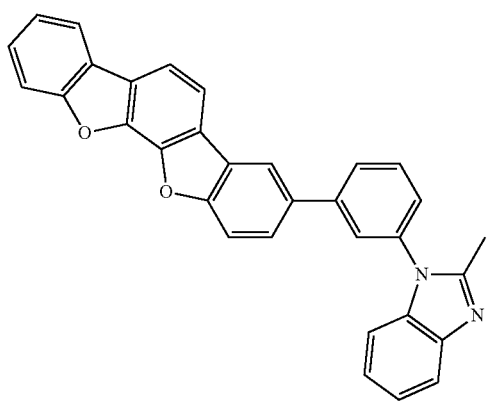
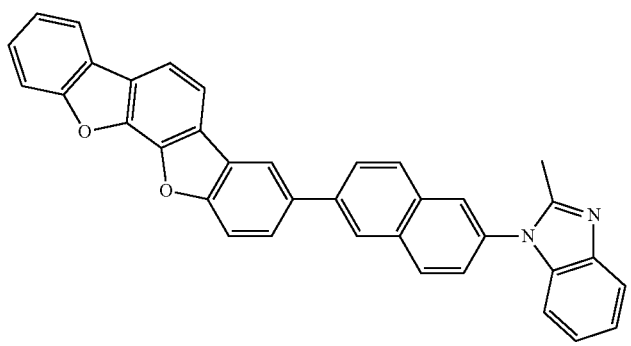

163
164
-continued
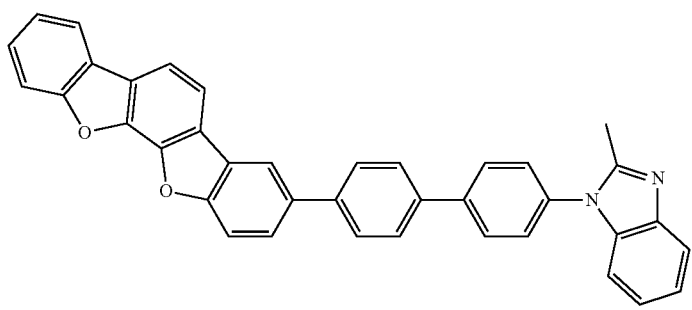
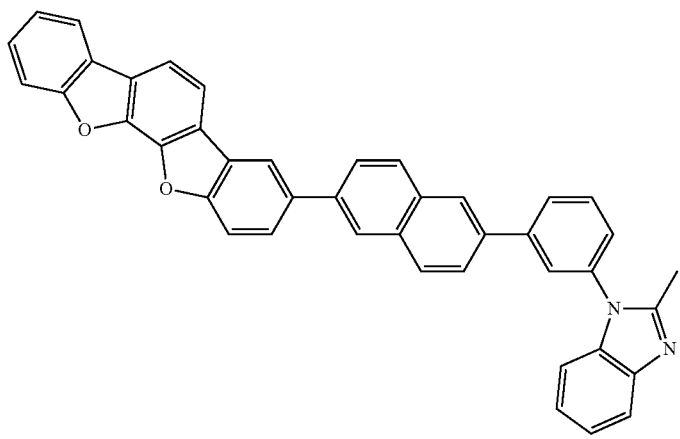
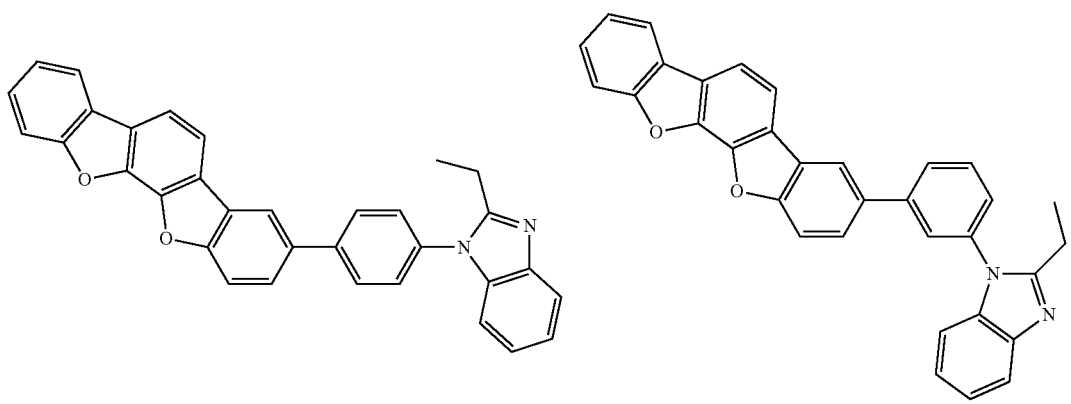
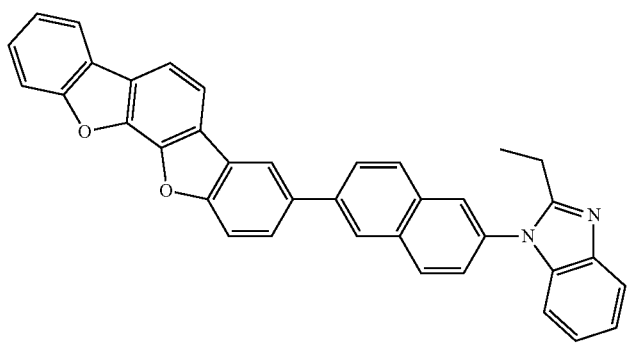

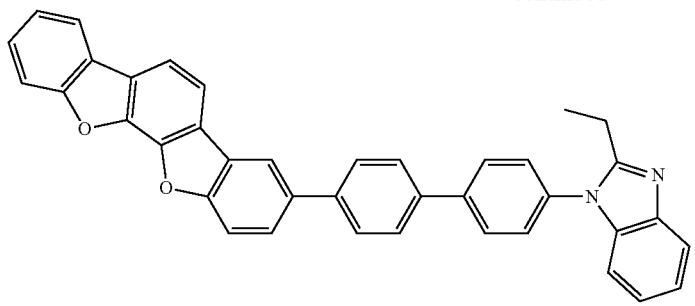
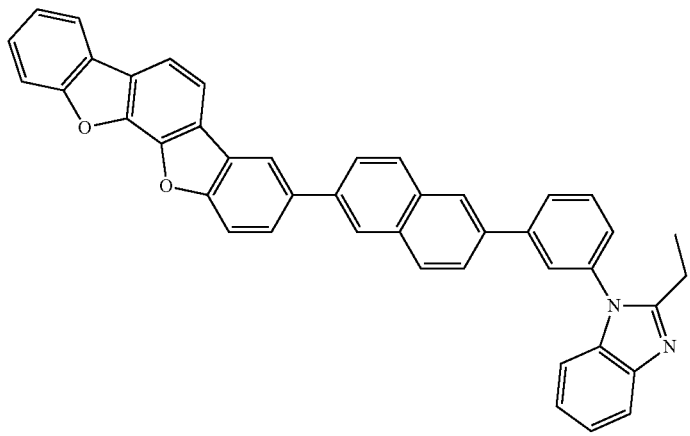
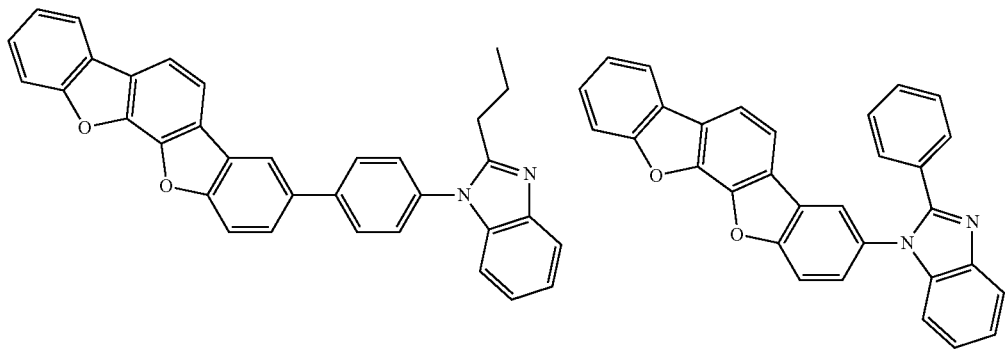
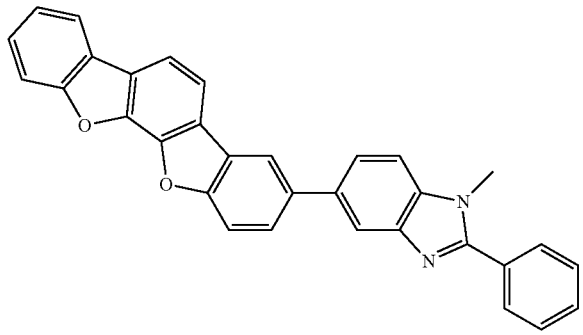

-continued
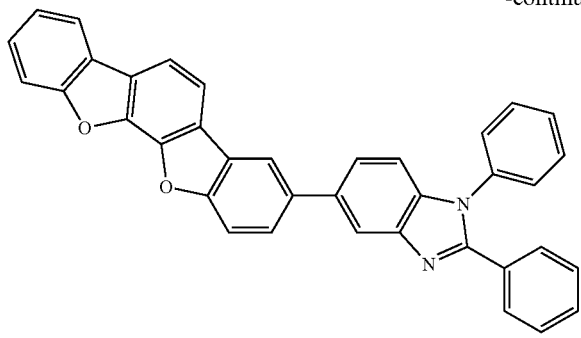
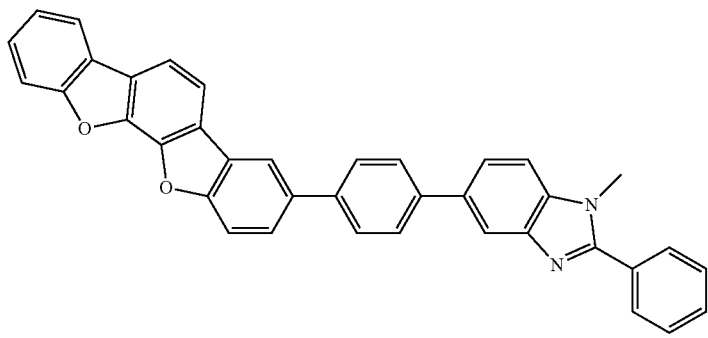
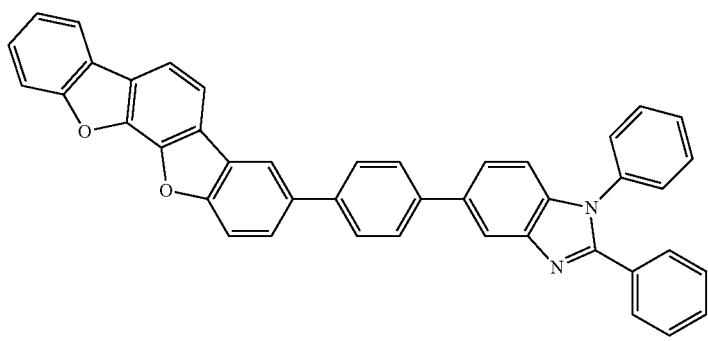
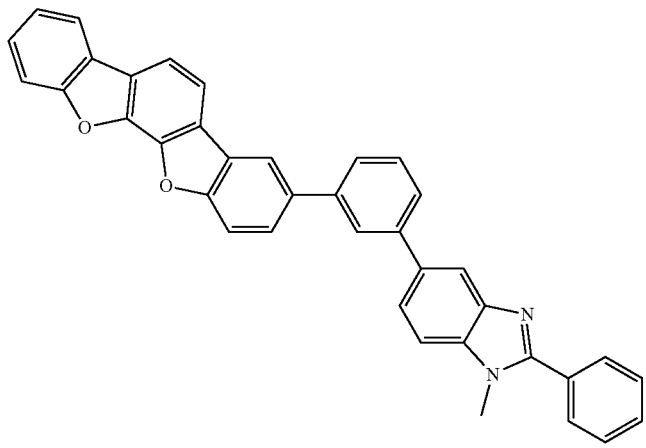

-continued
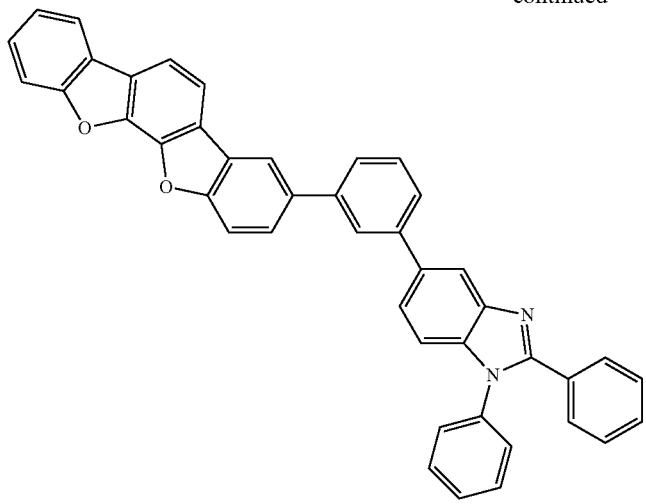
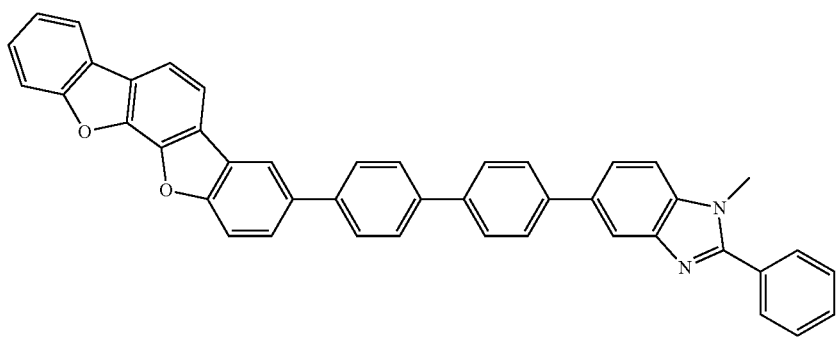
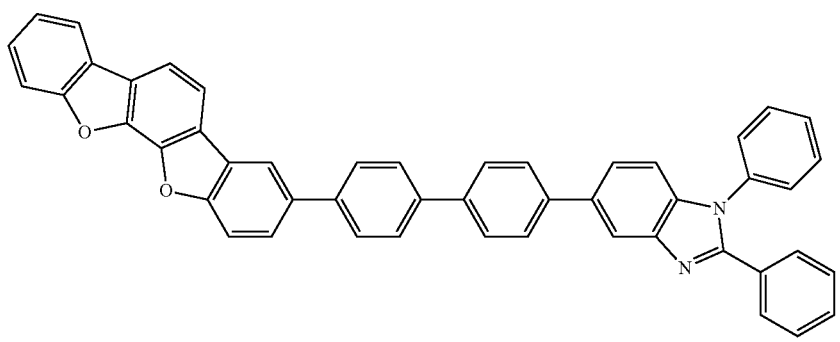
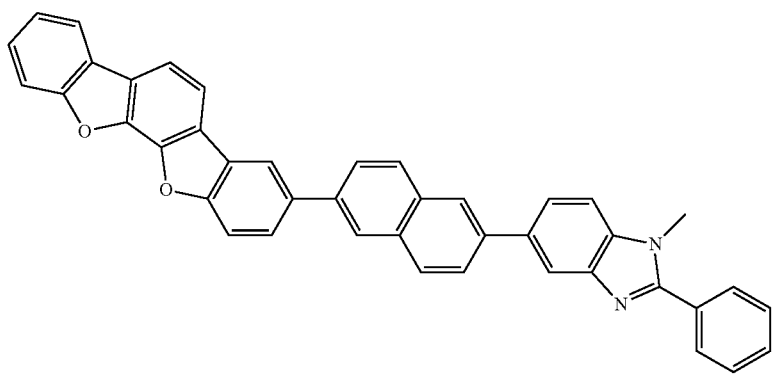

-continued
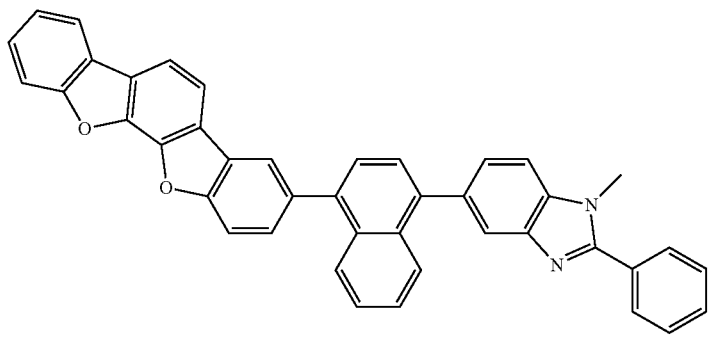
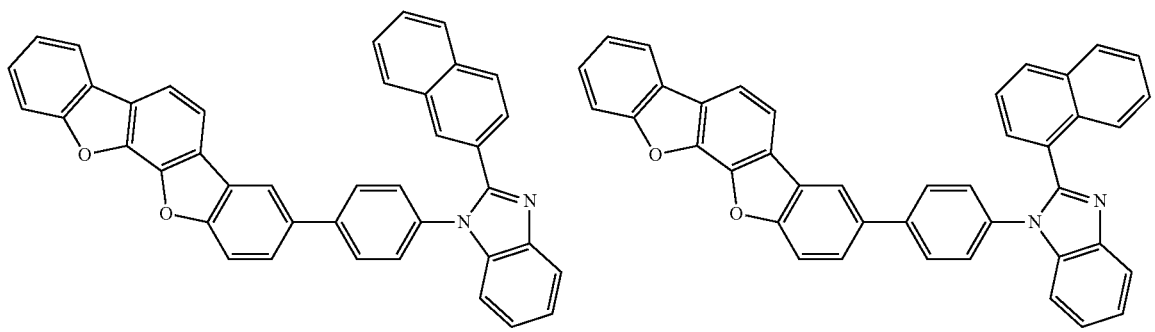
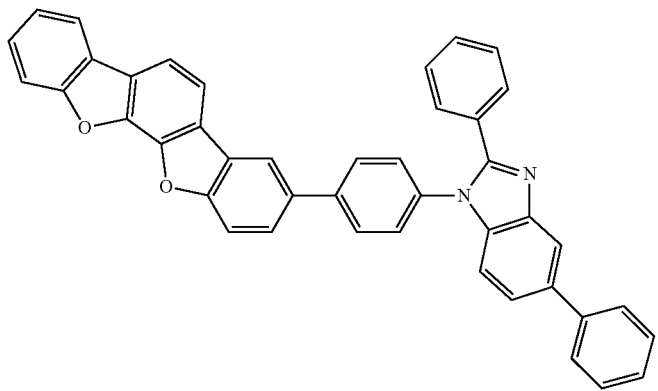
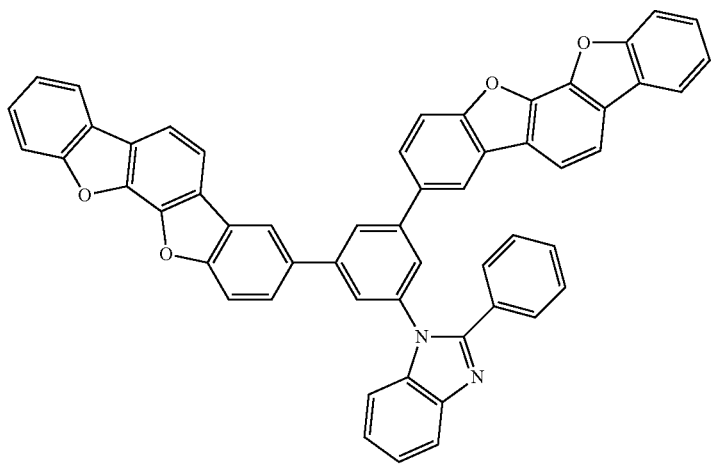 [SMILES: c1ccc(-c2nc3ccccc3n2-c2cc(-c3ccc4oc5c(ccc6c7ccccc7oc65)c4c3)cc(-c3ccc4oc5c(ccc6c7ccccc7oc65)c4c3)c2)cc1]

173
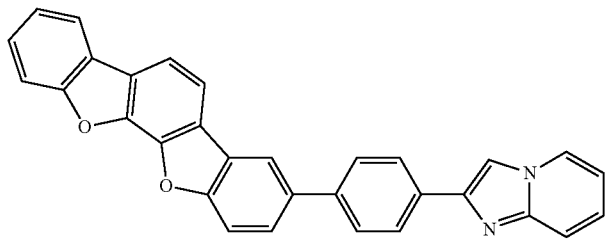
174
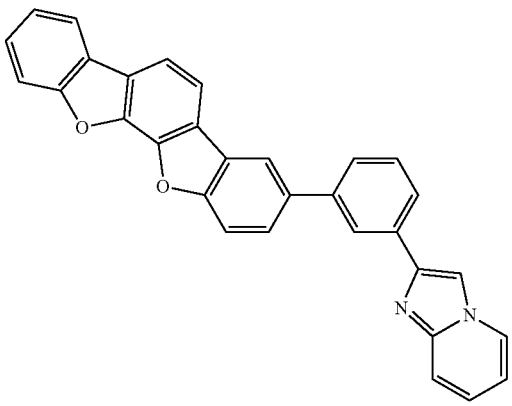
-continued
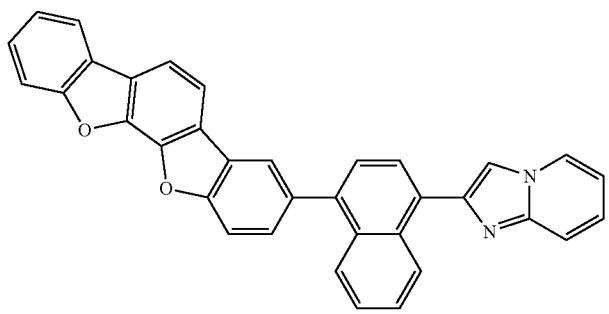
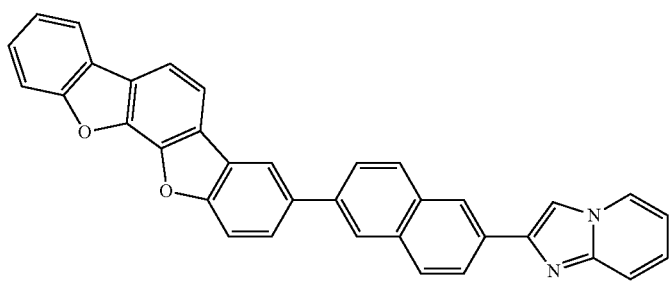
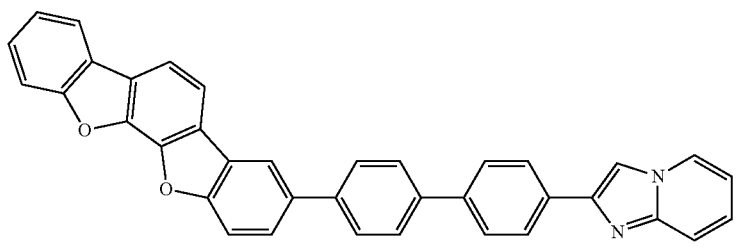
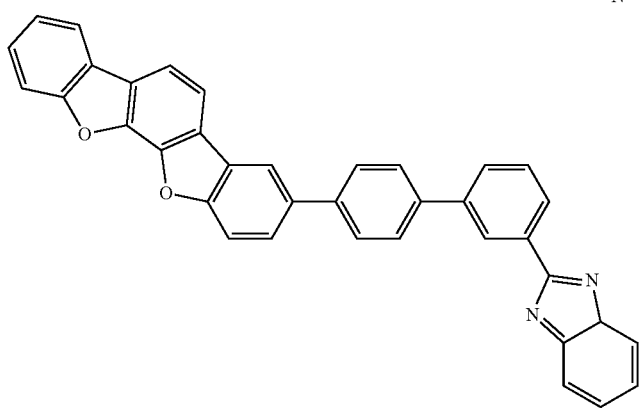

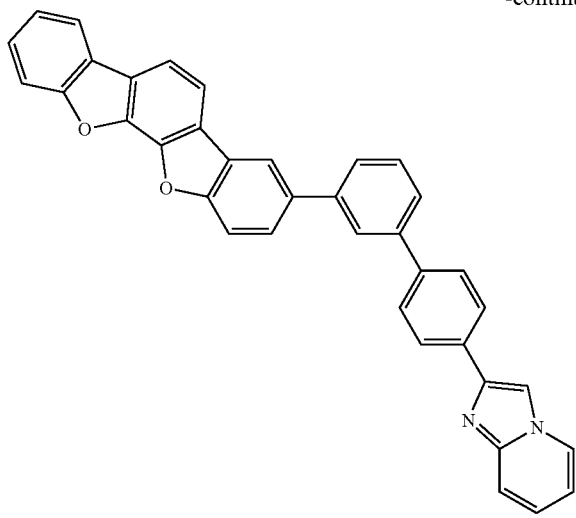
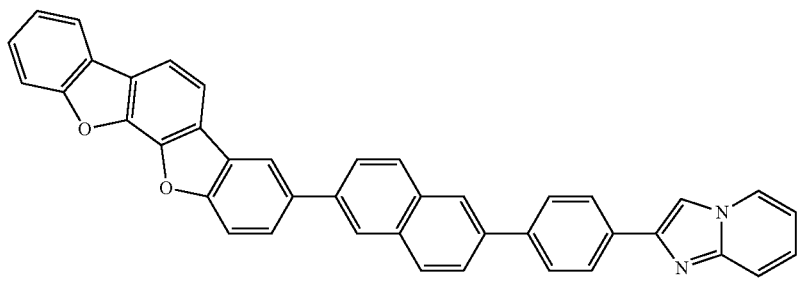
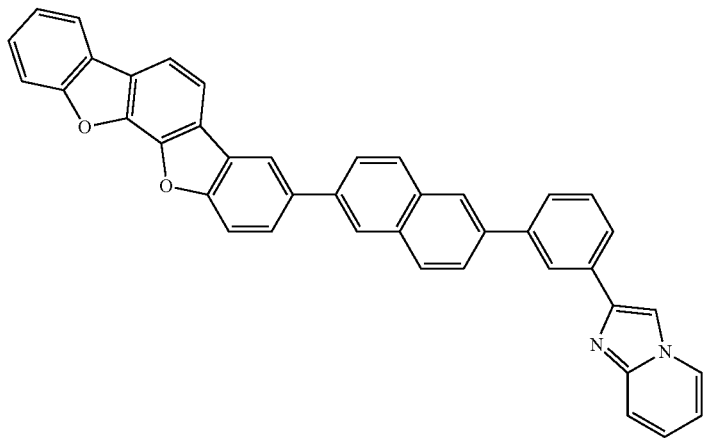
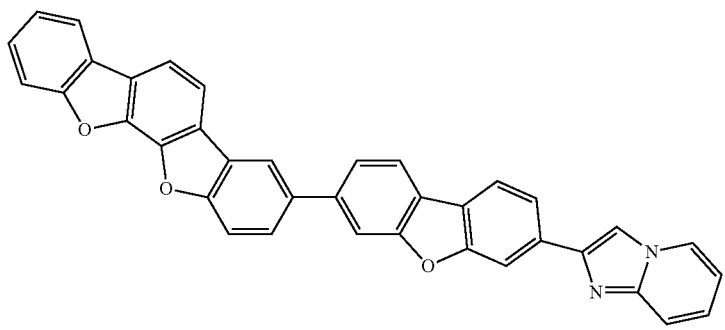

-continued
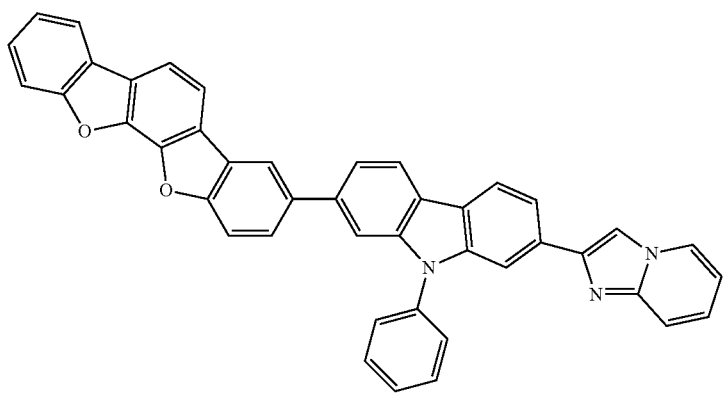
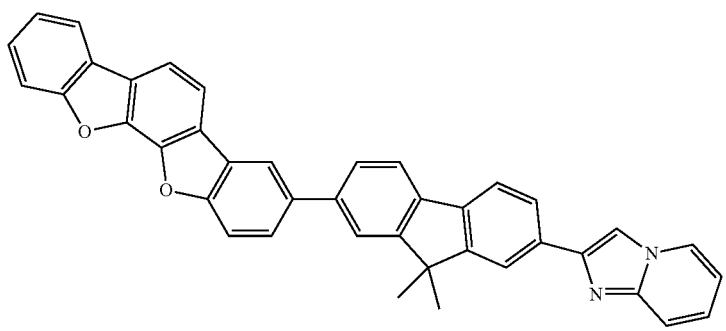
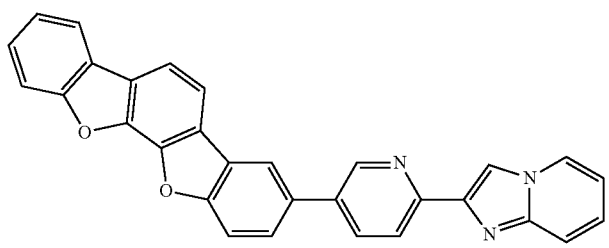
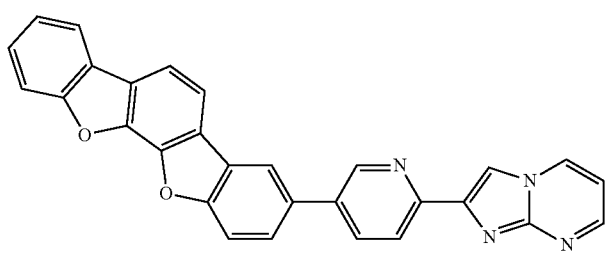
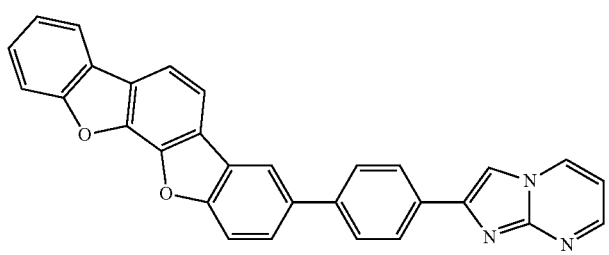
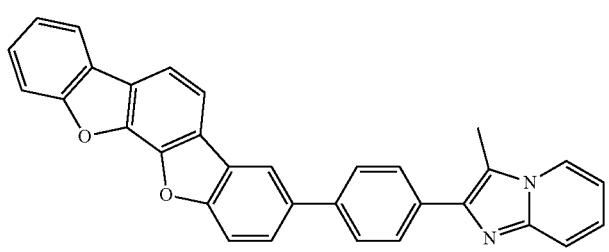

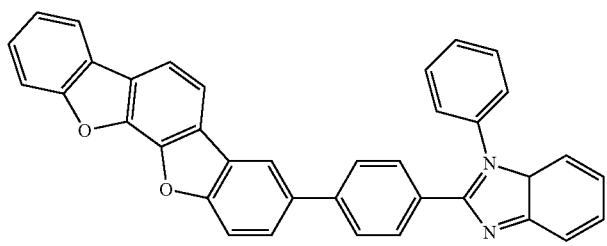
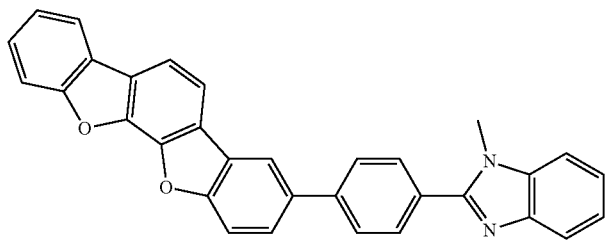
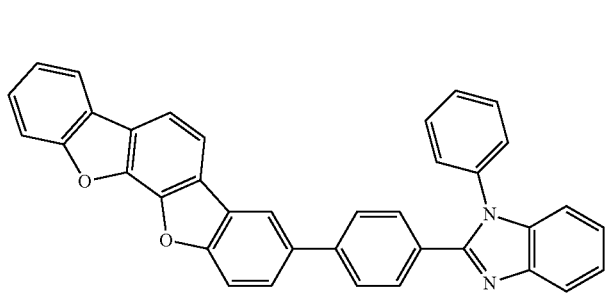
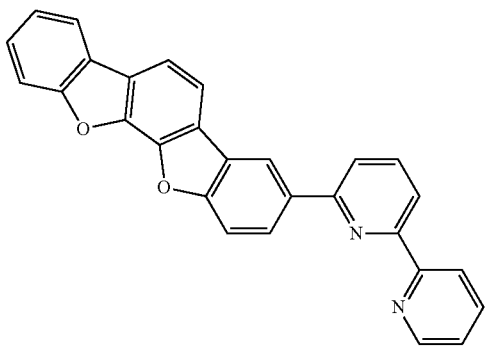
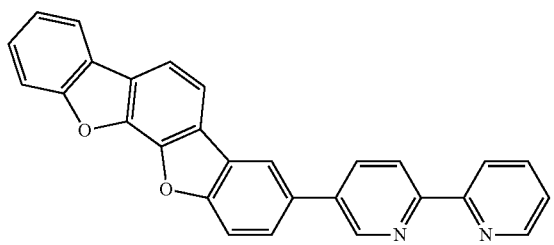
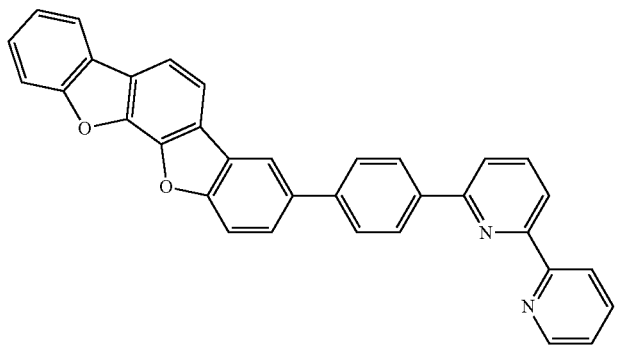

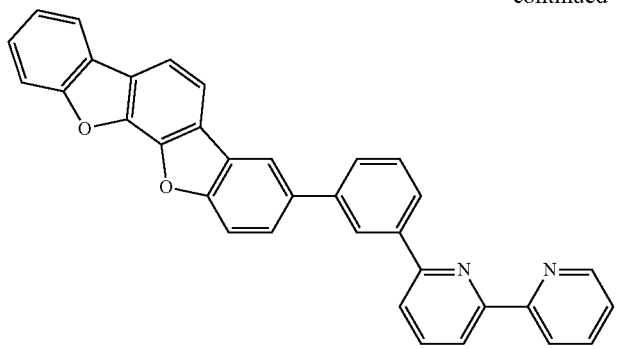
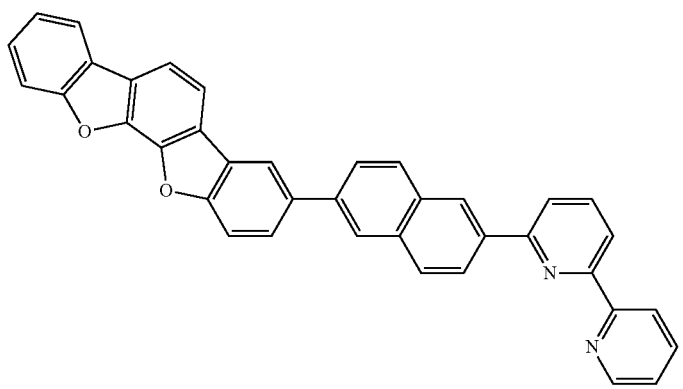
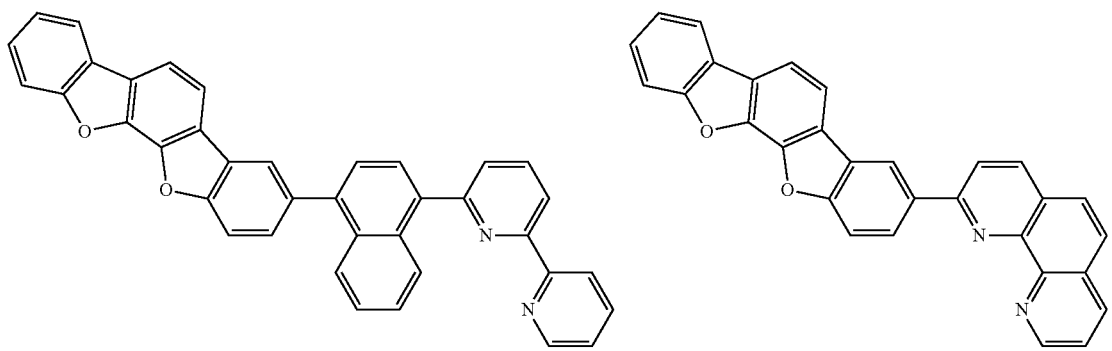
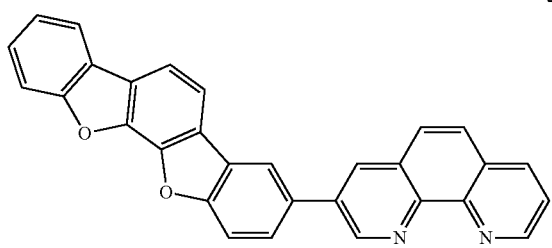
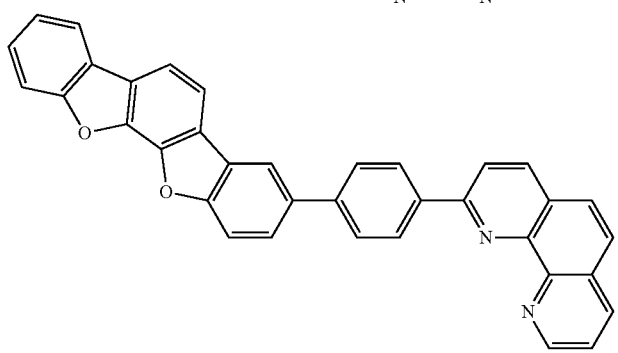

183
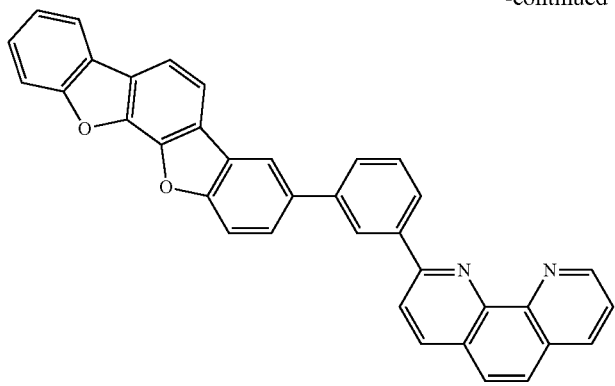
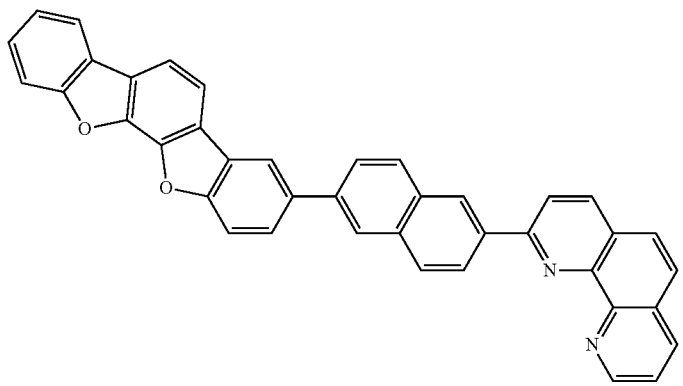
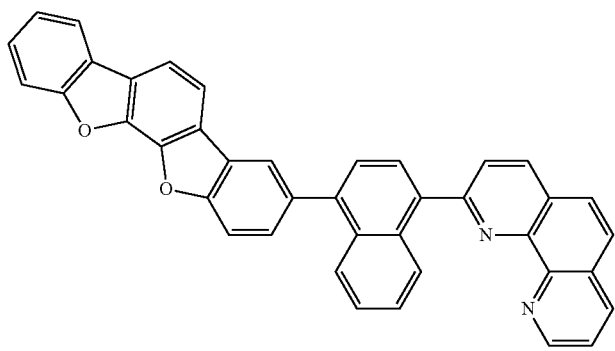
184
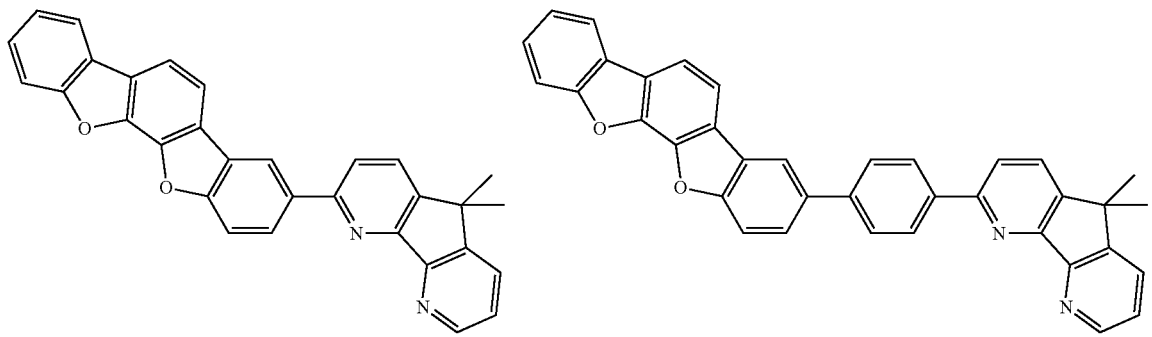

-continued
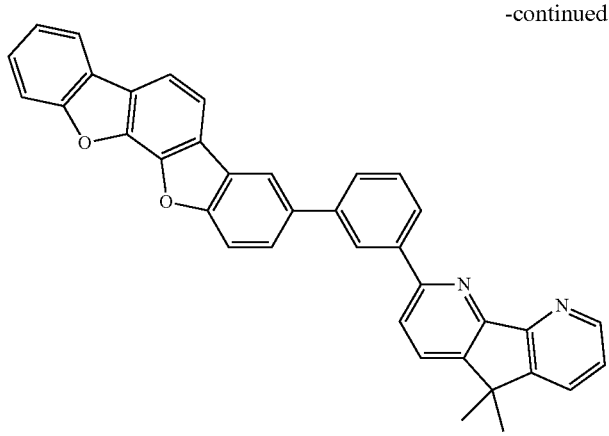
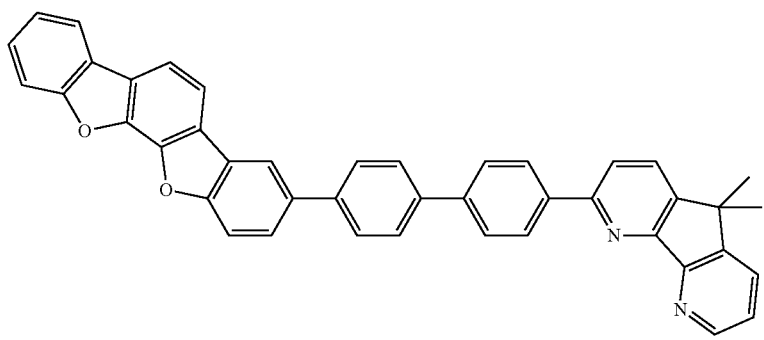
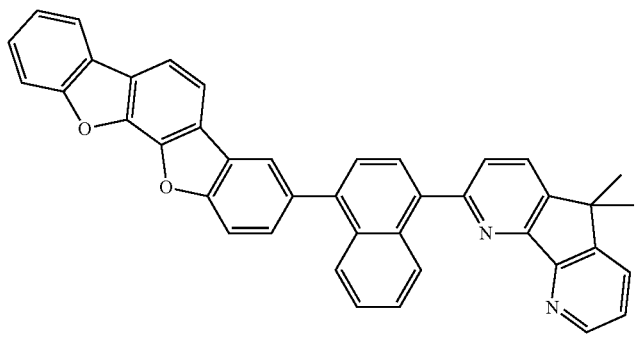
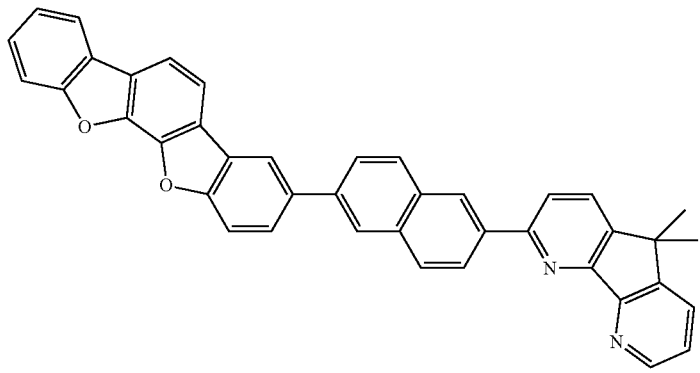

-continued
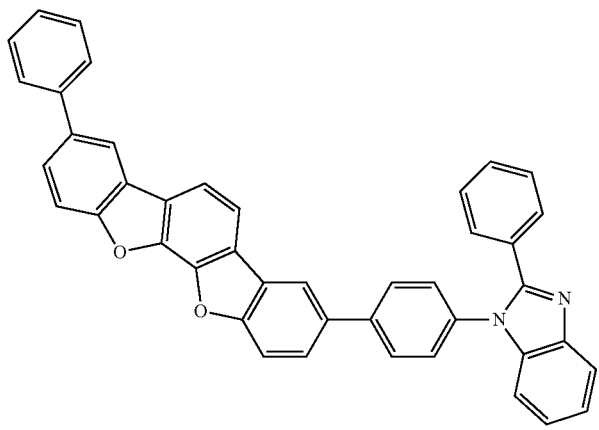
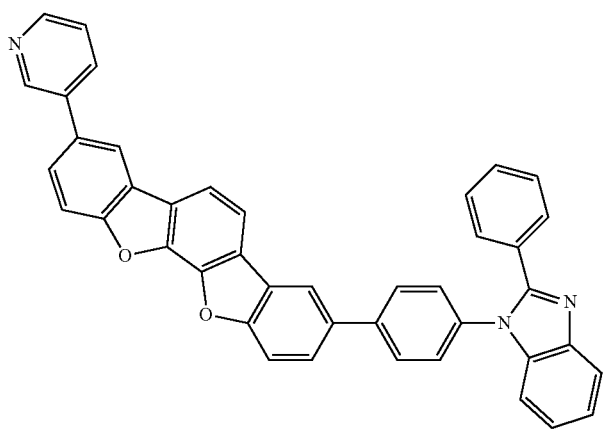
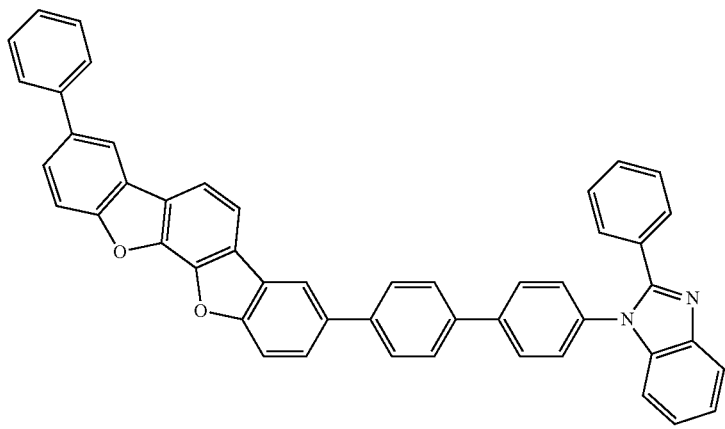
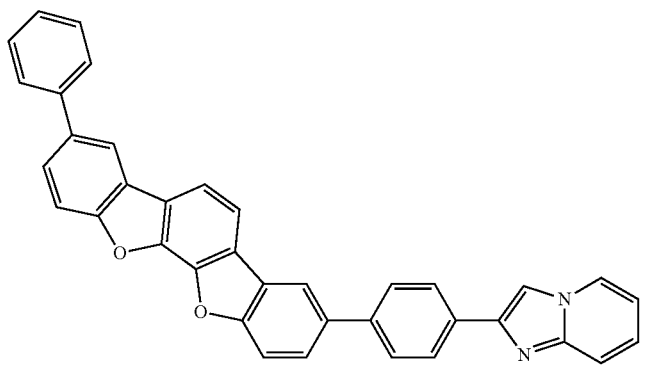

-continued
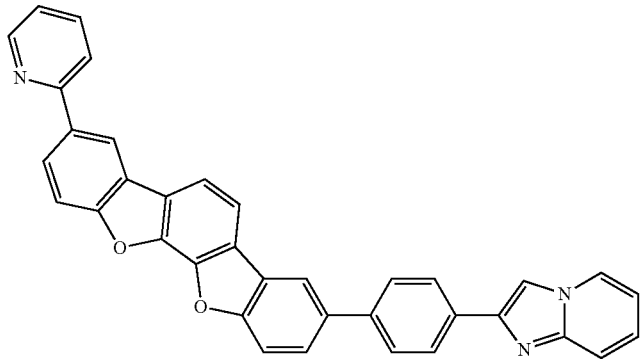
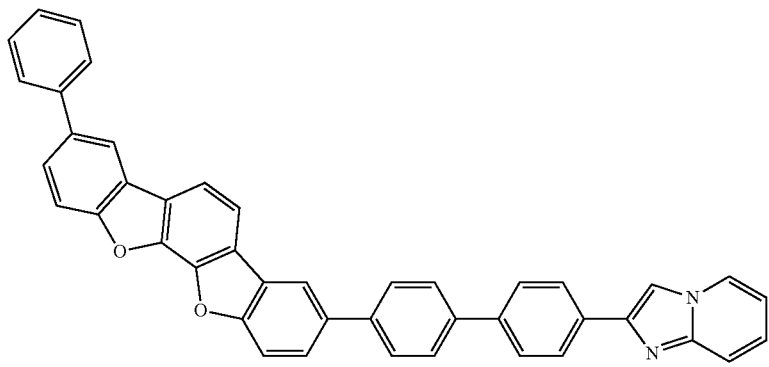
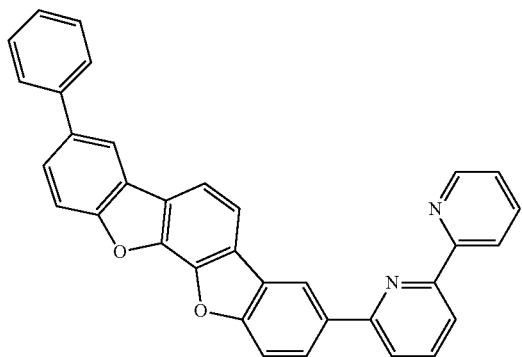
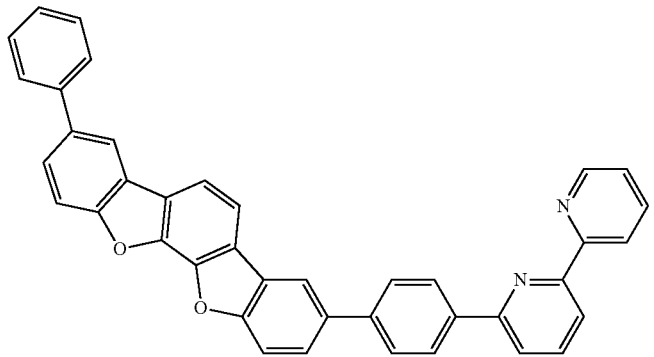

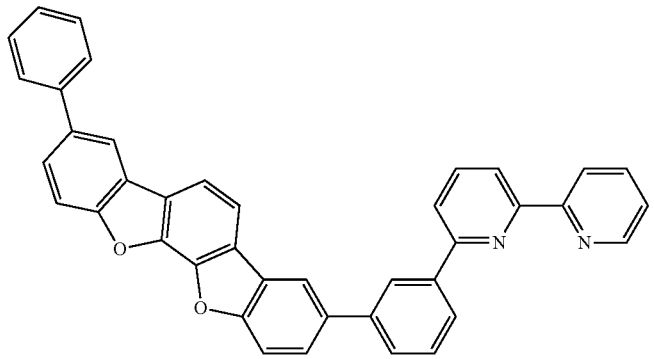
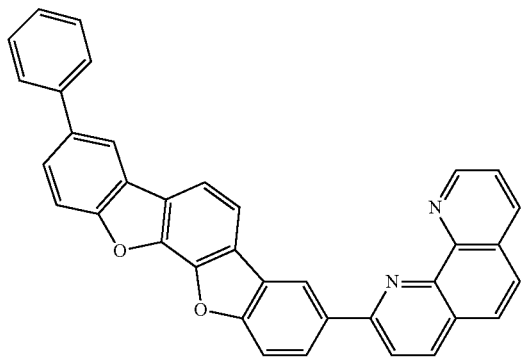
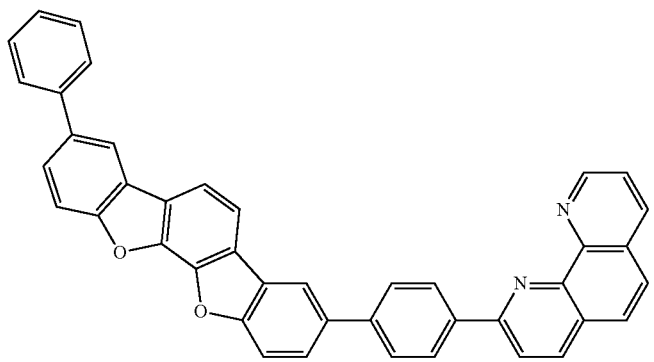
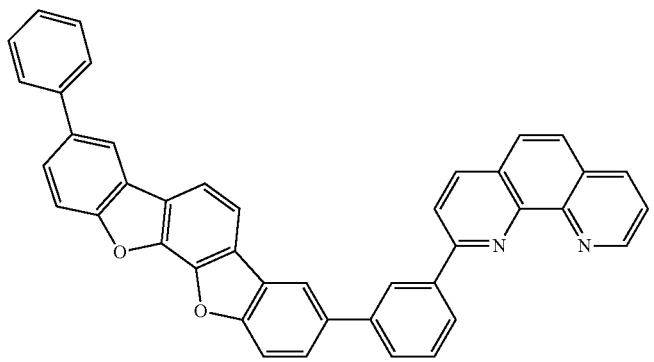

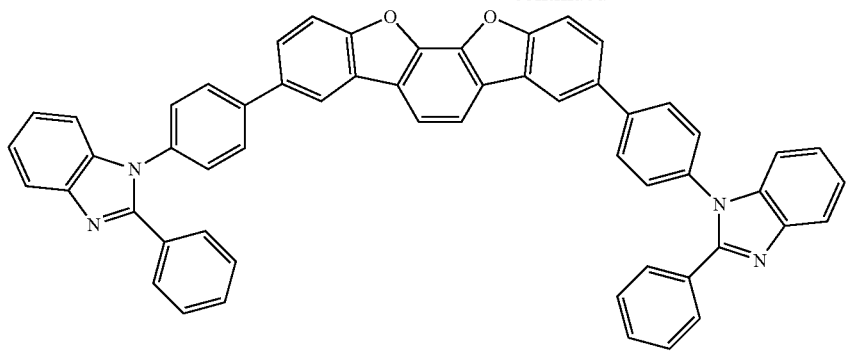
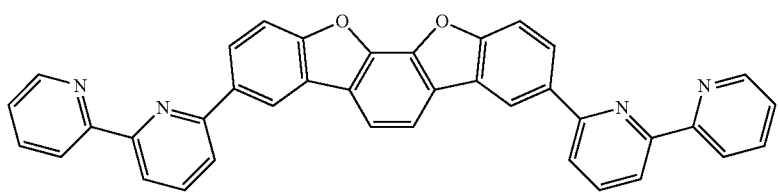
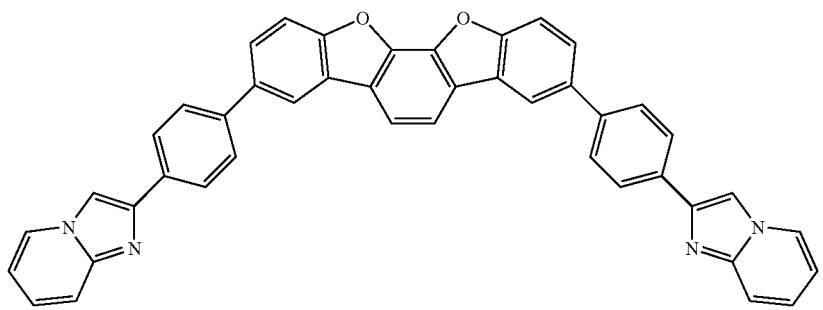
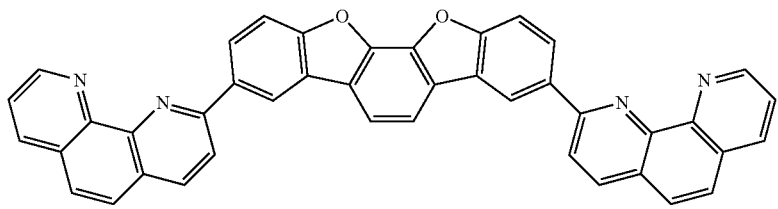
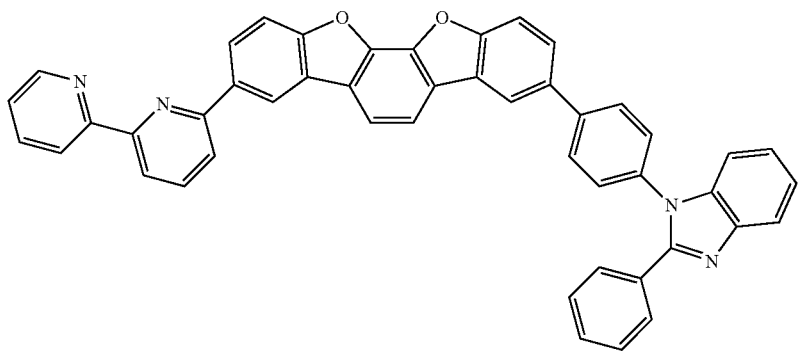

-continued
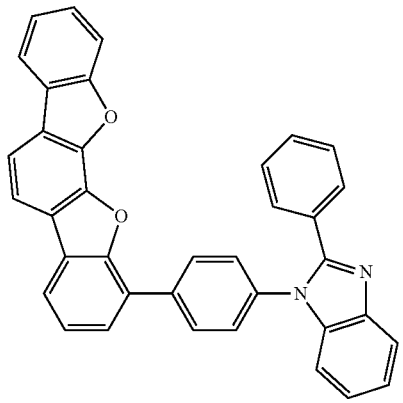
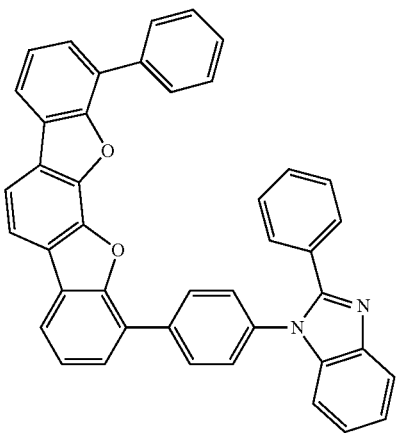
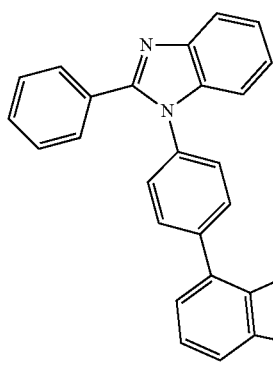
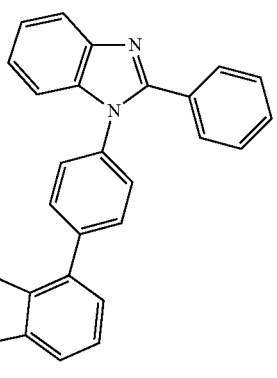
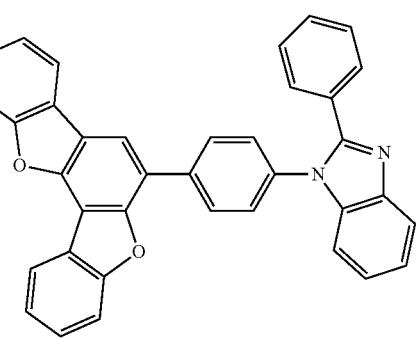
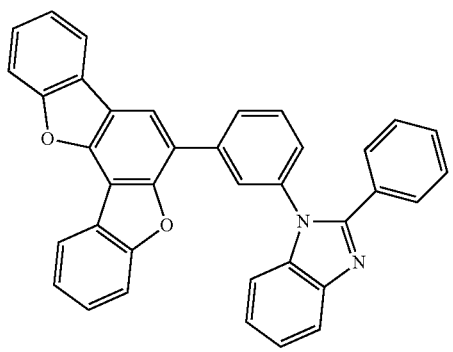
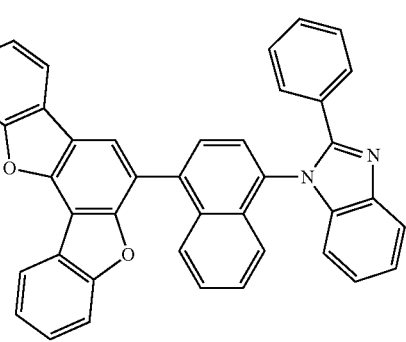
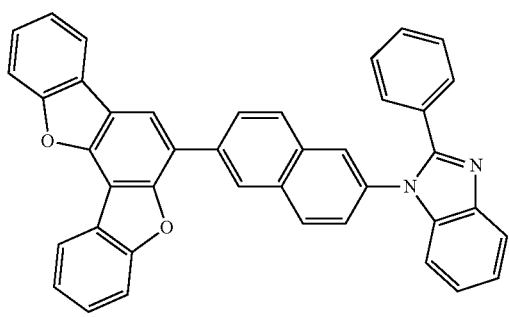

-continued
| 197 | 198 |
|---|---|
| 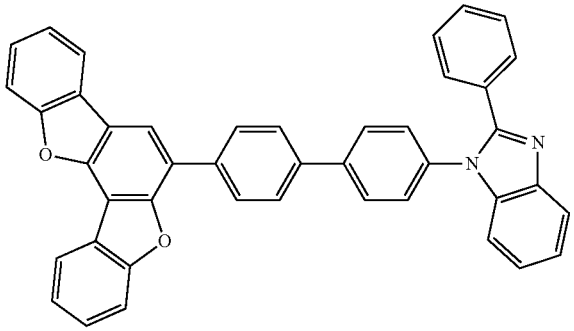 | 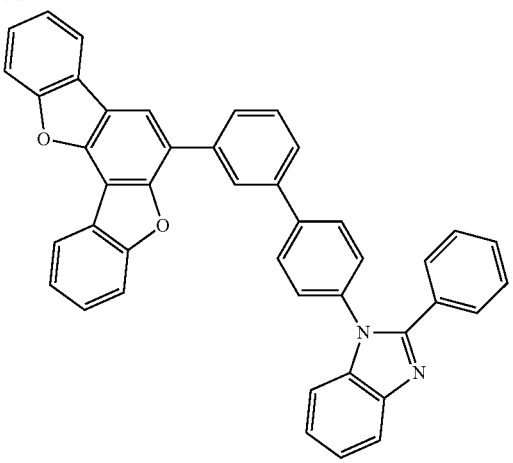 |
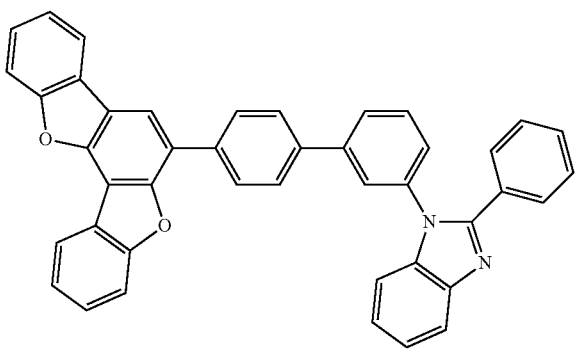
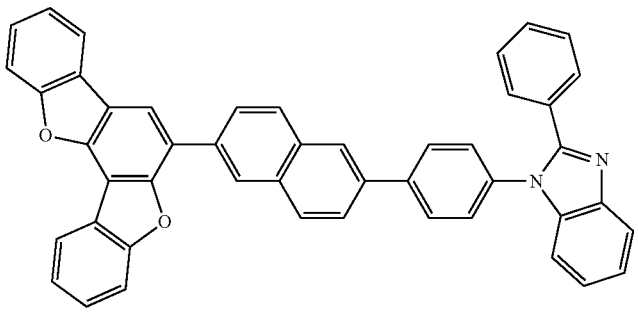
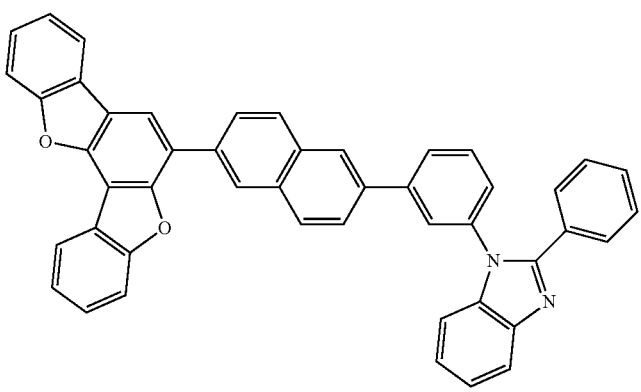

199 200
-continued
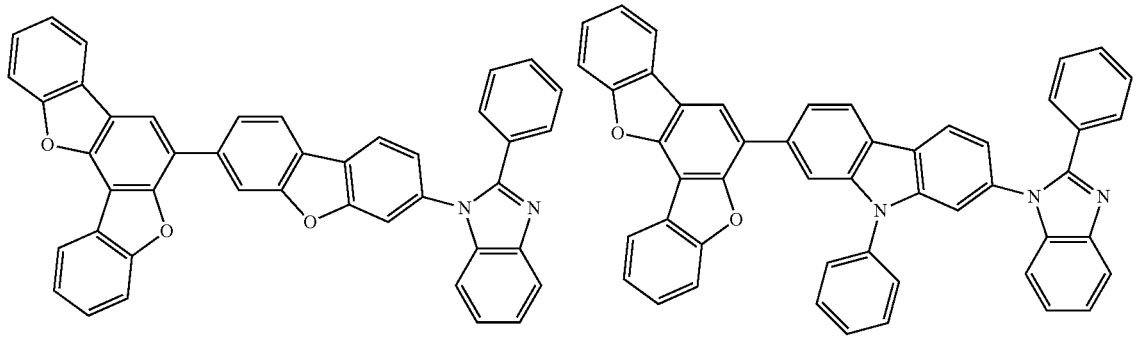
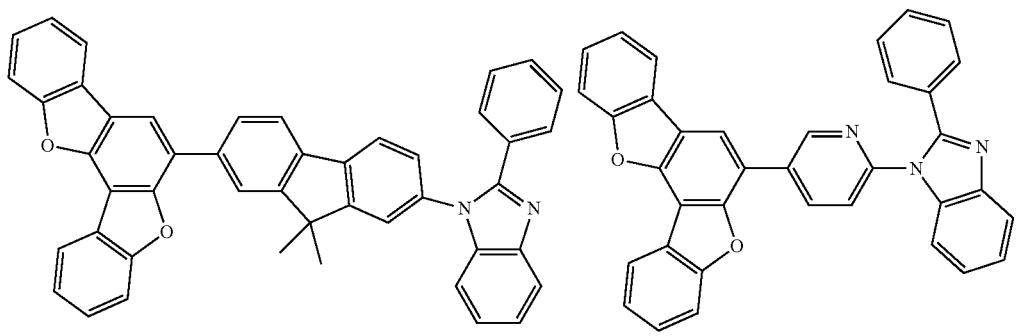
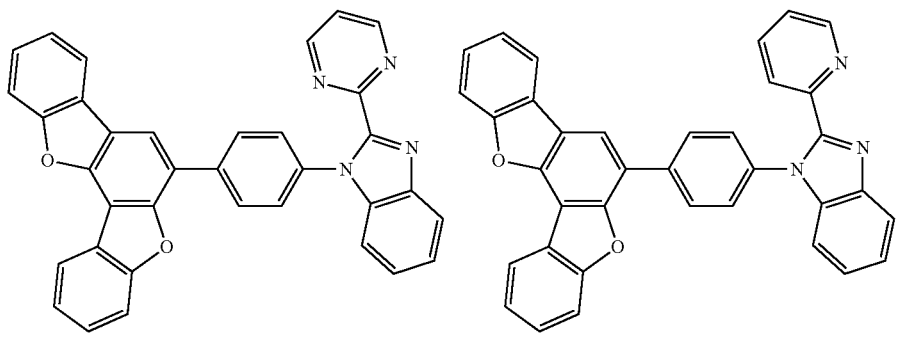
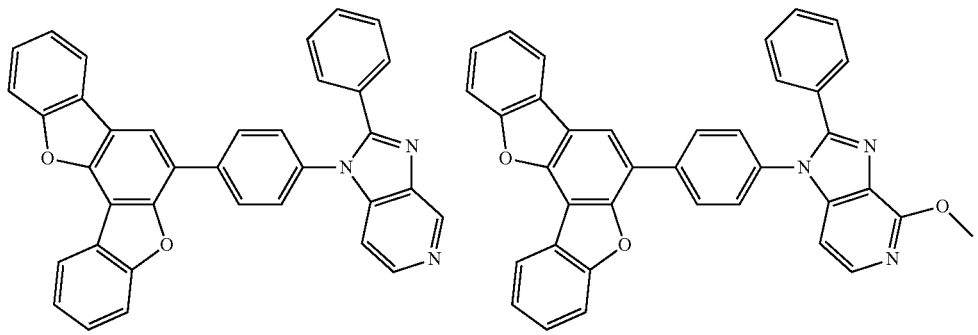

-continued
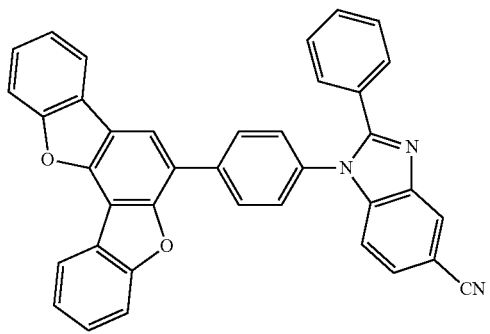
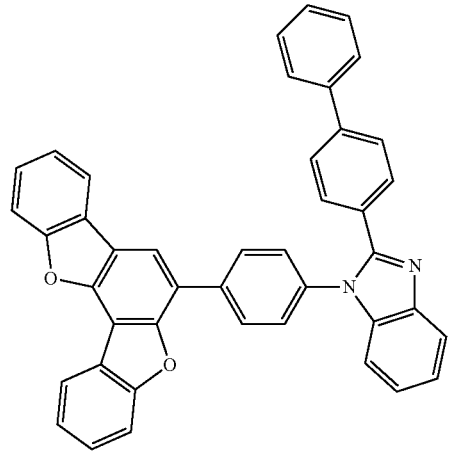
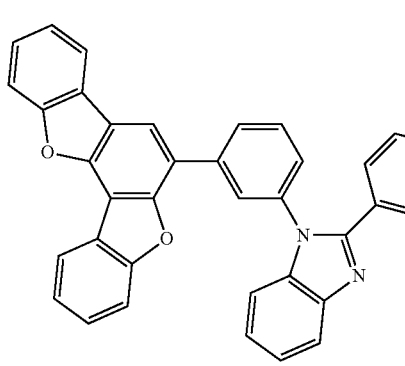
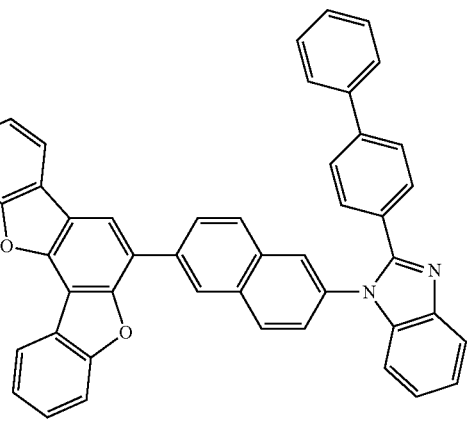
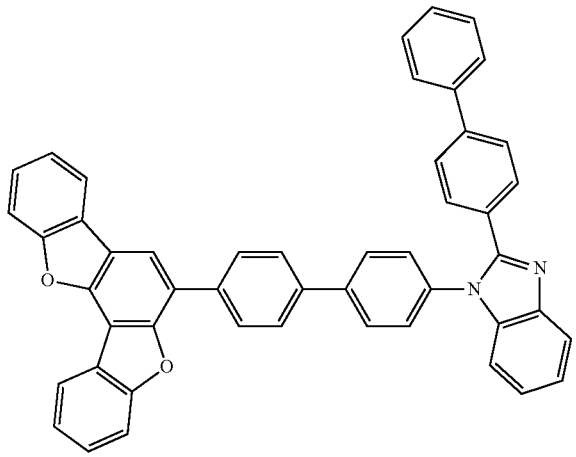
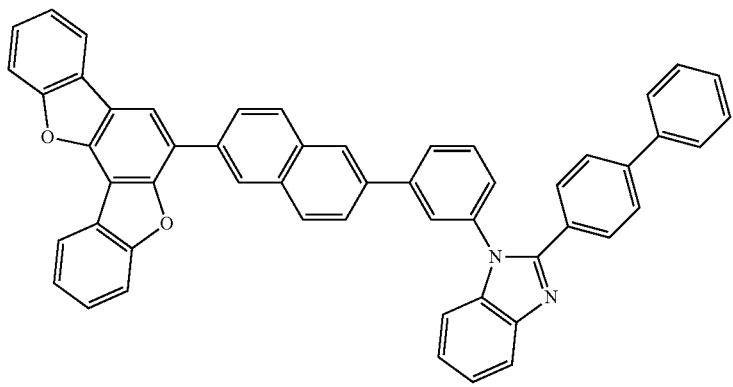

-continued
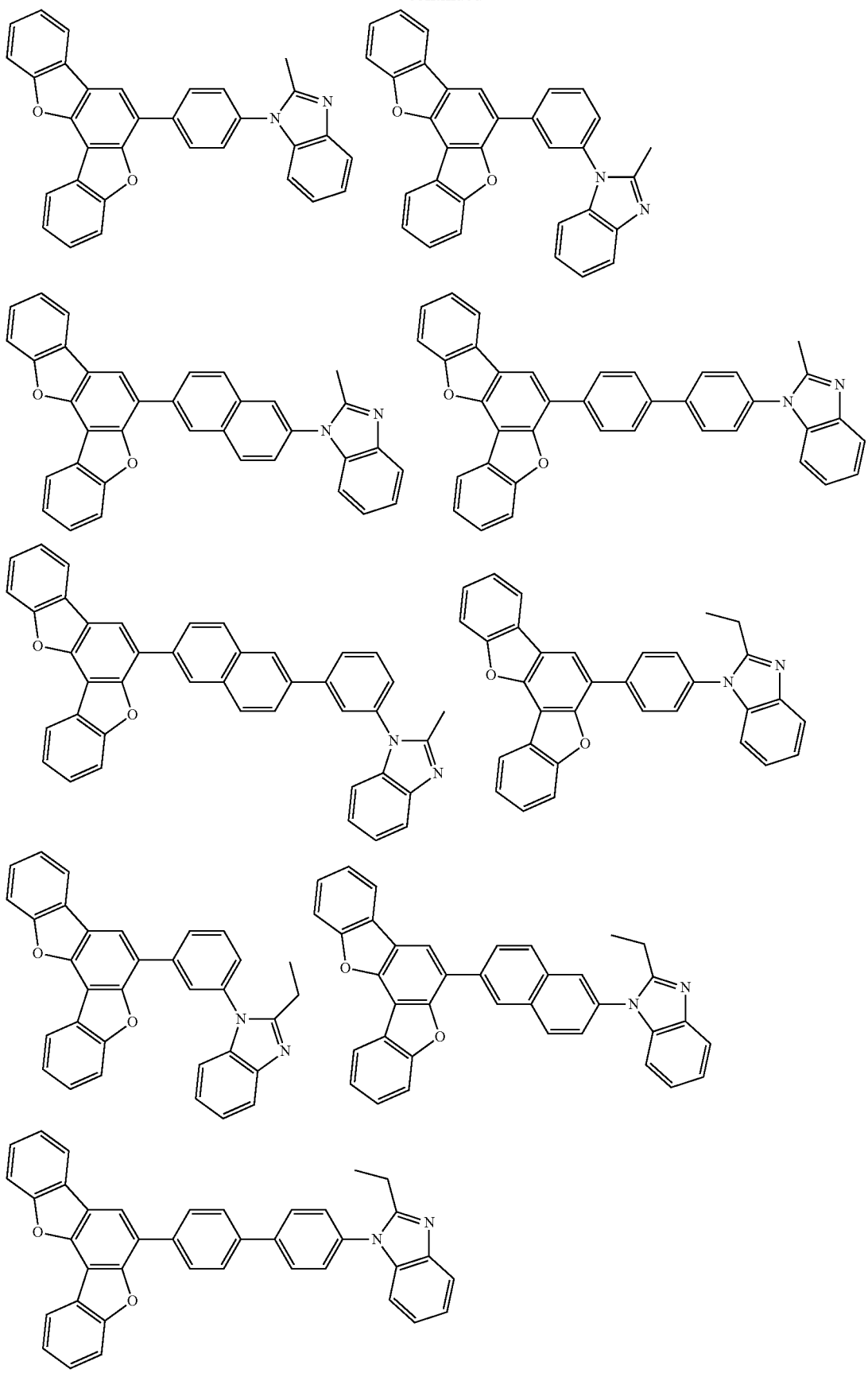

205 206
-continued
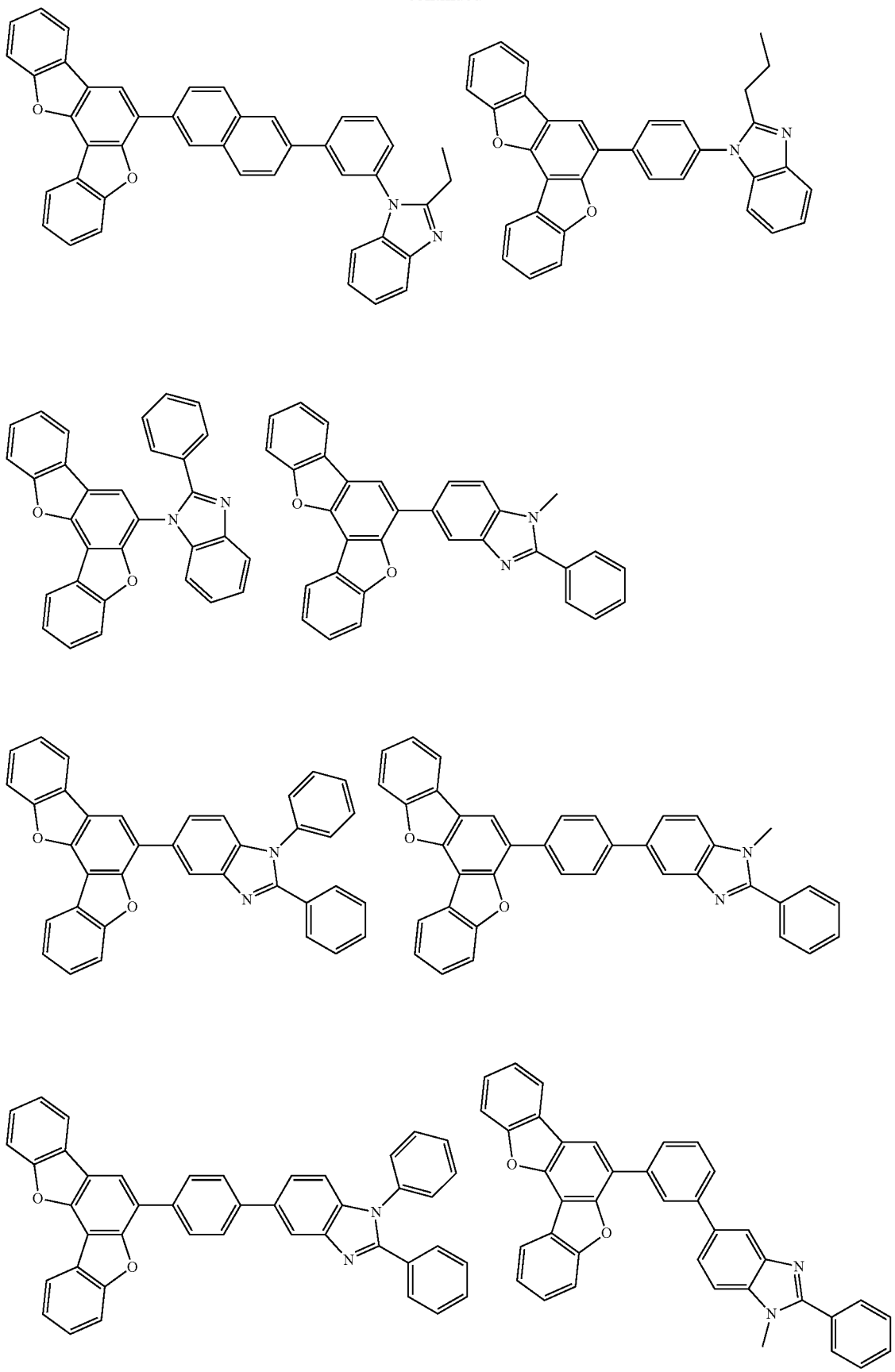

-continued
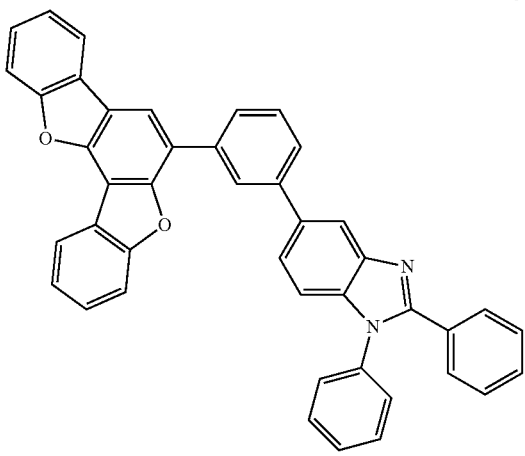
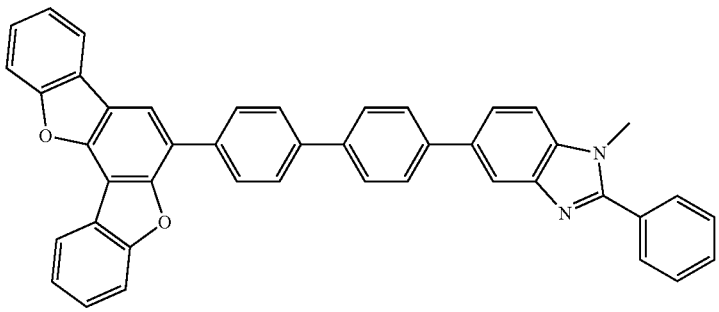
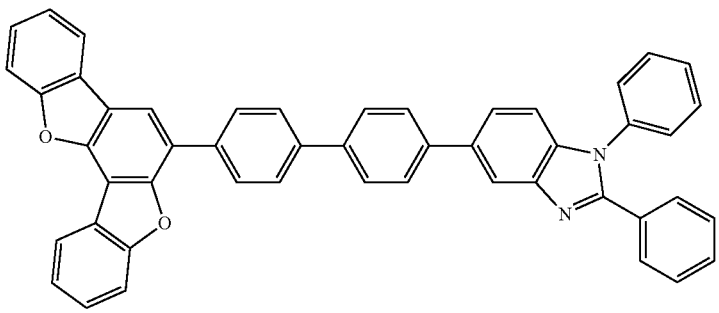
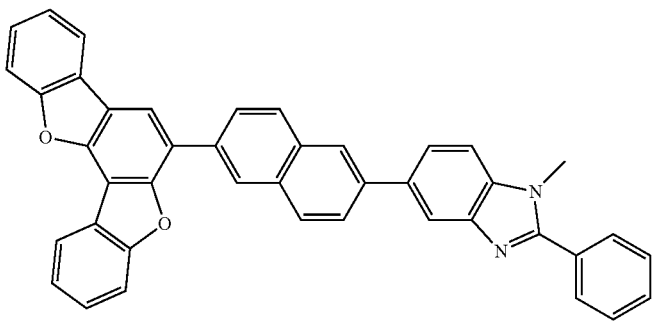

209 210
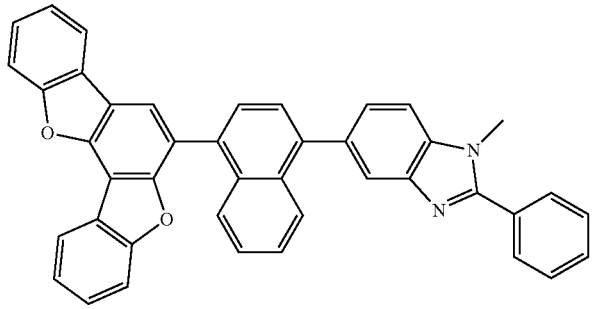 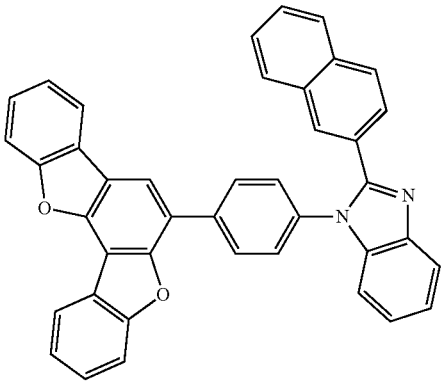
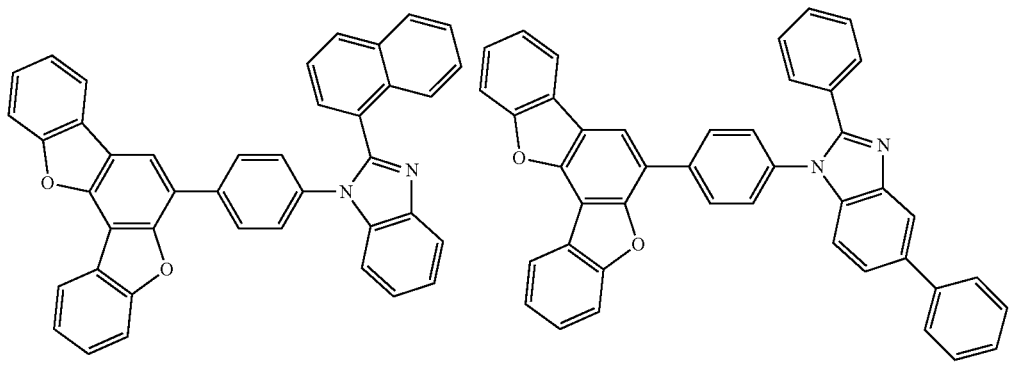
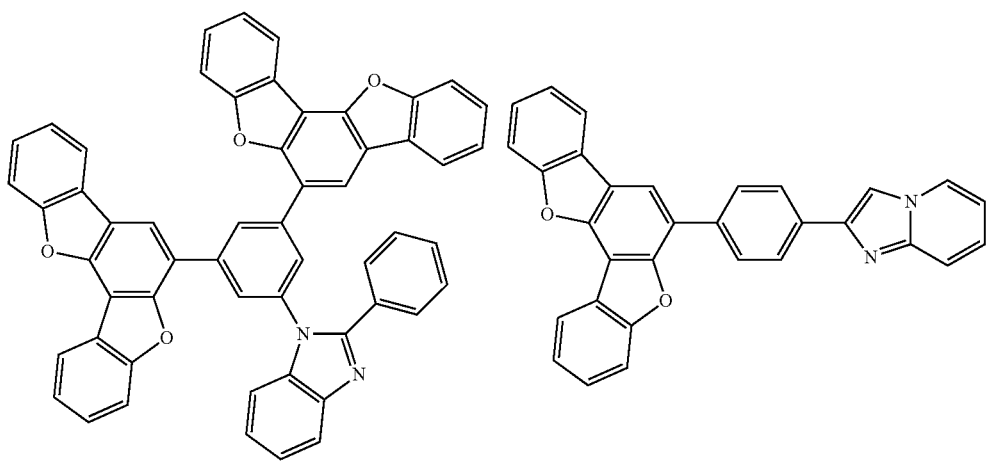
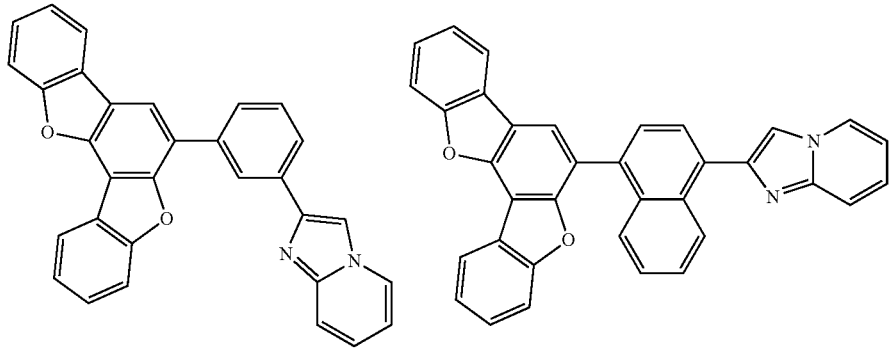

-continued
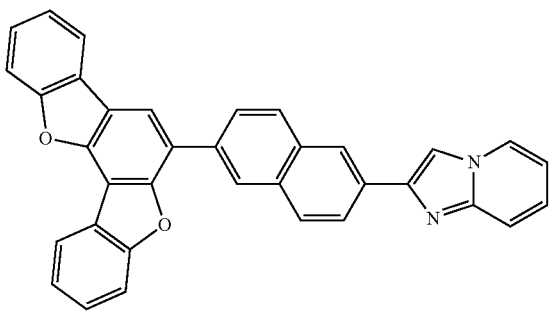
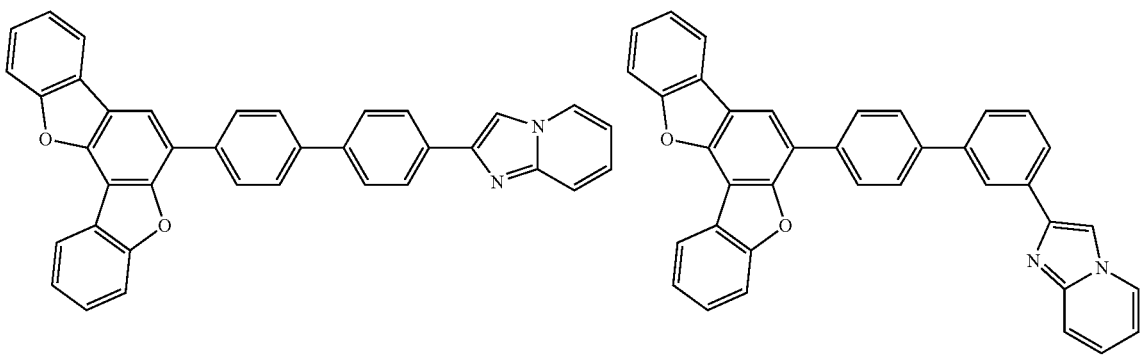
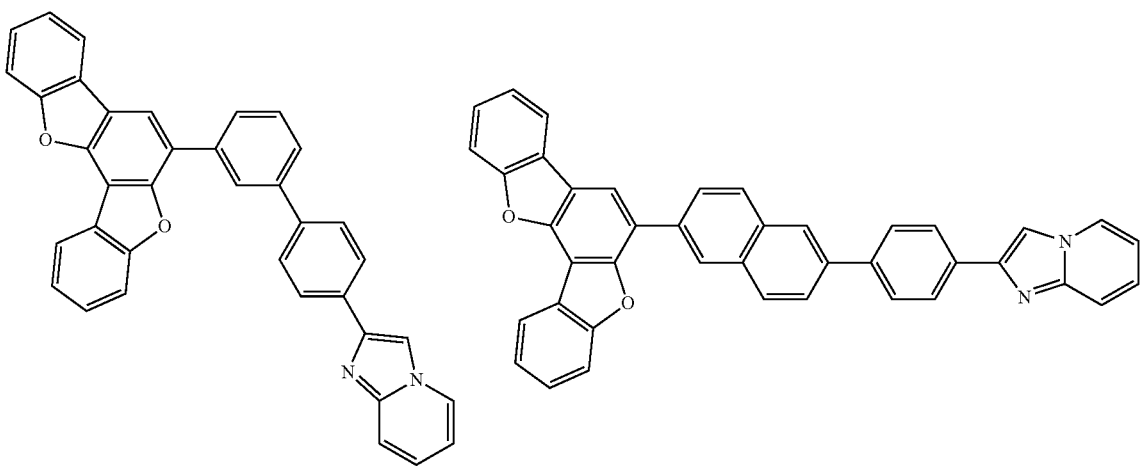
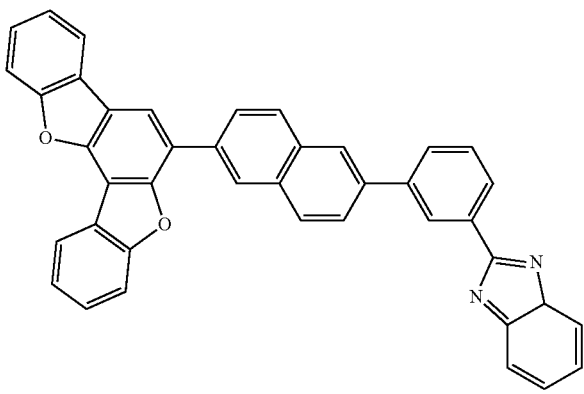

-continued
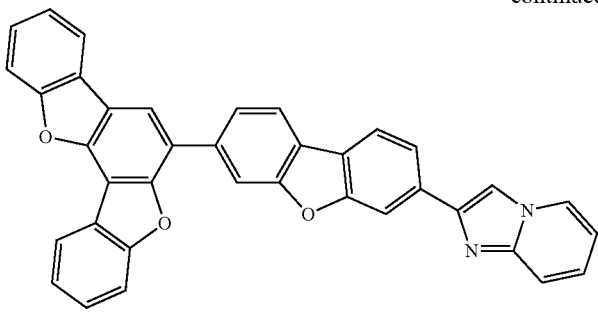
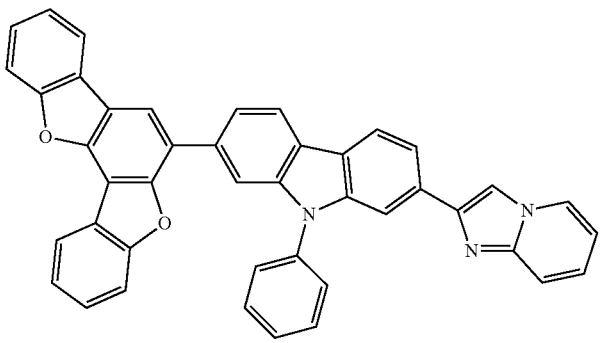
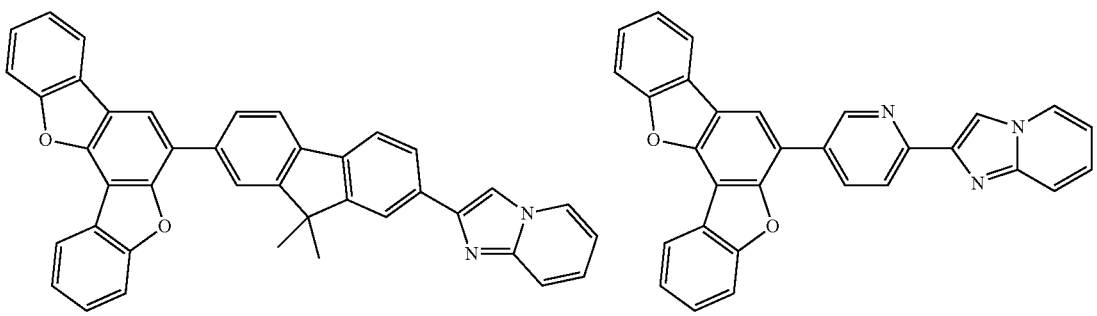
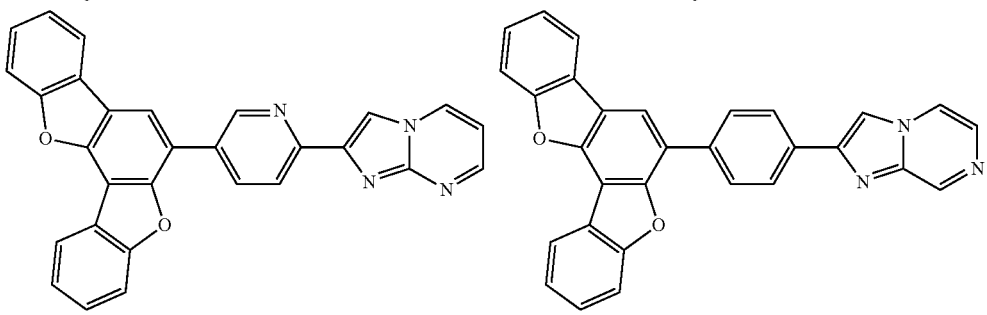
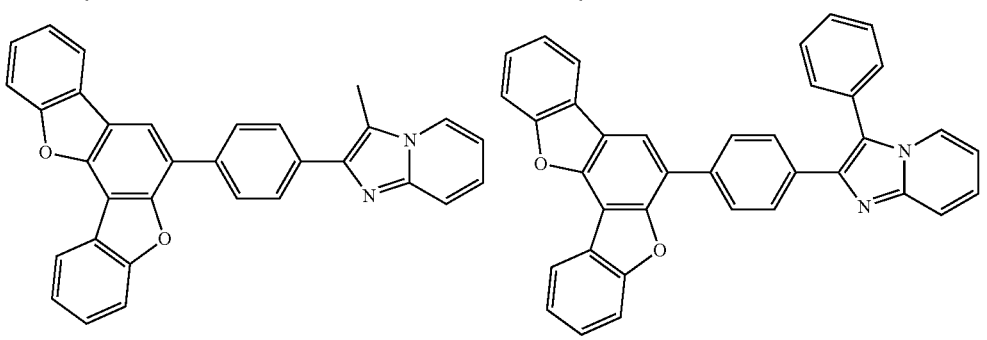

215 216
-continued
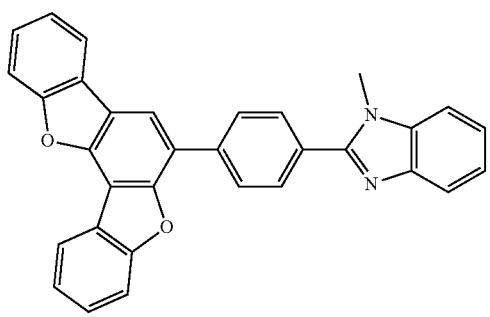 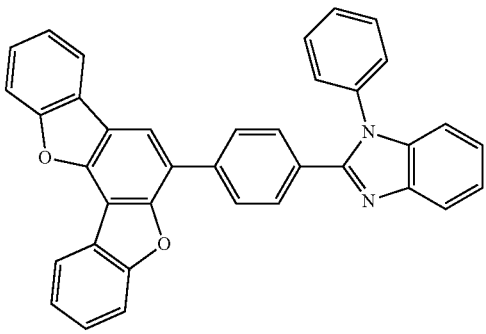
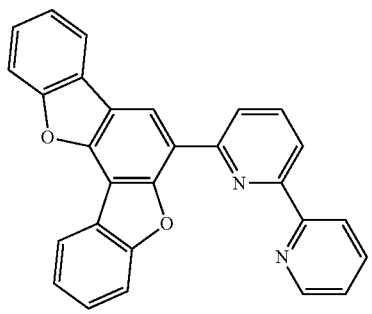 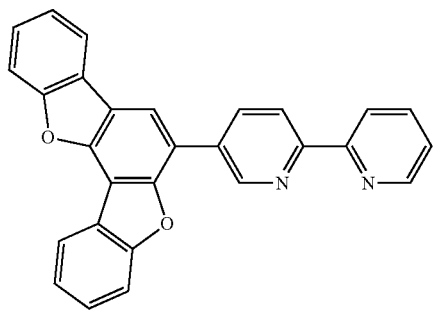
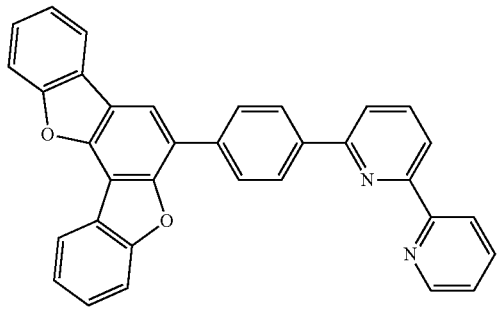 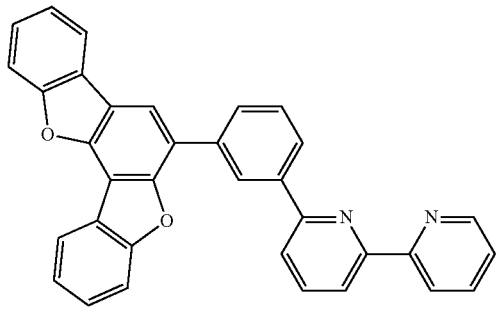
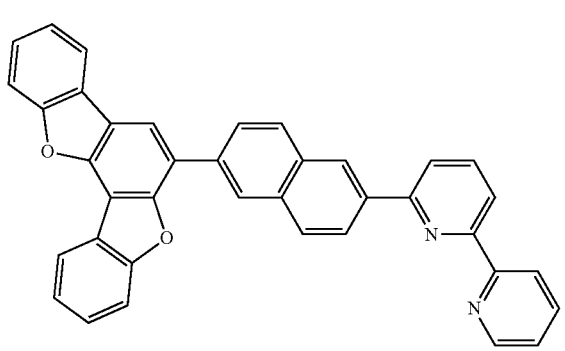 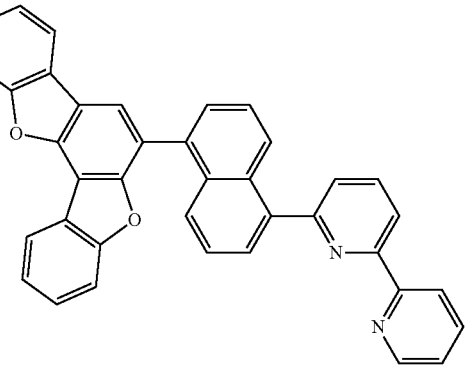
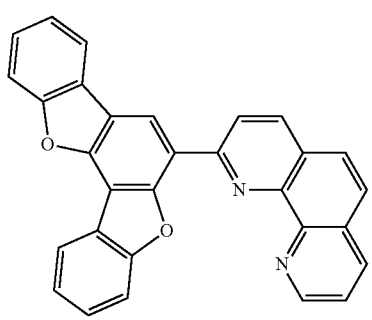 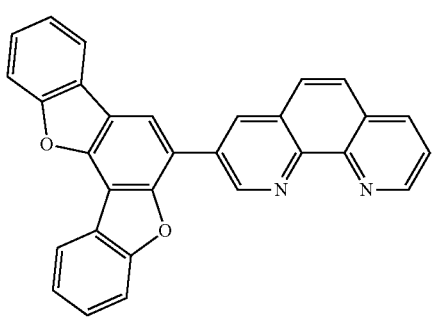

217 218
-continued
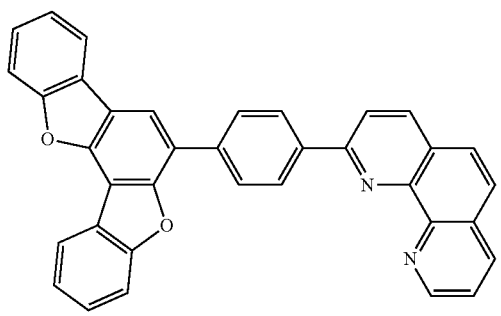 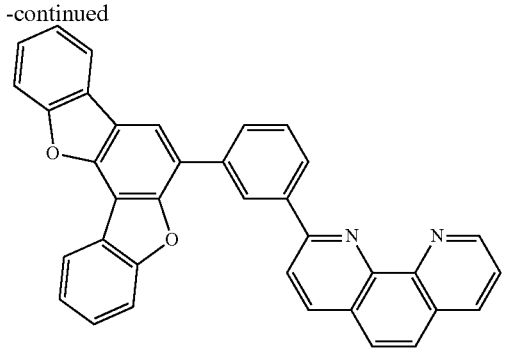
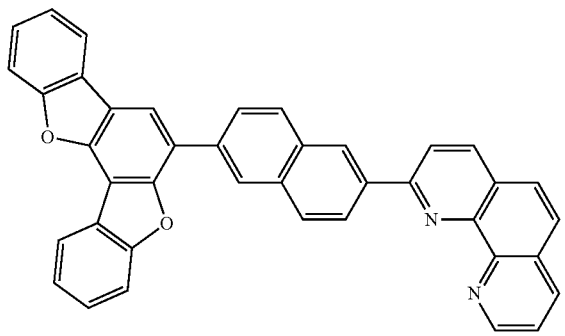 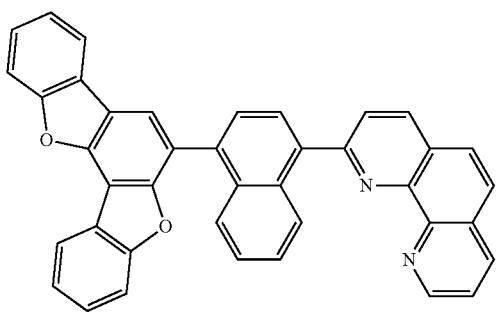
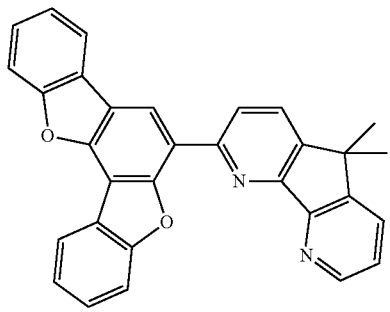 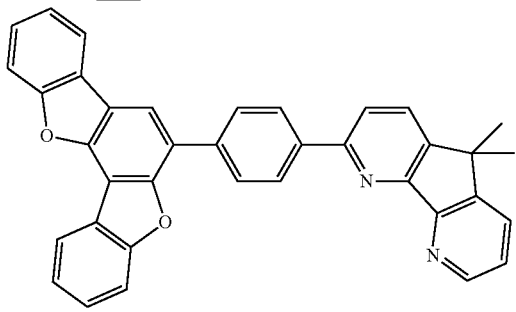
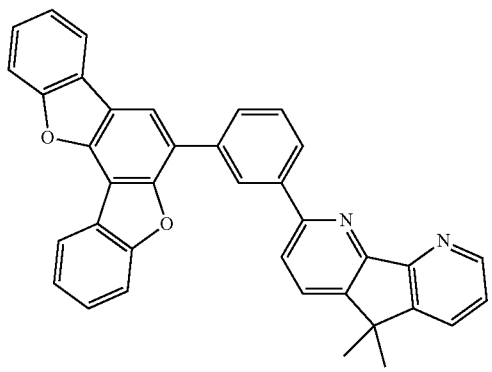 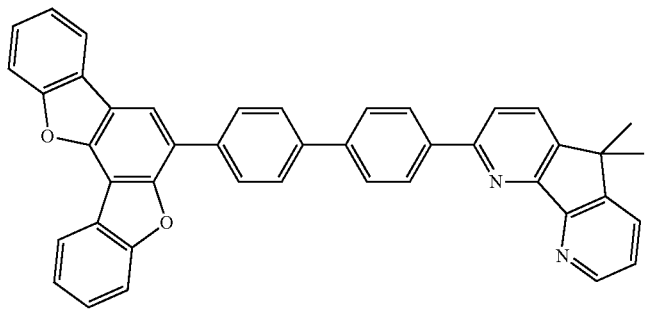
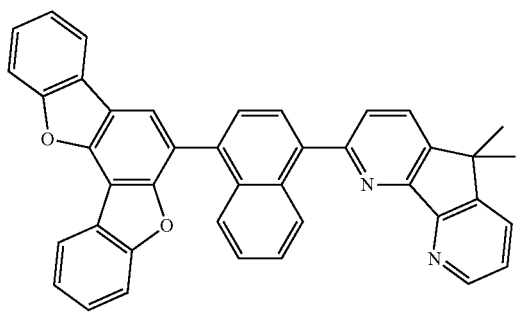 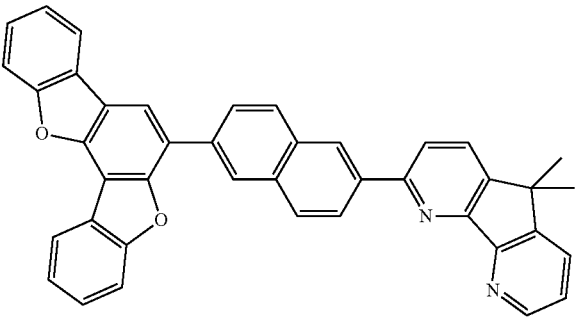

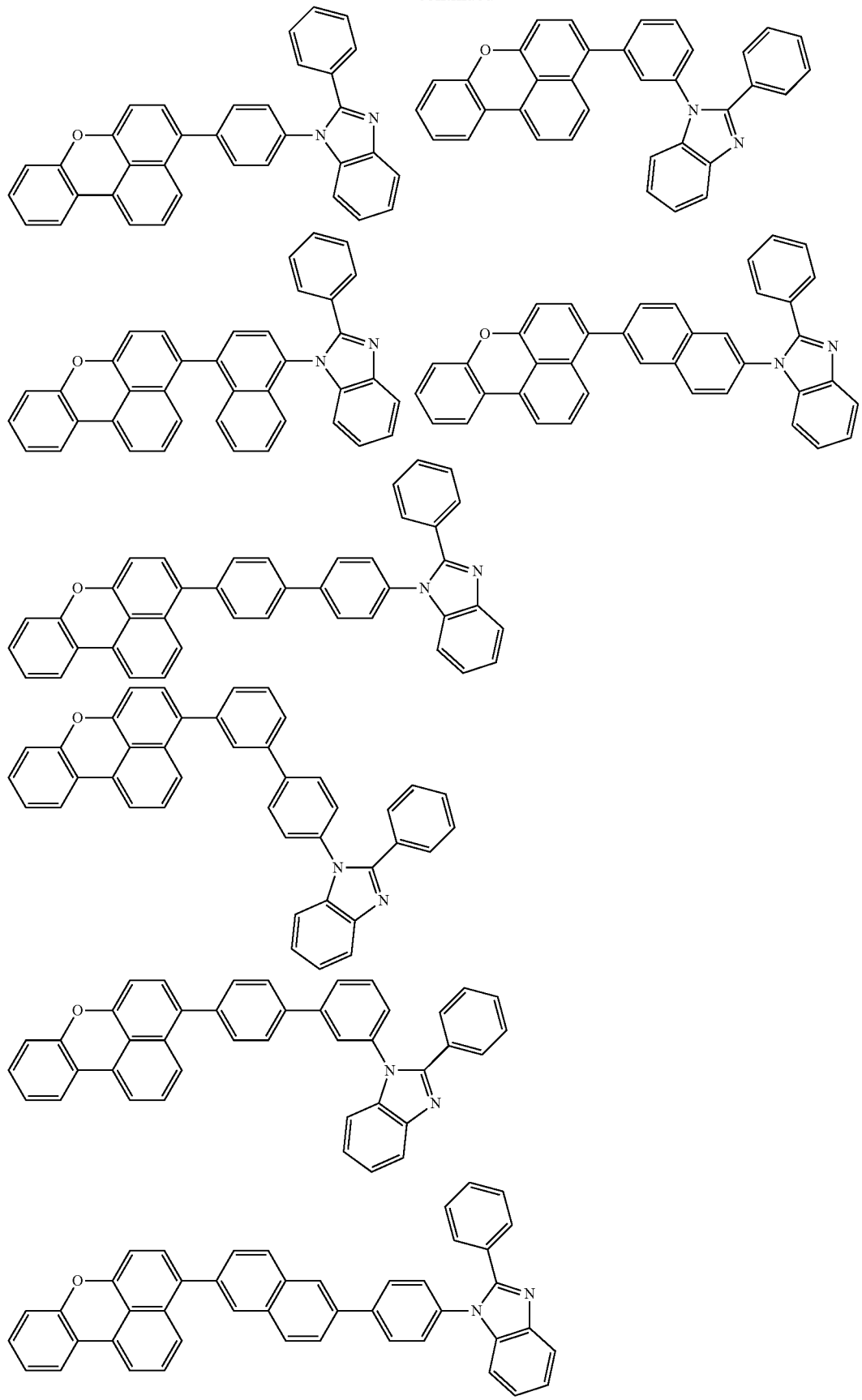

221
-continued
222
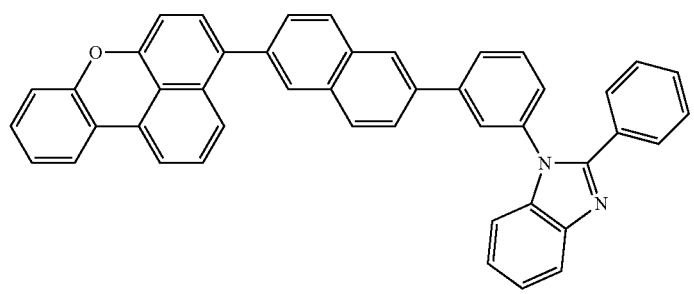
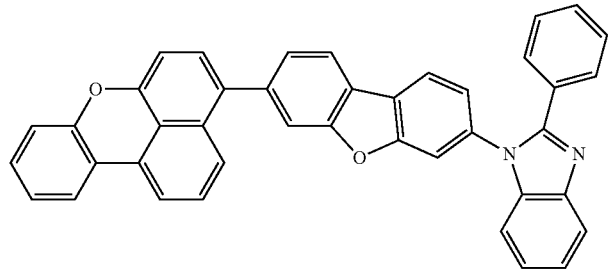
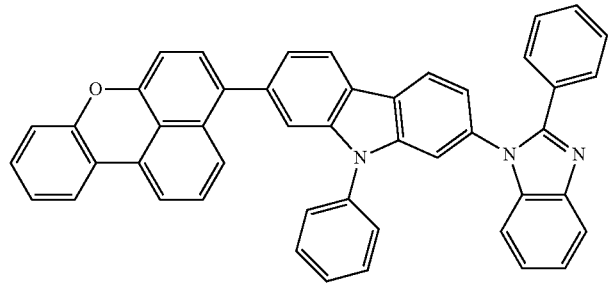
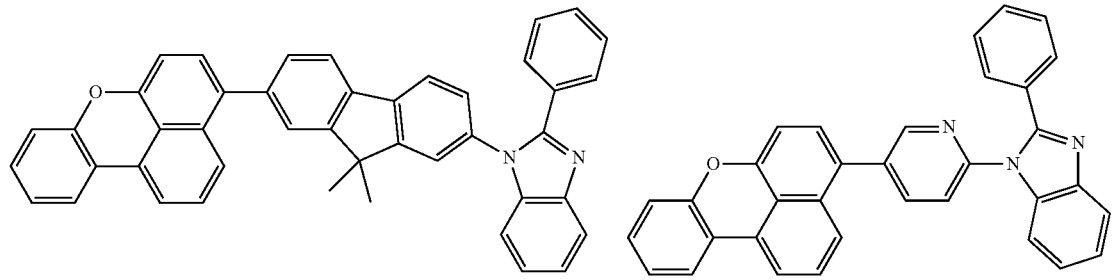
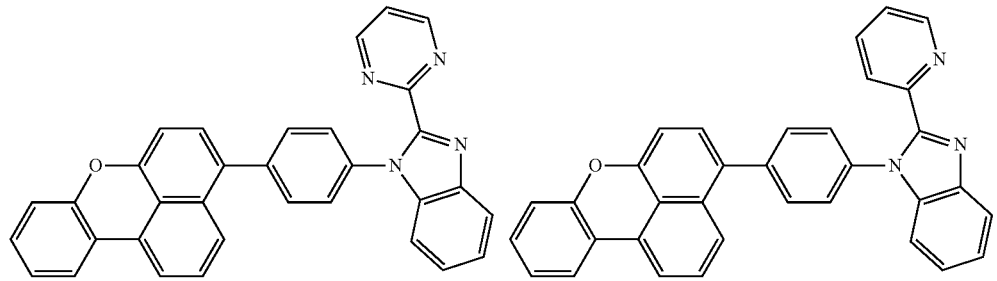
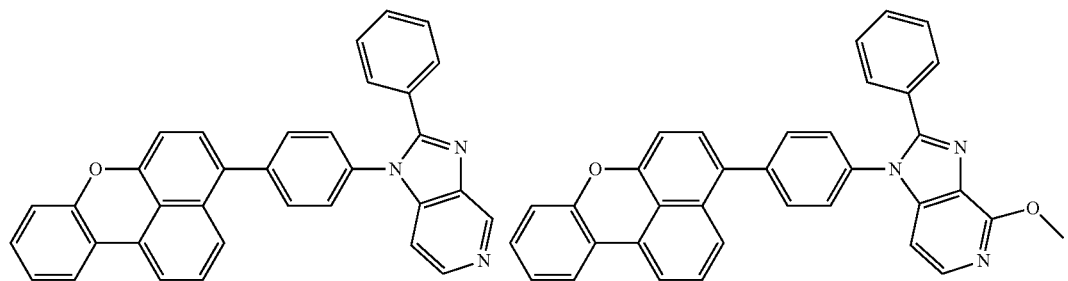

223 224
-continued
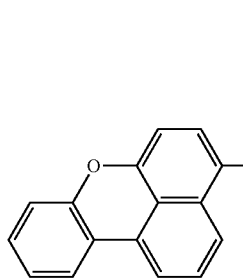 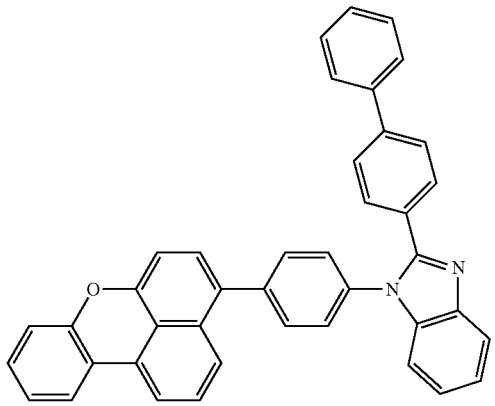
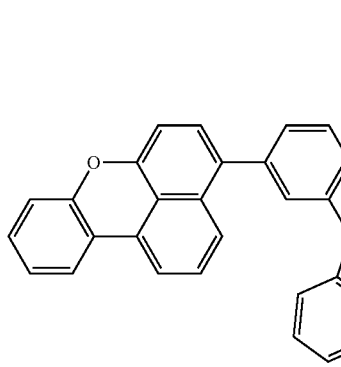 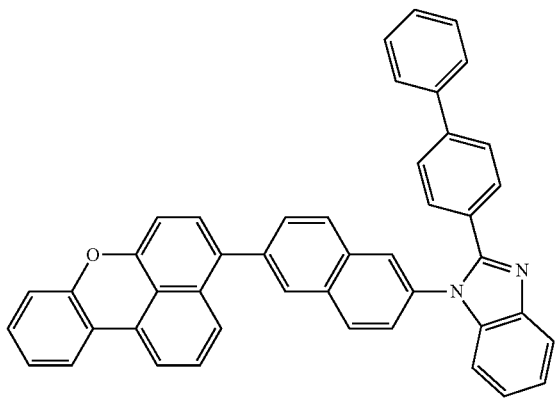
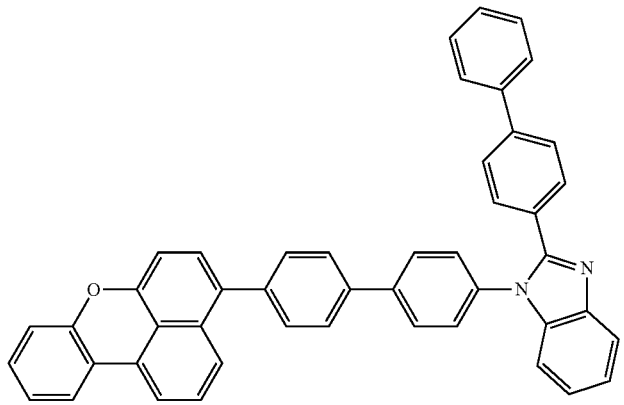
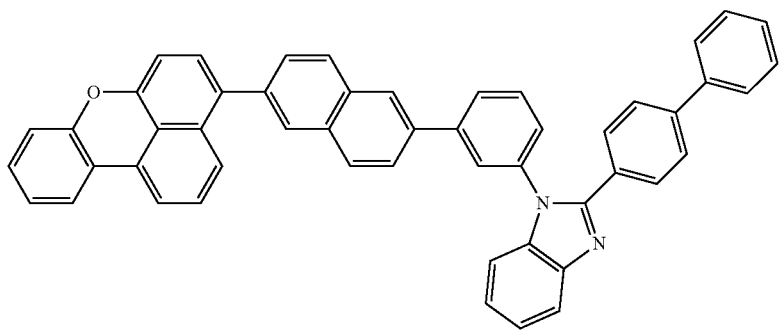

225 226
-continued
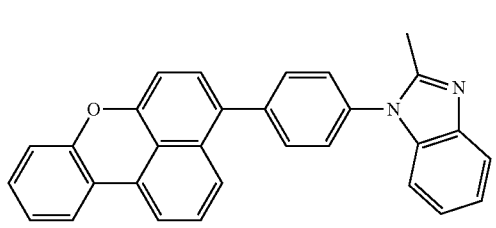
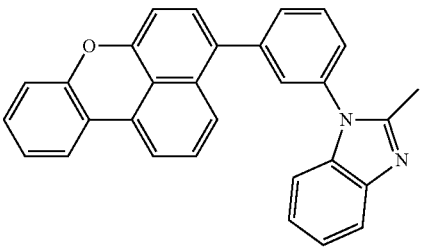
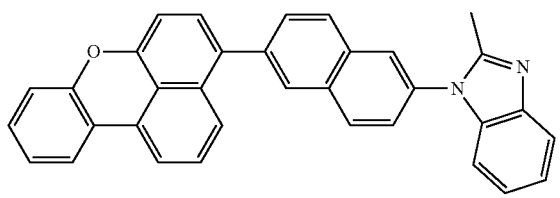
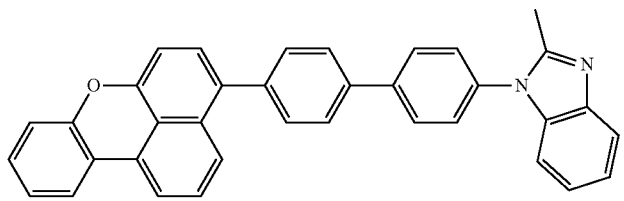
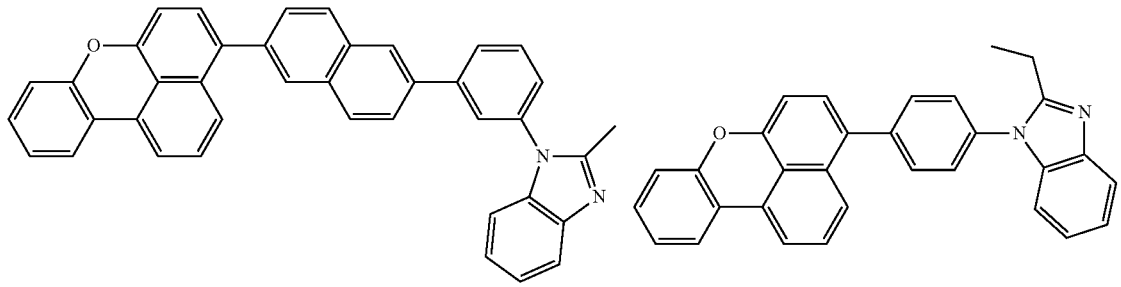
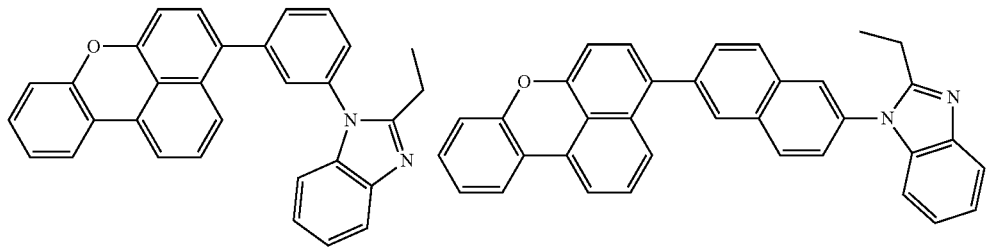
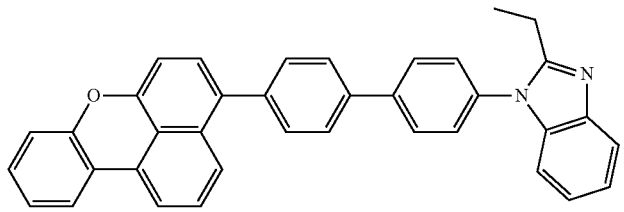
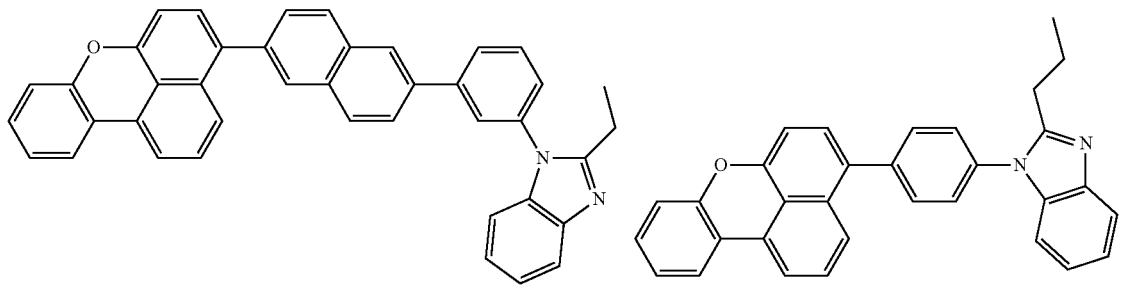

227
228
-continued
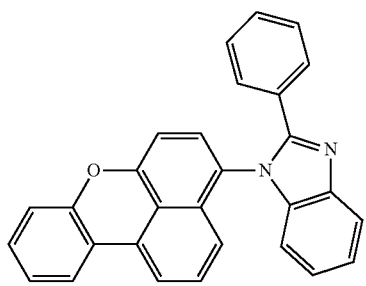 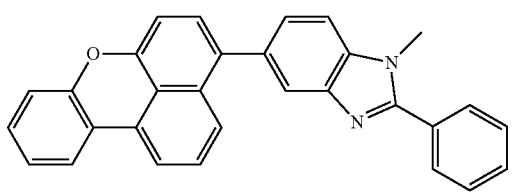
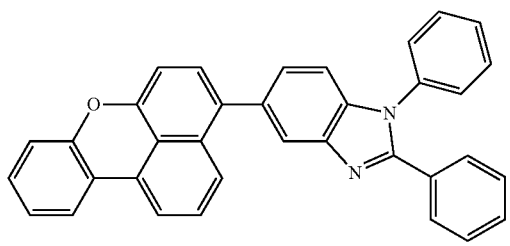 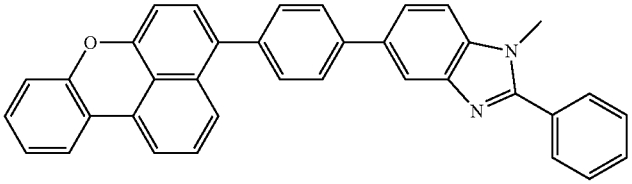
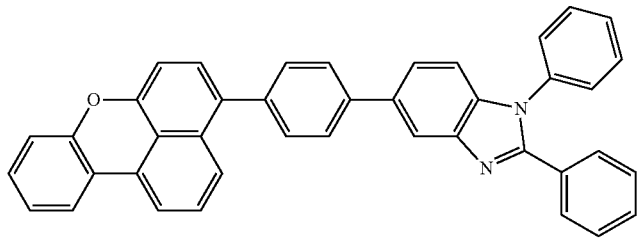
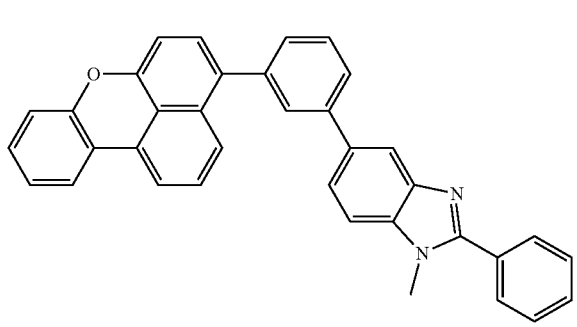 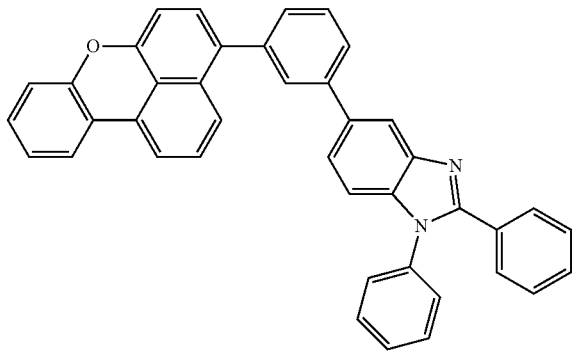
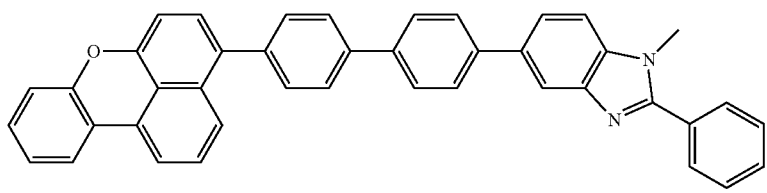
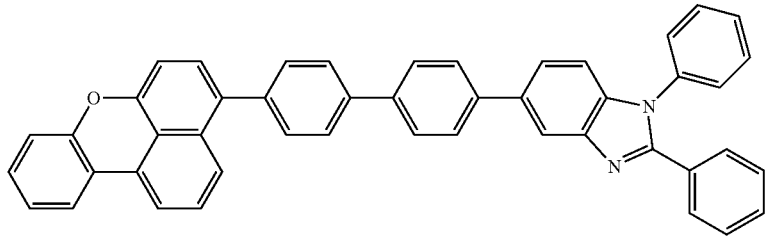

-continued
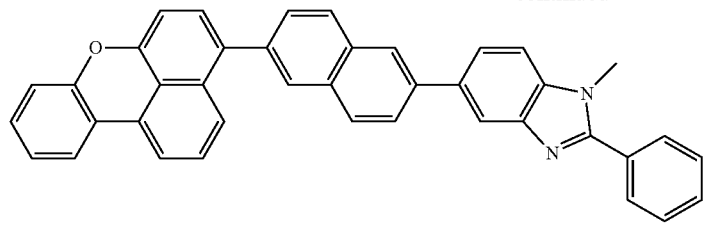
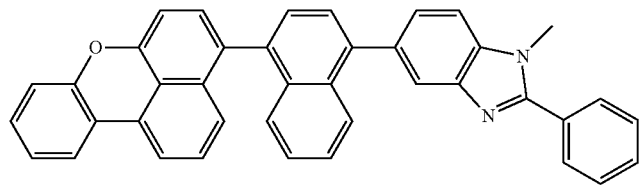
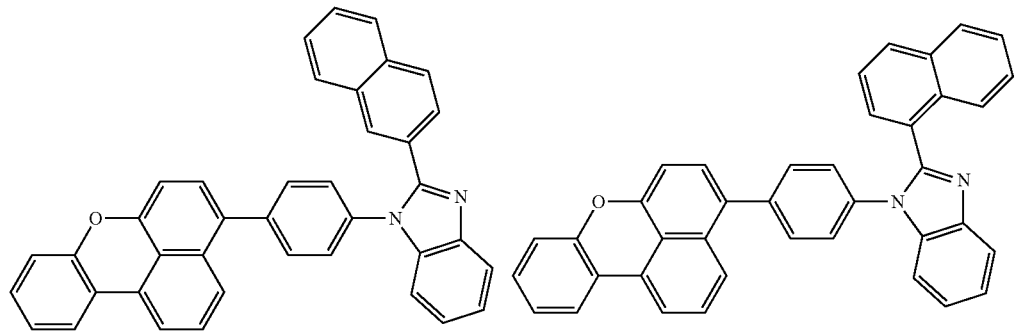
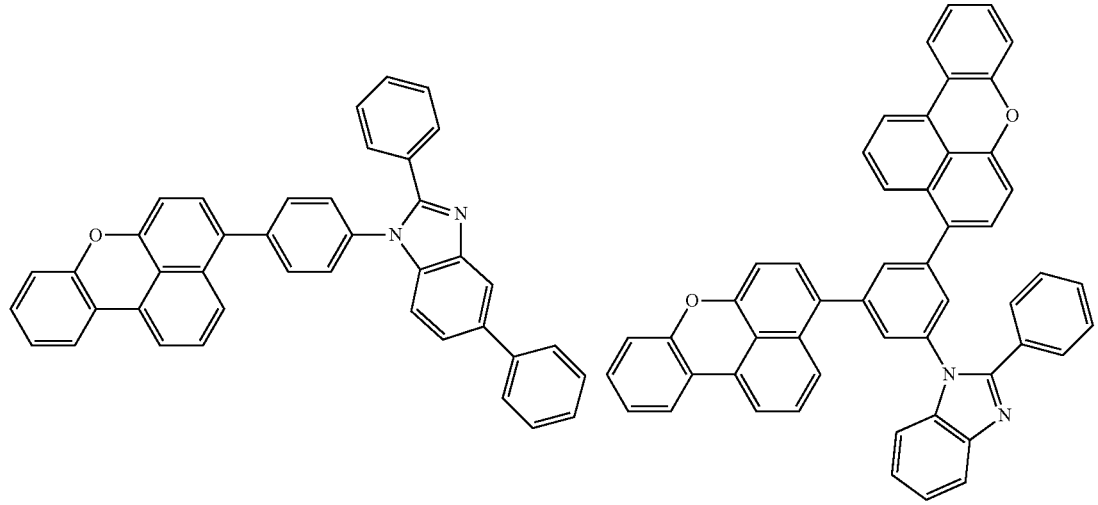
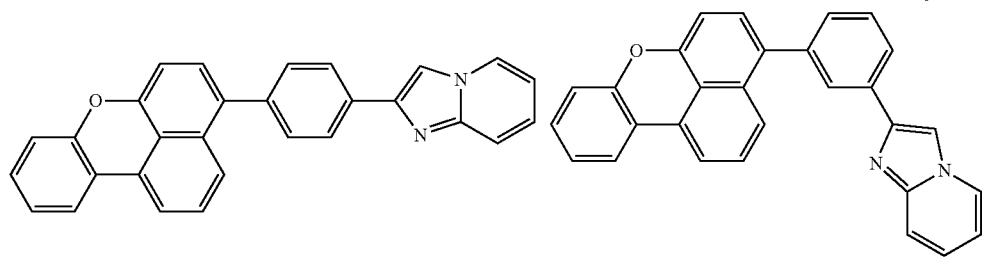
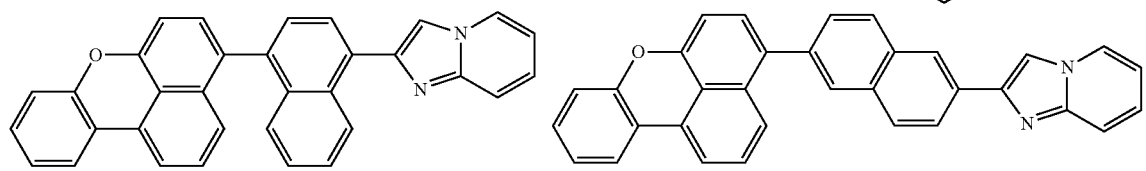

231
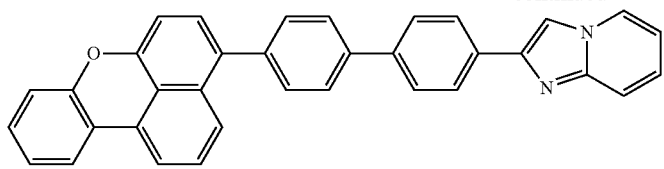
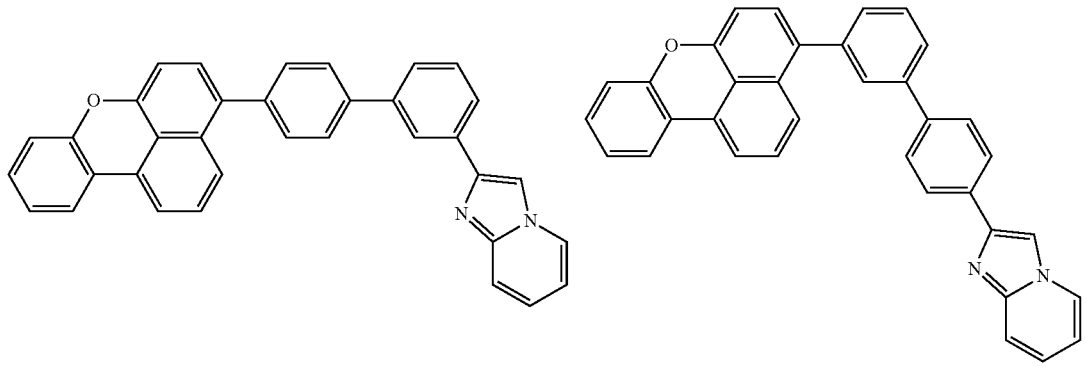
232
-continued
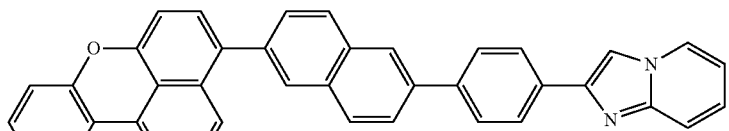
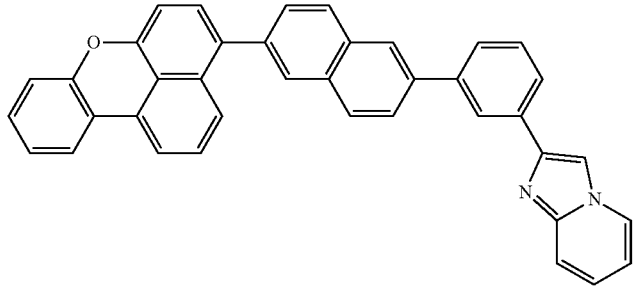
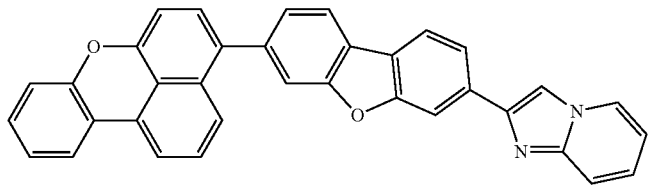
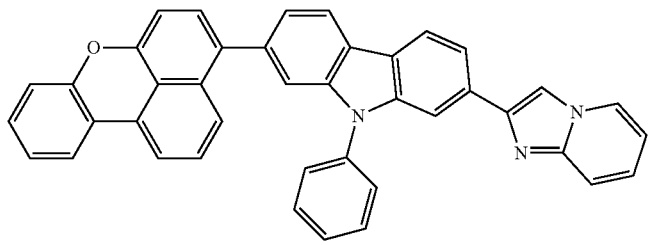
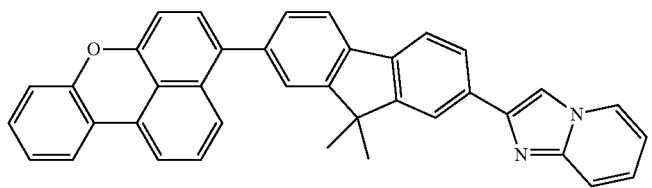

233 234
-continued
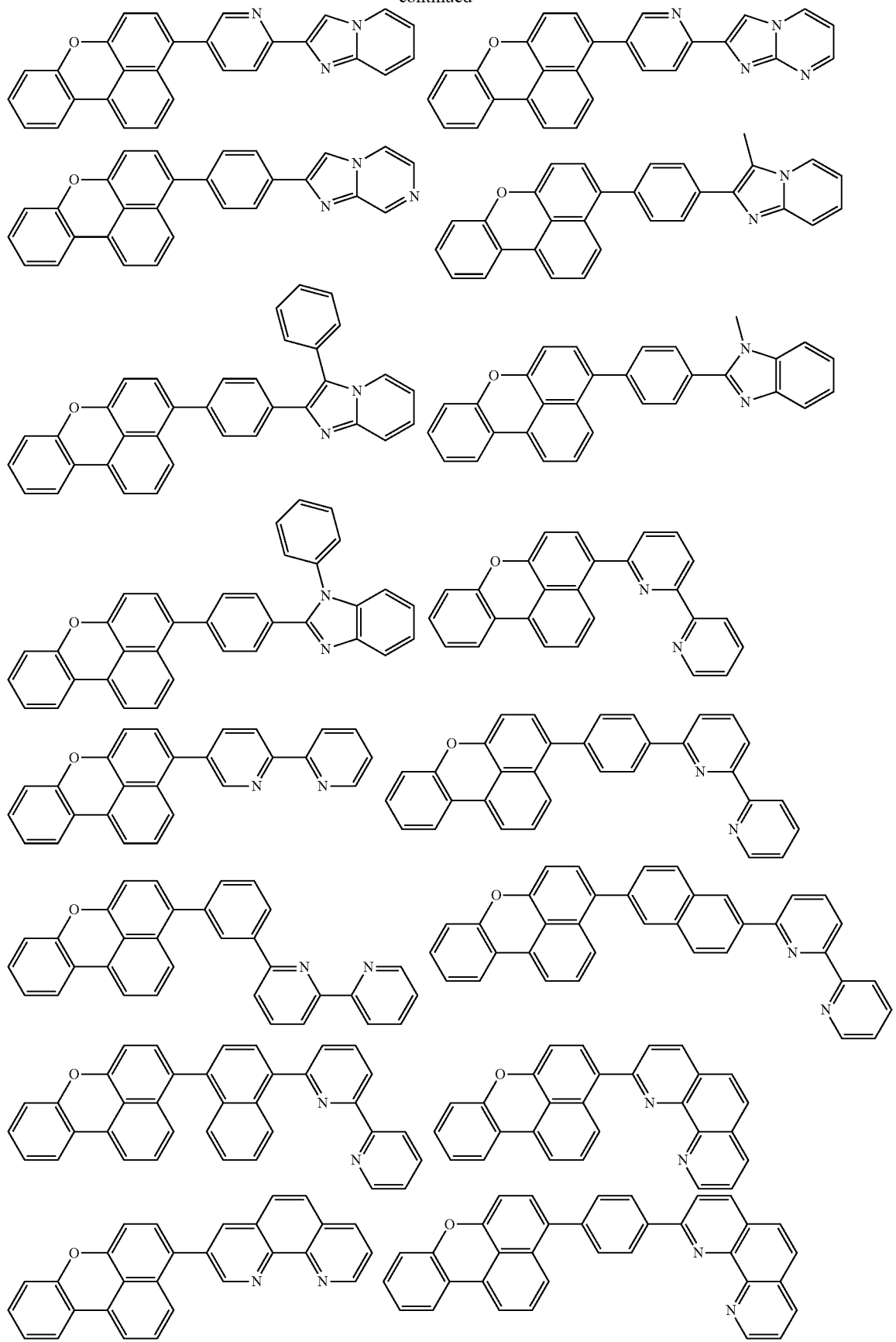

235 236
-continued
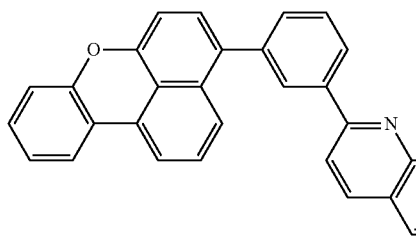
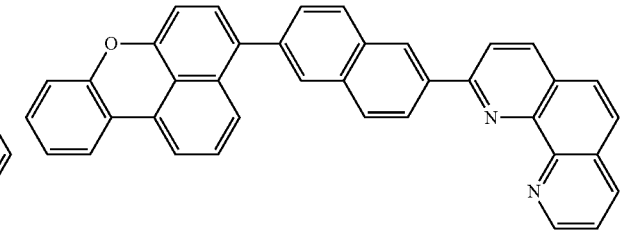
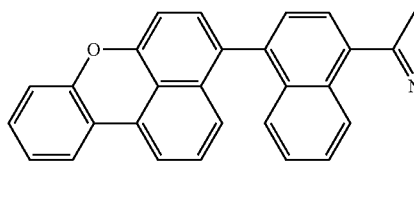
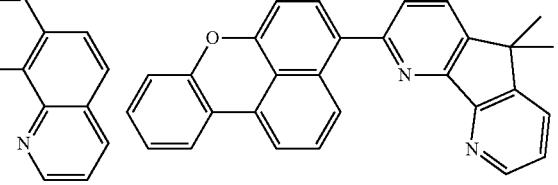
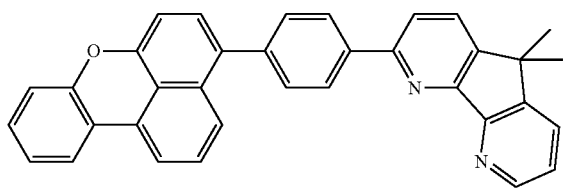
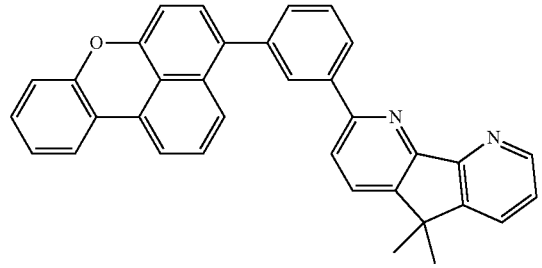
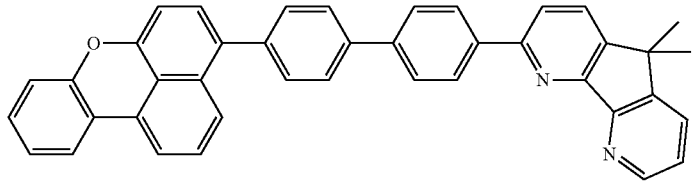
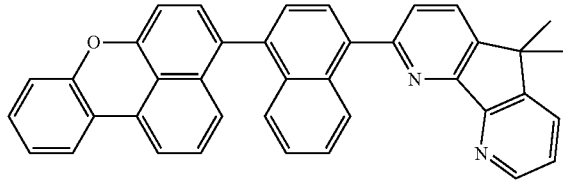
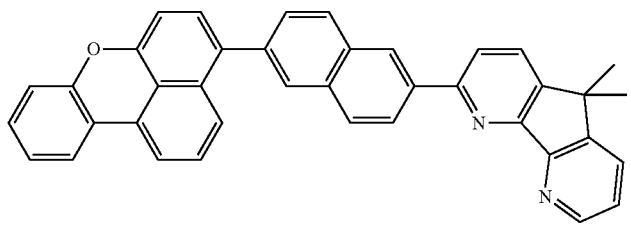
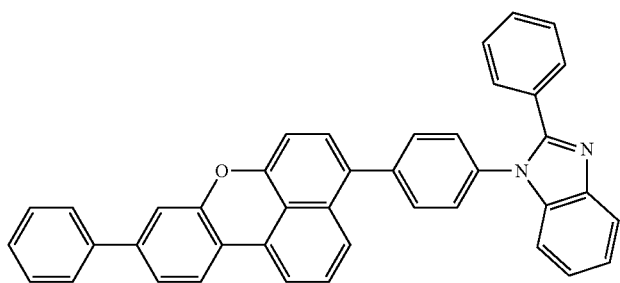

-continued
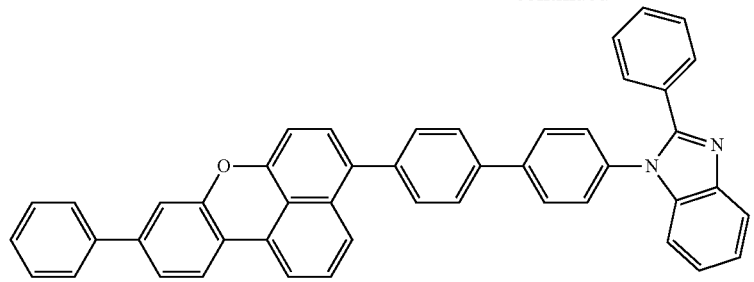
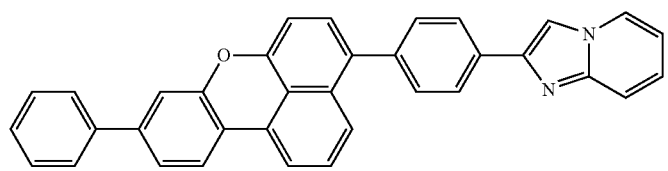
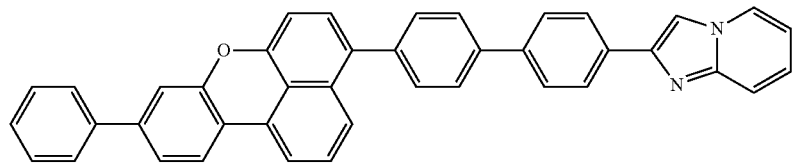
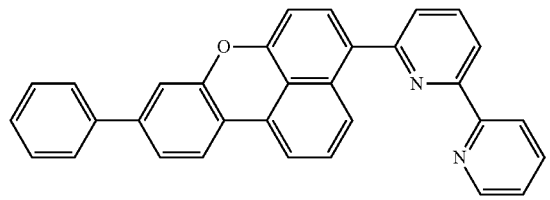
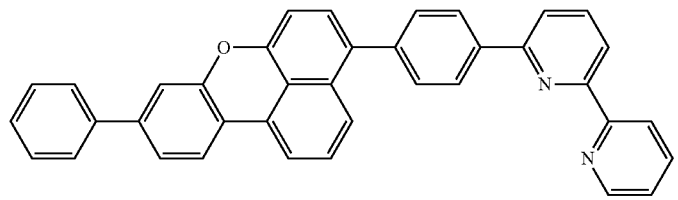
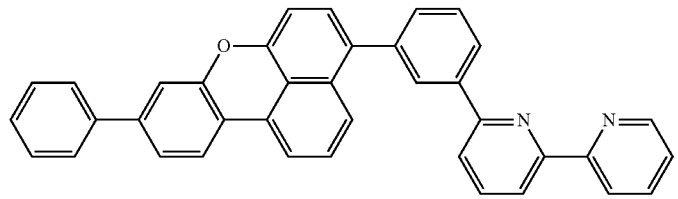
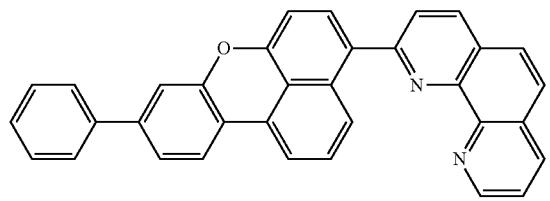
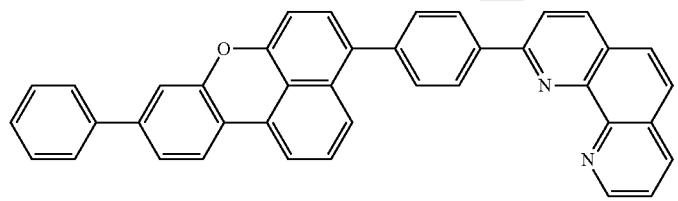

-continued
| 239 | 240 |
|---|---|
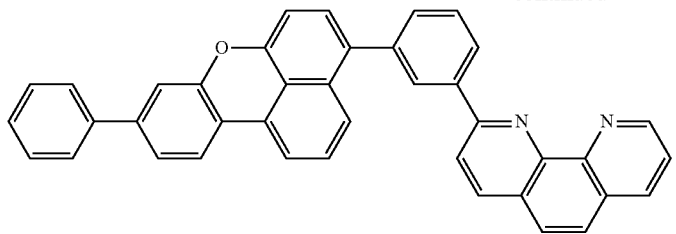
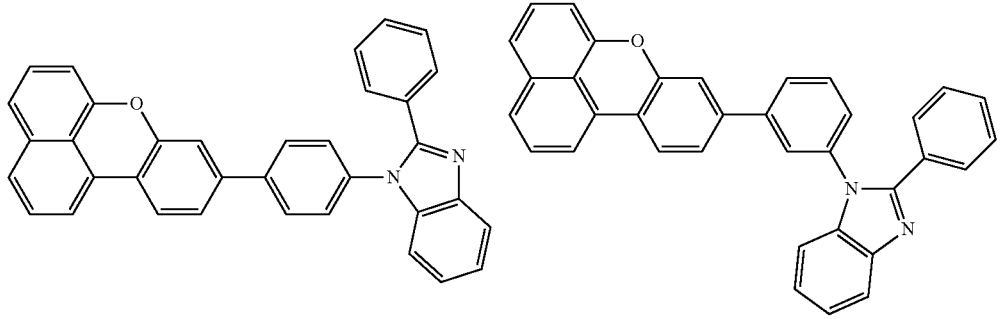
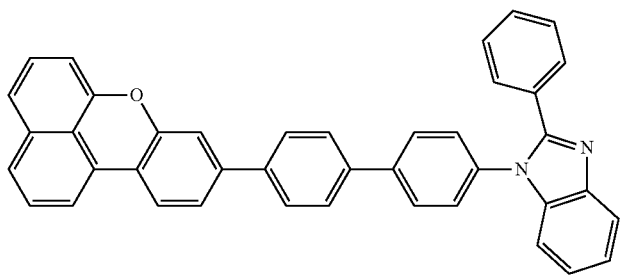
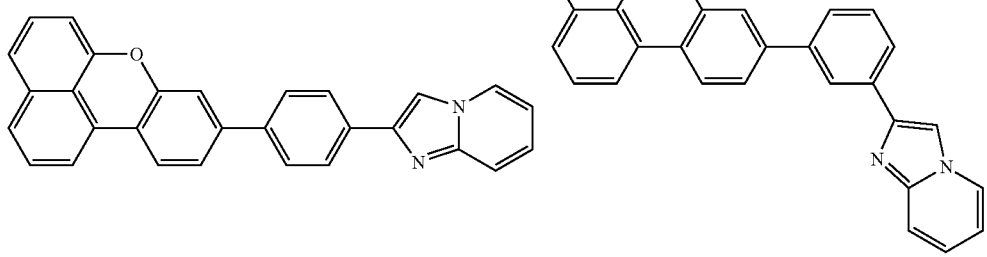
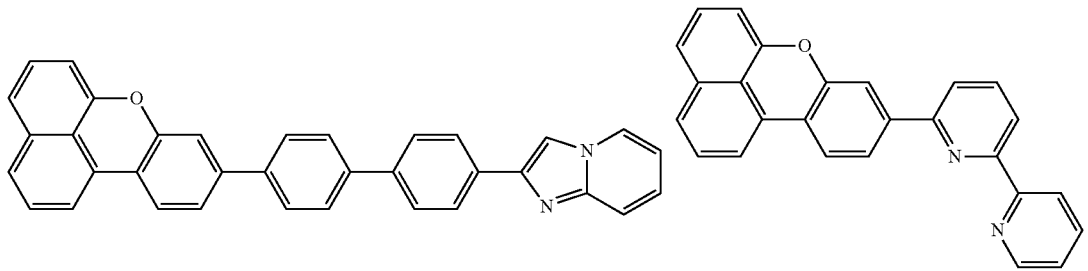
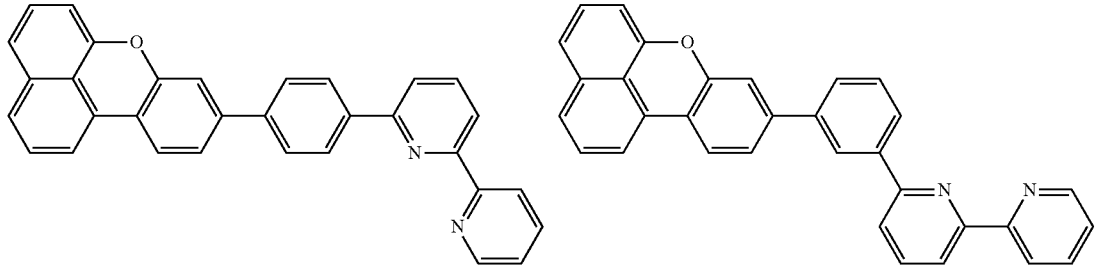

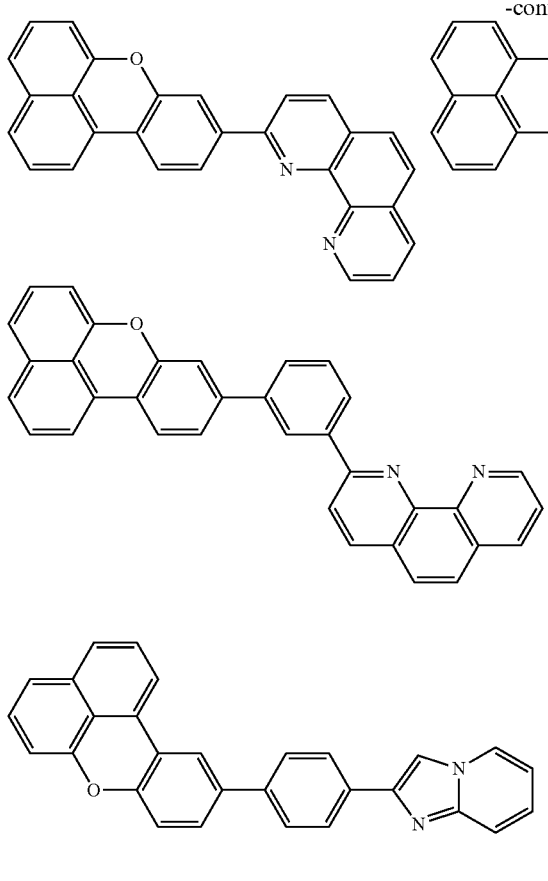

It is preferred that the oxygen-containing fused ring derivative of the invention be used as a material for an organic EL device. It is more preferred that it be used as a material for a blocking layer of an organic EL device.

A compound having a structure represented by the formulas (9) to (15), which is a basic skeleton of the oxygen-containing fused ring derivative of the invention, has a high triplet energy and is highly effective for confining triplet excitons. Therefore, when used as a material for a blocking layer which is in contact with the emitting layer of an organic EL device, for example, a TTF phenomenon can be promoted. Further, the oxygen-containing fused ring structure which is a basic skeleton of the oxygen-containing fused ring derivative of the invention has a feature that, stacking of molecules in the thin film is increased due to its high flatness, whereby electron-transporting property is increased. As a result, injection of electrons to the emitting layer is promoted, efficiency of recombination in the emitting layer are enhanced, whereby a TTF phenomenon can be effectively caused.

Conventionally, a TTF phenomenon is confirmed in the case where in the compounds used in the blocking layer, a part having the lowest triplet energy is a fused ring group of hydrocarbon. Further, it has been confirmed that, as in the case of the oxygen-containing fused ring derivative of the invention in which the heterocyclic part has the lowest triplet energy, a TTF phenomenon can be effectively occurred.

Further, since the oxygen-containing fused ring derivative of the invention contains a nitrogen-containing heterocyclic ring having a high injection property of electrons from a metal-containing layer such as an electrode, it is possible to realize a low-voltage-driving organic EL device without further stacking an electron-injecting layer.

A brief explanation will be given below referring to a TTF phenomenon.

When a voltage is applied to an organic EL device, holes are injected from an anode, and electrons are injected from a cathode, and the injected holes and electrons are recombined in an emitting layer to form an exciton. Regarding the spin state, singlet excitons and triplet excitons are formed in an amount ratio of 25%:75%. In a fluorescent device which has conventionally been known, light is emitted when singlet excitons are relaxed to the ground state. The remaining triplet excitons are returned to the ground state through a thermal deactivation process without emitting light. According to S. M. Bachilo et al (J. Phys. Cem. A, 104, 7711 (2000)), of 75% triplet excitons initially generated, one fifth thereof are changed to singlet excitons.

A TTF phenomenon is a phenomenon in which singlet excitons are generated by the collision and fusion of the triplet excitons. By utilizing the TTF phenomenon, not only 25% singlet excitons initially generated, but also singlet excitons which are generated by the collision and fusion of triplet excitons can be used for emission, whereby luminous efficiency of a device can be improved.

In order to allow a TTF phenomenon efficiently, it is required to confine triplet excitons, which have a significantly higher exciton life as compares with singlet excitons, in the emitting layer.

In the invention, it is preferred that a blocking layer comprising the oxygen-containing fused ring derivative of the invention be in adjacent to the emitting layer of a fluorescent device. In a fluorescent device using singlet excitons having a short exciton life, a blocking layer which causes the number of layer-stacking processes to be increased is not generally used. However, by using a blocking layer comprising the oxygen-containing fused ring derivative of the invention in a fluorescent device, a TTF phenomenon is generated, whereby a highly effective organic EL device can be realized. Further, since the oxygen-containing fused ring derivative of the invention has a high triplet energy, it has a function of a blocking layer even when used in a conventional phosphorescent device, whereby diffusion of triplet energy can be prevented.

In the invention, when reference is simply made to a "blocking layer", it means a layer of blocking triplet energy, and has a function different from a hole-blocking layer or a charge-blocking layer.

It is preferred that the blocking layer comprising the oxygen-containing fused ring derivative of the invention have an electron-donating dopant.

The electron-donating dopant is one or two or more selected from an alkali metal, an alkaline-earth metal, a rare earth metal and an oxide of an alkali metal, a halide of an alkali metal, an oxide of an alkaline-earth metal, a halide of an alkaline-earth metal, an oxide of a rare earth metal, a halide of a rare earth metal, an organic complex of an alkali metal, an organic complex of an alkaline-earth metal and an organic complex of a rare earth metal.

In the emitting layer of the organic EL device of the invention, rubrene, anthracene, tetracene, pyrene, perylene or the like can be used. An anthracene derivative is preferable. It is further preferred that an anthracene derivative represented by the following formula (16) be contained.

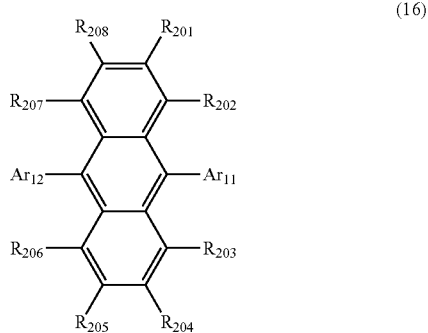

(16)

wherein $Ar_{11}$ and $Ar_{12}$ are independently a substituted or unsubstituted aryl group having 6 to 30 ring carbon atoms or a substituted or unsubstituted heterocyclic group having 5 to 30 ring atoms;

$R_{201}$ to $R_{208}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms or a substituted or unsubstituted heterocyclic group having 5 to 30 ring atoms. The aryl group and the heterocyclic group of $Ar_{11}$ and $Ar_{12}$, the aryl group, the heterocylic group, the alkyl group, the cycloalkyl group, the alkylsilyl group, the arylsilyl group, the alkoxy group and the aryloxy group of $R_{201}$ to $R_{208}$ are as explained in paragraphs 0027 to 0033.

It is preferred that the emitting layer comprising the anthracene derivative represented by the formula (16) be in contact with the blocking layer comprising the oxygen-containing fused ring derivative of the invention. When the emitting layer is in contact with the blocking layer comprising the oxygen-containing fused ring derivative of the invention, luminous efficiency can be improved by utilizing a TTF phenomenon.

When a TTF phenomenon is used, the triplet energy of a compound constituting the blocking layer comprising the oxygen-containing fused ring derivative of the invention should be higher than the triplet energy of a host mainly constituting the emitting layer. It is preferred that the oxygen-containing fused ring derivative of the invention and a host and a dopant contained in the emitting layer satisfy the following formulas (1) and (2):

$$E^T b > E^T h \qquad (1)$$

$$E^T d > E^T h \qquad (2)$$

wherein $E^T h$, $E^T b$ and $E^T d$ are a triplet energy of a host material, the oxygen-containing fused ring derivative of the blocking layer and the dopant, respectively.

Figure 2A:
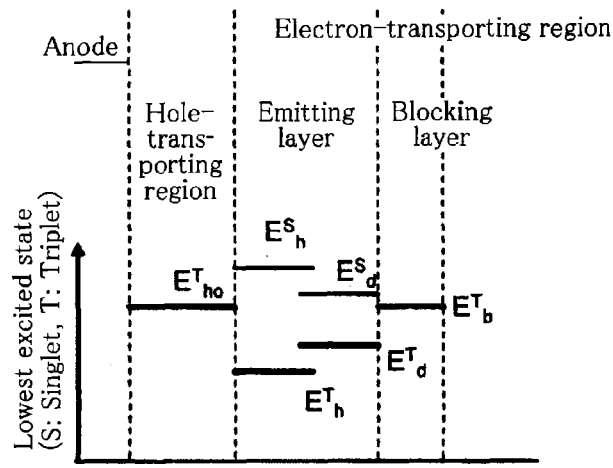
FIG. 2A is a view showing the relationship of the energy gap of each layer of the invention.

FIG. 1 is a schematic configuration view of an organic EL device showing one example of the first embodiment of the invention. FIG. 2A diagrammatically shows the lowest excited singlet energy state and the lowest excited triplet energy state of each layer. In the invention, the triplet energy means difference between the energy in the lowest excited triplet state and the energy in the ground state. The singlet energy (often referred to as the energy gap) means a difference between the energy in the lowest excited singlet state and the energy in the ground state. An organic EL device shown in FIG. 1 comprises an anode 10, a hole-transporting region 50, an emitting layer 20, an electron-transporting region 30 and a cathode 40 in this sequence. It is preferred that the hole-transporting region 50 be provided between the anode 10 and the emitting layer 20. In the embodiment shown in FIG. 2A, a configuration in which the electron-transporting region is formed only of a blocking layer is shown. However, the embodiment in which the electron-transporting region is formed only of the blocking layer does not prevent insertion of an electron-injecting layer having a higher injection property. When an electron-injecting layer is formed, a compound which has conventionally been used in the electron-injecting layer can be used. A hetero ring-containing compound is preferable.

In FIG. 2A, holes injected from an anode are then injected to the emitting layer through the hole-transporting region. Electrons injected from the cathode are then injected to the emitting layer through the electron-transporting region. Thereafter, holes and electrons are recombined in the emitting layer, whereby singlet excitons and triplet excitons are generated. There are two manners as for the occurrence of recombination. Specifically, recombination may occur either on host molecules or on dopant molecules. In this embodiment, as shown in FIG. 2A, if the triplet energy of a host and that of a dopant are taken as $E^T h$ and $E^T d$, respectively, it is preferred that the relationship $E^T h < E^T d$ be satisfied. By satisfying this relationship, as shown in FIG. 2B, the triplet excitons recombined and generated on the host do not transfer to a dopant having a further high triplet energy.

Further, the triplet excitons recombined and generated on dopant molecules energy-transferred to the host molecules rapidly. That is, singlet excitons are generated by a mechanism in which triplet excitons collide on the host efficiently by a TTF phenomenon without the transfer of the triplet excitons of the host to the dopant. Further, since the singlet energy of the dopant $E^S d$ is smaller than the singlet energy of the host $E^S h$, singlet excitons generated by a TTF phenomenon are energy-transferred from the host to the dopant, thereby contributing to the fluorescence emission of the dopant. In principal, in the dopant used in a fluorescent device, transfer from the excited triplet state to the ground state is prohibited. In such transition, the triplet excitons do not undergo optical deactivation, and undergo thermal deactivation. However, by allowing the relationship of the triplet energy of the host and the triplet energy of the dopant to be as mentioned above, singlet excitons are generated more efficiently by the collision of the triplet excitons before the triplet excitons undergo thermal deactivation.

In the electron-transporting region, the blocking layer is provided in a region which is in adjacent to the emitting layer. The blocking layer has a function of preventing diffusion of triplet excitons generated in the emitting layer to the electron-transporting region, and increasing the density of the triplet excitons by confining triplet excitons in the emitting layer, thereby to cause a TTF phenomenon to occur efficiently.

Figure 2B:
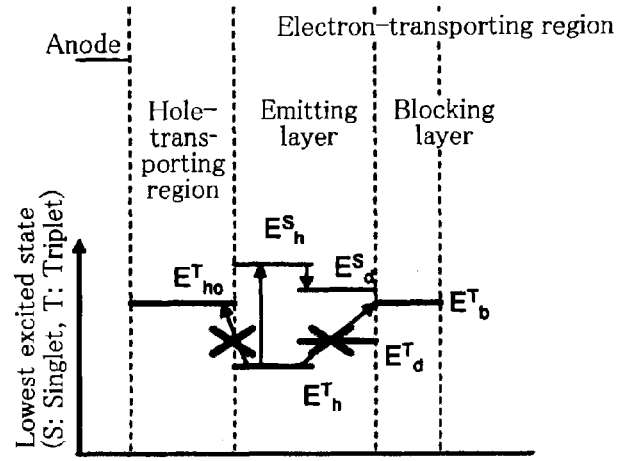
FIG. 2B is a view showing the action based on the relationship of the energy gap of each layer of the invention.
Figure 3:
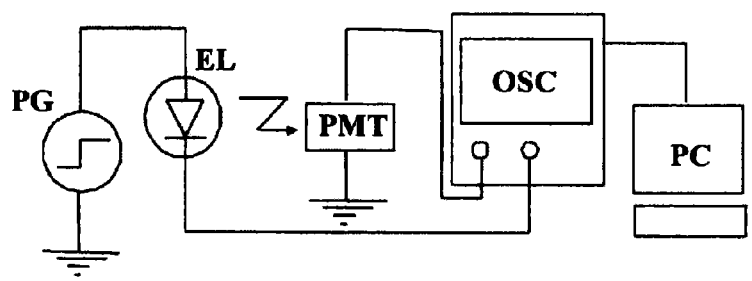
FIG. 3 is a view showing the method for measuring a transitional EL waveform.
Figure 4:
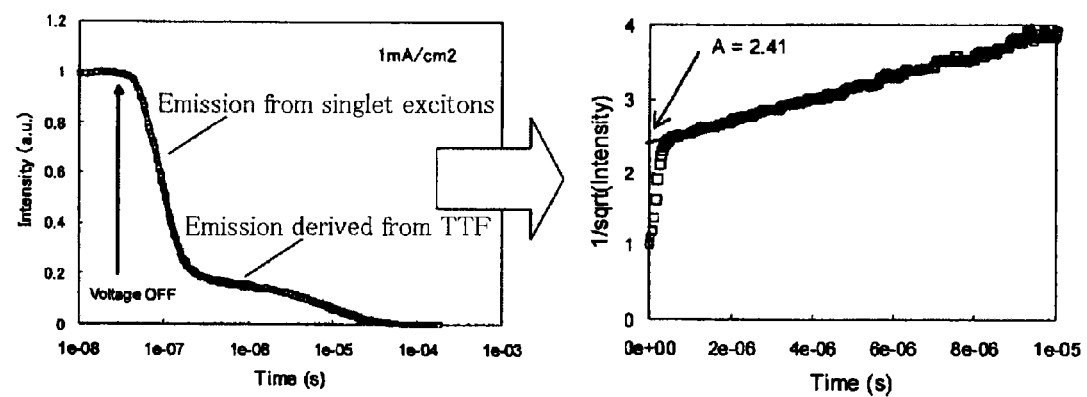
FIG. 4 is a view showing the method for measuring the ratio of the intensity of emission derived from TTF.

In order to prevent diffusion of triplet excitons, as shown in FIGS. 2A and 2B, it is preferred that the triplet energy $E^T b$ of a compound constituting the blocking layer be larger than $E^T h$, further $E^T d$. Since the blocking layer has a function of preventing diffusion of triplet excitons generated in the emitting layer to the electron-transporting region, triplet excitons of the host become singlet excitons efficiently in the emitting layer. The singlet excitons are transferred to the dopant and undergo optical energy deactivation. The material forming the blocking layer is the oxygen-containing fused ring derivative of the invention.

The blocking layer comprising the oxygen-containing fused ring derivative of the invention can also have the electron-injecting and transporting functions. This is because an unshared electron pair mediates receiving and transfer of electrons from adjacent layers. Electrons injected to a material of the blocking layer contribute to injection of electrons to the emitting layer by moving, through an electron-transporting structural part, to a part where electrons are donated more easily, i.e. the LUMO level is high.

Between the electron-transporting region and the cathode, a low-work-function metal layer may be provided. The low-work-function metal layer is a layer which has a low work function metal or a low-work-function metal compound. Even formed only of a low-work-function metal or a low-work-function metal compound, it is possible to add to a material used for the electron-transporting layer, a low work function metal, a low-work-function metal compound or a low-work-function metal complex as a donar. A low work function metal is a metal having a work function of 3.8 eV or less. As the metal having a low work function of 3.8 eV or less, an alkali metal, an alkaline earth metal or the like can be given. As the alkali metal, Li, Na, K, Cs or the like can be given. As the alkaline earth metal, Mg, Ca, Sr, Ba or the like can be given. As other low-work-function metals, Yb, Eu, Ce or the like can be given. As the low work function metal compound, an oxide, a halide, a carbonate and a borate of a low work function metal are preferable. As the halide, a fluoride, a chloride and a bromide can be given. Of these, a fluoride is preferable. For example, LiF can preferably be given. A low-work-function metal complex is a complex of a low-work-function metal, and an organic metal complex of an alkali metal, an alkaline earth metal or a rare earth metal is preferable.

Increasing efficiency utilizing a TTF phenomenon is significant in a blue fluorescent layer. In a blue fluorescent device (having a main peak wavelength of 500 nm or less), which is thought to be most difficult to enhance the luminous efficiency, by using the compound of the invention as the material for the blocking layer, a high luminous efficiency can be obtained.

In a phosphorescent emitting layer, it is possible to obtain effects of confining triplet energy in the emitting layer. Due to this confinement, it is possible to prevent diffusion of triplet energy, thereby contributing to luminous efficiency of a phosphorescent dopant.

Other elements of the organic EL device of the invention such as a substrate, an anode, a cathode, a hole-injecting layer, a hole-transporting layer or the like, known elements stated in PCT/JP2009/053247, PCT/JP2008/073180, U.S. patent application Ser. No. 12/376,236, U.S. patent application Ser. No. 11/766,281, U.S. patent application Ser. No. 12/280,364 or the like can be appropriately selected and used.

EXAMPLES

Synthetic Example 1

Synthesis of benzo[b]naphtho[2,1-d]furan-5-boronic acid

Benzo[b]naphtho[2,1-d]furan-5-boronic acid was synthesized according to the following scheme described.

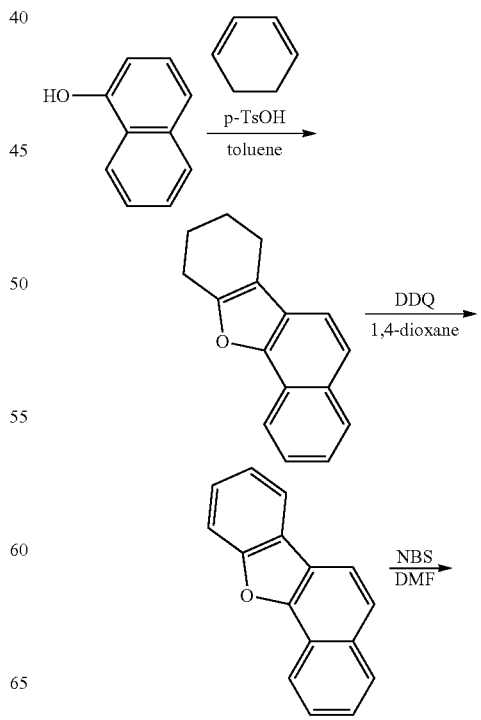

-continued

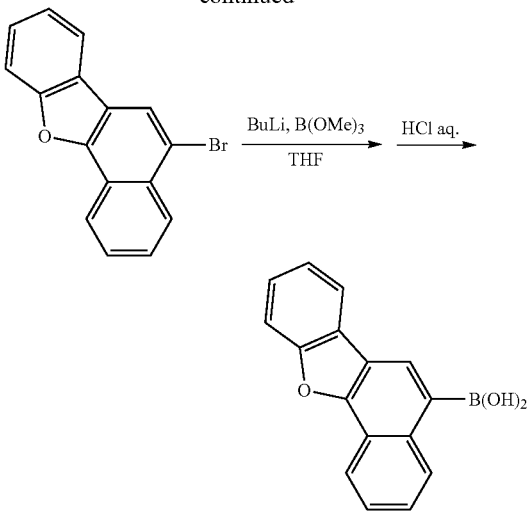

(a-1) Synthesis of 7,8,9,10-tetrahydrobenzo[b]naphtho[2,1-d]furan 144 g of 1-naphthol, p-toluenesulfonic acid monohydrate (190 g), 1,3-cyclohexanediene (80.1 g) and 4 L of toluene were charged in a flask, and refluxed for 24 hours. The reaction solution was cooled to room temperature, followed by washing with 600 mL of water. After dried an organic phase over magnesium sulfate, the solvent was evaporated under reduced pressure. The residue was purified by silica gel column chromatography, whereby 55.5 g of 7,8,9,10-tetrahydrobenzo[b]naphtho[2,1-d]furan was obtained (yield: 25%).

(a-2) Synthesis of benzo[b]naphtho[2,1-d]furan

Under an argon atmosphere, 7,8,9,10-tetrahydrobenzo[b]naphtho[2,1-d]furan (55.5 g), 2,3-dichloro-5,6-dicyano-1,4-benzoquinone (119 g) and 1 L of 1,4-dioxane anhydrous were charged in a flask, and refluxed for 12 hours. After cooled to room temperature, the reaction solution was extracted with toluene, and the precipitated solids were collected by filtration. After the filtrate was concentrated in a rotary evaporator, the residue was purified by silica gel column chromatography, whereby 32.7 g of benzo[b]naphtho[2,1-d]furan was obtained (yield: 60%).

(a-3) Synthesis of 5-bromobenzo[b]naphtho[2,1-d]furan

Benzo[b]naphtho[2,1-d]furan (32.7 g) was dissolved in 300 mL of N,N-dimethylformamide. After addition of a 50 mL N,N-dimethylformamide solution of N-bromosuccinimide (28.0 g), the reaction solution was stirred at 60° C. for 5 hours. After cooling to room temperature, the reaction solution was poured into 2 L of water. The solids obtained were washed with methanol, water and methanol sequentially. The crude product was purified by silica gel column chromatography, whereby 36.5 g of 5-bromobenzo[b]naphtho[2,1-d]furan was obtained (yield: 82%).

(a-4) Synthesis of benzo[b]naphtho[2,1-d]furan-5-boronic acid 5-bromobenzo[b]naphtho[2,1-d]furan (29.7 g) and 500 mL of tetrahydrofuran (dehydrated) were put into a flask, followed by cooling to −78° C. To the solution, n-BuLi ((1.60M in hexane) 66 mL) was added, and the resulting solution was stirred at 0° C. for 2 hours. Next, the solution was cooled to −78° C. again, followed by addition of B(OMe)$_3$ (27.3 g). The resulting solution was stirred at −78° C. for 10 minutes, and then stirred at room temperature for 5 hours. After completion of the reaction, 1N HCL aq. (200 mL) was added and the resulting solution was stirred at room temperature for 1 hour. Subsequently, the reaction solution was transferred to a separating funnel and extracted with ethyl acetate. After drying with MgSO$_4$, this solution was evaporated and resulting residue was washed with hexane, whereby 17.0 g of white solids of benzo[b]naphtho[2,1-d]furan-5-boronic acid were obtained (yield: 65%).

Synthetic Example 2

Synthesis of benzofurano[3,2-b]dibenzofuran-6-boronic acid

Benzofurano[3,2-b]dibenzofuran-6-boronic acid was synthesized according to the following synthesis scheme.

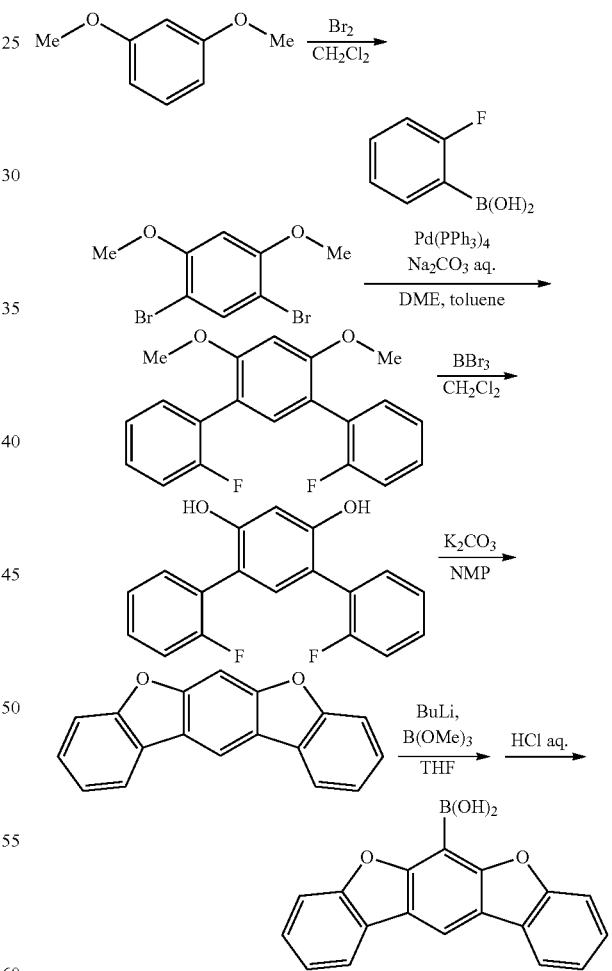

(b-1) Synthesis of 2,4-dibromo-1,5-dimethoxybenzene 1,3-dimethoxybenzene (53.9 g) was dissolved in 860 mL of dichloromethane, and the reaction atmosphere was replaced with argon. While cooled on ice, a 150 mL dichloromethane solution of bromine (129.3 g) was dropped for 2 and a half hour and warmed to room temperature gradually for 3 hours, further followed by stirring for one day. The reaction solution was cooled on ice, and neutralized with a 10% aqueous sodium hydrate solution. The dichloromethane phase was separated and collected, the water phase was extracted with dichloromethane, and the organic phases were dried over anhydrous sodium sulfate together. After filtration, the filtrate was concentrated. The residue obtained was dispersed and washed with hexane. The generated crystal was filtered out and then dried, whereby 110.5 g of white crystal of 2,4-dibromo-1,5-dimethoxybenzene was obtained (yield: 97%).

(b-2) Synthesis of 2,4-bis(2-fluorophenyl)-1,5-dimethoxybenzene 2,4-dibromo-1,5-dimethoxybenzene (88.8 g), 2-fluorophenyl boronic acid (100.74 g), Na$_2$CO$_3$ 2M aq. (600 mL), Pd(PPH$_3$)$_4$ (6.73 g), 150 mL of 1,2-dimethoxyethane and 150 mL of toluene were charged in a flask, and refluxed for 36 hours. After completion of the reaction, 500 mL of water and 1 L of toluene were added and the resulting solution was transferred to a separating funnel, then a toluene phase was separated and collected. After drying with MgSO$_4$, impurity at the original point was removed by a silica gel short column, and the solution was concentrated. The resulting solution was subjected to recrystallization from a toluene/hexane mixed solvent, whereby 86.5 g of white solids of 2,4-bis(2-fluorophenyl)-1,5-dimethoxybenzene were obtained (yield: 88%).

(b-3) Synthesis of 2,4-bis(2-fluorophenyl)-1,5-dihydroxybenzene 2,4-bis(2-fluorophenyl)-1,5-dimethoxybenzene (48.3 g) and 740 mL of dichloromethane (dehydrated) were put in a flask and cooled to 0° C. BBr$_3$ (89.0 g) was added, and then the resulting solution was stirred at room temperature for 24 hours. After completion of the reaction, the solution was cooled to −78° C., and the reaction was deactivated carefully with methanol, and further deactivated with a sufficient amount of water. The solution was transferred to a separating funnel and extracted with dichloromethane. After dried over MgSO$_4$, impurity at the original point was removed by a silica gel short column, and the solution was concentrated. The resulting solution was concentrated, and the obtained sample was dried in vacuum at 60° C. for 5 hours, whereby 44.1 g of white solids of 2,4-bis(2-fluorophenyl)-1,5-dihydroxybenzene were obtained (yield: 100%).

(b-4) Synthesis of benzofurano[3,2-b]dibenzofuran 2,4-bis(2-fluorophenyl)-1,5-dihydroxybenzene (44.14 g) and 888 mL of N-methyl-2-pyrrolidinone (dehydrated) were put in a flask, and solids were completely dissolved. K$_2$CO$_3$ (81.8 g) was added thereto, and then stirred at 200° C. for 2 hours. After completion of reaction, the solution was cooled to room temperature, and 2 L of toluene was added. The resulting solution was transferred to a separating funnel and washed with water. After dried over MgSO$_4$, removal of impurity at the original point was conducted through a silica gel short column, and the solution was concentrated. The resulting solution was subjected to recrystallization from a toluene/hexane mixed solvent, whereby 27.9 g of white solids of benzofurano[3,2-b]dibenzofuran were obtained (yield: 73%).

(b-5) Synthesis of benzofurano[3,2-b]dibenzofuran-6-boronic acid

Benzofurano[3,2-b]dibenzofuran (12.9 g) and tetrahydrofuran (dehydrated) (300 mL) were added to a flask, and the resulting solution was cooled to −78° C. n-BuLi ((2.63M in hexane) 20.0 mL) was added thereto, and then the resulting solution was kept at room temperature for 1 hour. Next, the solution was cooled to −78° C. again, followed by addition of B(OMe)$_3$ (10.4 g). The resulting solution was stirred at −78° C. for 10 minutes, and then kept at room temperature for 1 hour. After completion of the reaction, the solution was concentrated to about half amount in an evaporator. Then, 1N HCL aq. (200 mL) was added and the resulting solution was stirred at room temperature for 1 hour. Subsequently, the resulting solution was transferred to a separating funnel and extracted with ethyl acetate. After drying over MgSO$_4$, this solution was concentrated and dispersed and washed with a toluene/hexane mixed solvent, whereby 13.7 g of white solids of benzofurano[3,2-b]dibenzofuran-6-boronic acid were obtained (yield: 91%).

Synthetic Example 3

(c) Synthesis of 2-(benzo[kl]xanthene-4-yl)-4,4,5,5-tetramethyl-1,3,2-dioxaborolan 2-(benzo[kl]xanthene-4-yl)-4,4,5,5-tetramethyl-1,3,2-dioxaborolan was synthesized according to the synthesis scheme described below.

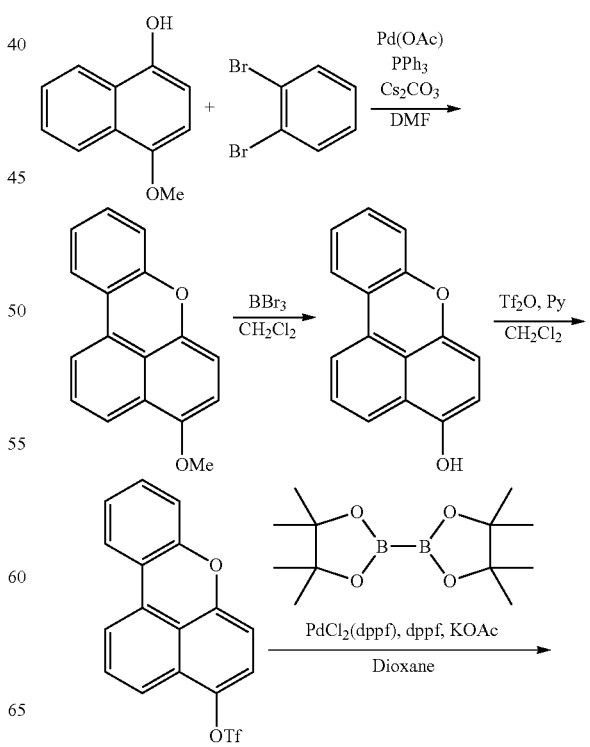

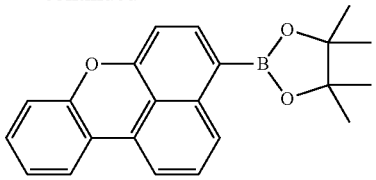

(c-1) Synthesis of 4-methoxybenzo[kl]xanthene 4-methoxy-1-naphthol (6.97 g) and 1,2-dibromobenzene (11.3 g) were dissolved in 200 mL of dimethylformamide. Cesium carbonate (52.13 g), triphenylphosphine (2.10 g) and palladium acetate (II) (0.45 g) were added sequentially, and stirred at 140° C. for 15 hours. The resulting solution was cooled to room temperature and separated by adding water and ethyl acetate. The water phase was extracted with ethyl acetate and washed with water and brine. After organic phases were combined and dried over anhydrous sodium sulfate and filtrated, the solution was evaporated. Water and methanol were added to the resulting residue. The resulting solution was extracted with diethyl ether and ethyl acetate, and washed with water and brine. After organic phases were combined and dried over anhydrous sodium sulfate and filtrated, the solution was evaporated. After purified by silica gel chromatography, the obtained residue was dispersed and washed and then dried, whereby 3.26 g of yellow solids of 4-methoxybenzo[kl]xanthene were obtained (yield: 33%).

(c-2) Synthesis of 4-hydroxybenzo[kl]xanthene 4-methoxybenzo[kl]xanthene (3.26 g) was dissolved in 100 mL of dichloromethane. Under an argon atmosphere, the resulting solution was cooled to −68° C. in a dry ice/methanol bath. Then, dichloromethane solution of boron tribromide (1M, 14 mL) was added dropwise for 20 minutes. Gradually warming to room temperature, the resulting solution was stirred for 4 hours. The obtained mixture was cooled on ice and carefully deactivated by adding several drops of water. 100 mL of water was further added. The generated precipitates were collected by filtration, and washed with water and dichloromethane, followed by drying. As a result, crystals of 4-hydroxybenzo[kl]xanthene (2.35 g) were obtained. The filtrate was separated, and a water phase was extracted with dichloromethane. After organic phases were combined and dried over anhydrous sodium sulfate and filtrated, the solution was evaporated. The residue obtained was dispersed and washed with a small amount of dichloromethane and dried, whereby crystals of 4-hydroxybenzo[kl]xanthene (0.53 g) were obtained. The total amount and yield of both crystals is 2.88 g and 94%, respectively.

[(c-3) Synthesis of 4-trifluoromethanesulfonylbenzo[kl]xanthene]

4-hydroxybenzo[kl]xanthene (2.88 g) was dispersed in 100 mL of dichloromethane and, cooled on ice, and pyridine (4.0 mL) was added under an argon atmosphere. Trifluoromethanesulfonic acid anhydride (3.0 mL) was added dropwise to the solution obtained for 10 minutes. After stirring while cooling on ice for 5 minutes, the solution was stirred for 3 hours while warming gradually to room temperature. 1M hydrochloric acid (50 mL) was added to the resulting solution while cooling in ice, the mixed solution was extracted with dichloromethane and washed with saturated sodium bicarbonate water. After that, the solution was dried over anhydrous sodium sulfate, filtrated and then concentrated. The resulting residue was dispersed and washed with a mixed solution of hexane/ethyl acetate and dried, whereby solids of 4-trifluoromethanesulfonylbenzo[kl]xanthene were obtained. The mother solution in the washing was concentrated and purified by means of silica gel chromatography. The residue obtained was dispersed and washed with hexane and dried, whereby solids of 4-trifluoromethanesulfonylbenzo[kl]xanthene was obtained. By bringing together both solids, 3.01 g of brownish white solids of 4-trifluoromethanesulfonylbenzo[kl]xanthene were obtained (yield: 67%).

(c-4) Synthesis of 2-(benzo[kl]xanthene-4-yl)-4,4,5,5-tetramethyl-1,3,2-dioxaborolane 4-trifluoromethanesulfonylbenzo[kl]xanthene (3.01 g), bispinacolate diboron (2.30 g), [1,1'-bis(diphenylphosphino)ferrocene]palladium(II)dichloride dichloromethane adduct (0.34 g), 1,1'-bis(diphenylphosphino)ferrocene (0.23 g) and potassium acetate (2.42 g) were dissolved in 50 mL of 1,4-dioxane and stirred at 80° C. for 17 hours. Bispinacolate diboron (1.15 g), [1,1'-bis(diphenylphosphino)ferrocene]palladium(II)dichloride dichloromethane adduct (0.34 g) and 1,1'-bis(diphenylphosphino)ferrocene (0.23 g) were added at 80° C. for 7 and a half hours. The reaction solution was cooled to room temperature, water and ethyl acetate were added thereto. Then, the resulting solution was filtrated. The mixed solution obtained was separated and extracted with ethyl acetate. After that, organic phases were combined and the resulting solution was washed with brine, dried over anhydrous sodium sulfate, filtered and then concentrated. The resulting residue was purified by silica gel chromatography, whereby 1.47 g of yellow solids of 2-(benzo[kl]xanthene-4-yl)-4,4,5,5-tetramethyl-1,3,2-dioxaborolane were obtained (yield: 52%).

Synthetic Example 4

(d) Synthesis of 2-(3-bromophenyl)-imidazo[1,2-a]pyridine 2-(3-bromophenyl)-imidazo[1,2-a]pyridine was synthesized according to the scheme described below.

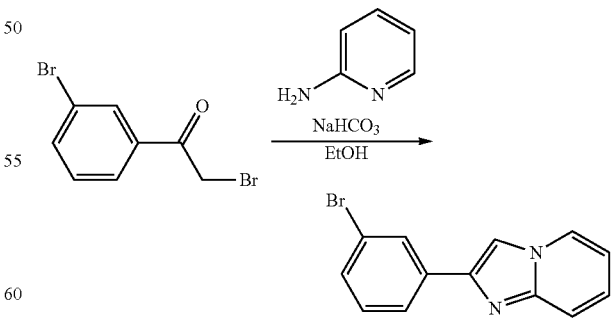

A mixture of 9.25 g of 3-bromophenacylbromide, 10.0 g of 2-aminopyridine and 4.19 g of sodium hydrogen carbonate in 150 ml of ethanol was refluxed for 5 hours. After completion of the reaction, generated crystals were collected by filtration, washed with water and acetone, and dried under reduced pressure, whereby 7.91 g of 2-(3-bromophenyl)-imidazo[1,2-a]pyridine was obtained (yield: 87%).

Oxygen-Containing Fused Ring Derivative

Example 1

Synthesis of Compound 1

A mixture of 3.00 g of 1-(4-bromophenyl)-2-phenyl-1H-benz[d]imidazole, 2.94 g of benzo[b]naphtho[2,1-d]furan-5-boronic acid, 0.50 g of tetrakis(triphenylphosphine)palladium(0), 26 ml of 1,2-dimethoxyethane and 13 mL of a 2M aqueous sodium carbonate solution were refluxed for 8 hours. The reaction mixture was cooled to room temperature, and water was added thereto, followed by stirring for 30 minutes. Ethyl acetate and hexane were added to the resulting solution, followed by stirring further for 30 minutes. The generated solids were collected by filtration, washed with water, methanol and hexane, and dried under reduced pressure. The solids obtained were dispersed and washed with a mixed solution of hexane/ethyl acetate. After that, the solids were purified by silica gel chromatography and dispersed and washed in hot toluene, whereby 3.01 g of white solids was obtained.

As a result of mass spectroscopy analysis, the compound obtained was identified as the following compound 1 (m/e=486 for molecular weight 486.17). The yield was 72%.

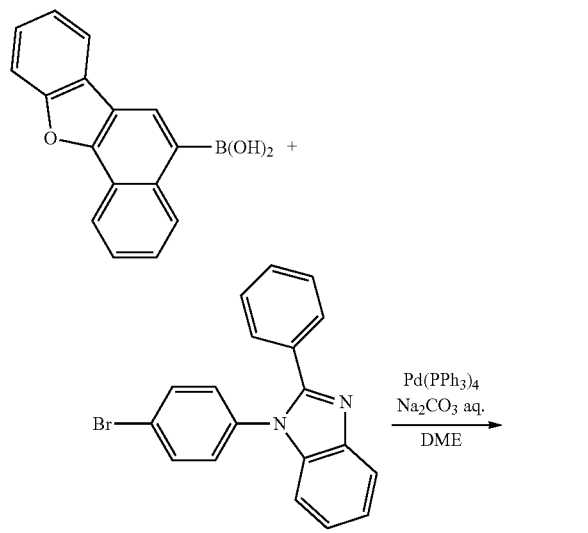

(Compound 1)

Example 2

Synthesis of Compound 2

A mixture of 3.00 g of 1-(4-bromophenyl)-2-phenyl-1H-benz[d]imidazole, 3.70 g of benzofurano[3,2-b]dibenzofuran-6-boronic acid, 0.60 g of tetrakis(triphenylphosphine)palladium(0), 26 ml of 1,2-dimethoxyethane and 13 mL of a 2M aqueous sodium carbonate solution were refluxed for 13 hours. The reaction mixture was cooled to room temperature, and water was added thereto, followed by stirring for 30 minutes. The generated solids were collected by filtration, washed with water, methanol and hexane, and dried under reduced pressure. The solids obtained were purified by silica gel chromatography, whereby 4.42 g of white solids were obtained.

As a result of mass spectroscopy analysis, the compound obtained was identified as the following compound 2 (m/e=526 for molecular weight 526.17). The yield was 97%.

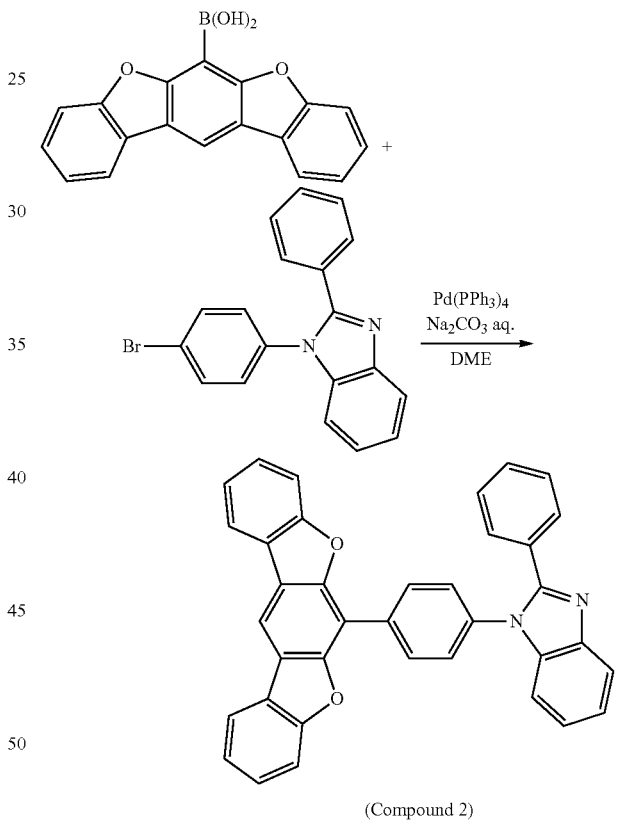

(Compound 2)

Example 3

Synthesis of Compound 3

A mixture of 1.36 g of 1-(4-bromophenyl)-2-phenyl-1H-benz[d]imidazole, 1.47 g of 2-(benzo[kl]xanthene-4-yl)-4,4,5,6-tetramethyl-1,3,2-dioxaborolane, 0.14 g of tetrakis(triphenylphosphine)palladium(0), 12 ml of 1,2-dimethoxyethane and 6 mL of 2M aqueous sodium carbonate solution were refluxed for 6 hours. The reaction mixture was cooled to room temperature, and water was added thereto, followed by stirring for 30 minutes. The generated solids were collected by filtration, washed with water, methanol and hexane, and dried under reduced pressure. The solids obtained were purified by silica gel chromatography, whereby 1.67 g of white solids were obtained.

As a result of mass spectroscopy analysis, the compound obtained was identified as the following compound 3 (m/e=486 for molecular weight 486.17). The yield was 88%.

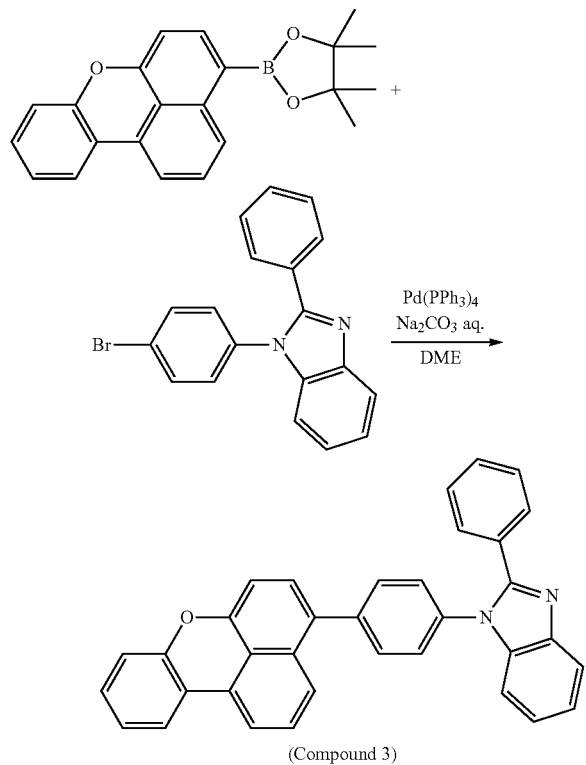

(Compound 3)

Example 4

Synthesis of Compound 4

Reaction was conducted in the same manner as in Example 2, except that 2-(3-bromophenyl)-imidazo[1,2-a]pyridine synthesized in Synthetic Example 4 was used instead of 1-(4-bromophenyl)-2-phenyl-1H-benz[d]imidazole.

As a result of mass spectroscopy analysis, the compound obtained was identified as the following compound 4 (m/e=450 for molecular weight 450.14). The yield was 73%.

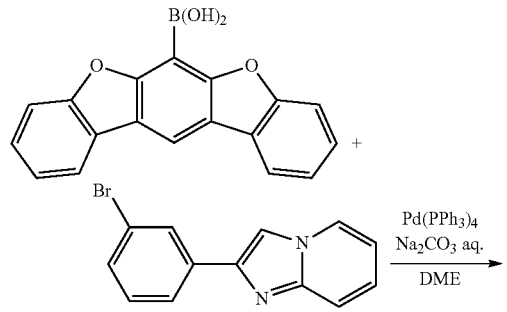

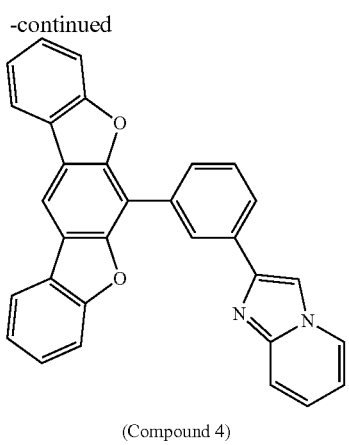

(Compound 4)

The physical property for each of Compounds 1, 2, 3 and 4 obtained was evaluated according to the following methods. The results were shown in Table 1.

(1) Triplet Energy ($E^T$)

The method for measuring the above-mentioned physical value is as follows.

The triplet energy was measured by a commercially available device (F-4500, manufactured by Hitachi Ltd.). The conversion formula of $E^T$ is as follows.

Conversion formula ET (eV)=1239.85/$\lambda_{ph}$

The "$\lambda_{ph}$" (unit: nm) means, when the phosphorescent intensity and the wavelength are taken at the vertical axis and the horizontal axis respectively to express a phosphorescent spectrum and a tangential line is drawn against the rise on the shorter wavelength side of the phosphorescent spectrum, a wavelength value of the intersection of the tangential line and the horizontal axis (unit: nm).

Each compound is dissolved in a solvent (sample 10 μmol/l, EPA (diethylether:isopentane:ethanol: 5:5:5 (volume ratio)). Each solvent is spectrally graded to obtain a sample for measuring phosphorescent emission. The sample for measuring phosphorescent emission put in a quarts cell was cooled to 77K, and then irradiated with excited light. The phosphorescent intensity was measured while changing the wavelength. In the phosphorescent spectrum, the vertical axis was the phosphorescent intensity and the horizontal axis was the wavelength.

A tangent line was drawn against the rise of the short-wavelength side of this phosphorescent spectrum, and a wavelength value $\lambda_{ph}$ (nm) of the intersection of the tangent line and the horizontal axis was obtained.

The tangent line against the rise on the short-wavelength side of the phosphorescent spectrum is drawn as follows. When moving on the spectrum curve from the short wavelength side of the phosphorescent spectrum to the maximum value of the shortest wavelength side, a tangent line at each point on the curve towards the long-wavelength side is taken into consideration. The slope of this tangent line increases with a rise in the curve (i.e. as the vertical axis is increased). This tangent line drawn at a point where this value of slope becomes the maximum is taken as the tangent line relative to the rise on the short wavelength side of the phosphorescent spectrum.

The maximum point having a peak intensity which is 10% or less of the maximum peak intensity of the spectrum is not included in the maximum value on the shortest wavelength side, and a tangent line which is taken at a point which is closest to the maximum value on the shortest wavelength side and where the value of the slope becomes the maximum is taken as a tangent line taken against the edge on the shorter wavelength side of the phosphorescent spectrum.

(2) Ionization Potential (Ip)

An ionization potential was measured by a method in which a single layer of each layer was formed on an ITO glass substrate separately by vacuum deposition, and measured by means of a photoelectron spectrometer (AC-3, manufactured by RIKEN Co., Ltd.) in the atmosphere by means of a thin film on the ITO glass substrate. Specifically, the material is irradiated with light, and the amount of electrons generated by charge separation is measured.

The one-half of the amount of photoelectrons emitted are plotted relative to the energy, and the threshold value of the photoelectron emission energy is taken as the ionization potential (Ip).

(3) Affinity (Af)

The affinity was calculated from the measured value of the ionization potential Ip and the energy gap Eg. The calculation was conducted as follows.

$$Af=Ip-Eg$$

The energy gap Eg was measured from the absorption edge of the absorption spectrum of the toluene solution. Specifically, an absorption spectrum was measured by means of a commercially available UV-visible spectrophotometer and the energy gap was calculated from the wavelength of the rise on the long-wavelength side of the spectrum.

The conversion formula is as follows:

$$Eg\ (eV) = 1239.85/\lambda_{ab}$$

One obtained by taking the absorption on the vertical axis and the wavelength on the horizontal axis is taken as the absorption spectrum. In the above-mentioned conversion formula regarding the energy gap Eg "$\lambda_{ab}$" (unit: nm) means the value of a wavelength at the intersection of the tangent line and the horizontal line.

Each compound was dissolved in a toluene solvent (sample $2\times10^{-5}$ mol/l) and a sample was prepared such that the optical path became 1 cm. The absorption was measured by changing the wavelength.

The tangent line against the rise on the long-wavelength side of the absorption spectrum is drawn as follows.

Of the maximum values of the absorption spectrum, when moving on the spectrum curve from the maximum value on the longest wavelength side to the long wavelength direction, a tangent line at each point on the curve is taken into consideration. As the curve rises down (i.e. as the vertical axis is decreased), the slope of this tangent line is decreased and then increased. This increase and decrease are repeated. A tangent line drawn at a point where the value of the slope become the minimum in the longest wavelength side (however, a case when the absorption becomes 0.1 or less is excluded) is taken as a tangent line against the rise on the longest wavelength side of the absorption spectrum.

The maximum point at which the value of absorption is 0.2 or less is not included in the maximum value on the longest wavelength side.

TABLE 1

| | Triplet energy (eV) | Ionization potential (eV) | Affinity (eV) |
|---|---|---|---|
| Compound 1 | 2.6 | 6.1 | 2.6 |
| Compound 2 | 2.8 | 6.1 | 2.7 |
| Compound 3 | 2.2 | 5.8 | 2.7 |
| Compound 4 | 2.8 | 6.0 | 2.6 |

Preparation of Organic EL Device

Example 5

Materials used for organic EL devices were as below:

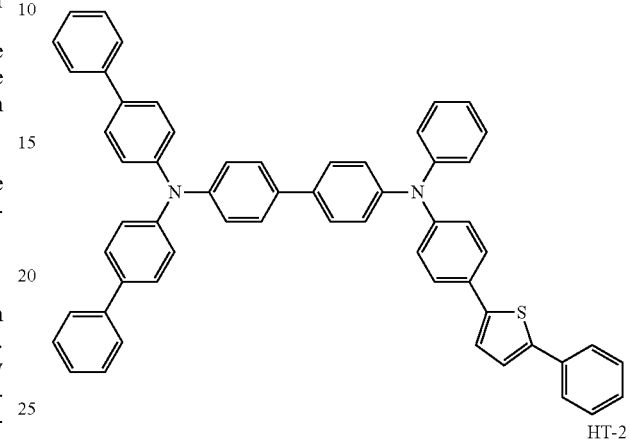

HT-1

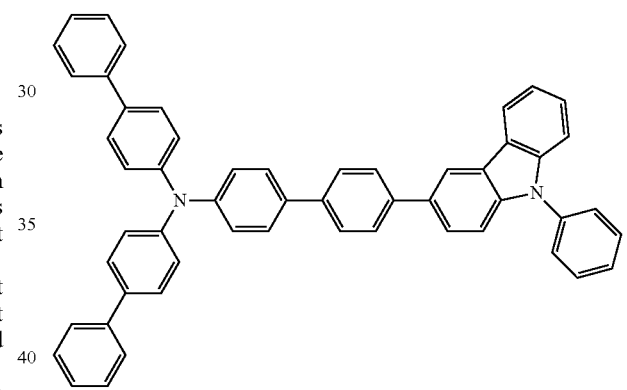

HT-2

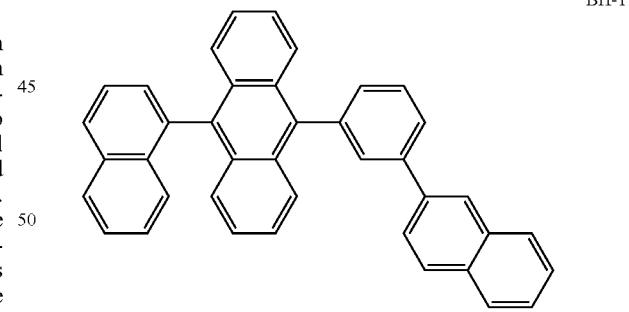

BH-1

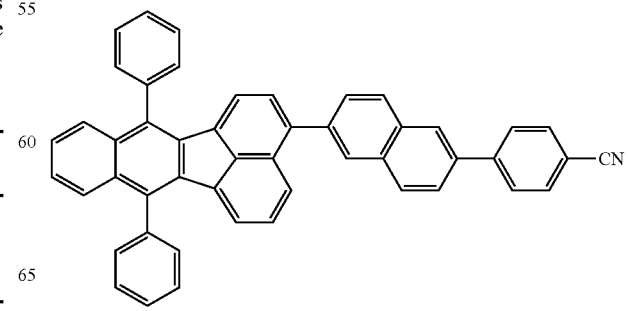

BD-1

-continued

ET-1

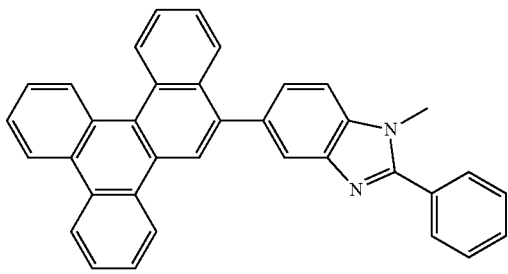

A glass substrate of 25 mm by 75 mm by 1.1 mm thick with an ITO transparent electrode (anode) (GEOMATEC CO., LTD.) was subjected to ultrasonic cleaning in isopropyl alcohol for 5 minutes, and cleaning with ozone for 30 minutes. The resultant substrate with transparent electrode lines was mounted on a substrate holder in a vacuum deposition device. First, compound HT-1 was deposited on the surface on which the transparent electrode lines were formed to form a 50 nm-thick film so as to cover the transparent electrode. The HT-1 film functions as a hole-injecting layer. Subsequently, compound HT-2 was deposited on the HT-1 film to form a 45 nm-thick film, HT-2 film. The HT-2 film functions as a hole-transporting layer.

Compound BH-1 (host material) and compound BD-1 (dopant material) were deposited on the HT-2 film such that the film thickness ratio of BH-1 to BD-1 became 20:1 to form an emitting layer with a thickness of 25 nm. On the emitting layer, compound 1 was deposited to form a blocking layer with a thickness of 5 nm. Furthermore, ET-1 as an electron-transporting material was deposited to form an electron-transporting layer with a thickness of 20 nm on the emitting layer. Then, LiF was deposited into a thickness of 1 nm. Metal Al was deposited on the LiF film into a thickness of 150 nm to form a metallic cathode, whereby an organic EL device was fabricated.

For the fabricated organic EL devices, device performance (driving voltage, luminous efficiency, external quantum yield and emission wavelength) at a current density of 10 mA/cm² when driven was evaluated. The results are shown in Table 2.

Examples 6, 7, 8 and 9, and Comparative Example 1

Organic EL devices were prepared and evaluated in the same manner as in Example 5, except that the blocking layer was stacked using compounds shown in Table 2 instead of compound 1, and compounds shown in Table 2 were used as a material for the dopant. The results are shown in Table 2.

BD-2 used in Example 8 and ET-2 used in Comparative Example 1 were following compounds.

ET-2

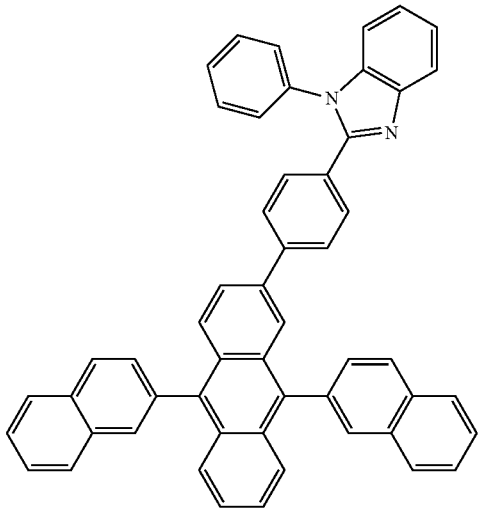

BD-2

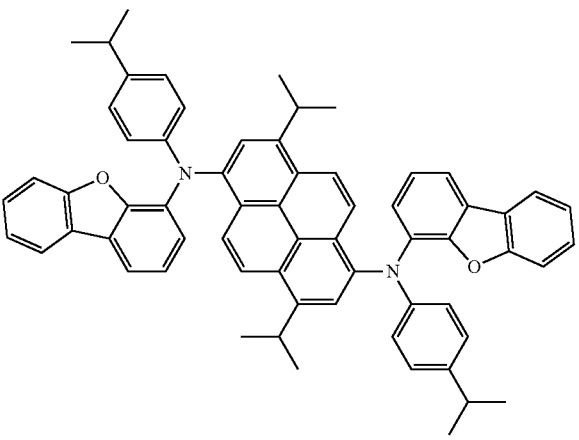

TABLE 2

|  | Blocking layer | Dopant material | Driving voltage (V) | Luminous efficiency (Cd/A) | External quantum yield (%) | Emission wavelength (nm) |
| --- | --- | --- | --- | --- | --- | --- |
| Example 5 | Compound 1 | BD1 | 4.3 | 9.1 | 9.3 | 450 |
| Example 6 | Compound 2 | BD1 | 3.6 | 10.0 | 10.0 | 450 |
| Example 7 | Compound 3 | BD1 | 3.6 | 10.1 | 10.0 | 451 |
| Example 8 | Compound 4 | BD1 | 4.1 | 9.4 | 9.2 | 451 |
| Example 9 | Compound 4 | BD2 | 4.2 | 10.2 | 9.5 | 464 |
| Com. Ex. 1 | ET-2 | BD1 | 4.6 | 8.2 | 7.9 | 451 |

The results above show that by using the compounds of the invention as a blocking layer (Examples 5 to 9), the organic EL devices of the invention can realize a higher luminous efficiency compared with the device which uses a conventional electron-transporting material (Comparative Example 1).

It is suggested that the above-mentioned high efficiency is due to the presence of blocking material. The triplet energy of BH-1 as a host material is 1.83 eV when calculated according to the same method as in compounds 1 to 4. The values for compounds 1 to 3 are sufficiently larger than the triplet energy of BH-1. As a result, it is considered that the confinement effect of triplet excitons in an emitting layer occurs.

Example 10

A glass substrate of 25 mm by 75 mm by 1.1 mm thick with an ITO transparent electrode (anode) (GEOMATEC CO., LTD.) was subjected to ultrasonic cleaning in isopropyl alcohol for 5 minutes, and cleaning with ozone for 30 minutes. The resultant substrate with transparent electrode lines was mounted on a substrate holder in a vacuum deposition device. First, compound HT-1 was deposited on the surface on which the transparent electrode lines were formed to form a 50 nm-thick film so as to cover the transparent electrode. The HT-1 film functions as a hole-injecting layer. Subsequently, compound HT-2 was deposited on the HT-1 film to form a 45 nm-thick HT-2 film. The HT-2 film functions as a hole-transporting layer.

Compound BH-1 (host material) and compound BD-2 (dopant material) were deposited on the HT-2 film such that the film thickness ratio of BH-1 to BD-2 became 20:1 to form an emitting layer with a thickness of 25 nm. Furthermore, on the emitting layer, compound 1 was deposited to form an electron-transporting layer with a thickness of 25 nm. Then, LiF was deposited into a thickness of 1 nm. Metal Al was deposited on the LiF film into a thickness of 150 nm to form a metallic cathode, whereby an organic EL device was fabricated.

For the fabricated organic EL devices, device performance (driving voltage, luminous efficiency, external quantum yield and emission wavelength) at a current density of 10 mA/cm² when driven was evaluated. The results are shown in Table 3.

Examples 11, 12 and 13, and Comparative Example 2

Organic EL devices were prepared and evaluated in the same manner as in Example 10, except that the electron-transporting layer was stacked using compounds shown in Table 3 instead of compound 1. The results are shown in Table 3.

TABLE 3

| | Blocking layer | Driving voltage (V) | Luminous efficiency (Cd/A) | External quantum yield (%) | Emission wavelength (nm) |
|---|---|---|---|---|---|
| Example 10 | Compound 1 | 4.9 | 9.0 | 8.6 | 463 |
| Example 11 | Compound 2 | 4.5 | 9.0 | 8.7 | 463 |
| Example 12 | Compound 3 | 4.3 | 10.0 | 9.6 | 463 |
| Example 13 | Compound 4 | 4.8 | 10.0 | 9.3 | 464 |
| Com. Ex. 2 | ET-2 | 4.9 | 6.8 | 6.4 | 464 |

It is understood that, even if used as a material for forming an electron-transporting layer singly, the compound of the invention can exhibit a high luminous efficiency as compared with conventional electron-transporting materials. This demonstrates that, the compound of the invention has not only effects of confining triplet excitons in the emitting layer by the effect of the blocking layer, as suggested above, it can also function as an electron-transporting material since it is a compound having a nitrogen-containing heterocyclic ring part that has electron-injecting/transporting property in the same molecule. By using the compound of the invention, a possibility is suggested that an electron-transporting region having a blocking performance with a smaller number of stacked layers can be formed.

INDUSTRIAL APPLICABILITY

An organic EL device comprising the oxygen-containing fused ring derivative of the invention can be used in a display panel for a large-screen television, an illumination panel or the like for which low consumption power is desired.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. An oxygen-comprising fused ring of formula (1):

(1)

wherein:

$Ar_1$ is an m-valent fused ring group of formula (9), (10), (11), (12), (13), (14) or (15):

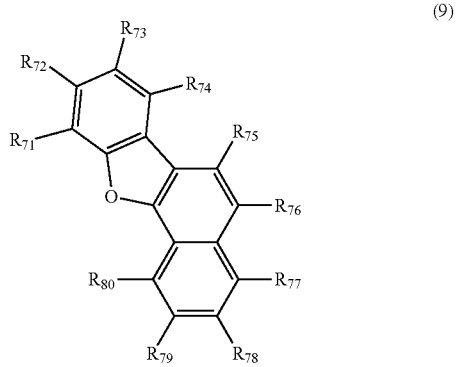

(9)

-continued

(10)
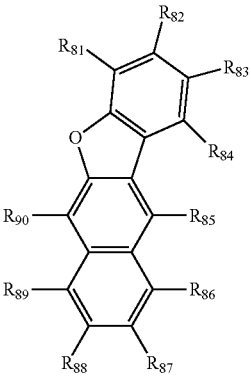

(11)
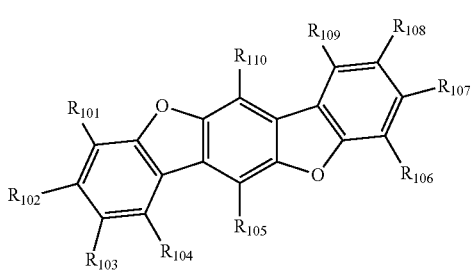

(12)

(13)
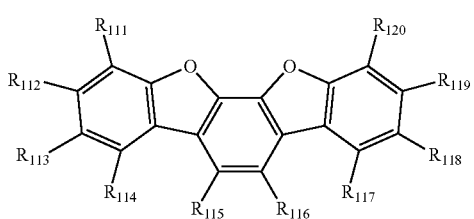

(14)
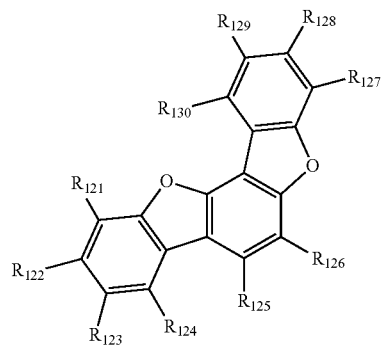

-continued

(15)
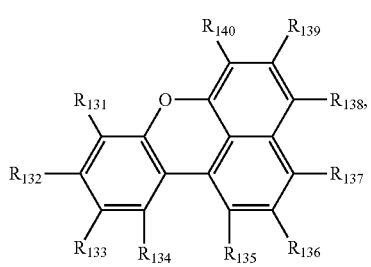

wherein $R_{71}$ to $R_{140}$ are each independently a hydrogen atom, a halogen atom, a substituted or unsubstituted alkyl group comprising 1 to 10 carbon atoms, a substituted or unsubstituted cycloalkyl group comprising 3 to 8 ring carbon atoms, a substituted silyl group comprising 3 to 30 carbon atoms, a cyano group, a substituted or unsubstituted alkoxy group comprising 1 to 20 carbon atoms, a substituted or unsubstituted aryl oxy group comprising 6 to 20 ring carbon atoms, a substituted or unsubstituted alkylthio group comprising 1 to 20 carbon atoms, a substituted or unsubstituted arylthio group comprising 6 to 30 carbon atoms, a substituted or unsubstituted arylamino group comprising 6 to 30 carbon atoms, a substituted or unsubstituted mono- or dialkylamino group comprising 1 to 20 carbon atoms, a substituted or unsubstituted aryl group comprising 6 to 30 ring carbon atoms, or a substituted or unsubstituted heterocyclic group comprising 5 to 30 ring atoms;

in formula (9), at least one of $R_{71}$ to $R_{80}$ is a single bond which bonds to L, the number of single bond being equal to m;

in formula (10), at least one of $R_{81}$ to $R_{90}$ is a single bond which bonds to L, the number of single bond being equal to m, in formula (11), at least one of $R_{91}$ to $R_{100}$ is a single bond which bonds to L, the number of single bond being equal to m;

in formula (12), at least one of $R_{101}$ to $R_{110}$ is a single bond which bonds to L, the number of single bond being equal to m;

in formula (13), at least one of $R_{111}$ to $R_{120}$ is a single bond which bonds to L, the number of single bond being equal to m;

in formula (14), at least one of $R_{131}$ to $R_{130}$ is a single bond which bonds to L, the number of single bond being equal to m;

in formula (15), at least one of $R_{131}$ to $R_{140}$ is a single bond which bonds to L, the number of single bond being equal to m;

HAr is nitrogen-comprising heterocyclic of formulae (2), (3), (4), or (5); with the proviso that when Ar1 is represented by formula (12) HAr is not represented by formula (4);

n and m are each independently an integer from 1 to 5, and at least one of n and m is 1; and L is a single bond, a substituted or unsubstituted n+1 valent aryl group comprising 6 to 30 ring carbon atoms, a substituted or unsubstituted n+1 valent heterocyclic group comprising 5 to 30 ring atoms, or an n+1 valent group obtained by combining, through a single bond, two or three selected from the group consisting of a substituted or unsubstituted aryl group comprising 6 to 30 ring carbon atoms and a substituted or unsubstituted heterocyclic group comprising 5 to 30 ring atoms:

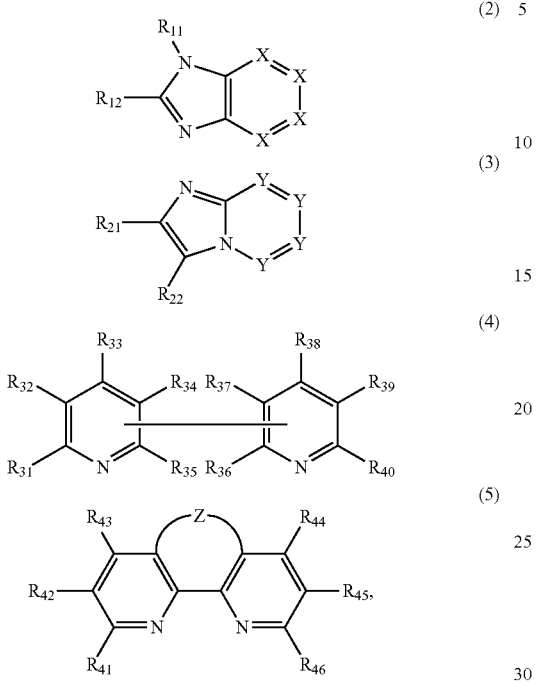

wherein:
R$_{11}$, R$_{12}$, R$_{21}$, R$_{22}$, R$_{31}$ to R$_{40}$, and R$_{41}$ to R$_{46}$ are each independently a hydrogen atom, a halogen atom, a substituted or unsubstituted alkyl group comprising 1 to 10 carbon atoms, a substituted or unsubstituted cycloalkyl group comprising 3 to 8 ring carbon atoms, a substituted silyl group comprising 3 to 30 carbon atoms, a cyano group, a substituted or unsubstituted alkoxy group comprising 1 to 20 carbon atoms, a substituted or unsubstituted aryloxy group comprising 6 to 20 ring carbon atoms, a substituted or unsubstituted alkylthio group comprising 1 to 20 carbon atoms, a substituted or unsubstituted arylthio group comprising 6 to 30 carbon atoms, a substituted or unsubstituted arylamino group comprising 6 to 30 carbon atoms, a substituted or unsubstituted mono- or dialkylamino group comprising 1 to 20 carbon atoms, a substituted or unsubstituted aryl group comprising 6 to 30 ring carbon atoms, or a substituted or unsubstituted heterocyclic group comprising 5 to 30 ring atoms;

any one of R$_{31}$ to R$_{35}$ and any one of R$_{36}$ to R$_{40}$ is a single bond which bonds two pyridine rings in formula (4);

X is N or CR$_{13}$, wherein R$_{13}$ is a hydrogen atom, a halogen atom, a substituted or unsubstituted alkyl group comprising 1 to 10 carbon atoms, a substituted or unsubstituted cycloalkyl group comprising 3 to 8 ring carbon atoms, a substituted silyl group comprising 3 to 30 carbon atoms, a cyano group, a substituted or unsubstituted alkoxy group comprising 1 to 20 carbon atoms, a substituted or unsubstituted aryloxy group comprising 6 to 20 ring carbon atoms, a substituted or unsubstituted alkylthio group comprising 1 to 20 carbon atoms, a substituted or unsubstituted arylthio group comprising 6 to 30 carbon atoms, a substituted or unsubstituted arylamino group comprising 6 to 30 carbon atoms, a substituted or unsubstituted mono- or dialkylamino group comprising 1 to 20 carbon atoms, a substituted or unsubstituted aryl group comprising 6 to 30 ring carbon atoms, or a substituted or unsubstituted heterocyclic group comprising 5 to 30 ring atoms;

when plural R$_{13}$s are present, the R$_{13}$s may be the same or different;

Y is N or CR$_{23}$, wherein R$_{23}$ is a hydrogen atom, a halogen atom, a substituted or unsubstituted alkyl group comprising 1 to 10 carbon atoms, a substituted or unsubstituted cycloalkyl group comprising 3 to 8 ring carbon atoms, a substituted silyl group comprising 3 to 30 carbon atoms, a cyano group, a substituted or unsubstituted alkoxy group comprising 1 to 20 carbon atoms, a substituted or unsubstituted aryloxy group comprising 6 to 20 ring carbon atoms, a substituted or unsubstituted alkylthio group comprising 1 to 20 carbon atoms, a substituted or unsubstituted arylthio group comprising 6 to 30 carbon atoms, a substituted or unsubstituted arylamino group comprising 6 to 30 carbon atoms, a substituted or unsubstituted mono- or dialkylamino group comprising 1 to 20 carbon atoms, a substituted or unsubstituted aryl group comprising 6 to 30 ring carbon atoms, or a substituted or unsubstituted heterocyclic group comprising 5 to 30 ring atoms;

when plural R$_{23}$s are present, the R$_{23}$s may be the same or different;

Z is a cross-linking group, which is a substituted or unsubstituted alkylene group or a substituted or unsubstituted alkenylene group; and any one of R$_{11}$ to R$_{13}$, any one of R$_{21}$ to R$_{23}$, any one of R$_{31}$ to R$_{40}$, and any one of R$_{41}$ to R$_{46}$ is a single bond which bonds to L.

2. The oxygen-comprising fused ring of claim 1, wherein Ar$_1$ is the fused ring group of formula (9) or (10).

3. The oxygen-comprising fused ring of claim 1, wherein Ar$_1$ is the fused ring group of formula (11), (12), (13), or (14).

4. The oxygen-comprising fused ring of claim 1, wherein Ar$_1$ the fused ring group of formula (15).

5. The oxygen-comprising fused ring of claim 1, wherein m is 1 and n is 1.

6. The oxygen-comprising fused ring of claim 1, which is a material for an organic electroluminescence device.

7. An oxygen-comprising fused ring, of formula (1):

wherein:
Ar$_1$ is an m-valent fused ring group in which four or more rings comprising one or more rings selected from the group consisting of a furan ring and a pyran ring are fused HAr is nitrogen-comprising heterocyclic of formulae (2), (3), (4), or (5); with the proviso that when Ar1 is represented by formula (12) HAr is not represented by formula (4);

n and m are each independently an integer from 1 to 5, and at least one of n and m is 1; and L is a single bond, a substituted or unsubstituted n+1 valent aryl group comprising 6 to 30 ring carbon atoms, a substituted or unsubstituted n+1 valent heterocyclic group comprising 5 to 30 ring atoms, or an n+1 valent group obtained by combining, through a single bond, two or three selected from the group consisting of a substituted or unsubstituted aryl group comprising 6 to 30 ring carbon atoms and a substituted or unsubstituted heterocyclic group comprising 5 to 30 ring atoms:

wherein:

$R_{11}$, $R_{12}$, $R_{21}$, $R_{22}$, $R_{31}$ to $R_{40}$ and $R_{41}$ to $R_{46}$ are each independently a hydrogen atom, a halogen atom, a substituted or unsubstituted alkyl group comprising 1 to 10 carbon atoms, a substituted or unsubstituted cycloalkyl group comprising 3 to 8 ring carbon atoms, a substituted silyl group comprising 3 to 30 carbon atoms, a cyano group, a substituted or unsubstituted alkoxy group comprising 1 to 20 carbon atoms, a substituted or unsubstituted aryloxy group comprising 6 to 20 ring carbon atoms, a substituted or unsubstituted alkylthio group comprising 1 to 20 carbon atoms, a substituted or unsubstituted arylthio group comprising 6 to 30 carbon atoms, a substituted or unsubstituted arylamino group comprising 6 to 30 carbon atoms, a substituted or unsubstituted mono- or dialkylamino group comprising 1 to 20 carbon atoms, a substituted or unsubstituted aryl group comprising 6 to 30 ring carbon atoms, or a substituted or unsubstituted heterocyclic group comprising 5 to 30 ring atoms;

any one of $R_{31}$ to $R_{35}$ and any one of $R_{36}$ to $R_{40}$ is a single bond which bonds two pyridine rings in formula (4);

X is N or $CR_{13}$, wherein $R_{13}$ is a hydrogen atom, a halogen atom, a substituted or unsubstituted alkyl group comprising 1 to 10 carbon atoms, a substituted or unsubstituted cycloalkyl group comprising 3 to 8 ring carbon atoms, a substituted silyl group comprising 3 to 30 carbon atoms, a cyano group, a substituted or unsubstituted alkoxy group comprising 1 to 20 carbon atoms, a substituted or unsubstituted aryloxy group comprising 6 to 20 ring carbon atoms, a substituted or unsubstituted alkylthio group comprising 1 to 20 carbon atoms, a substituted or unsubstituted arylthio group comprising 6 to 30 carbon atoms, a substituted or unsubstituted arylamino group comprising 6 to 30 carbon atoms, a substituted or unsubstituted mono- or dialkylamino group comprising 1 to 20 carbon atoms, a substituted or unsubstituted aryl group comprising 6 to 30 ring carbon atoms, or a substituted or unsubstituted heterocyclic group comprising 5 to 30 ring atoms, when plural $R_{13}$s are present, the $R_{13}$s may be the same or different;

Y is N or $CR_{23}$, wherein $R_{23}$ is a hydrogen atom, a halogen atom, a substituted or unsubstituted alkyl group comprising 1 to 10 carbon atoms, a substituted or unsubstituted cycloalkyl group comprising 3 to 8 ring carbon atoms, a substituted silyl group comprising 3 to 30 carbon atoms, a cyano group, a substituted or unsubstituted alkoxy group comprising 1 to 20 carbon atoms, a substituted or unsubstituted aryloxy group comprising 6 to 20 ring carbon atoms, a substituted or unsubstituted alkylthio group comprising 1 to 20 carbon atoms, a substituted or unsubstituted arylthio group comprising 6 to 30 carbon atoms, a substituted or unsubstituted arylamino group comprising 6 to 30 carbon atoms, a substituted or unsubstituted mono- or dialkylamino group comprising 1 to 20 carbon atoms, a substituted or unsubstituted aryl group comprising 6 to 30 ring carbon atoms, or a substituted or unsubstituted heterocyclic group comprising 5 to 30 ring atoms;

when plural $R_{23}$s are present, the $R_{23}$s may be the same or different;

Z is a cross-linking group, which is a substituted or unsubstituted alkylene group or a substituted or unsubstituted alkenylene group; and any one of $R_{11}$ to $R_{13}$, any one of $R_{21}$ to $R_{23}$, any one of $R_{31}$ to $R_{40}$ and any one of $R_{41}$ to $R_{46}$ is a single bond which bonds to L, and wherein the oxygen-comprising fused ring is a material for a blocking layer of an organic electroluminescence device.

8. An organic electroluminescence device, comprising, in the following sequence:

an anode;

an emitting layer;

a blocking layer; and a cathode, wherein the blocking layer comprises an oxygen-comprising fused ring of formula (1):

$$(Ar_1)_n\text{—}(L\text{—}HAr)_m \qquad (1)$$

wherein:

$Ar_1$ is an m-valent fused ring group in which four or more rings comprising one or more rings selected from the group consisting of a furan ring and a pyran ring are fused HAr is nitrogen-comprising heterocyclic of formulae (2), (3), (4), or (5); with the proviso that when Ar1 is represented by formula (12) HAr is not represented by formula (4);

n and m are each independently an integer from 1 to 5, and at least one of n and m is 1; and L is a single bond, a substituted or unsubstituted n+1 valent aryl group comprising 6 to 30 ring carbon atoms, a substituted or unsubstituted n+1 valent heterocyclic group comprising 5 to 30 ring atoms, or an n+1 valent group obtained by combining, through a single bond, two or three selected from the group consisting of a substituted or unsubstituted aryl group comprising 6 to 30 ring carbon atoms and a substituted or unsubstituted heterocyclic group comprising 5 to 30 ring atoms:

wherein:

$R_{11}$, $R_{12}$, $R_{21}$, $R_{22}$, $R_{31}$ to $R_{40}$, and $R_{41}$ to $R_{46}$ are each independently a hydrogen atom, a halogen atom, a substituted or unsubstituted alkyl group comprising 1 to 10 carbon atoms, a substituted or unsubstituted cycloalkyl group comprising 3 to 8 ring carbon atoms, a substituted silyl group comprising 3 to 30 carbon atoms, a cyano group, a substituted or unsubstituted alkoxy group comprising 1 to 20 carbon atoms, a substituted or unsubstituted aryloxy group comprising 6 to 20 ring carbon atoms, a substituted or unsubstituted alkylthio group comprising 1 to 20 carbon atoms, a substituted or unsubstituted arylthio group comprising 6 to 30 carbon atoms, a substituted or unsubstituted arylamino group comprising 6 to 30 carbon atoms, a substituted or unsubstituted mono- or dialkylamino group comprising 1 to 20 carbon atoms, a substituted or unsubstituted aryl group comprising 6 to 30 ring carbon atoms, or a substituted or unsubstituted heterocyclic group comprising 5 to 30 ring atoms;

any one of $R_{31}$ to $R_{35}$ and any one of $R_{36}$ to $R_{40}$ is a single bond which bonds two pyridine rings in formula (4);

X is N or $CR_{13}$, wherein $R_{13}$ is a hydrogen atom, a halogen atom, a substituted or unsubstituted alkyl group comprising 1 to 10 carbon atoms, a substituted or unsubstituted cycloalkyl group comprising 3 to 8 ring carbon atoms, a substituted silyl group comprising 3 to 30 carbon atoms, a cyano group, a substituted or unsubstituted alkoxy group comprising 1 to 20 carbon atoms, a substituted or unsubstituted aryloxy group comprising 6 to 20 ring carbon atoms, a substituted or unsubstituted alkylthio group comprising 1 to 20 carbon atoms, a substituted or unsubstituted arylthio group comprising 6 to 30 carbon atoms, a substituted or unsubstituted arylamino group comprising 6 to 30 carbon atoms, a substituted or unsubstituted mono- or dialkylamino group comprising 1 to 20 carbon atoms, a substituted or unsubstituted aryl group comprising 6 to 30 ring carbon atoms, or a substituted or unsubstituted heterocyclic group comprising 5 to 30 ring atoms;

when plural $R_{13}$s are present, the $R_{13}$s may be the same or different;

Y is N or $CR_{23}$, wherein $R_{23}$ is a hydrogen atom, a halogen atom, a substituted or unsubstituted alkyl group comprising 1 to 10 carbon atoms, a substituted or unsubstituted cycloalkyl group comprising 3 to 8 ring carbon atoms, a substituted silyl group comprising 3 to 30 carbon atoms, a substituted or unsubstituted alkoxy group comprising 1 to 20 carbon atoms, a substituted or unsubstituted aryloxy group comprising 6 to 20 ring carbon atoms, a substituted or unsubstituted alkylthio group comprising 1 to 20 carbon atoms, a substituted or unsubstituted arylthio group comprising 6 to 30 carbon atoms, a substituted or unsubstituted arylamino group comprising 6 to 30 carbon atoms, a substituted or unsubstituted mono- or dialkylamino group comprising 1 to 20 carbon atoms, a substituted or unsubstituted aryl group comprising 6 to 30 ring carbon atoms, or a substituted or unsubstituted heterocyclic group comprising 5 to 30 ring atoms;

when plural $R_{23}$s are present, the $R_{23}$s may be the same or different;

Z is a cross-linking group, which is a substituted or unsubstituted alkylene group or a substituted or unsubstituted alkenylene group; and any one of $R_{11}$ to $R_{13}$ any one of $R_{21}$ to $R_{23}$, any one of $R_{31}$ to $R_{40}$, and any one of $R_{41}$ to $R_{46}$ is a single bond which bonds to L.

9. The organic electroluminescence device of claim 8, further comprising:
an electron-injecting layer and/or an electron-transporting layer between the blocking layer and the cathode, wherein at least one layer of the electron-injecting layer and the electron-transporting layer comprises a hetero ring-comprising derivative.

10. The organic electroluminescence device of claim 9, wherein the electron-injecting layer and/or the electron-transporting layer comprises an electron-donating dopant.

11. The organic electroluminescence device of claim 10, wherein the electron-donating dopant is at least one selected from the group consisting of an alkali metal, an alkaline-earth metal, a rare earth metal, an oxide of an alkali metal, a halide of an alkali metal, an oxide of an alkaline-earth metal, a halide of an alkaline-earth metal, an oxide of a rare earth metal, a halide of a rare earth metal, an organic complex of an alkali metal, an organic complex of an alkaline-earth metal, and an organic complex of a rare earth metal.

12. The organic electroluminescence device of claim 8, wherein the emitting layer comprises an anthracene of formula (16):

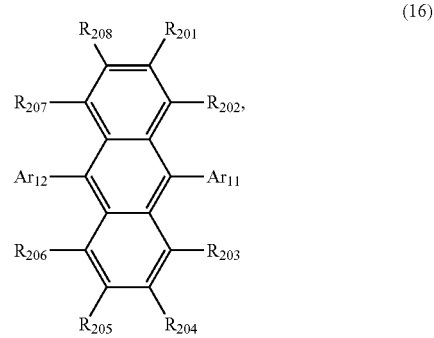

(16)

wherein:
$Ar_{11}$ and $Ar_{12}$ are each independently a substituted or unsubstituted aryl group comprising 6 to 30 ring carbon atoms or a substituted or unsubstituted heterocyclic group comprising 5 to 30 ring atoms; and $R_{201}$ to $R_{208}$ are each independently a hydrogen atom, a fluorine atom, a substituted or unsubstituted alkyl group comprising 1 to 10 carbon atoms, a substituted or unsubstituted cycloalkyl group comprising 3 to 10 ring carbon atoms, a substituted or unsubstituted alkylsilyl group comprising 3 to 30 carbon atoms, a substituted or unsubstituted arylsilyl group comprising 8 to 30 ring carbon atoms, a substituted or unsubstituted alkoxy group comprising 1 to 20 carbon atoms, a substituted or unsubstituted aryloxy group comprising 6 to 20 ring carbon atoms, a substituted or unsubstituted aryl group comprising 6 to 30 ring carbon atoms, or a substituted or unsubstituted heterocyclic group comprising 5 to 30 ring atoms.

13. The organic electroluminescence device of claim 12, wherein the emitting layer comprising the anthracene of formula (16) is in contact with the blocking layer comprising the oxygen-comprising fused ring.

14. The organic electroluminescence device of claim 8, wherein the emitting layer comprises a fluorescent dopant having a main peak wavelength of 500 nm or less.

* * * * *